US011697792B2

(12) United States Patent
Hinojosa et al.

(10) Patent No.: US 11,697,792 B2
(45) Date of Patent: Jul. 11, 2023

(54) EFFECTS OF SPACE TRAVEL ON HUMAN BRAIN CELLS

(71) Applicant: EMULATE, INC., Boston, MA (US)

(72) Inventors: Christopher David Hinojosa, Malden, MA (US); Josiah Sliz, Boston, MA (US); Iosif Pediaditakis, Boston, MA (US); Sonalee Barthakur, Boston, MA (US)

(73) Assignee: EMULATE, INC., Boston, MA (US)

( * ) Notice: Subject to any disclaimer, the term of this patent is extended or adjusted under 35 U.S.C. 154(b) by 317 days.

(21) Appl. No.: 16/712,439

(22) Filed: Dec. 12, 2019

(65) Prior Publication Data

US 2020/0181555 A1    Jun. 11, 2020

Related U.S. Application Data

(63) Continuation of application No. PCT/US2018/037505, filed on Jun. 14, 2018.
(Continued)

(51) Int. Cl.
| | |
|---|---|
| *C12M 1/00* | (2006.01) |
| *B01L 3/00* | (2006.01) |
| *C12M 3/06* | (2006.01) |
| *G01N 1/18* | (2006.01) |
| *C12M 1/26* | (2006.01) |

(52) U.S. Cl.
CPC ....... *C12M 29/10* (2013.01); *B01L 3/502738* (2013.01); *C12M 23/16* (2013.01); *C12M 29/14* (2013.01); *B01L 2300/0861* (2013.01); *B01L 2400/0605* (2013.01); *C12M 33/00* (2013.01); *G01N 1/18* (2013.01)

(58) Field of Classification Search
CPC ...... C12M 23/16; C12M 29/10; C12M 29/14; C12M 33/00; B01L 3/502738; B01L 2300/0861; B01L 2400/0605; G01N 1/18
See application file for complete search history.

(56) References Cited

U.S. PATENT DOCUMENTS

| | | | |
|---|---|---|---|
| 4,208,483 A | 6/1980 | Lee | ............................ 435/299.1 |
| 2002/0146817 A1* | 10/2002 | Cannon | .................. C12M 29/10 |
| | | | 435/289.1 |

(Continued)

FOREIGN PATENT DOCUMENTS

| | | | | |
|---|---|---|---|---|
| WO | WO/2016/010861 | | 1/2016 | |
| WO | WO-2016010861 A1 * | | 1/2016 | ............ B01L 3/5027 |

(Continued)

OTHER PUBLICATIONS

U.S. Appl. No. 62/024,361, Hinojosa, C. D. et al., filed Jul. 14, 2014.

(Continued)

*Primary Examiner* — Michael L Hobbs
(74) *Attorney, Agent, or Firm* — Medlen & Carroll, LLP

(57) ABSTRACT

The invention generally relates to a microfluidic platforms or "chips" for testing and conducting experiments on the International Space Station (ISS). More specifically, microfluidic Brain-On-Chip, comprising neuronal and vascular endothelial cells, will be analyzed in both healthy and inflamed states to assess how the circumstances of space travel affect the human brain.

8 Claims, 70 Drawing Sheets
(9 of 70 Drawing Sheet(s) Filed in Color)

Related U.S. Application Data

(60) Provisional application No. 62/648,715, filed on Mar. 27, 2018, provisional application No. 62/561,465, filed on Sep. 21, 2017, provisional application No. 62/519,739, filed on Jun. 14, 2017.

(56) References Cited

U.S. PATENT DOCUMENTS

| | | | |
|---|---|---|---|
| 2012/0329171 A1 | 12/2012 | Ismagliov et al. | 435/6.12 |
| 2014/0038279 A1 | 2/2014 | Ingber et al. | 435/297.2 |
| 2015/0119327 A1 | 4/2015 | Muotri et al. | 514/8.6 |
| 2015/0165436 A1 | 6/2015 | Chapman et al. | 435/287.2 |
| 2015/0306596 A1 | 10/2015 | Thompson et al. | 435/29 |
| 2017/0055522 A1 | 3/2017 | Levner et al. | 435/284.1 |

FOREIGN PATENT DOCUMENTS

| | | | |
|---|---|---|---|
| WO | WO/2017/027838 | 2/2017 | |
| WO | WO/2017/035484 | 3/2017 | |
| WO | WO/2017/070224 | 4/2017 | |
| WO | WO-2017074959 A1 * | 5/2017 | C12M 23/58 |

OTHER PUBLICATIONS

U.S. Appl. No. 62/127,438, Hinojosa, C. D. et al., filed Mar. 3, 2015.
ABCAM. Human skeletal muscle tissue lysate—total protein (ab29330), https://www.abcam.com/human-skeletal-muscle-tissue-lysate-total-protein-ab29330.html.
ABCAM. Human brain tissue lysate—total protein (ab29466), https://www.abcam.com/human-brain-tissue-lysate-total-protein-ab29466.html.
ABCAM. HepG2 whole cell lysate (ab7900), https://www.abcam.com/HepG2-whole-cell-lysate-ab7900.html.
ABCAM. Anti-Glucose Transporter GLUT1 antibody (ab15309), https://www.abcam.com/glucose-transporter-glut1-antibody-ab15309.html.
ABCAM. Anti-beta III Tubulin antibody (ab18207), https://www.abcam.com/beta-III-Tubulin-antibody-ab18207.html.
ABCAM. Anti-alpha smooth muscle Actin antibody (ab5694), https://www.abcam.com/alpha-smooth-muscle-actin-antibody-ab5694.html.
ABCAM. Anti-GFAP antibody [GF5] (ab10062), https://www.abcam.com/gfap-antibody-gf5-ab10062.html.
Avram, M. et al. (2008) "Plasma Surface Modification for Selective Hydrophobic Control," *Romanian Journal of Information Science and Technology* 11(4), 409-422.
Bake, S. et al. (2004)"17β-Estradiol Differentially Regulates Blood-Brain Barrier Permeability in Young and Aging Female Rats," *Endocrinology* 145(12), 5471-5475.
Bellone, J. A. et al. (2016) "Long-term effects of simulated microgravity and/or chronic exposure to low-dose gamma radiation on behavior and blood-brain barrier integrity," *npj Microgravity* 2(1), 16019.
Benam, K. H. et al. (2015) "Engineered in Vitro Disease Models," *Annual Review of Pathology: Mechanisms of Disease* 10(1), 195-262.
Benam, K. H. et al. (2016) "Small airway-on-a-chip enables analysis of human lung inflammation and drug responses in vitro," *Nature Methods* 13(2), 151-157.
Berridge, M. J. et al. (2000) "The versatility and universality of calcium signalling," *Nature Reviews Molecular Cell Biology* 1(1), 11-21.
Burek, M. et al. (2014) "Mechanisms of transcriptional activation of the mouse claudin-5 promoter by estrogen receptor alpha and beta," *Molecular and Cellular Endocrinology* 392(1), 144-151.
Cabezas, R. et al. (2014) "Astrocytic modulation of blood brain barrier: perspectives on Parkinson's disease," *Frontiers in cellular neuroscience* 8, 211-211.
Cao, S.-Y. et al. (2017) "Enhanced derivation of human pluripotent stem cell-derived cortical glutamatergic neurons by a small molecule," *Scientific Reports* 7(1), 3282.
Chanda, S. et al. (2014) "Generation of Induced Neuronal Cells by the Single Reprogramming Factor ASCL 1," *Stem Cell Reports* 3(2), 282-296.
Chen, C. et al. (1987) "High-efficiency transformation of mammalian cells by plasmid DNA," *Molecular and Cellular Biology* 7(8), 2745.
Chen, J. et al. (2012) "Computational simulation of the p-n doped silicon quantum dot," *International Journal of Quantum Chemistry* 112(24), 3879-3888.
Chi, O. Z. et al. (2004) "17beta-estradiol prevents blood-brain barrier disruption induced by VEGF," *Hormone and Metabolic Research* 36(5), 272-276.
Chodobski, A. et al. (2011) "Blood-brain barrier pathophysiology in traumatic brain injury," *Translational stroke research* 2(4), 492-516.
Crucian, B. et al. (2013) "Immune System Dysregulation Occurs During Short Duration Spaceflight on Board the Space Shuttle," *Journal of Clinical Immunology* 33(2), 456-465.
Delp, M. D. et al. (2016) "Apollo Lunar Astronauts Show Higher Cardiovascular Disease Mortality: Possible Deep Space Radiation Effects on the Vascular Endothelium," *Scientific Reports* 6(1), 29901.
Desai, B. S. et al. (2007) "Blood-Brain Barrier Pathology in Alzheimer's and Parkinson's Disease: Implications for Drug Therapy," *Cell Transplantation* 16(3), 285-299.
Engelhardt, B. et al. (2014) "Novel insights into the development and maintenance of the blood-brain barrier," *Cell and Tissue Research* 355(3), 687-699.
Fisherscientific. HUVEC(human umbilical vein) Whole cell lysate, Non-denatured; Abnova https://www.fishersci.com/shop/products/huvec-human-umbilical-vein-whole-cell-lysate-nondenatured-abnova-200-g/89014394.
Garbuzova-Davis, S. et al. (2012) "Impaired blood-brain/spinal cord barrier in ALS patients," *Brain Research* 1469, 114-128.
Gimbrone, M. A., Jr. et al. (2016) "Endothelial Cell Dysfunction and the Pathobiology of Atherosclerosis," *Circulation Research* 118(4), 620-636.
Gray, M. T. et al. (2015) "Striatal blood-brain barrier permeability in Parkinson's disease," *Journal of Cerebral Blood Flow and Metabolism* 35(5), 747-750.
Halvorson, K. G. et al. (2005) "A Blocking Antibody to Nerve Growth Factor Attenuates Skeletal Pain Induced by Prostate Tumor Cells Growing in Bone," *Cancer Research* 65(20), 9426-9435.
Hawkins, B. T. et al. (2005) "The Blood-Brain Barrier/Neurovascular Unit in Health and Disease," *Pharmacological Reviews* 57(2), 173.
Hong, S. M. et al. (2006) "Hydrophilic Surface Modification of PDMS Using Atmospheric RF Plasma," *Journal of Physics: Conference Series* 34(1), 656.
Huh, D. et al. (2010) "Reconstituting Organ-Level Lung Functions on a Chip," *Science* 328(5986), 1662.
Ivens, S. et al. (2006) "TGF-β receptor-mediated albumin uptake into astrocytes is involved in neocortical epileptogenesis," *Brain* 130(2), 535-547.
Jenson, D. et al. (2014) "Temporal dynamics of sensorimotor integration in speech perception and production: independent component analysis of EEG data," *Frontiers in psychology* 5, 656-656.
Kim, H. J. et al. (2012) "Human gut-on-a-chip inhabited by microbial flora that experiences intestinal peristalsis-like motions and flow," *Lab on a Chip* 12(12), 2165-2174.
Kuijlaars, J. et al. (2016) "Sustained synchronized neuronal network activity in a human astrocyte co-culture system," *Scientific Reports* 6(1), 36529.
Maggioli, E. et al. (2016) "Estrogen protects the blood-brain barrier from inflammation-induced disruption and increased lymphocyte trafficking," *Brain, Behavior, and Immunity* 51, 212-222.
Mai, J. et al. (2013) "An evolving new paradigm: endothelial cells—conditional innate immune cells," *Journal of Hematology and Oncology* 6(1), 61.
Maier, J. A. et al. (2015) "The impact of microgravity and hypergravity on endothelial cells," *BioMed Research International* 2015, 434803.
Minagar, A. et al. (2003) "Blood-brain barrier disruption in multiple sclerosis," *Multiple Sclerosis* 9(6), 540-549.

(56) References Cited

OTHER PUBLICATIONS

Nimon, J. (2011) Gardening in Space withHydroTropi, https://phys.org/news/2011-01-gardening-space-hydrotropi.html.

Odijk, M. et al. (2015) "Measuring direct current trans-epithelial electrical resistance in organ-on-a-chip microsystems," *Lab on a Chip 15*(3), 745-752.

Pedersen, B. K. et al. (1994) "The immune system during exposure to extreme physiologic conditions," *International Journal of Sports Medicine 15 Suppl 3*, S116-121.

Ramasamy, S. et al. (2016) "Tle1 tumor suppressor negatively regulates inflammation in vivo and modulates NF-κB inflammatory pathway," *Proceedings of the National Academy of Sciences 113*(7), 1871-1876.

Robinson, P. B. et al. (2001) "Interaction of cavitation bubbles with a free surface," *Journal of Applied Physics 89*(12), 8225-8237.

Rosenberg, G. A. (2012) "Neurological diseases in relation to the blood-brain barrier," *Journal of Cerebral Blood Flow and Metabolism 32*(7), 1139-1151.

Sebastiano, V. et al. (2011) "In situ genetic correction of the sickle cell anemia mutation in human induced pluripotent stem cells using engineered zinc finger nucleases," *Stem Cells 29*(11), 1717-1726.

Sofronova, S. I. et al. (2015) "Spaceflight on the Bion-M1 biosatellite alters cerebral artery vasomotor and mechanical properties in mice," *Journal of Applied Physiology 118*(7), 830-838.

Sommer, C. A. et al. (2009) "Induced Pluripotent Stem Cell Generation Using a Single Lentiviral Stem Cell Cassette," *Stem Cells 27*(3), 543-549.

Thermofisher. ZO-1 Monoclonal Antibody (Z1-1A12), https://www.thermofisher.com/antibody/product/Z0-1-Antibody-clone-ZO1-A12-Monoclonal/33-9100.

Thorsen, T. et al. (2002) "Microfluidic Large-Scale Integration," *Science 298*(5593), 580.

Weislogel, M. M. et al. (2011) "Quasi-steady capillarity-driven flows in slender containers with interior edges," *Journal of Fluid Mechanics 685*, 271-305.

Xu, L. et al. (2010) "The iPS technique provides hope for Parkinson's disease treatment," *Stem Cell Reviews and Reports 6*(3), 398-404.

Zenaro, E. et al. (2017) "The blood-brain barrier in Alzheimer's disease," *Neurobiology of Disease 107*, 41-56.

Zhang, Y. et al. (2013) "Rapid Single-Step Induction of Functional Neurons from Human Pluripotent Stem Cells," *Neuron 78*(5), 785-798.

PCT International Search Report of International Application No. PCT/US2018/037505 dated Oct. 26, 2018.

\* cited by examiner

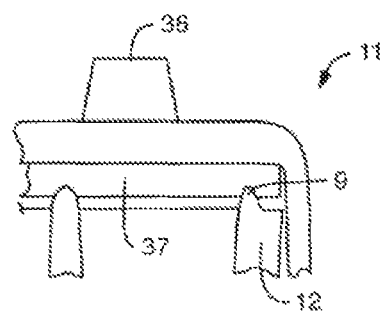
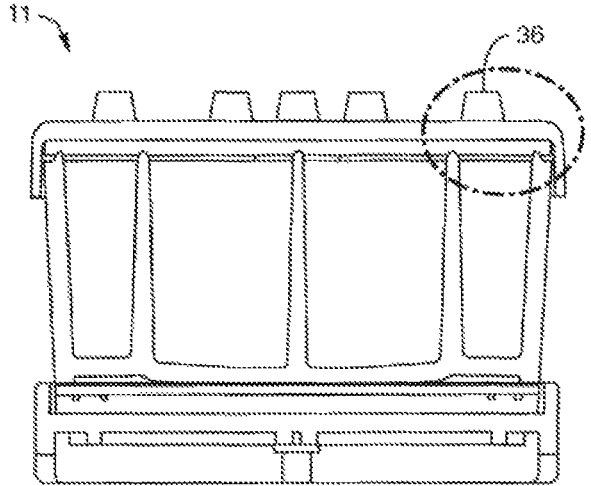
FIG. 2E-2
FIG. 2E-1

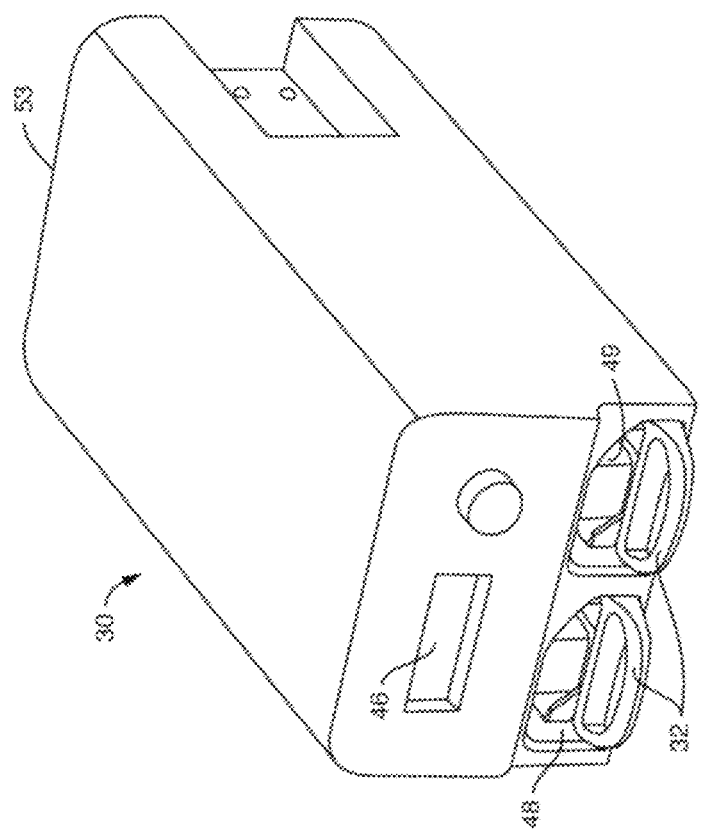
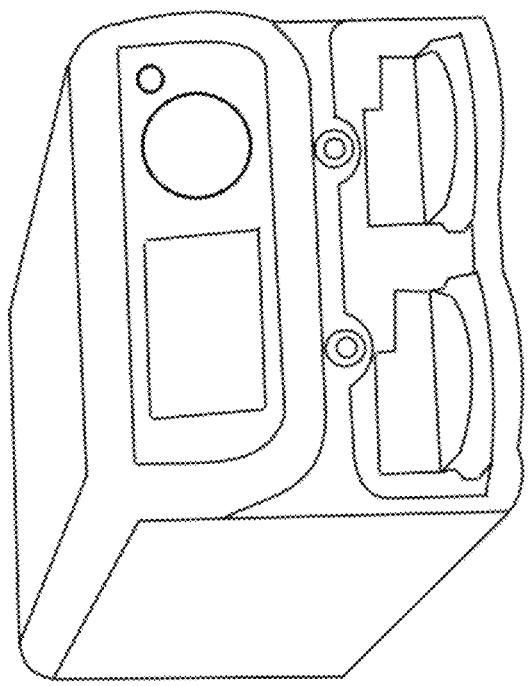
FIG. 7B

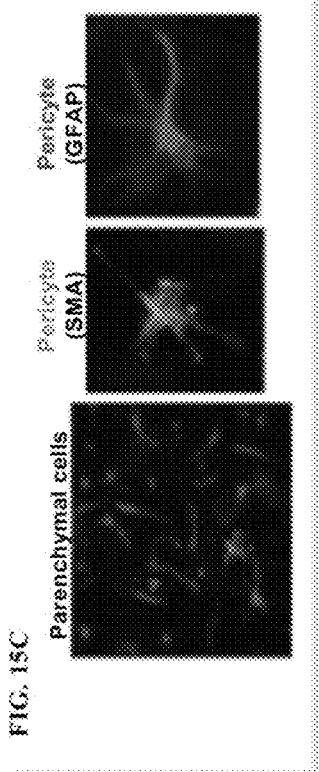
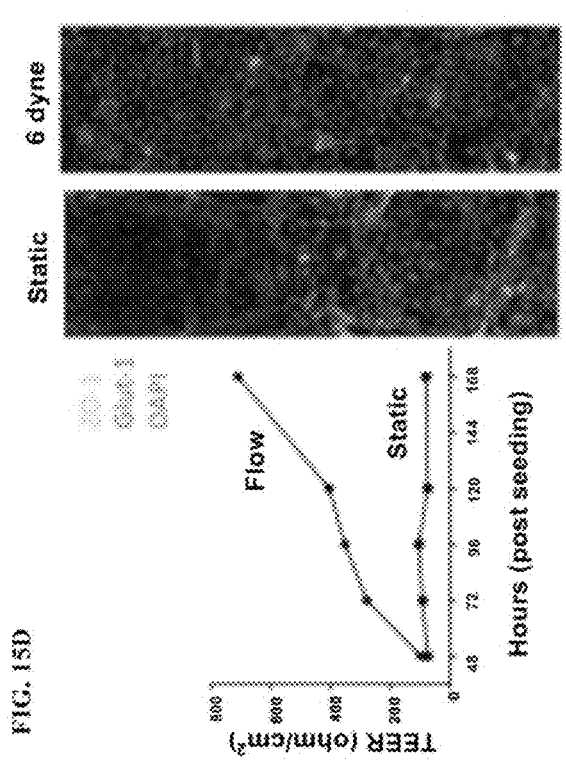
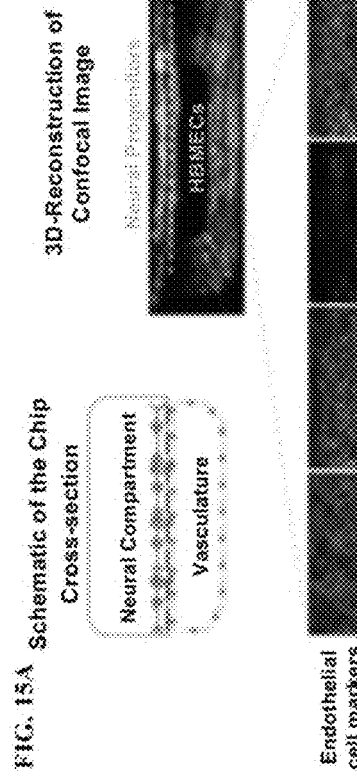
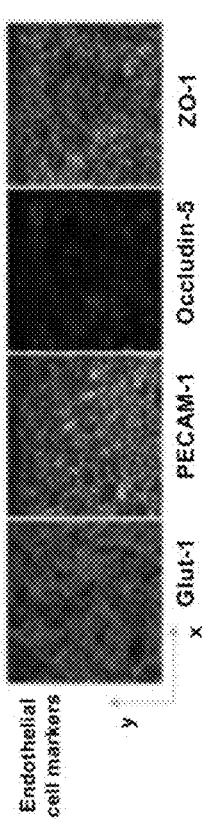
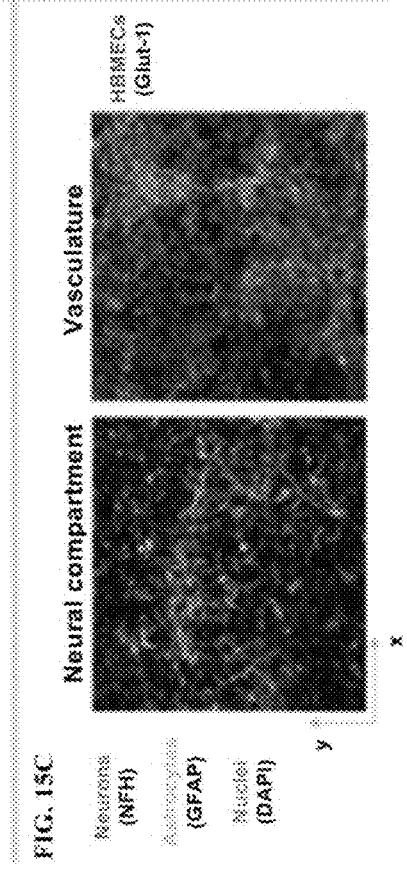
FIG. 15A-D

FIG. 17 A-D

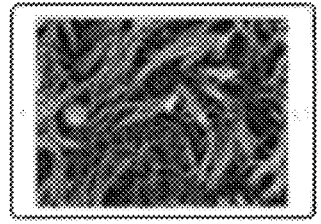
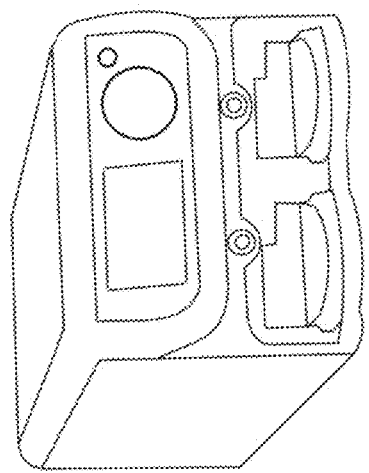
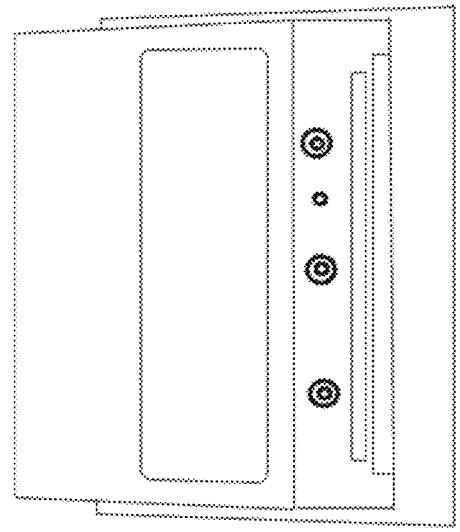
FIG. 18A-18C
FIG. 18A
FIG. 18C
FIG. 18B
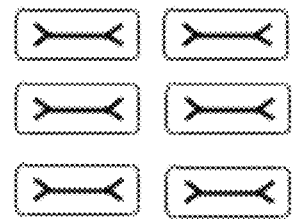

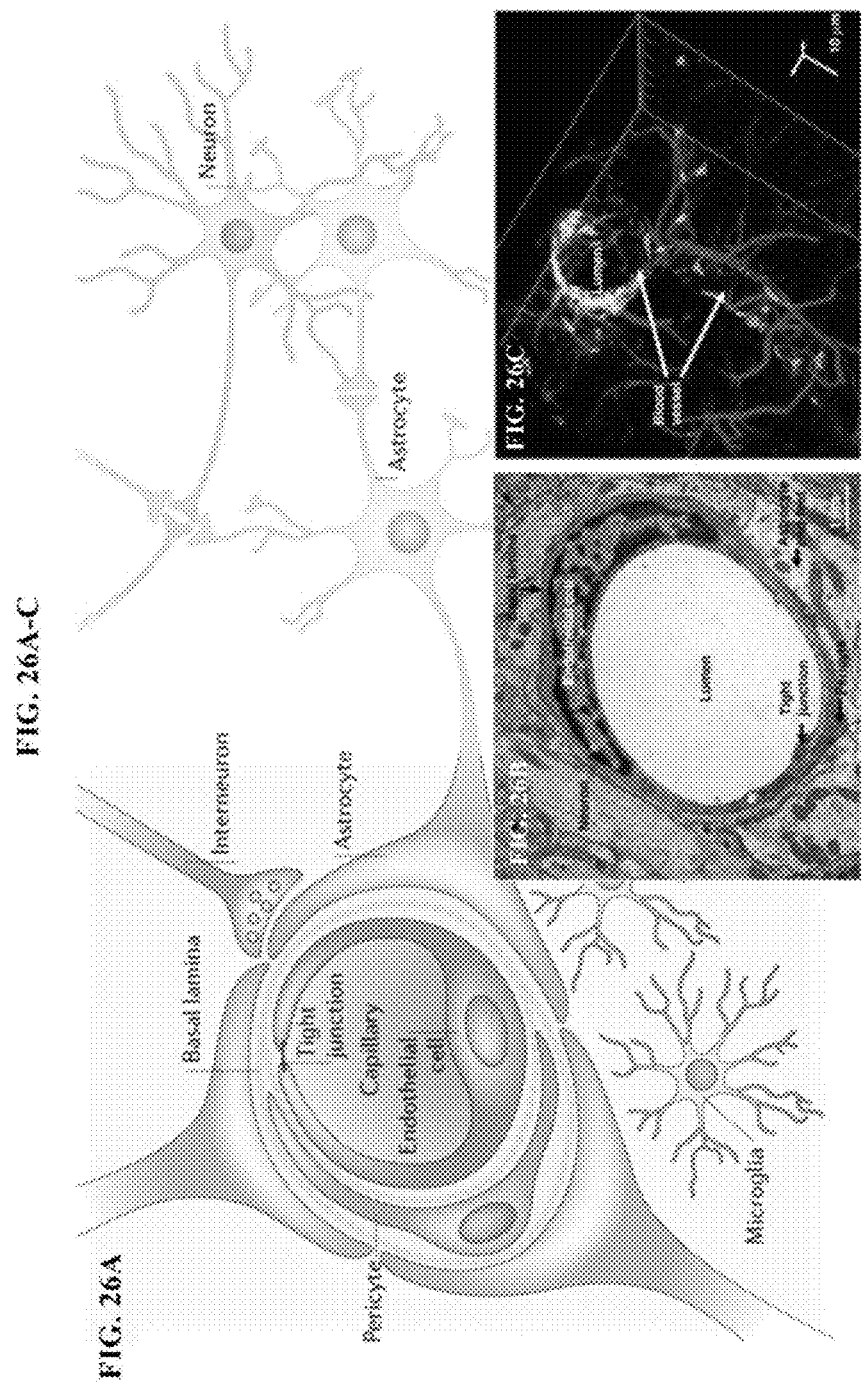
FIG. 26A-C

Fig. 27A-B
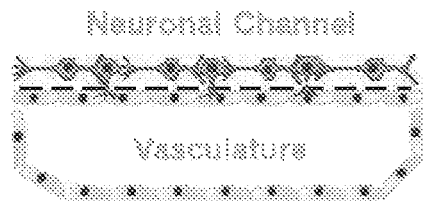
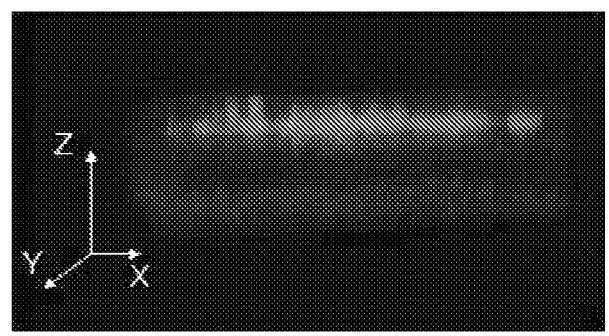
Fig. 27A
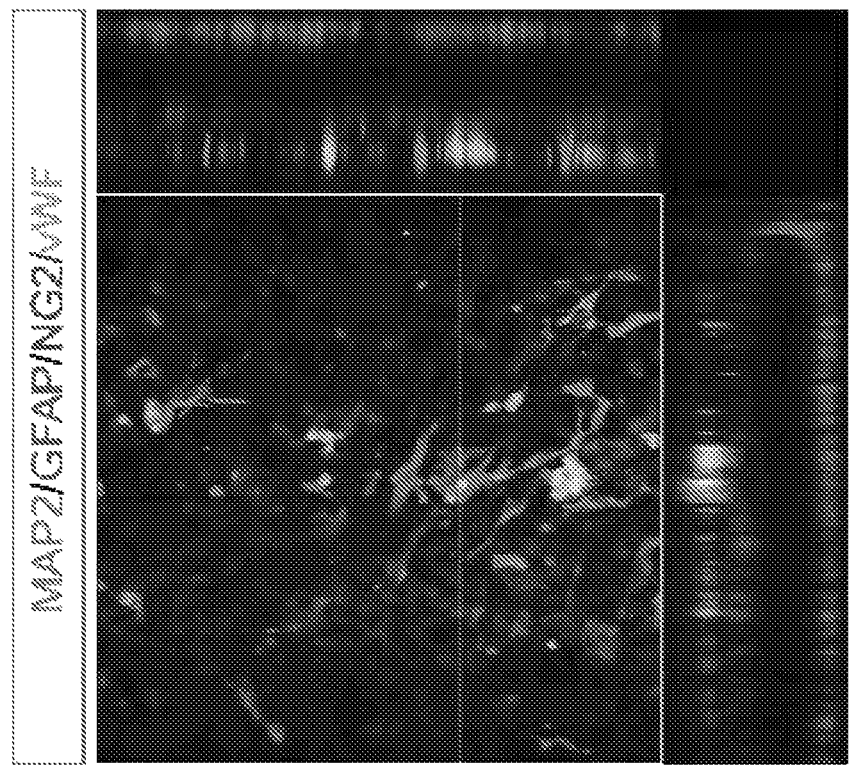
Fig. 27B

FIG. 44B - 44C
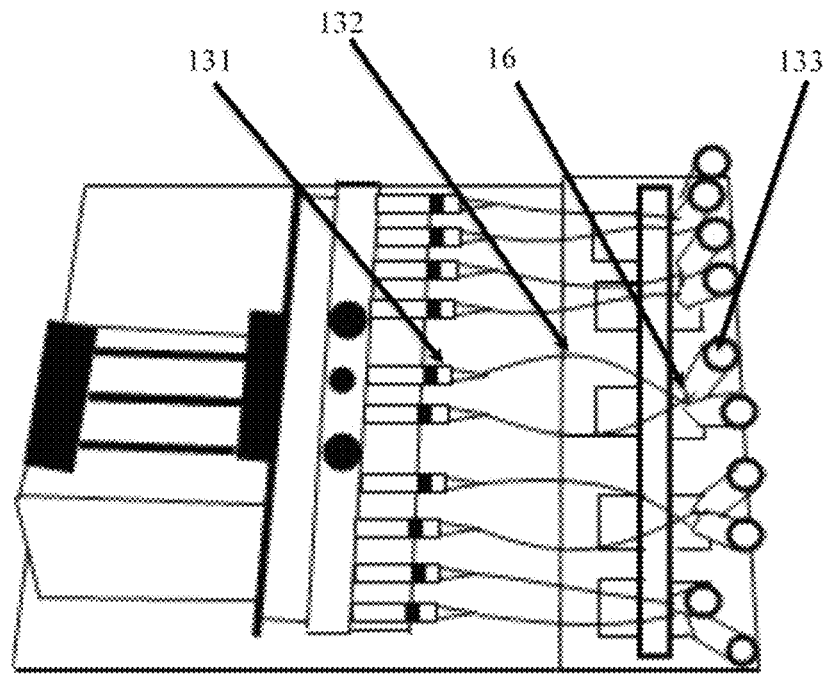
FIG. 44B
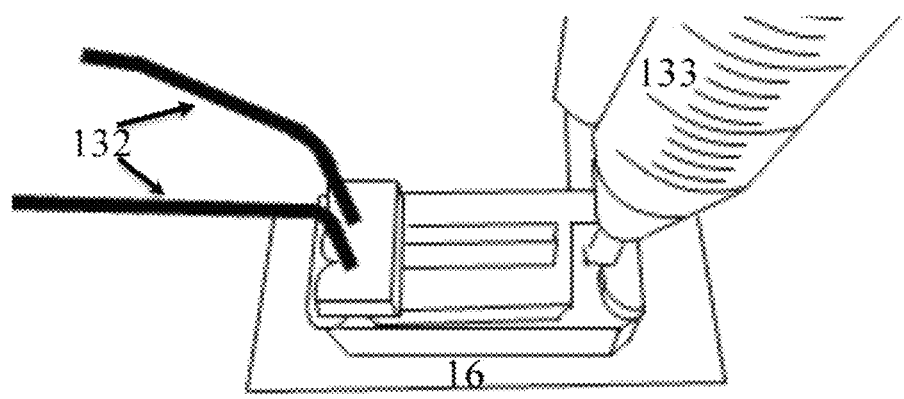
FIG. 44C

Fig. 45A-C

FIG 47A- 47B
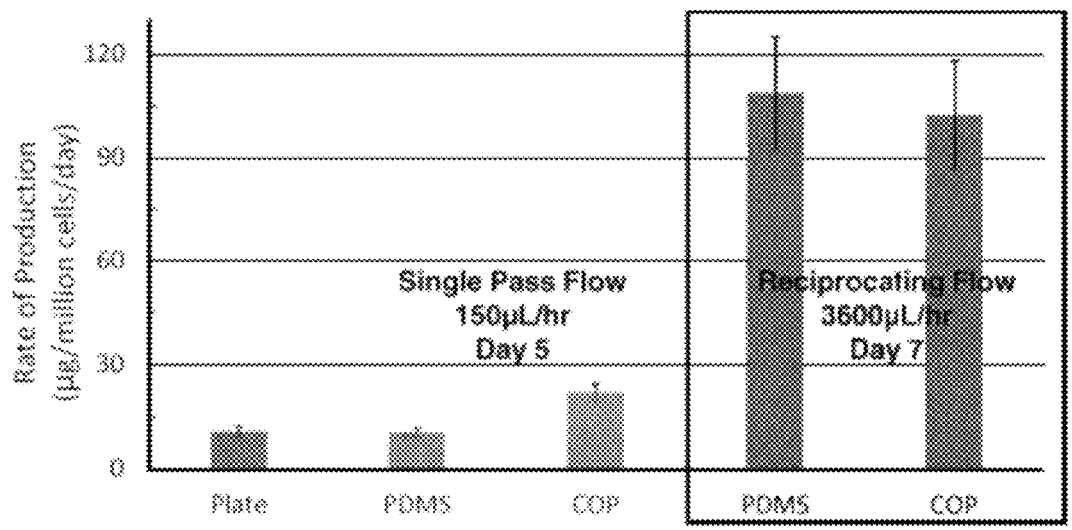
FIG 47A
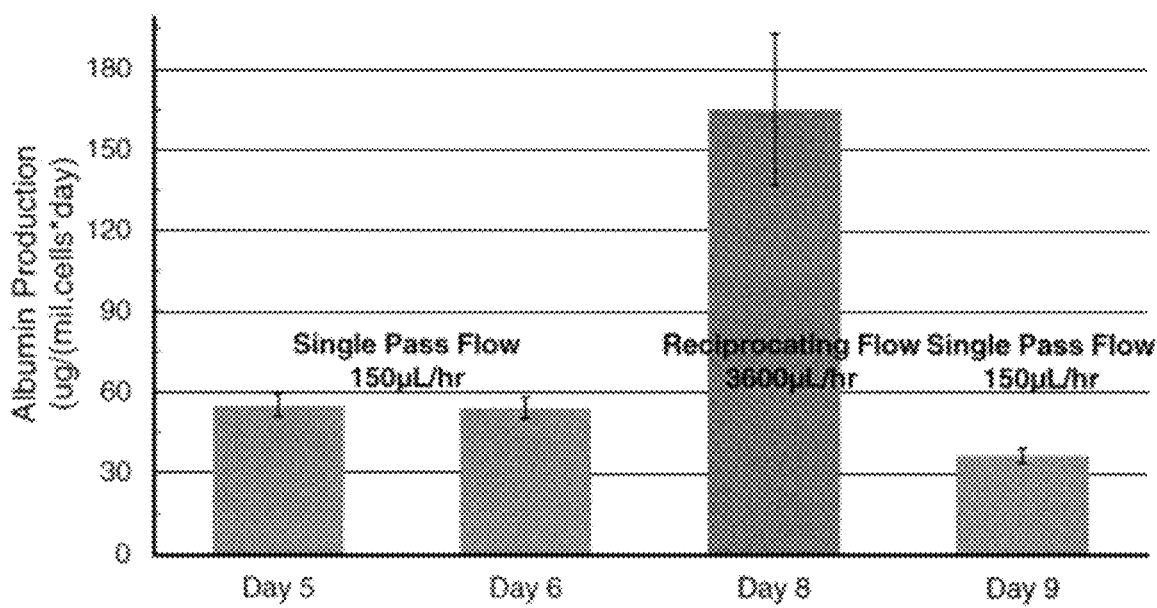
FIG 47B

EFFECTS OF SPACE TRAVEL ON HUMAN BRAIN CELLS

CROSS REFERENCE TO RELATED APPLICATIONS

This application claims priority to PCT/US18/37505, filed Jun. 14, 2018, now expired; which claims priority to Provisional Application Serial No. 62/648,715 filed on Mar. 27, 2018, now expired, which claims priority to Provisional Application Serial No. 62/561,465, filed on Sep. 21, 2017, now expired, and which claims priority to Provisional Application Serial No. 62/519,739, filed on Jun. 14, 2017, now expired, the contents of which are incorporated herein in their entirety.

FIELD OF THE INVENTION

The invention generally relates to a microfluidic platforms or "chips" for testing and conducting experiments on the International Space Station (ISS). More specifically, microfluidic Brain-On-Chip, comprising neuronal and vascular endothelial cells, will be analyzed in both healthy and inflamed states to assess how the circumstances of space travel affect the human brain.

BACKGROUND

Space exploration imposes new challenges on human physiology and offers a unique opportunity to study human biology beyond the conditions found on Earth. There is growing evidence that conditions in space have an impact on cardiovascular health and the immune response in humans (Delp et al., 2016). Prior research has shown that some of the forces experienced during liftoff or simulated microgravity conditions have been associated with a decrease in tight junction proteins and barrier integrity in multiple endothelial models (Maier et al., 2015), (Bellone et al., 2016).

Interestingly, similar pathophysiological conditions have been previously associated to early stages of vasculopathies and neurodegenerative diseases such as multiple sclerosis (MS) (Hawkins 2005, Rosenberg, 2012). However, relatively little work has been done to understand the mechanisms that might contribute to this outcome.

What is needed are better compounds and methods for decoupling gravity effects from other factors causing neuronal dysfunction. Further, information on factors separate from gravity effects are contemplated to provide new insights into neuronal degenerative disease, such as Parkinson's for providing new therapeutics.

SUMMARY OF THE INVENTION

The invention generally relates to a microfluidic platforms or "chips" for testing and conducting experiments on the International Space Station (ISS). More specifically, microfluidic Brain-On-Chip, comprising neuronal and vascular endothelial cells, will be analyzed in both healthy and inflamed states to assess how the circumstances of space travel affect the human brain.

In one embodiment, the invention contemplates a method, comprising: a) providing living cells on a membrane, said membrane in contact with one or more fluidic channels; and b) exposing said cells to a zero gravity environment. In one embodiment, said cells are neurons. In one embodiment, said neurons are in a layer on said membrane. In one embodiment, said layer has at least one characteristic in common with a blood brain barrier. In one embodiment, said membrane and said one or more fluidic channels are within a microfluidic device. In one embodiment, said zero gravity environment is in a spacecraft or space station.

Temperatures encountered over the course of spaceflight, i.e. takeoff through landing, and aboard ISS, include low temperature conditions, e.g. −80° C., for up to 12 weeks, or more, depending upon the length of space travel. Therefore, −80° C. storage conditions are added to capabilities for 4° C. storage and transition temperatures, and sample temperatures of 37° C. onboard space craft and ISS. Samples on-chips are fixed, and/or lysed, then stored at −80° C. Samples at 37° C. may be samples under incubation or during at least a part of the assay, readout. Reagents such as media, buffer, lysis buffer, fixative, etc., in addition to being stored at 4° C., also go through a −80° C. time period, e.g., prior to landing.

Thus, in some embodiments, methods described herein, include low temperature conditions, e.g. −80° C., as shown in exemplary FIG. 23. FIG. 23 shows an exemplary Thermal timeline showing temperatures of chips, reagents, and samples over the course of the flight.

For another example, Thermal design parameters are contemplated to include: Chip culture temperature (37° C.); Media storage (4° C.); Effluent storage (4° C.); Chip storage, including unfixed chips, fixed chips, and lysed chips, etc., temperature during return to earth (between 4° C. or −80° C.), etc.

Thus, in some embodiments, Hypergravity Chips are fixed then stored at −80° C. after takeoff. In some embodiments, Microgravity Chips are sampled daily and fixed at >10 days then stored at −80° C. In some embodiments, Microgravity Chips are automatically sampled daily and fixed at >10 days. In some embodiments, chips frozen at −80° C., are brought to 4° C. or ambient temperature, e.g. room temperature, then stained with antibodies. Nonlimiting examples of fixatives are fixatives are MeOH and NDS+ Glycine.

Furthermore, fixation of cells on chips were modified due in part to long storage conditions at −80° C. In part, due to the long term storage at −80° C., fixatives were tested for capabilities to retain antigen structure upon thawing for accurate staining of specific molecules, e.g. E-cadherin, showing little or no background staining.

Moreover, methods described herein were modified in part due to constraints of ISS. Therefore, fixation of chips were modified due in part to limitation of automation and cold storage options on ISS; fluid recirculation was incorporated to allow for physiological shear stress without requiring large fluidic reservoirs. Space hardware are contemplated to have new materials and components that may influence biological function. For comparisons, terrestrial parallel methods are modified accordingly.

Observed characteristics of the in vitro "BBB-on-chip" of the present invention include: (1) tight junctions between endothelial cells (which creates selective permeability to substances); (2) optional cell-to-cell communication exemplified by contact of the endothelial cells with astrocytes (e.g. endfoot contact by partial transmigration of the membrane separating these cells); (3) optional extended neurite projections, (4) optional fluid flow that influences cell differentiation and tight junction formation; and (5) high electrical resistance representing the maturity and integrity of the BBB components.

In one embodiment, the invention contemplates a method of collecting samples, comprising: a) providing an assembly comprising i) a sample-generating device comprising a first fluid and ii) a sampling conduit in fluidic communication with said sample-generating device; b) directing at least a first portion of said first fluid at a first time-point to enter said sampling conduit so as to create a first sample; and c) directing at least a second portion of said first fluid at a second time-point to enter said sampling conduit so as to create a second sample. In one embodiment, said method further comprises the step d) collecting one or more samples from said sampling conduit. In one embodiment, said method further comprises the step d) testing one or more samples from said sampling conduit. In one embodiment, said first fluid is a liquid. In one embodiment, said first and second samples are separated by a gas. In one embodiment, said first fluid is a gas. In one embodiment, said first and second samples are separated by liquid. In one embodiment, said first and second samples are separated by an immiscible fluid. In one embodiment, said sample-generating device comprises a microfluidic device and said first fluid comprises culture media. In one embodiment, said first sample comprises effluent from said micro fluidic device. In one embodiment, said microfluidic device comprises cells on a surface, in one embodiment, said surface is a microchannel. In one embodiment, said surface is a membrane. In one embodiment, said sampling conduit comprises a capillary tube.

In one embodiment, the invention contemplates a method of collecting samples from microfluidic devices, comprising: a) providing an assembly, comprising one or more reservoirs comprising cell culture media in fluidic communication with one or more microfluidic devices, said one or more microfluidic devices in fluidic communication with a sampling conduit and comprising cells on a surface, said cells perfused with fluid; b) causing culture media in said one or more reservoirs to flow into said one or more microfluidic devices, thereby causing fluid to exit said one or more microfluidic devices as effluent; and c) directing at least a portion of said effluent to enter said sampling conduit so as to create samples. In one embodiment, said method further comprises the step d) collecting one or more samples from said sampling conduit. In one embodiment, said method further comprises the step d) testing one or more samples from said sampling conduit. Collecting or testing of a first sample can be at a first time-point; collecting or testing of a second sample can be at a second lime-point. In one embodiment, said testing comprises detecting one or more proteins (e.g. enzymes, cytokines, etc.) secreted by said cells. In one embodiment, said method further comprises introducing gas into said sampling conduit to separate said samples into discrete volumes. In one embodiment, said introducing comprises activating a T-junction so as to create a gas gap between samples (so as to avoid any significant mixing of the samples). In one embodiment, said method further comprises directing a portion of said effluent to a waste reservoir. In one embodiment, said directing of step c) comprises opening a valve. In one embodiment, said amount of opening of said valve determines the amount of said effluent that enters into said sampling conduit. In one embodiment, said method further comprises closing said valve, thereby stopping effluent from entering said sampling conduit. In one embodiment, said sample collecting is continuous. In one embodiment, said sample collecting is discontinuous. In one embodiment, said sample testing is continuous or discontinuous. In one embodiment, said sampling conduit comprises a tube. In one embodiment, said sampling conduit comprises a capillary tube. In one embodiment, said sampling conduit comprises a microfluidic channel. In one embodiment, said method further comprises introducing an immiscible fluid into said sampling conduit to separate said samples into discrete volumes.

In one embodiment, the invention contemplates a method of recirculating culture media through microfluidic devices, comprising: 1) providing an assembly, comprising a) one or more reservoirs comprising cell culture media in fluidic communication with one or more microfluidic devices, said one or more microfluidic devices comprising i) cells on a surface and ii) inlet and outlet ports, said inlet and outlet ports in fluidic communication with a recirculation pathway, said cells perfused with fluid; and 2) causing culture media in said one or more reservoirs to flow into said one or more microfluidic devices, thereby causing fluid to exit said outlet port of said one or more microfluidic devices and enter said recirculation pathway. In one embodiment, said surface is a microchannel. In one embodiment, said surface is a membrane.

In one embodiment, the invention contemplates a method of perfusing cells comprising: a) providing a fluid source, said fluid source in fluidic communication with a microfluidic device having at least one microchannel comprising surfaces, wherein at least one surface comprise living vascular cells; and b) contacting said vascular cells with said fluid at a flow rate of between 300 and 1500 ul per hour (but more typically between 600 and 900 ul per hour). In one embodiment, said flow rate of step b) is applied for at least 6 days (which has been found empirically to increase the functionality and viability of the vascular cells). In one embodiment, said vascular cells are brain endothelial cells. In one embodiment, said brain endothelial cells are selected from group consisting of pluripotent stem cells (iPSc)-derived mammalian brain-microvascular endothelial cells (hBMEC) and primary brain microvascular endothelial cells. In one embodiment, said brain endothelial cells are derived from fibroblasts. In one embodiment, said brain endothelial cells are human cells. In one embodiment, said method further comprises, providing, brain cells in a second microchannel. In one embodiment, said brain cells are selected from group consisting of astrocytes, pericytes, microglia and neurons. In one embodiment, said brain cells are brain neuronal cells. In one embodiment, said brain neuronal cells are selected from group consisting of primary cells, iPSc-derived neurons, glutamatergic neurons, cortical neurons, cortical glutamatergic neurons, GABAergic neurons and CGE-like GABAergic neurons. In one embodiment, said brain neuronal cells are selected from group consisting of cortical neurons, cortical glutamatergic neurons, cortical GABAergic neurons and cortical CGE-like GABAergic neurons. In one embodiment, said brain neuronal cells are human glutamatergic neurons. In one embodiment, said method further comprises step e) collecting at least a portion of the fluid that exits said microfluidic device. In one embodiment, said flow rate of step b) is between 600 and 900 ul per hour.

In one embodiment, the invention contemplates a method of seeding vascular cells in a microfluidic device, comprising: a) providing i) a microfluidic device having at least one microchannel comprising surfaces, wherein at least one surface support adhesion of living vascular cells; ii) a plurality of living vascular cells; and iii) a fluid; and b) seeding said plurality of living vascular cells into said microchannel so as to create seeded vascular cells on a surface; c) contacting said seeded vascular cells with fluid at a flow rate of between 1 and 150 ul per hour for at least 2 days; and d) increasing the flow rate of said fluid to a rate between from 300-1500 ul per hour for at least 2 days after step c). In one embodiment, said seeded cells are allowed to attach to said at least one surface prior to step c), e.g. in a static culture condition without flow. In one embodiment, said flow rate of step d) is applied for at least 6 days (so as to promote functionality and viability). In one embodiment, said vascular cells are brain endothelial cells. In one embodiment, said brain endothelial cells are selected from group consisting of pluripotent stem cells (iPSc)-derived mammalian brain-microvascular endothelial cells (hBMEC) and primary brain microvascular endothelial cells. In one embodiment, said method further comprises, providing, mammalian neuronal cells and seeding said neuronal cells in a second microchannel. In one embodiment, said neuronal cells are brain neuronal cells selected from group consisting of astrocytes, pericytes, microglia and neurons. In one embodiment, said brain neuronal cells are selected from group consisting of primary cells, iPSc-derived neurons, glutamatergic neurons, cortical neurons, cortical glutamatergic neurons, GABAergic neurons and CGE-like GABAergic neurons. In one embodiment, said brain neuronal cells are selected from group consisting of cortical neurons, cortical glutamatergic neurons, cortical GABAergic neurons and cortical CGE-like GABAergic neurons. In one embodiment, said brain neuronal cells are human glutamatergic neurons. In one embodiment, said method further comprises step e) causing fluid to exit said microfluidic device. In one embodiment, said method further comprises step f) collecting at least a portion of said fluid exiting said microfluidic device. In one embodiment, said flow rate of step c) is between 30 and 60 ul per hour. In one embodiment, said flow rate is applied for at least 4 days. In one embodiment, said flow rate of step d) is between 600 and 900 ul per hour. In one embodiment, said flow promotes the formation of tight cell-to-cell junctions among said brain microvascular endothelial cells. In one embodiment, said method further comprises detecting said tight cell-to-cell junctions. In one embodiment, said tight cell-to-cell junctions are detected by TEER measurements. In one embodiment, said tight cell-to-cell junctions are detected by cell permeability assays. In one embodiment, said tight cell-to-cell junctions are characteristic of the blood-brain barrier.

In one embodiment, the invention contemplates a method comprising: a) providing i) a microfluidic device comprising a membrane having first and second surfaces, wherein second surface of said membrane supports adhesion of a living vascular cells and said first surface of said membrane supports adhesion of living neuronal cells; ii) a plurality of living mammalian vascular cells; and iii) a fluid; and b) seeding said plurality of living mammalian vascular cells onto said second surface so as to create seeded vascular cells; c) contacting said seeded vascular cells with said fluid at a flow rate of between 1 and 150 ul per hour for at least 2 days; and d) increasing said a flow rate of said fluid to a rate between 300-1500 ul per hour for at least 2 days. In one embodiment, said seeded cells are allowed to attach to said second surface prior to step c), e.g. under static conditions. In one embodiment, said flow rate of step d) is applied for at least 6 days. In one embodiment, said vascular cells are brain endothelial cells. In one embodiment, said brain endothelial cells are selected from group consisting of pluripotent stem cells (iPSc)-derived human brain-microvascular endothelial cells (hBMEC) and primary brain microvascular endothelial cells. In one embodiment, said method further comprises, providing mammalian neuronal cells and seeding said neuronal cells onto said first surface. In one embodiment, said neuronal cells are brain neuronal cells selected front group consisting of astrocytes, pericytes, microglia and neurons. In one embodiment, said brain neuronal cells are selected from group consisting of primary cells, iPSc-derived neurons, glutamatergic neurons, cortical neurons, cortical glutamatergic neurons, GABAergic neurons and CGE-like GABAergic neurons. In one embodiment, said brain neuronal cells are human glutamatergic neurons. In one embodiment, said method further comprises step e) causing fluid to exit said microfluidic device. In one embodiment, said method further comprises step f) collecting at least a portion of said fluid that exits said microfluidic device. In one embodiment, said flow rate of step c) is between 30 and 60 ul per hour. In one embodiment, said flow rate is applied for at least 4 days. In one embodiment, said flow rate of step d) is between 600 and 900 ul per hour.

In one embodiment, the invention contemplates a method comprising: a) providing i) a microfluidic device having at least one microchannel comprising surfaces, wherein at least one surface supports adhesion of living mammalian glutamatergic neuron cells; ii) a plurality of living mammalian glutamatergic neuron cells; and iii) a test compound; and b) seeding said plurality of living mammalian glutamatergic neuron cells into said microchannel so as to create seeded glutamatergic neuron cells on a surface; and c) contacting said seeded glutamatergic neuron cells with said test compound. In one embodiment, said microfluidic device comprises a membrane having first and second surfaces, wherein said glutamatergic neuron cells are seeded on said first surface. In one embodiment, said method further comprises seeding living mammalian vascular cells on said second surface so as to create seeded vascular cells. In one embodiment, said first surface of the membrane comprises a surface of a first microchannel and said second surface of the membrane comprises a surface of a second microchannel. In one embodiment, said method further comprises perfusing said seeded cells with culture fluid. In one embodiment, said vascular cells are brain endothelial cells. In one embodiment, said brain endothelial cells are selected from group consisting of pluripotent stem cells (iPSc)-derived human brain-microvascular endothelial cells (hBMEC) and primary brain microvascular endothelial cells. In one embodiment, said glutamatergic neuron cells are primary cells or iPSc-derived cells. In one embodiment, said glutamatergic neuron cells are cortical glutamatergic neurons. In one embodiment, said test compound alters the influx of calcium into said neuron cells. In one embodiment, said test compound is an inhibitor for a N-methyl-D-aspartate (NMDA) receptor expressed by said glutamatergic neuron cell. In one embodiment, said inhibitor is D-2-aminopentanoic acid (DAP5). In one embodiment, said test compound is an inhibitor for an α-amino-3-hydroxy-5-methyl-4-isoxazolepropionic acid (AMPA) receptor expressed by said glutamatergic neuron cell. In one embodiment, said inhibitor is 6-cyano-7-nitroquinoxaline-2,3-dione (CNQX). In one embodiment, said test compound is an inhibitor of glutamate activity of said glutamatergic neuron cell. In one embodiment, said glutamate inhibitor is Memantine. In one embodiment, said glutamatergic neuron cells are from subject with a brain disorder. In one embodiment, said brain disorder is Alzheimer's disease. In one embodiment, said brain endothelial cells are derived from fibroblasts. In one embodiment, said glutamatergic neuron cells are derived from fibroblasts. In one embodiment, said glutamatergic neuron cells are derived from transfected cells.

In one embodiment, the invention contemplates a method, comprising: a) providing living cells on a membrane, said membrane in contact with one or more fluidic channels; and b) exposing said cells to a zero gravity environment. In one embodiment, said cells are neurons. In one embodiment, said neurons are in a layer on said membrane. In one embodiment, said layer has at least one characteristic in common with a blood brain barrier. In one embodiment, said membrane and said one or more fluidic channels are within a microfluidic device. In one embodiment, said zero gravity environment is in a spacecraft or space station.

BRIEF DESCRIPTION OF THE DRAWINGS

The patent or application file contains at least one drawing executed in color. Copies of this patent with color drawing(s) will be provided by the Office upon request and payment of the necessary fee.

FIG. 2C-2 is a magnified view of one portion of FIG. 2C-1 (circled). In the illustrated embodiment, the cross section shape of the sealing tooth is a trapezoidal shape, but other contemplated embodiments employ other tooth shapes including but not limited to semi-circular, rectangular, polygonal, and triangular. FIG. 2E-1 is a cross-section view of one embodiment of the cover assembly seal in connection with the reservoir, showing the cover gasket and sealing tooth. FIG. 2E-2 is a magnified view of one portion of FIG. 2E-1 (circled). As the pressure manifold (discussed below) engages the cover assembly, the pressure drives the cover assembly (including the cover gasket) onto the sealing tooth, forming seals between each of the reservoir chambers.

FIG. 7B is a schematic of another embodiment showing the trays (or racks) inserted within the housing of the culture module, which has a user interface. The illustrated nested design in which (in the present example) a tray carries multiple removable sub-trays provides the user with the flexibility to remove or carry various numbers of PDs depending on use. For example, the user may carry a full tray to a bio-safety cabinet in order to replenish media or collect samples from PDs in the tray, move a sub-tray of 3 PDs to a microscope stage in order to image them without permitting the remaining PDs from dysregulating in terms of temperature or gas content, or remove or load a single PD for careful inspection or replacement.

FIG. 10B shows an exploded view of the device of FIG. 10A, showing a bottom piece (97) having channels (98) in a parallel configuration, and a top piece (99) with a plurality of ports (2), with a tissue-tissue interface simulation region comprising a membrane (101) between the top (99) and bottom (97) pieces and an exemplary microfluidic chip (16).

FIG. 11 also shows an embodiment where a reservoir 121, containing gas, air, or fluids for use as plugs between samples, is in fluidic communication with sampling conduits. In some embodiments, a pump (113) is used for introducing a plug between samples and/or moving samples through the conduit. Additional valves (114) downstream of the organ-chip allow for effluent fluid to be recirculated through the chip (l 18 or another fluid connector) or through a different connector (exemplary 123 upper channel) sending effluent fluid (exemplary 122 lower channel) to a common waste reservoir (116) or to sample collector, e.g. via conduit exemplary 126 and 127 upper channel (pointed out after a valve 114) or 124 and 125 lower channel pointed out before the valve 114. The system highlighted in gray (210) will fit in one CubeLab 2U and contain the organ-chips, fluidic manifold, and waste container and will be maintained at 37° C. The system highlighted in blue (220) will fit in a separate and adjacent CubeLab 2U containing media, reagents and samples and will be maintained at 4° C.

FIG. 15A-D shows an exemplary Human BBB-Chip characterization as a standard BBB-Chip design. FIG. 15A shows the bottom channel is fully lined by iPSc induced to brain endothelial cells that have been shown to express typical junction markers of the BBB vascular tissue. FIG. 15B shows the top compartment (brain compartment) includes astrocytes, neurons and FIG. 15C pericytes. FIG. 15D Additionally, perfusing the vascular channel at physiologically relevant shear rate (6 dyne) has been proven to increase barrier function (measured via TEER).

FIG. 17B TNF mediated inflammation causing extravasation of blood, generate neural toxicity in the brain as indicated by the significant increase in the LDH of the brain compartment and FIG. 17C observed via confocal imaging (FIG. 17D).

FIG. 18A-C shows exemplary devices as FIG. 18A Human Emulation System, which includes Organ-Chips (left), an automated plug-and-play instrument for controlling with cellular microenvironment within an Organ-Chip (center), and the software for simple user control (right). FIG. 18B illustrates a folly automated instrument/device (left) for interconnecting multiple organ-chips. FIG. 18C illustrates a compact, microfluidic selector valve (right) for interconnecting Organ-chips. A modified version of this technology is contemplated to enable a high-density valving architecture for automated experiments on the ISS.

FIG. 20B Shows absorption of coumarin from media into PDMS surfaces and an alternative material over time (lower). The magnitude of two different molecules partitioning into either PDMS or an alternative material. The amount of compound partitioned into PDMS from media is relatively high, while it is below the limit of detection for the alternative material.

FIGS. 26A, 26D and 26E Shows exemplary illustrations of brain microvascular endothelial cells in vivo as the first barrier between blood vessels and brain parenchyma while FIG. 26B shows a transmission electron micrograph of a brain blood vessel in vivo and FIG. 26C shows an immunostained fluorescent micrograph of a histological section. FIG. 26F shows an illustration of one embodiment of a Blood Bruin Barrier (BBB) chip. FIGS. 26A, 26D (Zenaro et al., Neurobiology of Disease 107:41-56 (2017)) and 26E shows Endothelial cells linked by tight junctions (TJs), closely surrounded by pericytes. Astrocytic endfeet support endothelial function and provide the cellular link to neuronal cells. Activated microglia respond to neuronal injury by releasing inflammatory cytokines that can disrupt the BBB (blood brain barrier). FIG. 26F Shows an exemplary illustration of one embodiment of a blood brain barrier on-chip. 1. Upper Channel. 2. Lower Channel. 3. Human iPSC-derived neuronal cells cultured with human primary astrocytes and pericytes. 4. Human iPSC-derived brain microvascular endothelial cells. 5. Porous Membrane. 6. Vacuum Channels.

FIG. 27A-B One example of a 3D Reconstruction of the Brain-Chip. High-magnification cross-sections shown are projections of confocal Z-stacks. FIG. 27A One embodiment of a Brain-Chip illustrated (above) as comprising a vascular channel lined by iPSC-derived HBMECs (pale blue cells) and a neural channel seeded with neurons, astrocytes and pericytes (shown as dark blue cells). One embodiment of a Brain on-Chip is shown (below) as a micrograph where red/magenta/cyan identifies the cells in the neuronal channel and green identifies endothelial cells in the vasculature channel. FIG. 27B An exemplary higher magnified micrograph of one embodiment of a brain on-chip where green indicates MAP2 staining (neuronal marker), magenta represents GFAP-stained astrocytes, red indicates NG2 marker for pericytes, and cyan corresponds to Von Willebrand factor (vWF) staining, an endothelial cell marker. Scale bar: 50 µm.

FIG. 29A, upper to lower channel florescent micrographs, blue indicates Hoechst staining of nuclei, green indicates MAP2 staining (neuronal matter), magenta represents GFAP-stained astrocytes, red indicates NG2 marker for pericytes. The lower micrograph shows a merged image of the upper 4 fluorescent channels. Scale bar: 5 mm. FIG. 29B Shows a higher magnified image of a merged channel. Scale bar: 50 µm (left) and a lower power micrograph (upper right) of a merged channel where green indicates MAP2 staining (neuronal marker), magenta represents GFAP-stained astrocytes. The same magnified area is shown (lower right) where red indicates NG2 marker for pericytes. Scale bars: 100 µm.

FIG. 30A Spontaneous activity was studied by means of calcium imaging, enabling the investigation of neuronal activity of single cells and the network as a whole. Fluo-4 AM, a calcium sensitive fluorescent dye, was loaded onto the cells, and intracellular calcium fluctuations were monitored over time using high-speed imaging. FIG. 30B Shows vascular flow contributes to maintain the neuronal activity on the Brain-Chip. On the other hand, there was no significant difference between the condition where both channels flow and the condition with the vascular channel under flow. An exemplary graph comparing active cells in the neuronal channel (%) demonstrates that flow in the vascular channel alone contributes significantly to the percentage of active cells in the neuronal channel. FIG. 30C shows an exemplary diagram of the relationship between a sampling area on a chip (for left) to flow through a capillary in relation to glia end-feet (in vivo) to a diagram of an in vivo placement of pericytes, glia end-fool (far right). The box contains a diagram summarizing flow in relation to neuronal activity.

FIG. 31A No Vascular Flow showing numerous red TUNEL positive cells (white arrowheads) vs. FIG. 31B Vascular Flow where few TUNEL positive cells are observed. Immunohistochemistry (ICC): green identifies Neurons (MAP-2), magenta identifies Astrocytes (GFAP). blue identifies Pericytes (NG2), and red identifies apoptotic and dying cells stained using a Cell Death Assay (TUNEL). Scale bar: 50 µm. FIG. 31C shows a graph comparing percent TUNEL-positive cells in the neuronal channel where 20% of the cells were dying or dead without flow compared to less than 5% under vascular flow.

FIG. 32A Neuronal Channel with calcium imaging shows spontaneous neuronal activity (green-Fluo-4 florescent dye) when neurons are cultured alongside astrocytes. Scale bar: 100 µm. FIG. 31B florescent images shows immunostaining for GFAP (magenta)/MAP2 (green). Scale bar: 50 µm.

FIG. 37A MAP2 Neurons (green); FIG. 37B Synaptic Vesicles (red); FIG. 37C Merged florescent channels where double positive areas are yellow.

FIG. 38A is a graph demonstrating control-baseline staining for Fluo-4AM neuronal activity. FIG. 38B shows staining for Fluo-4AM neuronal activity under Glutamatergic Inhibition with a combination of NMDA and AMPA receptor inhibition (DAP5 (blocks NMDAR) and CNQX (blocks AMPAR) respectively) which reduced the percentage of active neurons by blocking the influx of calcium in glutamaterigic neurons on the Brain-Chip as compared to a control (baseline) without inhibitors, FIG. 38A. Scale bars=200 μm.

FIG. 38C is an exemplary graph showing around 100% active neurons in controls while less than 25% show activity after addition of inhibitors.

FIG. 44A-C illustrates and shows photographs of embodiments for recirculation (reciprocation) and introduction of a test compound into a microfluidic chip as one embodiment of a non-drug absorbing setup (e.g. device). Setup: for ensuring adequate oxygenation; is non-drug absorbing; and decreases system volume. FIG. 44A shows an illustration of one embodiment of a syringe (131) fluidically connected by tubing (132) to a microchannel of a microfluidic chip (16) in turn fluidically connected to a reservoir (133). FIG. 44B shows a photograph image of one embodiment of a syringe (131) fluidically connected by tubing (132) to a microchannel of a microfluidic chip (100) in turn fluidically connected to a reservoir (133). FIG. 44C shows a photograph image of one embodiment of a Chip with both channels attached to a reservoir and attachments for syringes fluidically connected by tubing (132) to a microchannel of a microfluidic chip (16) in turn fluidically connected to a reservoir (133).

FIG. 45A show's one embodiment for a Pull Mode—Recirculate as Step 1: Pull 30 μL of media into the chip, exposing cells to freshly oxygenated media. A syringe (131) fluidically connected by tubing (132) to a microchannel (134) of a microfluidic chip (16) in turn fluidically connected to a reservoir (133). FIG. 45B shows one embodiment for exposing chips, i.e. cells, to a test compound as Step 2: Incubate for 1 minute, allowing exposure of cells to a test compound. FIG. 45C shows one embodiment for a Push Mode Oxygen Exposure. Step 3: Push 30 μL of media into outlet, exposing media to oxygen. Then repeat Steps 1-3 as desired.

FIG. 46A Inlet reservoir (135); outlet reservoir (136); check valve (137); lines indicate tubing (138) fluidically connecting reservoirs with one channel (70) in a microfluidic chip (16). FIG. 46B shows a more detailed illustration of one embodiment for incorporation of a check Valve into a Pod. Inlet reservoir (135); outlet reservoir (136); check valve (137); Shortcut channel in Pod fluid layer (139). FIG. 46C shows an illustration of an engineering drawing for one embodiment of a check valve (137) as an exemplary Duckbill Check Valve. FIG. 46D shows exemplary photographs of pod reservoirs. Inlet reservoir (135); outlet reservoir (136); Shortcut channel in Pod fluid layer (139); Shortcut channel vias into reservoirs (140). FIG. 46E shows an illustration of a side view of the check valve in FIG. 46C. Dimension a of FIG. 46C may be between 2.03 and 2.10 mm (.080 and 0.083 in) in one embodiment. Dimension b of FIG. 46C may be between 0.6 and 0.7 mm (0.022 and 0.026 in) in one embodiment. Dimension c of FIG. 46C may be at a minimum 3.1 mm in diameter (0.122 in) in one embodiment. Dimension d of FIG. 46C may be at a minimum of 1.4 mm in diameter (0.055 in) in one embodiment. Dimension e of FIG. 46C may be a minimum 3.3 mm(0.130 in) in one embodiment.

FIG. 47A-B shows graphs demonstrating hepatocyte viability and function as albumin production (ug/million cells/day) when media is recirculated. COP Liver-Chip shows comparable (high) albumin production to PDMS Liver-Chip after dosing with compounds during reciprocation. Comparative chips were not dosed. Chips were "perfused" with media each day during the experiment including both single-pass flow and reciprocation.

FIG. 47A shows exemplary data graphs comparing albumin production after 7 days of dosing. Static plates and microfluidic chips, constructed with PDMS or COP, are compared by several test conditions over time, albumin production after dosing with no recirculation, i.e. a single pass flow at 150 ul/hr. on Day 5 was compared to Day 7 albumin production with reciprocating flow 3600 uL/hr.

FIG. 47B shows exemplary data graphs comparing albumin production after dosing PDMS chips under conditions of a single pass flow at 150 ul/hr. on Days 5 and 6, then Day 8 production with reciprocating fluid flow at 3600 uL/hr compared to a single pass flow at 150 ul/hr. on Day 9.

DEFINITIONS

Figure 1A:
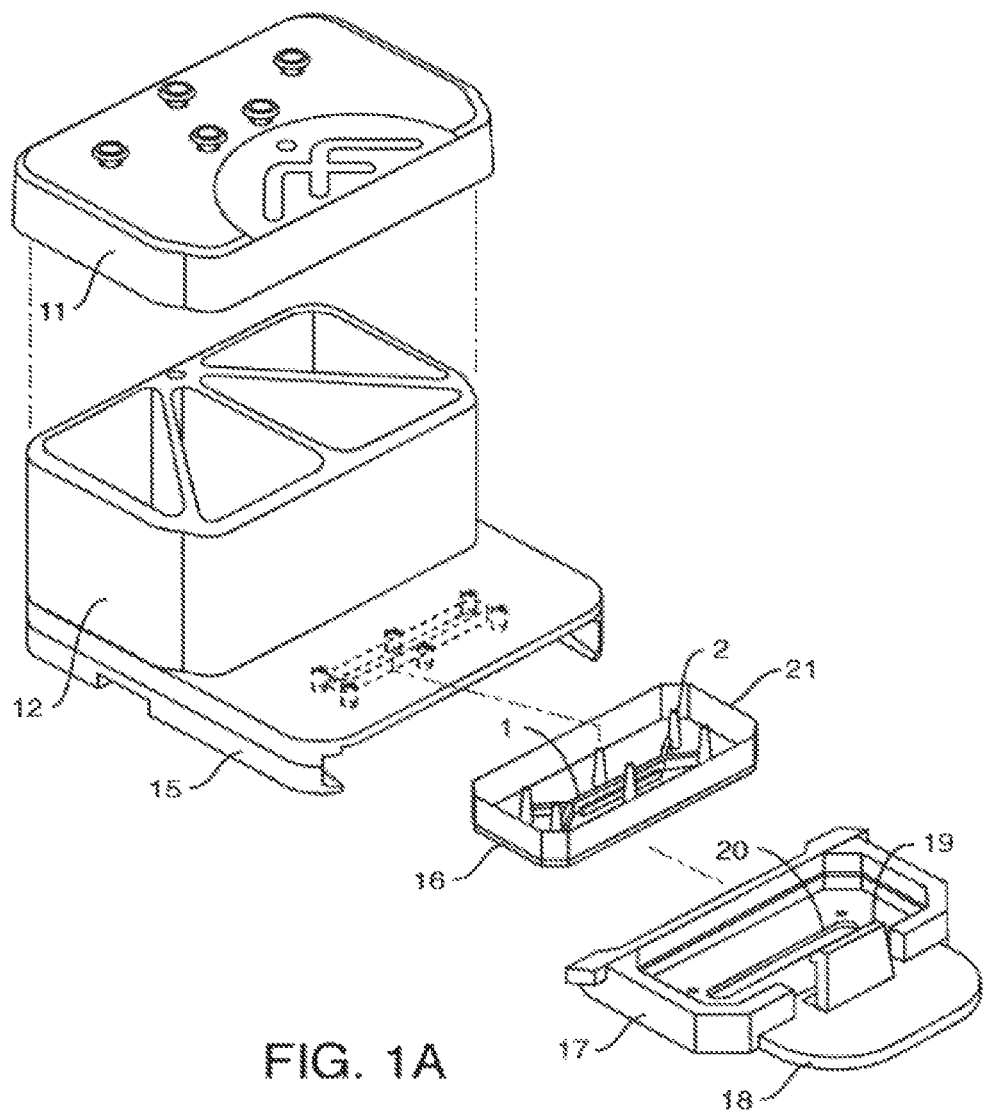
FIG. 1A is an exploded view of one embodiment of the perfusion manifold assembly showing the cover (or cover assembly) off of the reservoirs (the reservoir body can be made of acrylic, for example), the reservoirs positioned above the backplane, the backplane in fluidic communication with the reservoirs, the skirt with a side track for engaging a representative microfluidic device or "chip" (which can be fabricated out of plastic, such as PDMS, for example) having one or more inlet, outlet and (optional) vacuum ports, and one or more microchannels, the chip shown next to (but not in) one embodiment of a chip carrier (which can be fabricated out of a thermoplastic polymer, such as acrylonitrile butadiene styrene (ABS), for example), the carrier being configured to support and carrier the chip, e.g. dimensioned so that the chip fits within a cavity.

An organ-on-a-chip is contemplated for use as described in the U.S. Pat. No. 8,647,861, and the International Patent App. No. PCT/US2014/071611, the contents of each of which are incorporated herein by reference in their entireties.

Brain microvascular endothelial cells (BMEC) are interconnected by specific junctional proteins forming a highly regulated barrier separating blood and the central nervous system (CNS), the so-called blood-brain-barrier (BBS). Together with other cell-types such as astrocytes or pericytes, they form the neurovascular unit (NVU), which specifically regulates the interchange of fluids, molecules and cells between the peripheral blood and the CNS.

The blood-brain barrier is of major clinical relevance because dysfunction of the blood-brain barrier leads to degeneration of the neurovascular unit, and also because drugs that are supposed to treat neurological disorders often fail to permeate the blood-brain barrier. Due to its importance in disease and medical treatment, it would be highly advantageous to have a predictive model of the human blood-brain barrier that recapitulates aspects of the cerebral endothelial microenvironment in a controlled way.

There are many ways to evaluate the integrity and physiology of an in vitro system that mimics the blood brain barrier. Two of the most common methods are Transepithelial Electric Resistance (TEER) and Lucifer Yellow (LY) rejection. Manipulations should be performed using aseptic techniques in order for the cells to remain in culture without contamination. TEER measures the resistance to pass current across one or more cell layers on a membrane. The measurement may be affected by the pore size and density of the membrane, but it aims to ascertain cell and/or tissue properties. The TEER value is considered a good measure of the integrity of the cell monolayer.

For TEER measurements, an embodiment is contemplated wherein the layered structure or microfluidic device has electrodes configured for measuring the electrophysiology of said brain microvascular endothelial cells. However, it is not intended that the present invention be limited to TEER measurements. In one embodiment, the present invention contemplates a method of testing, comprising 1) providing a layered structure comprising i) fluidic channels covered by ii) a porous membrane, said membrane comprising iii) a layer of brain microvascular endothelial cells in contact with said fluidic channels, said membrane position below iv) a gel matrix (or other porous volume), said gel matrix (preferably) under a removable cover; and 2) measuring the electrophysiology of said brain microvascular endothelial cells. A variety of techniques are contemplated including but not limited to using a multi-electrode array or patch clamping. An "open top" design allows for patch clamping through the opening.

Lucifer Yellow (LY) travels across cell monolayers through passive paracellular diffusion (through spaces between cells) and has low permeability. Therefore it is considerably impeded in passing across cell monolayers with tight junctions. Permeability (Papp) for LY of ≤5 to 12 nm/s has been reported to be indicative of well-established monolayers.

"Bond number" is a dimensionless ratio of gravity forces to capillary forces on a liquid interface. When the Bond number is high air, liquid interfaces tend to be shaped by gravity. When the Bond number is low, those surfaces tend to be shaped by the capillary force.

"Hydrophobic reagents" are used to make "hydrophobic coatings" on surfaces (or portions thereof), including projections, platforms or pedestals at or near ports, as well as mating surfaces (or portions thereof). It is not intended that the present invention be limited to particular hydrophobic reagents. In one embodiment, the present invention contemplates the use of silanes to make hydrophobic coatings, including but not limited to halogenated silanes and alkylsilanes. In this regard, it is not intended that the present invention be limited to particular silanes; the selection of the silane is limited in a functional sense, i.e. that it render the surface hydrophobic. Tire present invention also contemplates using commercially available products, such as the Rain-X™ product which is a synthetic hydrophobic surface-applied product that causes water to bead, most commonly used on glass automobile surfaces.

A surface or a region on a surface is "hydrophobic" when it displays (e.g. advancing) contact angles for water greater than approximately ninety (90) degrees (in many cases, it is preferable that both advancing and receding contact angles are greater than approximately 90 degrees). In one embodiment, the hydrophobic surfaces of the present invention display advancing contact angles for water between approximately ninety (90) and approximately one hundred and ten (110) degrees. In another embodiment, hydrophobic surfaces have regions displaying advancing contact angles for water greater than approximately one hundred and ten (110) degrees. In another embodiment, hydrophobic surfaces hove regions displaying receding contact angles for water greater than approximately 100 degrees. We note that some liquids, and particularly some biological liquids, contain elements that may coat a surface after wetting it, thereby affecting its hydrophobicity. In the context of the present invention, a surface resists such as coating from a liquid of intended use, tor example, such coating does not create an advancing and/or receding contact angle that is less than 90 degrees over the duration that the surface remains welted by the said liquid.

A surface or a region on a surface is "hydrophilic" when it displays (e.g. advancing) contact angles for water less than approximately ninety (90) degrees, and more commonly less than approximately seventy (70) degrees (in many cases it is preferable that both the advancing and receding contact angles are less than approximately 90 degrees or approximately 70 degrees).

Measured contact angles can fall in a range, i.e. from the so-called advancing (maximal) contact angle to the receding (minimal) contact angle. The equilibrium contact is within those values, and can be calculated from them.

Hydrophobic surfaces "resist wetting" by aqueous liquids. A material is said to resist wetting by a first liquid where the contact angle formed by the first liquid on the material is greater than 90 degrees. Surfaces can resist wetting by aqueous liquids and non-aqueous liquids, such as oils and fluorinated liquids. Some surfaces can resist wetting by both aqueous liquids and non-aqueous liquids. Hydrophobic behavior is generally observed by surfaces with critical surface tensions less than 35 dynes/cm. At first, the decrease in critical surface tension is associated with oleophilic behavior, i.e., the wetting of the surfaces by hydrocarbon oils. As the critical surface tensions decrease below 20 dynes/cm, the surfaces resist wetting by hydrocarbon oils and are considered oleophobic as well as hydrophobic.

Hydrophilic surfaces "promote wetting" by aqueous liquids. A material is said to promote wetting by a first liquid where the contact angle formed by the first liquid on the material is less than 90 degrees, and more commonly less than 70 degrees.

As used herein, the phrases "linked," "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

"Channels" are pathways (whether straight, curved, single, multiple, in a network, etc.) through a medium (e.g., silicon, plastic, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents.

"Microchannels" are channels with dimensions less than 1 millimeter and greater than 1 micron. Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

Figure 3A:
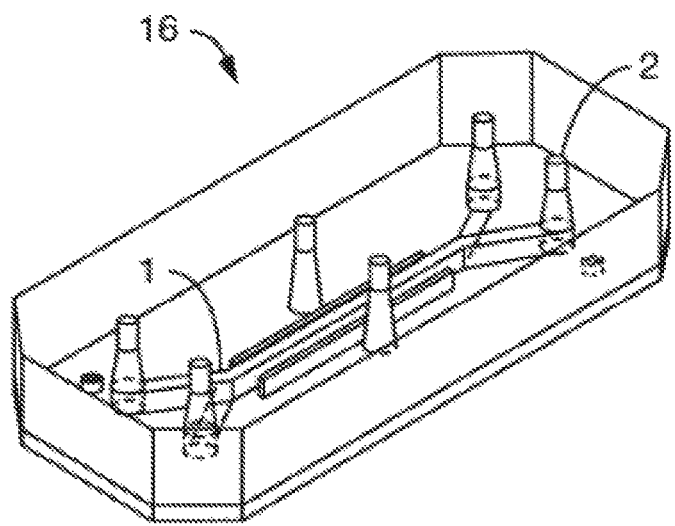
FIG. 3A shows one embodiment of the microfluidic device or chip, showing two channels, each with an inlet and outlet port, as well as (optional) vacuum ports.
Figure 3B:
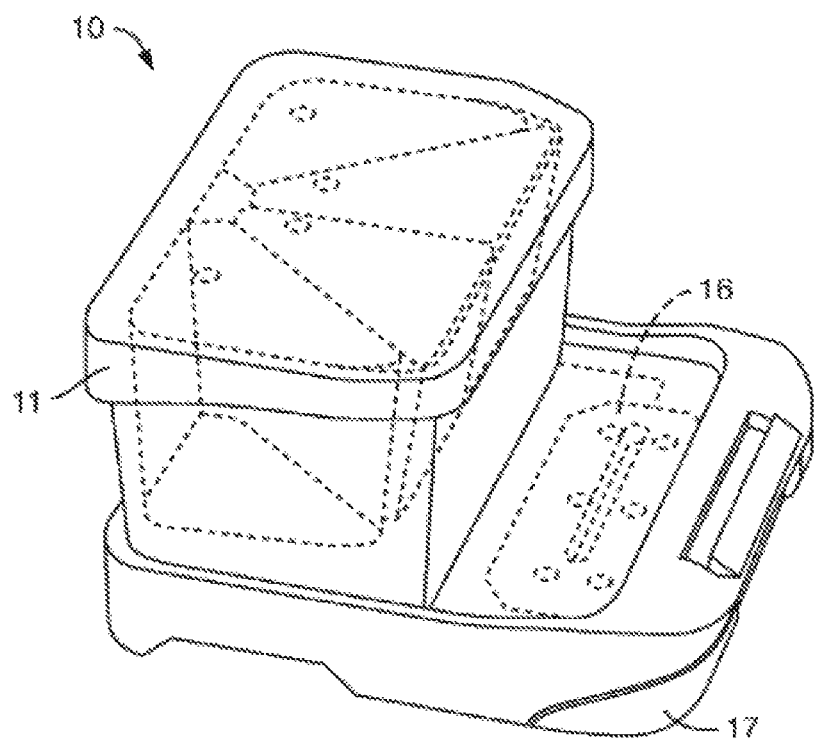
FIG. 3B is a topside schematic of an alternative embodiment of the perfusion disposable or "pod" featuring the transparent (or translucent) cover over the reservoirs, with the chip inserted. The chip can be seeded with cells and then placed in a carrier for insertion into the perfusion disposable.
Figure 3C:
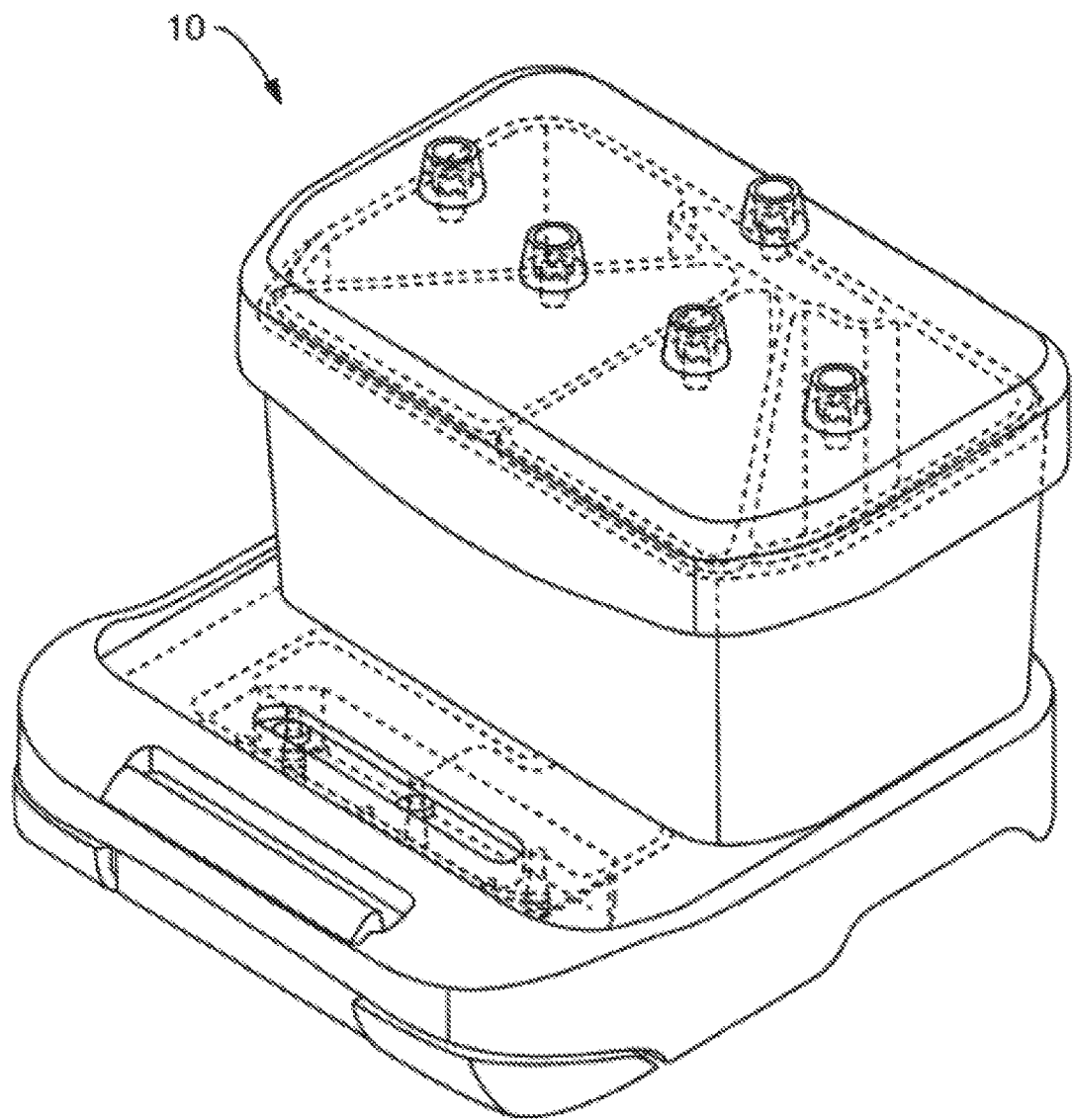
FIG. 3C is a schematic of the same assembled perfusion disposable embodiment shown in FIG. 3B, except that the ports on the cover assembly and the cutout (above the inserted chip for visualization, imaging, etc.) are now shown.
Figure 3D:
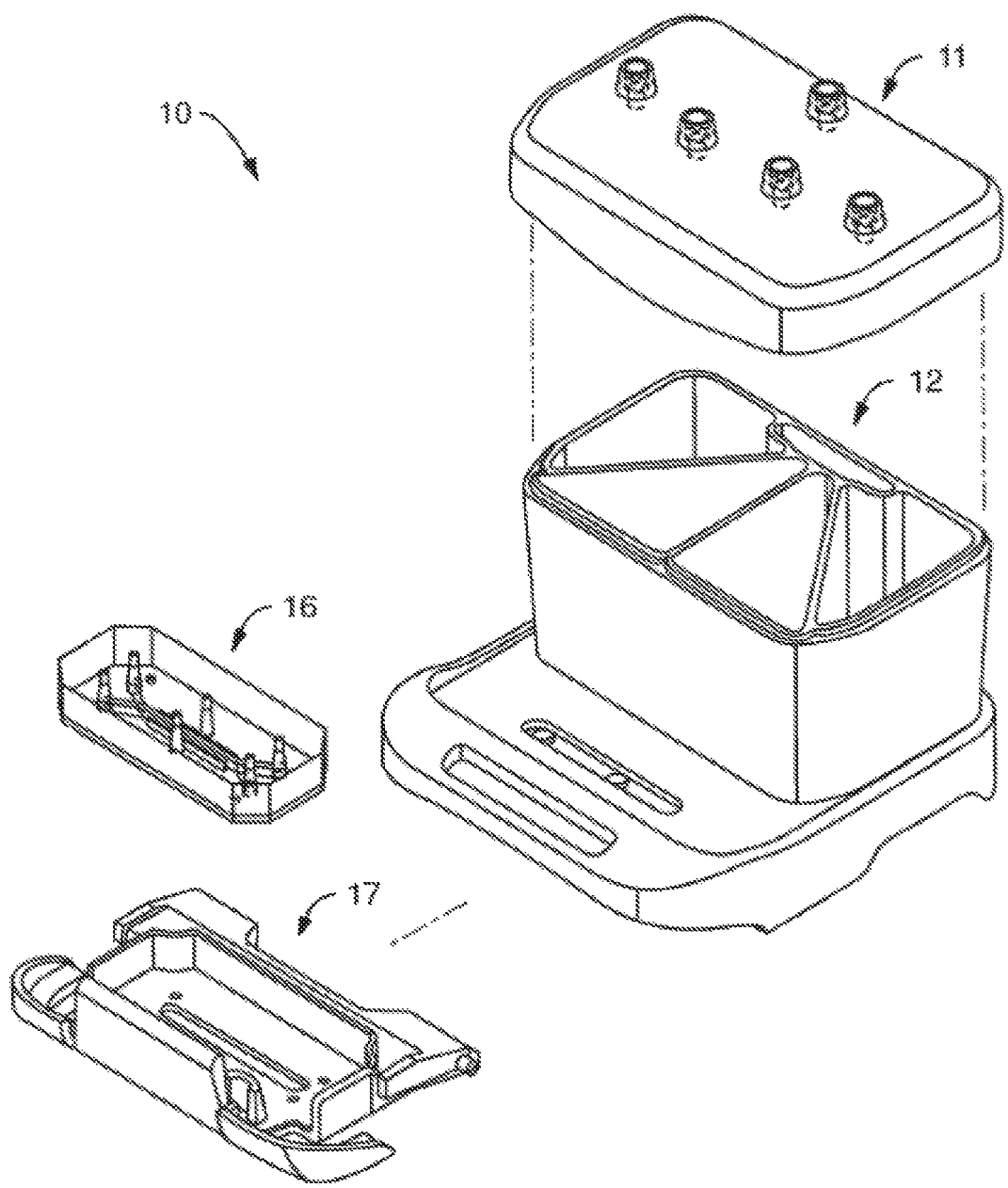
FIG. 3D is a schematic of the same perfusion disposable embodiment of FIG. 3C, but unassembled to show the relationships of the cover, reservoirs, skirt, chip and carrier.
Figure 4A:
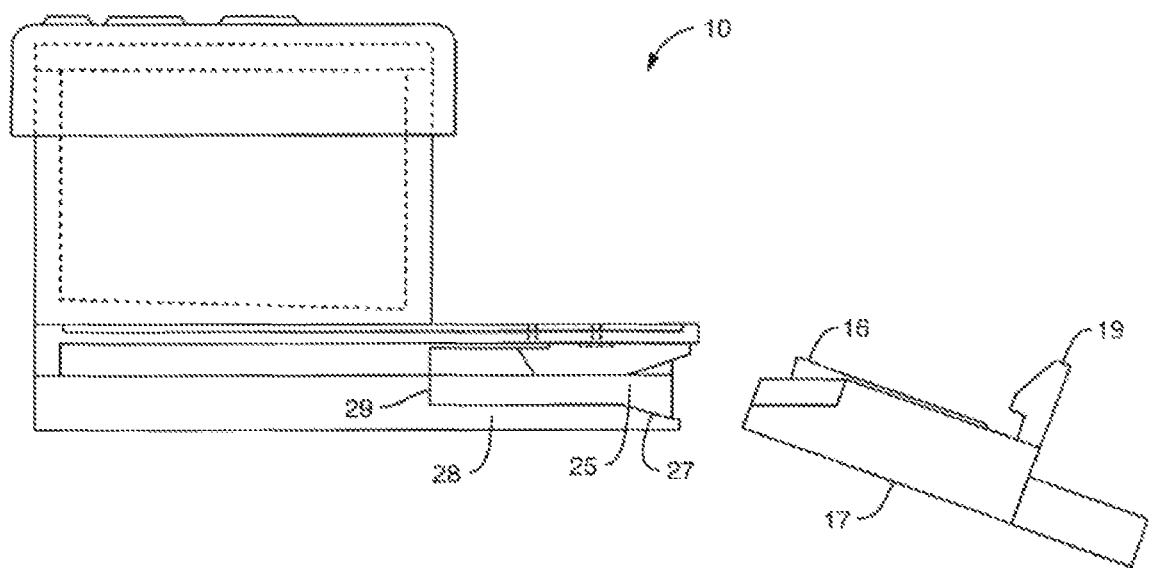
FIG. 4A shows a side view of one embodiment of a chip carrier (with the chip inside) approaching (but not yet engaging) a side track of a skirt of one embodiment of the perfusion manifold assembly, the carrier aligned at an angle matching an angled front end portion of the side track, the carrier comprising a retention mechanism configured as a upwardly protecting clip. Without being bound by theory, a suitably large angle permits chip engagement without smearing or premature engagement of liquid droplets present on the chip and/or the perfusion manifold assembly during the insertion and alignment processes.
Figure 4B:
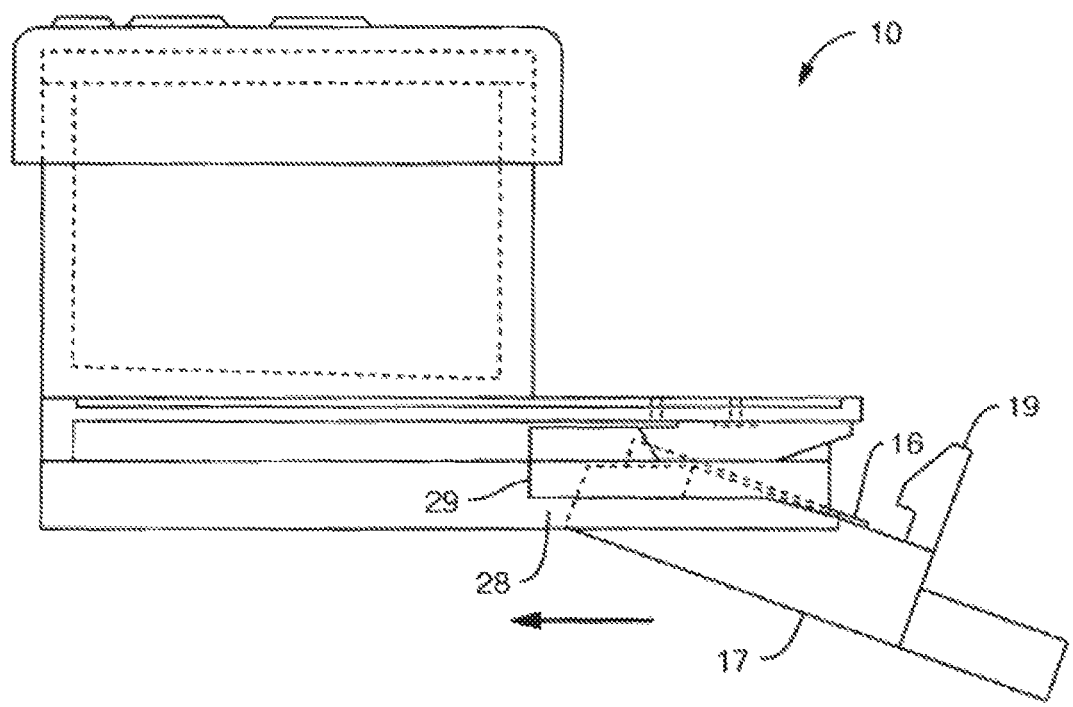
FIG. 4B shows a side view of one embodiment of a chip earner (with the chip inside) engaging a side track of a skirt of one embodiment of (but not yet linked to) the perfusion manifold assembly.
Figure 4C:
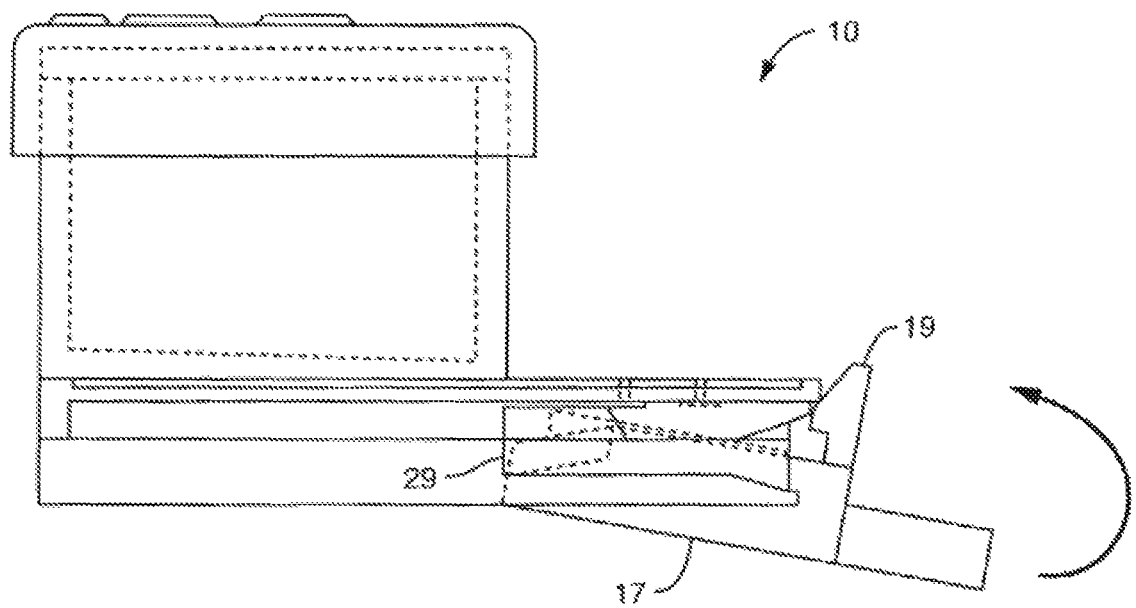
FIG. 4C shows a side view of one embodiment of a chip carrier (with the chip inside) folly engaging a side track of a skirt of one embodiment of (but not yet linked to) the perfusion manifold assembly (with an arrow showing the necessary direction of movement to get a snap fit whereby the retention mechanism will engage to prevent movement).
Figure 4D:
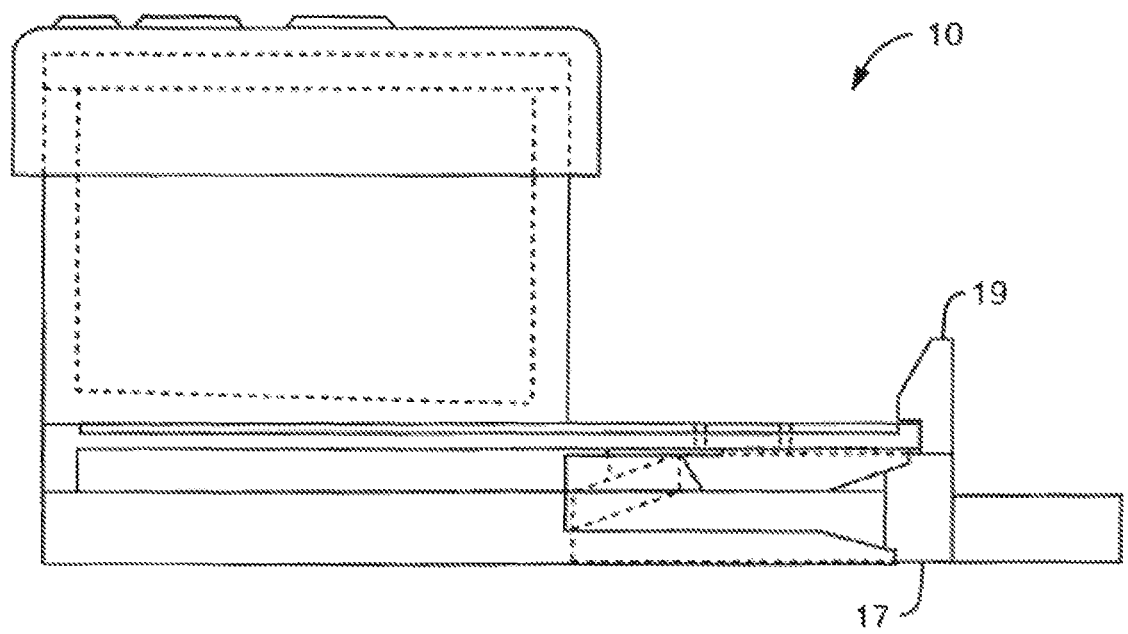
FIG. 4D shows a side view of one embodiment of a chip carrier (with the chip inside) detachably linked to the perfusion manifold assembly, where the retention mechanism is engaged to prevent movement. While detachability and optionally re-attachability is desirable in certain applications (for example, permitting chip removal to enable the addition of cells, imaging, performing various assays), in alternative embodiments, the linking is not detachable. For example, an adhesive layer, glue and/or heat staking may be employed to provide a robust linkage that may pose a challenge in detachment or reattachment.
Figures 1, 4E:
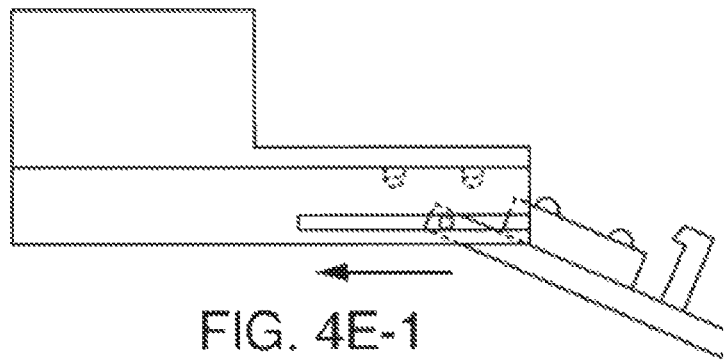
FIG. 4E is a summary slide schematically showing one embodiment of a linking approach to the perfusion manifold comprising a 1) sliding action (4E-1), 2) pivoting (4E-2), and 3) snap fit (4E-3) so as to provide alignment and fluidic connection in a single action. In the 1) sliding step, the chip (or other microfluidic device) is inserted into the carrier, which slides along to align the fluidic ports. In the 2) pivot step, the chip (or other micro fluidic device) is pivoted until ports come into fluid contact. In the 3) clip or snap fit step, the force needed to provide a secure seal is provided.
Figures 2, 4E:
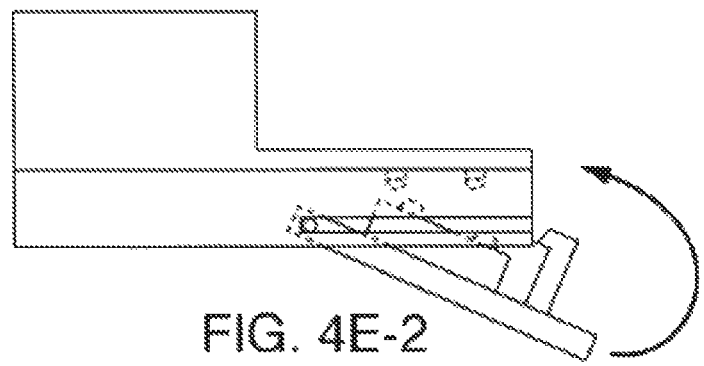
Figures 3, 4E:
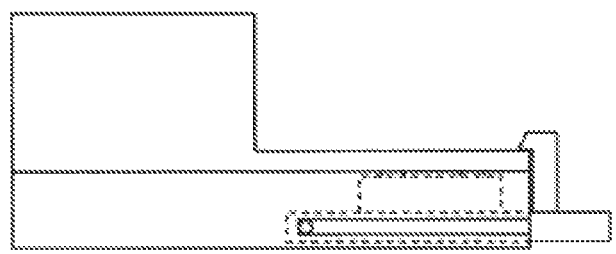

The present invention contemplates a variety of "microfluidic devices," including but not limited to microfluidic chips (such as that shown in FIG. 3A), perfusion manifold assemblies (without chips), and perfusion manifold assemblies engaged with microfluidic chips (such as that shown in FIG. 3B). However, the methods described herein for engaging microfluidic devices (e.g. by drop-to-drop connections), and for perfusing microfluidic devices are not limited to the particular embodiments of microfluidic devices described herein, and may be applied generally to microfluidic devices, e.g. devices having one or more microchannels and ports.

A "stable droplet" is a droplet of media that does not experience significant movement away from its intended location (e.g. to remain in contact with a fluidic port) and preferably does not experience a significant (>10%) change in volume or placement on a microfluidic device over the course of several seconds, and more preferably one minute, and even more preferably several minutes (2-10 minutes). In a preferred embodiment, the present invention contemplates a stable droplet during drop-to-drop engagement. A surface may intrinsically (e.g. because of what it is made of) be able to stably retain, or be made to stably retain, a droplet, meaning that the droplet will not spontaneously expand or shift beyond a limited (or designated) area. Stable droplets do not experience a significant change in volume or placement. The present invention contemplates this spatial control of droplets, i.e. retaining the droplet within a defined spatial extent and/or retaining the droplet within the spatial extent of the one or more regions. In a preferred embodiment, the present invention contemplates both preventing the droplet from extending too far, and ensuring that it is centered on the port (i.e. making sure that the area right on top of the fluidic port remains covered by the droplet). In terms of preventing the droplet from extending or spreading too wide, the present invention contemplates, in one embodiment, retaining the droplet within the spatial extent of the one or more regions. In a particularly preferred embodiment, the present invention contemplates preventing the droplet from shifting away during manipulation (i.e. rolling away on the surface as the microfluidic device or chip is moved around or even inverted. Of course, such movements are contemplated without violent shaking. A droplet that is found to be stable if a particular engagement procedure is used, may be found unstable if another procedure (e.g. more violent procedure) is utilized.

"Controlled engagement" refers to engagement of two devices that allows for both adequate alignment of vias or ports, and smooth drop-to-drop connection, which does not result in loss of droplet stability. If the devices, for example, snap violently into place or the droplets on opposite devices touch prior to engagement, droplet stability will be compromised.

"Conduits" can be any device for delivering or conveying gas, fluid or electricity and include (but are not limited to) channels, ducts, pipes and tubes. For electricity, conduits are typically wires or cables.

"Parenchyma" refers in general to functional cells or parts of an organ that may also be referred to descriptively as "parenchymal". As one example, in brain tissue, "parenchyma" refers to the functional tissue comprising at least two types of "parenchyma cells", i.e. brain cells, e.g. neurons and glia (glial) cells.

Glia cells include but are not limited to oligodendrocytes (including myelin producing cells), ependymal cells, astrocytes and microglia (resident specialized brain macrophages). Such cells comprise a ventricular system (examples include oligodendrocytes and ependymal cells) and a neurovascular unit comprising neurons, astrocytes, pericytes and endothelial cells.

"Non-parenchymal" in reference to the brain includes but is not limited to endothelial cells, macrophages, ependymal cells, etc.

"Brain cells" in general refer to any cell type found in vivo in any part of the brain. Examples of brain cells include but are not limited to parenchymal cells, non-parenchymal cells, neuroepithelial cells, pericytes, etc.

GENERAL DESCRIPTION OF THE INVENTION

The invention generally relates to a microfluidic platforms or "chips" for testing and conducting experiments on the International Space Station (ISS). More specifically, microfluidic Brain-On-Chip, comprising neuronal and vascular endothelial cells, will be analyzed in both healthy and inflamed states to assess how the circumstances of space travel affect the human brain.

An automated research platform is contemplated for use to conduct experiments on the International Space Station (ISS). In some embodiments, the automated platform will be fully automated. Studies will analyze the Brain-Chip, which in some embodiments, consists of neuronal and vascular endothelial cells, and in other embodiments comprises neuronal and vascular endothelial cells in healthy and/or inflamed states to assess how the circumstances of space travel affect the human brain. In one embodiment of a brain chip used to mimic the human brain and the biologically active surfaces that cells normally contact and sense in vivo (see, example FIG. 26F), iPSC-derived glutamatergic neurons, human primary astrocytes and pericytes were seeded into the neuronal channel (upper chamber), and human brain microvascular endothelial cells in the vascular channel (lower chamber).

Freed from the effects of gravity found on Earth, an International Space Station provides an environment where researchers can study human health in microgravity, allowing them to decouple the force of gravity from other effects that can impact brain cell function. Different experiments using the Brain-Chip will study how other space travel stressors, such as hyper-gravity experiments during launch can reduce availingly of oxygen known as hypoxia, and increased levels of stress hormones, etc., influence brain function. Adaptation to stressors is a highly considered mechanism to preserve health and avoid disease development. Bus research will provide unique insights on the adaptive mechanisms of human brain cells in space, with a potentially unforeseen spectrum of applications for understanding both diseases and associated therapies. In some embodiments, it is contemplated to apply the system described herein in the laboratory, e.g. Organ-Chips, in space for the benefit of astronauts as well as humankind. Thus, embodiments described herein provide a unique research environment for enhancing knowledge to improve human health. An Organ-Chip refers to a living, microengineered environment that recreates the natural physiology and mechanical forces that cells experience within the human body.

There is no limit on the amount of gravitational force (or other factors encountered in space, such as radiation), present for any embodiments described herein. In other words, gravitational forces include but are not limited to those present on the ISS, or on spacecraft during take-off and landing. In fact, there are no limits on gravitational forces such that normal gravity, higher levels of gravity, and lower levels of Earth's gravity are contemplated for use, e.g. gravitation forces simulating or on long space flights, gravitational forces such as found on the Moon or Mars, for examples, is contemplated for use.

This project is also designed to provide insights into the relation between inflammation and blood brain barrier functionality, which is an area of investigation for neurodegenerative diseases, such as Alzheimers and Parkinson's. Other studies will use the Brain-Chip to evaluate the efficacy of anti-inflammatory intervention on the blood-brain barrier in space.

Thus, application of microfluidic Organ-Chip technology is contemplated for use to assess the effects of space flight in human organs in vitro. The proposed work focuses on the development of automated hardware for space to enable experiments in human, in vivo relevant microphysiological systems for understanding of the impact of microgravity and other space flight-imposed stressors on human physiology, e.g. temperature and other conditions during take-off, flight and landing, etc., disease development and response to drugs. The exemplary organ described herein, is the blood-brain barrier (BBB)-Chip, both in normal and inflamed states, which causes a major compromise in the BBB and allows for evaluation of clinically relevant endpoints. Organ-Chip technology will be validated with automated instrumentation in terrestrial experiments simulating space flight protocols/environment. A platform is contemplated to conduct two separate organ-chip experiments on the International Space Station (ISS) to understand the effects of this unique environment on BBB physiology. Further, terrestrial experiments assessing specific contribution of each of the individual, primary cell stressors in space can be simulated on Earth. Imaging, biochemical, and transcriptomic data from studies over different time points will be analyzed, compared and provide the inputs for building a model of the system. This integrative approach will reveal new aspects of the effects of microgravity on the BBB in normal and disease states, and provide insights into drug discovery for this organ that maintains homeostasis or propagates a number of serious diseases. Successful implementation of space compatible hardware and BBB-Chip findings is contemplated to provide an in viva relevant, in vitro platform available to the scientific community for the evaluation of the impact of microgravity in physiology and disease of a number of human organs, and support drug development in novel, clinically relevant ways.

Examples of microfluidic chips, e.g. products, that includes integrated flow control, stretching, and fresh media/effluent storage are described herein, at least in part, in addition to descriptions in WO2017035484 (PCT/US2016/049033), herein incorporated by reference in its entirety.

1. Embodiments of a Perfusion Manifold Assembly.

Figure 1B:
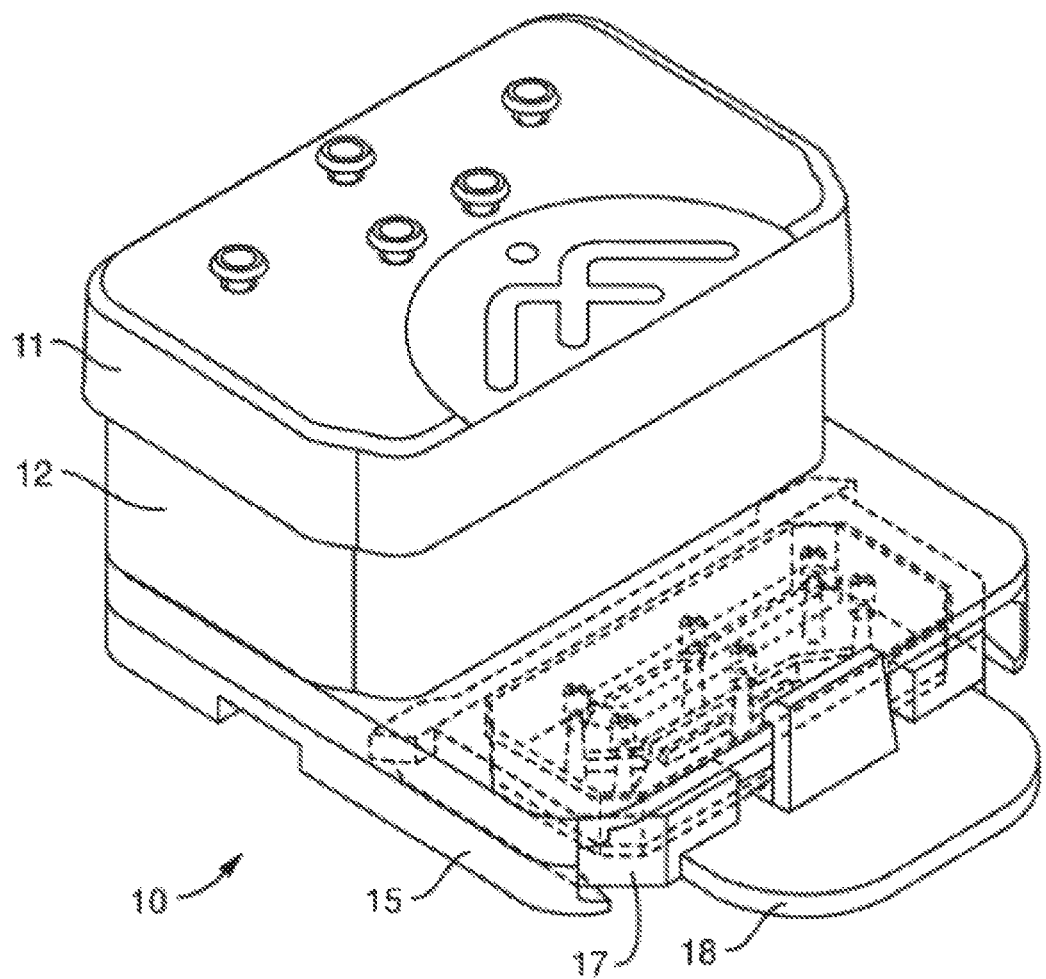
FIG. 1B shows the same embodiment of the perfusion manifold assembly with the cover on and over the reservoirs, and the chip inside the chip carrier fully linked to the skirt of the perfusion manifold assembly, and thereby in fluidic communication with the reservoirs. In one embodiment, each chip has two inputs, two outputs and (optionally) two connections for the vacuum stretch. In one embodiment, putting the chip in fluidic communication connects up to and at least six individual connections into one action, rather than connecting them one at a time.
Figure 1C:
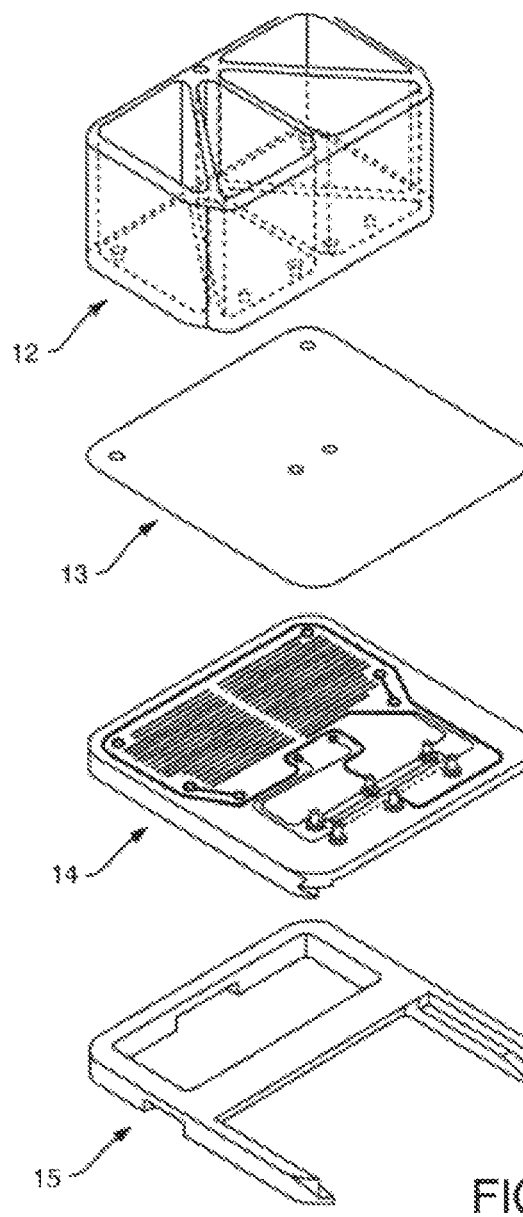
FIG. 1C is an exploded view of one embodiment of the perfusion manifold assembly (before the components have been assembled) comprising reservoirs positioned over a fluidic backplane (comprising a fluid resistor), that is fluidically sealed with a capping layer and is positioned over a skirt, with each piece dimensioned to fit over the next. In one embodiment, the skirt comprises structure (e.g. made of polymer) that holders or defines two open spaces, one of the spaces configured to receive the carrier with the chip inside. In one embodiment, the skirt has structure that completely surrounds one open space and two "arms" that extend outwardly that define a second open space for receiving the carrier. In one embodiment, the two arms have side tracks for slidably engaging the carrier edges.

In one embodiment, the present invention contemplates a perfusion manifold assembly that allows for perfusion of a microfluidic device, such as an organ on a chip microfluidic device comprising cells that mimic cells in an organ in the body or at least one function of an organ, that is (preferably detachably) linked with said assembly so that fluid enters ports of the microfluidic device from a fluid reservoir, optionally without tubing, at a controllable flow rate. In one embodiment (as shown in FIGS. 1A, 1B and 1C), the perfusion manifold assembly (10) comprises i) a cover or lid (11) configured to serve as to top of ii) one or more fluid reservoirs (12), iii) a capping layer (13) under said fluid reservoirs), iv) a fluidic backplane (14) under, and in fluidic communication with, said fluid reservoirs), said fluidic backplane comprising a fluidic resistor, and v) a projecting member or skirt (15) for engaging the microfluidic device (16) or chip which is preferably positioned in a carrier (17), the chip having one or more microchannels (l) and in fluidic communication with one or more ports (2). The assembly can be used with or without the lid or cover. Other embodiments (discussed below) lack a skirt or projecting member. In one embodiment, the carrier (17) has a tab or other gripping platform (18), a retention mechanism such as a clip (19), and a visualization cutout (20) for imaging the chip. The cutout (20) can enable placing a carrier (e.g. a carrier engaged with the perfusion manifold assembly or "pod" or not so engaged) onto a microscope or other inspection device, allowing the chips to be observed without having to remove the chip from the carrier. In one embodiment, the fluidic resistor comprises a series of switchbacks or serpentine fluid channels.

A variety of fluid resistors designs are contemplated, as described more fully in U.S. Provisional Application Ser.

Nos. 62/024,361 and 62/127,438, which became PCT/US2015/040026, hereby incorporated by reference (and in particular, the discussion of resistors, resistor design, and pressures is incorporated herein by reference). In one embodiment, the perfusion manifold assembly is made of plastic and is disposable, i.e. it is disposed of after docking with and perfusing a microfluidic device. While the present invention contemplates "disposable" embodiments, the element may (alternatively) be reusable (e.g. as a cost consideration).

In one embodiment, the microfluidic device (e.g. chip) (16) may first be placed in a carrier (17) (e.g. chip carrier) before engaging the perfusion manifold assembly (10) or may engage the assembly directly. In either case, the (optional) detachable linking of the microfluidic device with the manifold should either a) prevent air from entering the microchannels, or b) provide a way for undesirable air to be removed or vented out of the system. Indeed, air removal may be needed in some embodiments during both chip attachment and use of the microfluidic device.

In one embodiment for preventing air from entering the microchannels, the microfluidic device is detachably linked using a "drop-to-drop" "chip-to-cartridge" connection. In this embodiment, an inlet port of the microfluidic device has a droplet (22) projecting therefrom, and the surface of the perfusion manifold assembly or "cartridge" (10) for engaging the device has a corresponding droplet (23). When the two are brought together, the droplets merge allowing for fluidic communication without the introduction of air into the channels. In one embodiment, the chip carrier is designed so as to not interfere with the "drop-to-drop" connection. For example, the carrier, in one embodiment, surrounds the sides, but not the mating surface (21) of the microfluidic device. It should be noted that in one embodiment, a skirt-free perfusion manifold (10) may be located where the microfluidic device or chip engages from underneath (rather than from the side).

It is not intended that the present invention be limited to one manner for detachably linking the microfluidic device. In one embodiment, the microfluidic device, such as an organ on a chip microfluidic device comprising cells that mimic one or more functions of cells in an organ in the body or at least one function of an organ, approaches the assembly from the side or underneath, with the droplet (22) projecting upward, while the corresponding droplet (23) on the assembly (or other type of fluid source) projects downward. The microfluidic device (or the device carrier) may comprises a portion (24) configured to engage a side track (25) or other guide mechanism. In another embodiment, the microfluidic device, such as an organ on a chip microfluidic device comprising cells that mimic cells in an organ in the body or at least one function of an organ, approaches the assembly from above, with the droplet projecting downward, while the corresponding droplet on the assembly projects upward. In still another embodiment, the microfluidic device, such as an organ on a chip microfluidic device comprising cells that mimic cells in an organ in the body or at least one function of an organ, approaches the assembly from the side and is positioned by pivoting about a hinge, socket, or other pivot point (26). In still another embodiment, the microfluidic device engages in the manner of an audio cassette or CD with the droplet projecting upward, while the corresponding droplet on the assembly projects downward, where there is a combined sideways movement and upward movement.

In one embodiment, the microfluidic device (16) is detachably linked with the perfusion manifold assembly (10) by a clipping mechanism that temporarily "locks" the microfluidic device, including organ-on-chip devices, in place (FIGS. 4A, 4B, 4C and 4D). In one embodiment, the clipping or "snap fitting" involves a projection on the carrier (19) which serves as a retention mechanism when the microfluidic device (16) is positioned. In one embodiment, the clipping mechanism is similar to the interlocking plastic design of a Lego™ chip and comprises a straight-down clip, friction fit, radial-compression fit or combination thereof. However, in another embodiment, the clipping mechanism is triggered after the microfluidic device, or more preferably, the carrier (17) comprising the microfluidic device (16), engages the perfusion manifold assembly (or cartridge) on a guide rail, side slot, internal or external track (25) or other mechanism that provides a stable glide path for the device as it is conveyed (e.g. by machine or by hand) into position. The guide rail, side slot, internal or external track (25) or other mechanism can be, but need not be, strictly linear and can be positioned in a projecting member or skirt (15) attached to the main body of the perfusion manifold assembly (10). In one embodiment, the beginning portion of the guide rail (25) (or side slot, internal or external track or other mechanism) comprises an angled slide (27) which provides a larger opening for easier initial positioning, followed by a linear or essentially linear portion (28). In one embodiment, the end portion (29) (close to the corresponding ports of the assembly) of an otherwise linear (or essentially linear) guide rail (25) (or side slot, internal track or other mechanism) is angled (or curves) upward so that there is a combination of linear movement (e.g. initially) and upward movement to achieve linking.

In several embodiments, droplets remain placed at their corresponding fluidic port despite the motion of their substrate or any period of upside-down orientation. In addition, it is desirable that the droplets retain their size, for example, so that the drop-to-drop process is consistent regardless of the speed of the engagement process. Accordingly, the present invention contemplates designs and method to provide stable droplets. Stable droplets are contemplated for aqueous as well as non-aqueous liquids. Although examples without loss of generality on aqueous droplets, one familiar with the art should be able to adapt the examples and particularly the use of hydrophilic and hydrophobic regions or materials based on the wetting properties of the liquid. In some embodiments, a droplet may be restricted within a first region of a substrate by surrounding the first region with a second region, wherein the second region is hydrophobic (or more generally, with a propensity against wetting by the droplet's liquid). The said second region may be hydrophobic due to selection of one or more hydrophobic materials that it comprises (e.g. PTFE, FEP, certain grades of Nylon, etc.), surface treatment (e.g. plasma treatment, chemical treatment, ink treatment), the use of a gasket (e.g. a film, an o-ring, an adhesive gasket), by masking during treatment of at least one other region of the substrate, or a combination thereof. In some embodiments, a droplet may be restricted within a first region of a substrate by surrounding the first region with a geometric feature. In some embodiments, the geometric feature may be a ridge or a depression. Without being bound by theory, such features may act to restrict the droplet by means of their edges, which interact with the surface layer of the droplet (and correspondingly with the surface tension of the droplet), for example, by "pinning" the surface of the droplet. In some embodiments, a droplet may be restricted to cover a first region of a substrate by adapting the first region to be hydrophobic (or more generally, with a propensity for wetting by the droplet's liquid). The said first region may be hydrophilic due to selection of one or more hydrophilic materials that is comprises (e.g. PMMA, PLA), surface treatment (e.g. plasma treatment, chemical treatment, ink treatment), the use of a gasket (e.g. a film, an o-ring, an adhesive gasket), by masking during the treatment of at least one of other region of the substrate, or a combination thereof.

In one embodiment, the mating surface (21) of a microfluidic device (or at least a portion thereof adjacent the port opening) is hydrophobic or made hydrophobic (or protected with a mask during plasma treatment to keep it from becoming hydrophilic). In one embodiment, the mating surface of a perfusion manifold assembly or cartridge (or at least a portion thereof adjacent the port opening) is hydrophobic or made hydrophobic (or protected with a mask during plasma treatment to keep it from becoming hydrophilic). In one embodiment, both the mating surface of the microfluidic device (or at least a portion thereof adjacent the port opening) and the mating surface of the perfusion manifold (or at least a portion thereof adjacent the port opening) is hydrophobic or made hydrophobic (or protected with a mask during plasma treatment to keep it from becoming hydrophilic).

The advantage of the carrier is that the surfaces of the microfluidic device need not be touched during the detachable linkage with the perfusion manifold assembly. The carrier can have a plate, platform, handle or other mechanism for gripping the carrier (18), without contacting the mating surface (21) of the microfluidic device (16). The retention mechanism (19) can comprise a projection, hook, latch or lip that engages one or more portions of the perfusion manifold assembly, and more preferably the skirt of the perfusion manifold assembly, to provide a "snap fit."

In other embodiments, one or more gaskets can be used to vent air (e.g. any air that has been introduced because of the detachable linking of the microfluidic device with the perfusion manifold assembly). While in one embodiment, bubbles can be trapped (and their impact thereby limited), in an alternative embodiment, they are vented. One method involves use of hydrophobic vent material (molded or sheet). For example, the hydrophobic vent material may comprise PTFE, PVDF, hydrophobic grades of Nylon, or a combination thereof. In some embodiments venting can be accomplished by employing materials that display high gas permeability (e.g. PDMS). In other embodiments, venting can be accomplished by employing porous materials, for example, sintered materials, porous membranes (e.g. track-etched membranes, fiber-based membranes), open-cell foams, or a combination thereof. In a preferred approach, air escapes from a vented (or venting) gasket. In some embodiments, the perfusion manifold assembly or microfluidic device comprise a vent adapted to provide a path for undesired gas to escape.

Figure 5:
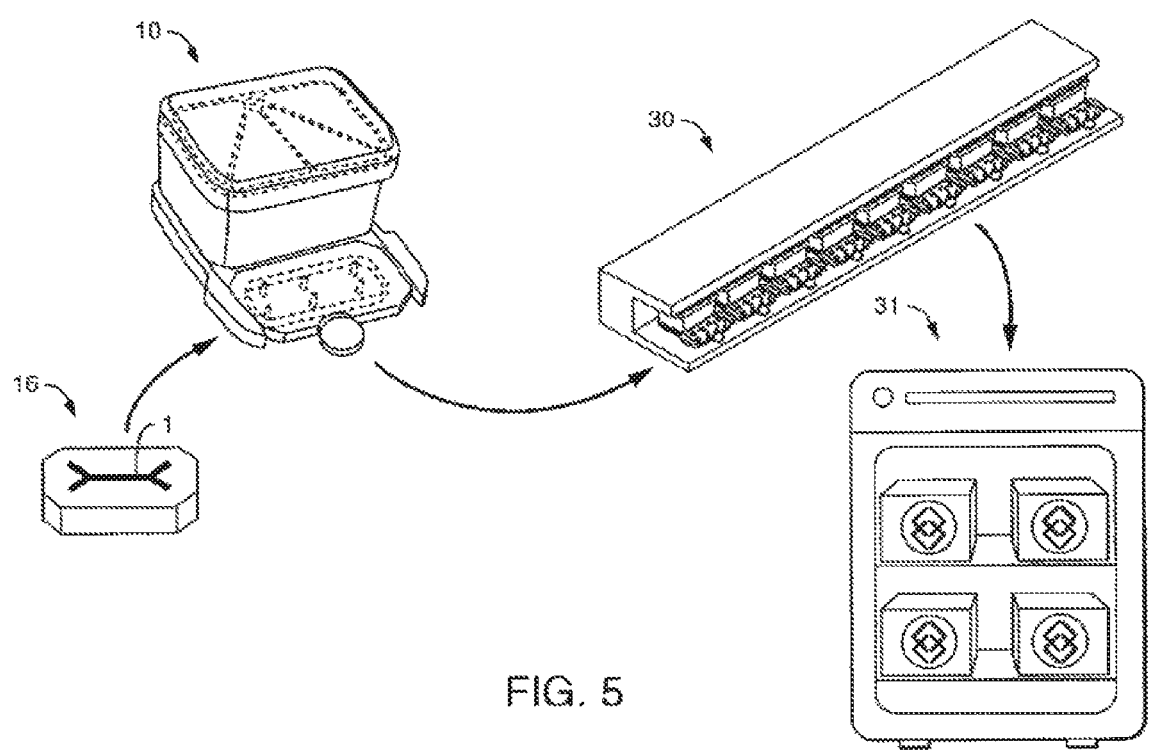
FIG. 5 is a schematic of one embodiment of a work flow (with arrows showing each progressive step), where the chip is linked (e.g. snapped in) to a disposable perfusion manifold assembly ("perfusion disposable"), which in turn is positioned with other assemblies on a culture module, which is placed in an incubator. In alternative embodiments, the culture module may comprise features of an incubator (e.g. a heat source and/or a source of warm moist air), so as to avoid the need for a separate incubator. While the present invention contemplates "disposable" embodiments, the element may (alternatively) be reusable (e.g. as a cost consideration). In a further embodiment of the work flow or method, the chip can be placed in a carrier, the carrier can be placed in a seeding guide (discussed and illustrated below), cells can be seeded into the chip, the carrier can be removed from the seeding guide, and the carrier can engage the perfusion disposable (with the rest of the work flow as illustrated in FIG. 5).
Figure 7A:
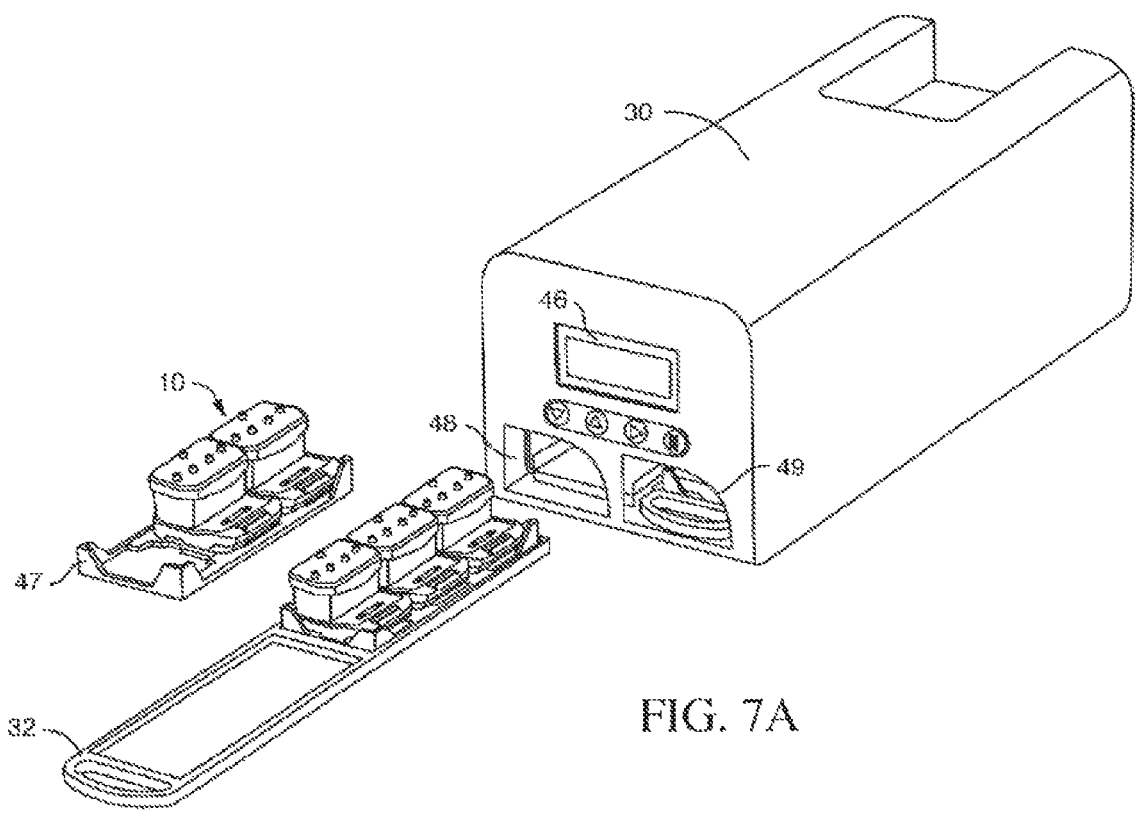
FIG. 7A is a schematic of another embodiment showing the tray (or rack) and sub-tray (or nest) for transporting and inserting the perfusion disposables (PDs) into the pressure module, which has a user interface on outside of the housing.

Once a microfluidic device (or "chip") has docked with the perfusion manifold assembly, the assembly-chip combination can be placed into an incubator (31) (typically set at a temperature above room temperature, e.g. 37° C.), or more preferably, into a culture module (30) capable of holding a plurality of assembly-chip combinations, the culture module configured to fit on an incubator shelf (see FIG. 5). This allows for the easy handling of many (e.g. 5, 10, 20, 30, 40, 50 or more) microfluidic devices at one time. For example, where the culture module comprises 9 assembly-chip combinations, and an incubator is sized for 6 to 9 culture modules, between 54 and 81 "organs-on-chip" can be handled in a single incubator (FIG. 5 and FIG. 7A-B). In another example, where the culture module comprises 12 assembly-chip combinations, and an incubator is sized for 4 to 6 culture modules, between 48 and 72 "organs-on-chip" can be handled in a single incubator. The perfusion manifold can be easily removed and inserted into the culture module without breaking the fluidic connections to the chip. In one embodiment, the culture module is capable of maintaining the temperature above room temperature, e.g. 37° C., without being placed in an incubator.

The culture module (30), in one embodiment (FIG. 6), comprises a removable tray (32) for positioning the assembly-chip combinations, a pressure surface (33), and pressure controllers (34), along with an optional user interface (46) to control the movement of the various elements. In one embodiment, the tray (32) can slide. In one embodiment, the tray is positioned on the culture module and the tray is moved up via a tray mechanism (35) to engage the pressure surface (33) of the culture module, i.e. the cover or lid (11) of the perfusion manifold assembly (10) engages the pressure surface of the culture module (30). Multiple perfusion assemblies (10) can be attached to the pressure controllers in a single action by the tray mechanism. In another embodiment, the tray is positioned on the culture module and the pressure surface of the culture module (30) is moved down to engage the tray (32), i.e. the cover or lid (11) of the perfusion manifold assembly (10). In either case, in one embodiment (FIGS. 2A and 2B), the cover or lid comprises ports such as through-hole ports (36) that are engaged by corresponding pressure points on the pressure surface (33) of the culture module. These ports (36), when engaged, transmit applied pressure inward through the cover and through a gasket (37) and apply the pressure to the fluid in the reservoirs (12) of the perfusion manifold assembly (10). Thus, in this embodiment, pressure is applied through the lid (11) and the lid seals against the reservoir(s). For example, when on applies 1 kPa, this nominal pressure results, in one embodiment, in a flow rate of approximately 30-40 uL/hr. Alternatively, these ports (36), when engaged, move inward on the cover so as to contact the gaskets (i.e. the ports act essentially like plungers).

FIG. 7A is a schematic of another embodiment of the culture module (30) showing the tray (or rack) (32) and sub-tray (or nest) for transporting and inserting the perfusion disposables (10) into the culture module, which has two openings (48, 49) in the housing to receive the trays, and a user interface (46) to control the process of engaging the perfusion disposables and applying pressure. A typical incubator (not shown) can hold up to six modules (30). FIG. 7B is a schematic of the same embodiment of FIG. 7A, but showing both of the trays (or racks) (32) inserted into the two openings (48, 49) in the housing (53) of the pressure module (30), which has a user interface (46) (e.g. LCD screen) to control the process.

Figure 8A:
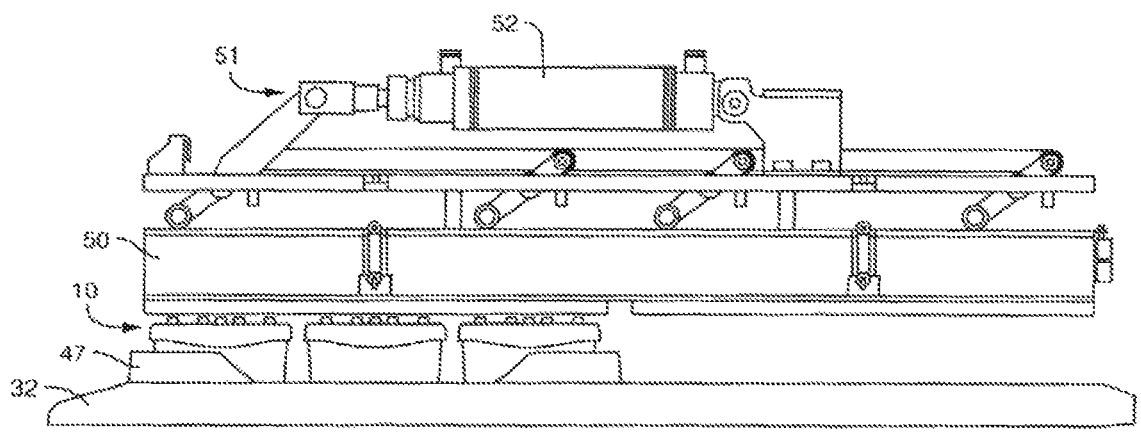
FIG. 8A is a schematic of the interior of one embodiment of the pressure module (in an open position), showing the positioning of the tray (or rack), sub-tray (or nest), perfusion disposables (PDs) under a pressure manifold (but not engaging it, so the clearance is sufficient to remove them), with the actuation assembly (including the pneumatic cylinder) above. Three microfluidic devices or perfusion disposables are shown to illustrate, although more (e.g. 6, 9 or 12) are typically used at once.

FIG. 8A is a schematic of the interior of one embodiment of the module (i.e. the housing has been removed), showing the pressure manifold (50) in an open position, with the positioning of the tray or rack (32), sub-tray or nest (47), perfusion disposables (10) under the pressure manifold (50) but not engaging it (so the clearance is sufficient to remove them), with the actuation assembly (51) including the pneumatic cylinder (52) above.

Figure 8B:
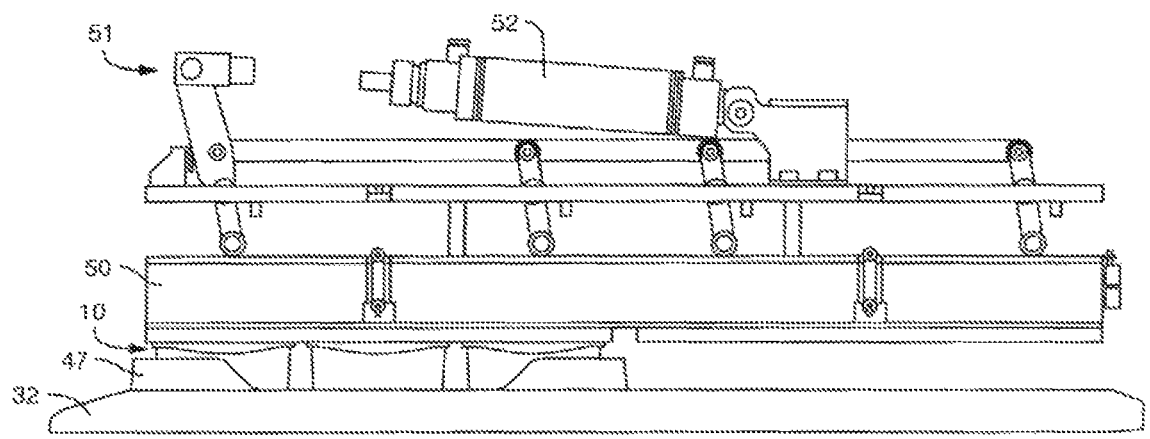
FIG. 8B is a schematic of the interior of one embodiment of the pressure module (in a closed position), showing the positioning of the tray (or rack), sub-tray (or nest), perfusion disposables (PDs) under the pressure manifold (and engaging it), with the actuation assembly (including the pneumatic cylinder) above. Again, three microfluidic devices or perfusion disposables are shown to illustrate, although more (e.g. 6, 9 or 12) are typically used at once.

FIG. 8B is a schematic of the interior of one embodiment of the module (i.e. the housing has been removed), showing the pressure manifold (50) in a closed position, with the positioning of the tray or rack (32), sub-tray or nest (47), perfusion disposables (10) under the pressure manifold (50) and engaging it, with the actuation assembly (51) including the pneumatic cylinder (52) above. The pressure manifold (50) simultaneously engages of the perfusion disposables

(10) while media perfusion is required or needed. Independent control of the flow rate in the top and bottom channels of the chip (16) can be achieved. The pressure manifold (50) can disengage (without complicated fluid disconnects) as desired to allow removal of the trays (32) or nests (47) for imaging or other tasks. In one embodiment, the pressure manifold (50) can simultaneously disengage from a plurality of perfusion manifold assemblies. In one embodiment, the perfusion disposables (10) are not rigidly fixed inside the nests (47), allowing them to locate relative to the pressure manifold (50) as it closes, in a preferred embodiment, integrated alignment features in the pressure manifold (50) provide guidance for each perfusion disposable (10).

In one embodiment, the cover or lid is made of polycarbonate. In one embodiment, each through-hole port is associated with a filter (38) (e.g. a 0.2 um filter), in one embodiment, the filters are aligned with holes (39) in a gasket positioned underneath the cover.

A culture module comprising a pressure manifold is contemplated that allows the perfusion and optionally mechanical actuation of one or more microfluidic devices, such as organ-on-a-chip microfluidic devices comprising cells that mimic at least one function of an organ in the body.

Figure 9A:
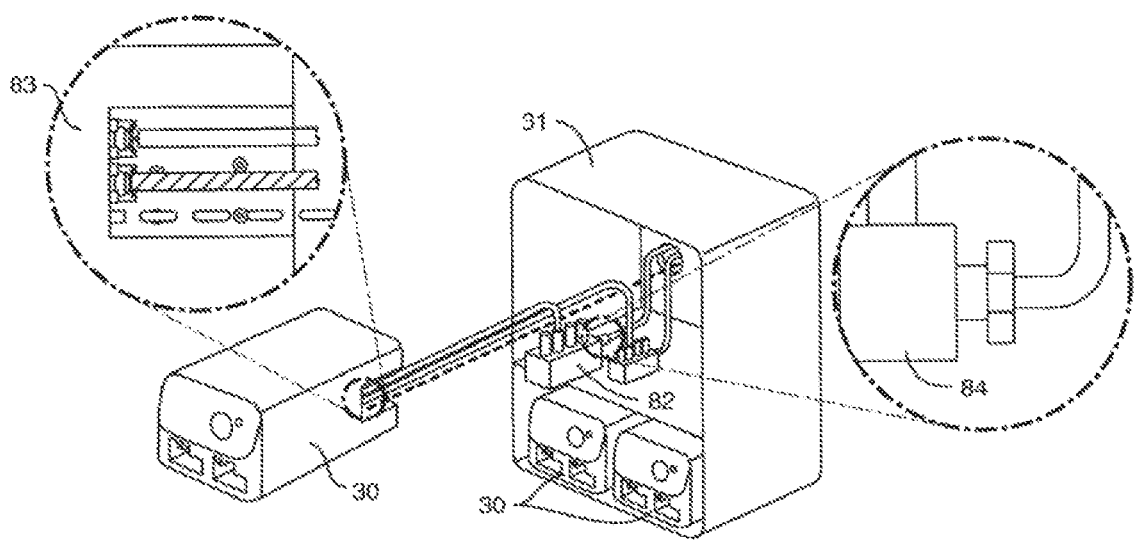
FIG. 9A is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections).
Figure 9B:
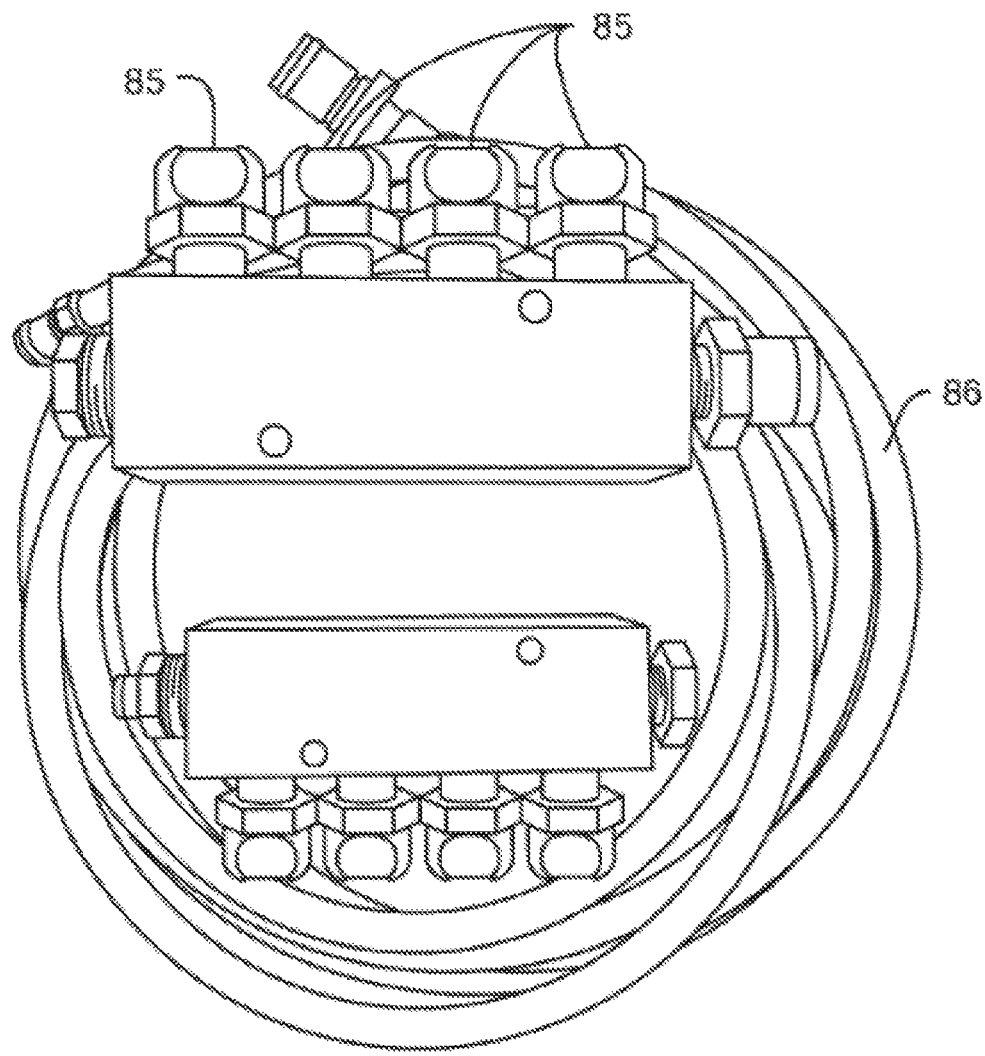
FIG. 9B is a photograph of gas hubs and vacuum hubs (collectively 85), along with the tubing (86) for the connection shown in FIG. 9A.

FIG. 9A is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections). FIG. 9B is a photograph of gas hubs and vacuum hubs (collectively 85), along with the tubing (86) for the connection shown in FIG. 9A. While this connection scheme is optional, it provides a convenient way to utilize multiple culture modules with a single incubator.

A. Pressure Lid

The present invention contemplates in one embodiment "perfusion manifold assemblies" or "perfusion disposables," which facilitate the culture of Organs-on-Chips within a culture instrument. While the present invention contemplates "disposable" embodiments, the element may (alternatively) be reusable (e.g. as a cost consideration).

In one embodiment, these perfusion disposables (PDs) include one or more input and one or more output reservoirs, as well as elements required for pumping.

In particular, in one embodiment, perfusion disposables include one or more resistors, which are used for pressure-driven pumping. In the pressure-driven embodiment, the instrument creates or controls fluid flow by applying a pneumatic pressure (whether positive or negative) to one or more of the reservoirs. One advantage of this approach is that the pressure-driven design can avoid liquid contact with the instrument, which offers benefits in terms of sterility and ease of use (e.g. avoiding gas bubbles in liquid lines).

In some embodiments, the instrument applies pressure directly to the one or more reservoirs (with no lid). A sufficient pressure seal may be attained by integrated one or more gaskets on the perfusions disposable and/or the instrument (for example, as part of a pressure manifold). However, it is desirable that when the perfusion disposables are outside of the instrument the reservoirs are protected from contamination, for example, from environmental particles or airborne microbes.

Accordingly, in the same embodiments it may be desirable to provide a lid that a user can employ to cover the reservoirs when outside of the instrument and/or to employ PD embodiments that comprise a substrate that conveys pressure but blocks contamination (for example, a suitable filter disposed on a reservoir's opening). However, such solutions typically pose drawbacks. In particular, expecting a user to place a lid requires the user to manage lids while the perfusion disposables are engaged with the instrument and ideally place the lids as soon as the PDs leave the instrument; in most circumstances, these actions adversely affect user experience. In turn, a filler disposed on a reservoir's opening typically blocks access to the said reservoir by pipettes and other typical lab tools, thereby adversely limiting their ease of use.

According to an aspect of the present invention, a "pressure lid" is disclosed as a lid that may be disposed on a microfluidic device or a device adapted to accept a microfluidic device (e.g. a perfusion disposable) even while the said device is engaged with an instrument, with the pressure lid adapted to permit the communication of pressure between the instrument and the said device. The present invention contemplates that in some embodiments, a pressure lid is a removable cover adapted to be disposed onto one or more reservoirs of a microfluidic device or a device adapted to accept a microfluidic device (e.g. a perfusion disposable), the pressure lid comprising at least one instrument-interface port and at least one reservoir-interface port, wherein the pressure lid is adapted to convey pressure between at least some of the instrument-facing port and at least some of the reservoir-facing ports. In some embodiments, the pressure lid comprises at least one "through hole" port—an opening that connect a first and second surface of the lid, wherein the opening on the first surface is adapted to form an instrument-facing port and the opening on the second surface is adapted to form a reservoir-facing port. In some embodiments, the though-hole port is round, rectangular, triangular, polygonal, rectilinear, curvilinear, elliptical, and/or curved, in some embodiments, however, the lid comprises a channel that links at least one instrument-facing port and at least one reservoir-facing ports, which may not be disposed directly opposite each other. Such embodiments may be useful, for example, where there is a need to adapt between locations of instrument interface and reservoir locations, for example, when it is desired for the same instrument to support the actuation of a plurality of versions of perfusion disposables.

In some embodiments, the pressure lid is adapted to form a pressure seal between said pressure lid and at least one reservoir. In some embodiments, the pressure lid is engaged with at least one reservoir forming a lid-to-reservoir pressure seal. In some embodiments, the pressure lid is adapted to form a pressure seal between said pressure lid and at least one instrument, in some embodiments, the pressure lid is engaged with at least one instrument forming a lid-to-instrument pressure seal. Any of the lid-to-reservoir seals and lid-to-instrument seals may employ any sealing methodology known in the art and can be selected for example, from the list of face seal, radial seal, tapered seal, friction fit or a combination thereof. Any of the said seals may employ one or more gaskets, O-Rings, elastic materials, pliable materials, adhesive, sealants, greases or combination thereof. It is not intended that the present invention be limited to a design that has a perfect pressure seal, as this may not be required. Rather, some amount of gas leakage can be tolerated, since the instrument may actively regulate pressure, thereby compensating for the leak. The relaxing of a requirement to obtain a perfect seal on one or both sides can simplify design and reduce costs.

In some embodiments, the pressure lid comprises a load concentrator. For example, in some embodiments, the pressure lid comprises a ridge surrounding at least one instrument-facing port. In some embodiments, the pressure lid comprises a ridge surrounding at least one reservoir-facing port, it is known in the art that such load concentrators can act to improve pressure seals by enhancing reliability or reducing the required force; designs known in the art include, for example, rectangular, semi-circular, triangular, trapezoidal and polygonal ridges. Accordingly, a load concentrator surrounding an instrument-facing port may be employed to improve a lid-to-instrument pressure seal, and a load concentrator surrounding a reservoir-facing port may be used to improve a lid-to-reservoir pressure seal.

In some embodiments, the pressure lid comprises a filter. For example, the pressure lid may comprise a membrane filter, sintered filter, fiber-based filter and/or track-etched filter. In some embodiments, the said filter is disposed within or abutting a through-hole port and/or one of its openings. In some embodiments, the said filter is disposed within or abutting a channel included in the lid and/or one of the openings of said channel.

In some embodiments, the filter is selected to improve the sterility of a reservoir and/or block particles, contaminated or microbes. In some embodiments, the filter features have an effective pore size of 0.4 um or less, 0.2 um to 2 um, 1 um to 10 um, 5 um to 20 um, 10 um to 50 um. It is known in the art that filters that feature an effective pore size of 0.4 um or less are preferable for maintaining sterility. However, a filter such as the Porex 4901 possess a 25 um effective pore size has been shown to be effective in maintaining sterility.

In some embodiments, the pressure lid comprises one or more gaskets. In some embodiments, the one or more gaskets are adapted to permit or improve a pressure seal (which may nevertheless not be a perfect seal). In some embodiments, at least one gasket is disposed on a reservoir-contact surface of the said lid. In some embodiments, at least one gasket is disposed on an instrument-contact surface of the said lid. In some embodiments, a gasket is adapted to permit or improve pressure seals with a plurality of reservoirs. In some embodiments, a gasket is adapted to permit or improve pressure seals at a plurality of instrument-facing ports. In some embodiments, the one or more of the gaskets comprise an elastomer, pliable material, O-Ring and/or a combination thereof. In some embodiments, one or more of the gaskets are formed by extrusion, casting, injection molding (including reaction-injection molding), dye cutting and/or a combination thereof. In some embodiments, at least one gasket is mechanically coupled to the lid by adhesion (e.g. using adhesive tape), clamping, screwing down, bonding, heat-staking, welding (e.g. ultrasonically, by laser), fusing (e.g. using solvent-assisted bonding), and/or a combination thereof.

For example, in some embodiments of the lid includes a port (5) that allows pneumatic (e.g. vacuum) control of (optional) chip stretching to be communicated through the lid (see FIGS. 2A-2E). It is not intended that the lid be limited to communicating pneumatic pressure; it is contemplated that the lid can communicate additionally fluidic or electrical interfaces.

In one embodiment, the lid can include sensors. For example, the lid may comprise a pressure sensor to determine, for example, the pressure incident on one or more reservoirs. Further, the lid may include liquid-level sensing to determine the amount of liquid present in the reservoir or whether specific fill (or depletion) thresholds have been passed. This can be done in a variety of ways. In one embodiment, the detecting liquid optically using the difference of refractive indexes is contemplated. In this embodiment, air-filled compartments and channels disperse light, while liquid or fluid-filled channels focus light. More specifically, the refractive indexes of liquid are from 1.3 to 1.5 while that of air is 1.0. In one embodiment, each optical sensor consists of a matched pair of an IR emitter (SEP8736, 880 nm, Honeywell) and a phototransistor (SDP8436, 880 nm, Honeywell). In this embodiment, IR is chosen over visible light for it is less susceptible to interfering light.

The ability to easily remove fluids from the various reservoirs (e.g. take sample, replenish media, add test agents, etc.) is a desired feature. An especially desired feature is to be able to use standard laboratory pipettes and syringes for such operations. However, such fluidic access (especially using a pipette) requires the accessed reservoir to be open to the environment. This, in terms, is undesirable particularly when the chip or disposable are in transit or in use outside of the instrument, as the opening can provide a means for contamination of the reservoir. A typical solution to this problem is to include a lid that can be applied to one or more of the reservoirs when they are not being accessed. However, including a simple lid can complicate the use of the technology, since the user typically would have to actively install and remove the lid, as well as maintain lids near the instrument in a sterile way.

One solution is to include a means for automatically removing and/or installing lids as part of the system (whether integrated in the culture instrument or a separate module). For example, the system can include a mechanical actuator that is capable of engaging a lid installed on a disposed perfusion disposable and removing it prior to engagement with the pressure system. This mechanical actuator can re-install the lid upon removal of the perfusion disposable. In an alternate embodiment, the system includes a means for applying a lid to a perfusion disposable prior to or upon removal, for example, with the lid originating from a magazine of stored lids.

A shortcoming of the system with the means for automatically removing and/or installing lids (discussed in the prior paragraph) is that it requires one or more mechanical actuators whose operation can be challenging in practice. Another challenge is the following: the design of the reservoirs and in particular its opening aims to satisfy the demands of liquid access (e.g. manual sample taking or replenishing using a pipette), the pressure-driven system (e.g. ensuring a good pressure seal against the instrument) and manufacturing (e.g. injection-molding of the reservoirs). In practice, these requirements can oppose each other. For example, manual access may demand a broad reservoir opening; in contrast, it may be desirable for the pressure interface to be narrower, to reduce the force on the instrument.

A better solution disclosed herein is to include a "pressure lid" (see FIGS. 2A, 2B, 2C and 2D). This pressure lid is a lid that may be installed on to the reservoirs to reduce the likelihood of contamination, and is designed to stay predominantly in place while the perfusion disposable is engaged with the instrument. In order to stay predominantly in place while engaged with the instrument, the lid preferably includes a) one or more features designed to interface with the instrument (e.g. to received positive or negative pressure), b) one or more features designed to interface with one or more reservoirs (e.g. create a pressure seal or minimize gas leakage so that pressure can be applied to the reservoir at), and c) a means for pressure to be communicated from at least some of the features (a) and at least some of the features (b). The pressure lid or portions thereof may be transparent or translucent. This can allow, for example, viewing liquid levels within the reservoirs. The pressure lid may include markings that indicate the nature or name of respective reservoirs.

In one embodiment of the pressure lid, the opening in the pressure ltd (e.g. on its top) may be smaller than the reservoir, to reduce the surface area open for contamination and/or reduce the area subject to a pressure seal. In another embodiment, the lid may include a filter or a plurality of filters (38) to prevent solids and particles from entering (see FIG. 2A). For example, the lid may include a 0.2 um or 0.4 um filter known to reduce entry of bacteria and other contaminants. Many materials and technologies can be used for such filters. For example, track-etched filters (e.g. PTFE, polycarbonate, PET), paper filters, porous and expanded materials (e.g. cellulose and derivatives, polypropylene, etc.), sintered materials (e.g. Porex filters) may be used since the filter need conduct pressure and not liquids.

In one embodiment, the lid may include a means for permitting gas flow but predominantly no liquid flow. This can include, for example, hydrophobic porous membranes or filters, gas permeable membranes or filters, etc. This approach can also help reduce the likelihood of spillage.

In one embodiment, the lid may include a deformable portion that can deform to conduct pressure. For example, this can be an elastic or plastic membrane that stretches into the reservoir as positive pressure is applied. Similarly, the lid may include a plunger used to transmit pressure from the instrument to one or more reservoirs. Care should be taken to ensure that the desired pressure is applied to the inside of the reservoir, as the membrane or plunger can apply a back force. This can be done, for example, by a) ensuring that the back force is small or understood through design of the membrane, plunger or the operating pressure range, b) measuring the pressure inside the reservoir and using it to control the applied pressure, c) monitoring the resulting flow to control the applied pressure. The deformable portion offers one way for pressure to be communicated.

Either side of the pressure lid (instrument-facing or perfusion disposable-facing) as well as each of the opposing surfaces (instrument and perfusion-disposable features that interact with the pressure lid) can be designed to enable a pressure seal in a number of different ways. In one embodiment, the present invention contemplates one or more regions comprising one or more elastic or pliable materials. In one embodiment, this is done with one or more gaskets (see FIG. 2A), which can be made for example from elastomeric or pliable materials (e.g. silicone, SEBS, polypropylene, Viton, rubber, etc.). The gaskets can be shaped in a variety of ways, including cut flat sheets, o-rings (not necessarily round in shape or cross-section), etc. in one embodiment, this is done with one or more ridges that act as load concentrators (see FIG. 2C). Without wishing to be bound by theory, these act to localize the sealing force to create elevated localized sealing pressure. These ridges may potentially engage a gasket or pliable material on the opposing surface. Care should be taken to design the shape of the ridge (particularly the portion of the shape that engages the opposing surface), as this shape can have a substantial effect on the required sealing pressure. A variety of shapes are contemplated (e.g. rectangular, triangular, trapezoidal, half-circular or circular section, etc.). In one embodiment, the sealing tooth has a trapezoidal shape for improved sealing (see FIG. 2C). Alternatively, the gasket could be integrated into either the Reservoir or Lid in the form of an overmolded elastomer (e.g. silicone, SEBS, etc). This overmolded elastomer could then, itself, have an appropriate shape to act as a seal (e.g. a tooth or o-ring half-round section).

The approach need not be limited to a single design. In one embodiment, the present invention contemplates a combination of one or more regions comprising one or more elastic or pliable materials. Moreover, gasketing or ridges can be done per-reservoir, so that each is isolated m terms of applied pressure, or it can encompass two or more reservoirs, which may reduce complexity. In one embodiment (see FIG. 2D) the path encircles chambers of the reservoir chamber—cover assembly seal, so each chamber is isolated from the other, in one embodiment (see FIG. 2D), there are two reservoirs, each with an inlet chamber (6A, 6B) and an outlet chamber (7A, 7B), and a separate (optional) vacuum chamber (8) that allows for transfer of a vacuum to the chip or other microfluidic device. In one embodiment (FIG. 2E), the reservoir chamber—cover assembly seal comprises a sealing tooth (9).

It is not intended that the present invention be limited to a design that has a perfect pressure seal, as this may not be required. Rather, some amount of gas leakage can be tolerated, since the instrument may actively regulate pressure, thereby compensating for the leak. The relaxing of a requirement to obtain a perfect seal on one or both sides can simplify design and reduce costs.

The pressure lid can be affixed or rest upon the reservoirs (whether on the perfusion disposable or directly on chip) in a variety of different ways. Embodiments can involve instances wherein the liquid or gas seal between the lid and reservoirs) is present even outside of the instrument (e.g. the lid is held tightly in place by something other than the instrument), and wherein the seal is created by action of the instrument (e.g. the instrument presses the lid against the reservoirs during perfusion). In another embodiment, the present invention contemplates a combined approach, e.g. the lid is designed to create at least a partial seal as in the first option above, but the seal is approved or assured by action of the instrument as in the second option above. An advantage of approaches that provide at least some degree of sealing of the lid against the reservoir even outside of the instrument is that they may reduce the risk of spills and contamination (e.g. due to handling or transport).

Examples of approaches to affix or rest the pressure lid (regardless of which of the above three approaches they fall under) include a) where the lid can simply rest upon the reservoirs or perfusion disposable (this can be aided by overhanding portions of the lid, so that the lid cannot simply slide off); b) the lid can be screwed, glued or pinned into place; and c) the lid can be clipped into place. In an alternative embodiment, it could also be held down by a spring, e.g. a hinged lid with a spring that forces the lid closed.

Clip features may reside in the lid, the perfusion disposable, chip or combination thereof. Furthermore, some embodiments make use of a separate substrate that provides clipping elements (i.e. a separate piece that one brings in to clip the lid into place). An advantage of the clipping approach is that it can facilitate easy application and removal of a lid while still securing the lid in place. The clipping may be optional; for example, it may be applied when shipping or transporting the device and ignored during regular use.

In some embodiments, the lid is asymmetric or includes lock-and-key features to ensure that the lid is correctly oriented with respect to a perfusion disposable and/or an instrument.

Many of the features of the perfusion disposable (PD) could potentially be included in the "chip" itself or a different device for coupling to a chip. If the reservoirs, for example, are included in the chip, one could use a pressure lid directly on top of the chip.

While the pressure lid has been discussed above in connection with the pressurization of one or more reservoirs within a perfusion disposable or perfusion manifold assembly, it is not intended that the pressure lid be limited by use with these embodiments. Indeed, it is contemplated that the pressure lid can be used with other microfluidic devices. The pressure lid can be movable or removably attached to other microfluidic devices to allow improved access to elements (e.g. reservoirs) within. The pressure lid can be removed from such other devices, and the other devices can be used without the lid. In one embodiment, the other microfluidic devices comprise cells on a membrane and/or in or on one or more microchannels.

C. Tray System

It is desirable to be able to remove chips and/or perfusion disposables from the instrument without having the remove the instrument itself from, for example, an incubating enclosure. It is also desirable to be able to remove groups of chips and/or perfusion disposables together. Tills is because the operations that are performed on the chips/disposables often need to be done in batches at a time (e.g. media replenishing, dosing with an agent, sample taking), regardless of whether the operations are performed automatically or manually. For example, it is convenient to remove groups of chips/disposables at a time if to help transport them to a bio-safety cabinet or culture hood.

Figure 6:
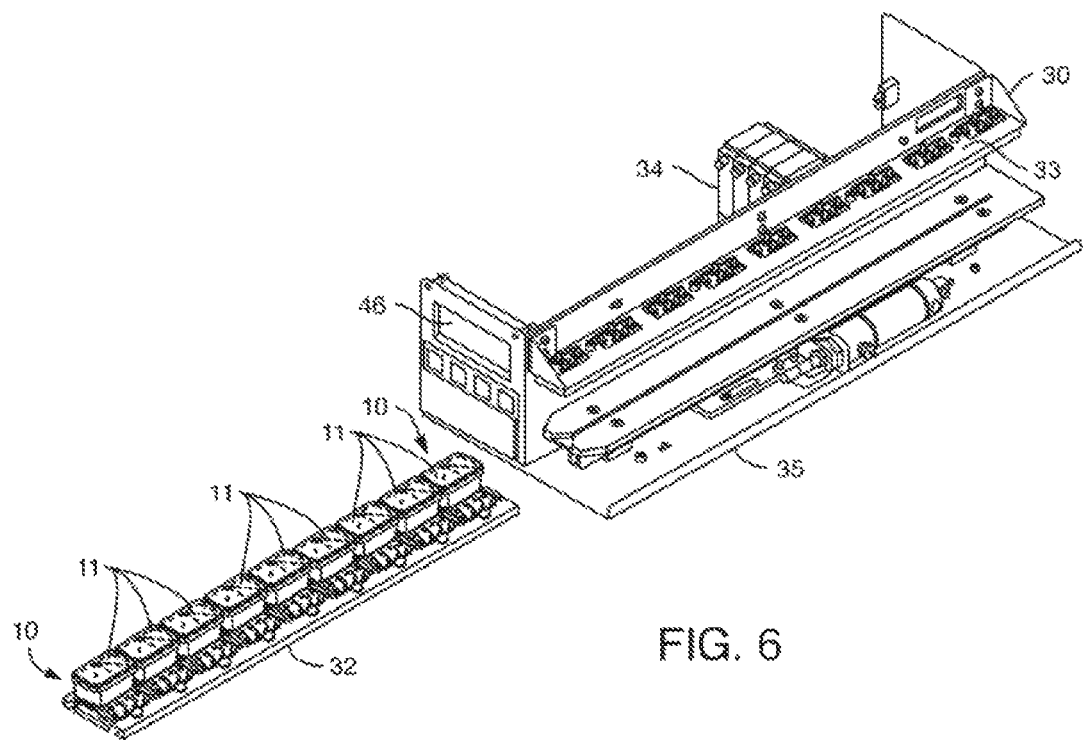
FIG. 6 shows one embodiment of a removable tray with a plurality of assemblies (with linked chips) positioned thereon, next to one embodiment of a culture module with pressure points on a mating surface that correspond to the ports on the cover of each perfusion manifold assembly held in the tray, such that they can be brought together by the tray mechanism so that pressure can be applied via the pressure controllers. The tray mechanism thereby attaches the perfusion manifold assemblies to pressure or flow controllers in a single action (whether lifting the tray up or coming down to meet the tray), allowing for a simultaneous linking.

To address these needs, the present invention contemplates, in one embodiment, a system in which perfusion disposables can be inserted or removed from an instrument (or module) in groups by means of a tray system (see FIG. 6). For example, a current embodiment allows each instrument to accept two trays (or racks) of six perfusion-disposables each (8A and 8B).

In one embodiment, the tray (or rack) (32) may facilitate the alignment of the perfusion disposables (10) with the instrument (30) (e.g. aligning reservoirs or port locations with corresponding pressure or fluid interfaces included in the instrument). This can be done in a number of ways, including providing locating features for the perfusion disposables (or any additional elements that carry them) within the tray, and providing locating features for the tray within the instrument and alignment features (57) for the perfusion disposables. Features that can be used to support such alignment include reference surfaces, pins, guides, shaped surfaces (e.g. fillets and/or chamfers), spring or elastic elements to promote registration, etc. These may be included in the tray, instrument, perfusions disposables or combinations thereof.

The tray may optionally be designed to capture leaks originating from the perfusion disposables or instrument interfaces. The tray may optionally include one or more optical windows that may facilitate microscopy or inspection. This can enable placing a tray onto a microscope or other inspection device, allow the chips to be observed without having to remove each disposable from the tray. Correspondingly, the tray may be optionally designed to minimize imaging working distance, e.g. lay flat on or fit into a microscope stage, etc. The system may optionally include a means for retaining one or more of the perfusion disposable within the tray. For example, the perfusion disposable may clip into the tray, with clip features present on the perfusion disposable, tray, an additional substrate or combinations thereof.

In some embodiments, the tray system includes one or more sub-trays (or nests) (47) that fit into a carrier tray (32) (see FIG. 8A). Sub-trays allow subsets of perfusion disposables (e.g. three) to be removed from the tray simultaneously. This can be useful, for example, where one or more operations performed on the chips-disposables benefits from a smaller number of chips that are present on the carrier tray. For example, in some embodiments, up to three disposables on a microscope stage at one time, to minimize the time that the chips/disposables spend outside of their preferred incubation and perfusion environments. Consequently, a current embodiment includes earner trays (32) that support two sub-trays (47) each, each sub-tray supporting three perfusion disposables (10) (see FIG. 8A).

The sub-trays may facilitate the alignment of the perfusion disposables with the instrument. This can be done in a number of ways, including by providing locating features for the perfusion disposables within the tray, by providing locating features for the sub-tray within the carrier tray, and by providing locating features for the carrier tray within the instrument. Features that can be used to support such alignment include reference surfaces, pins, guides, shaped surfaces (e.g. fillets and/or chamfers), and spring or elastic elements to promote registration, etc. These may be included in the carrier tray, sub-tray, instrument, perfusions disposables or combinations thereof. By way of an example, the present invention contemplates an embodiment wherein the perfusion disposables align to the sub-tray, which in turn aligns to the earner tray, which in turn aligns to the instrument (see FIGS. 9A and 9B). It is not intended that of these alignments or necessary; indeed, some steps in this chain may be skipped. For example, the sub-tray may align directly to the instrument using any of the described features, and not requiring the carrier tray for alignment purposes.

The sub-tray may optionally be designed to capture leaks originating from the perfusion disposables or instrument interfaces. The sub-tray may optionally include one or more optical windows that may facilitate microscopy or inspection. This can enable placing a sub-tray onto a microscope or other inspection device, allow the chips to be observed without having to remove each disposable from the tray. Correspondingly, the sub-tray may be optionally designed to minimize imaging working distance, e.g. lay flat on or fit into a microscope stage, etc. The system may optionally include a means for retaining one or more of the perfusion disposables within the sub-tray. For example, the perfusion disposable may clip into the sub-tray, with clip features present on the perfusion disposable, sub-tray, an additional substrate or combinations thereof. The system may optionally include a means for retaining the sub-tray within the carrier tray. For example, the sub-tray may clip into the carrier tray, with clip features present on the sub-tray, carrier tray, an additional substrate, or combinations thereof.

It may be convenient to divide some of the desired features between the carrier tray and the one or more sub-trays. For example, the sub-trays can provide an optical window and the carrier tray can be designed to capture leaks. As this example illustrates, it may be desired to include a sub-tray even if the carrier tray is designed to support one sub-tray.

The same instrument may support different tray or sub-tray types, as well as different numbers of trays. For example, an instrument may accept two different tray types, each tray type designed for a different type of perfusion disposable, in such a case, the tray can in essence act as an adaptor that adapts the different perfusion-disposable types to the same instrument.

The present invention also contemplates in one embodiment, microscope stages, stage-inserts or adapters (e.g. that plug into the stage inserts) designed to accept one or more chips, perfusion disposables, trays or sub-trays. These can make it easy to "drop in" a number of chips for imaging, with the chips securely retained on the stage (thereby avoiding drift, for example, as the microscope stage moves).

D. Engaging Perfusion Disposables with the Instrument.

In one embodiment, the present invention contemplates a pressure-driven system for the biological culture in fluidic devices, which applies pressure (whether positive or negative) to one or more fluidic elements. These fluidic elements can include, for example, chips, reservoirs, perfusion disposables, pressure lids or combinations thereof, in such system, the instrument interfaces with the respective fluidic element or elements in order to apply the pressure where desired. Such interfacing typically involves establishing a gas seal, although in some embodiments a tight seal is not required (e.g. the pressure-regulation can maintain the desired pressure despite gas leak). Without loss of generality, the following description refers to establishing a seal, but the intent is to also encompass embodiments that do not require a seal.

In the present disclosure, a system and method are contemplated for establishing a pressure interface between a biological culture instrument and one or more fluidic elements. In particular, a system is contemplated wherein, in one embodiment, the one or more fluidic elements are lifted into contact with one or more pressure manifolds included in the instrument, the said one or more pressure manifolds are lowered into contact with the said one or more fluidic elements, or a combination thereof. In some embodiments, the said raising or lowering engages multiple fluidic elements with the instrument in unison (e.g. through a single operation or single movement) (see FIGS. 8A and 8B), simultaneously linking a plurality of microfluidic devices (such as one or more of the embodiments of the perfusion manifold assembly discussed herein).

Some embodiments wherein the fluidic elements are raised include one or more platforms onto which one or more of the fluidic elements are disposed. In such embodiments, one or more of the platforms may be raised in order to affect the said raising of the one or more fluidic elements (FIG. 6). In some embodiments, the instrument or system includes a mechanical means (35) for manually achieving the said raising or lowering involved in the said establishing of a pressure interface. Such mechanical means (35) for manual actuation can include the moving of a user-accessible control surface, which may include, for example, a level, pull-push knob, rotational control, or combinations thereof.

In some embodiments, the instrument or system includes a mechanical actuator (51) in order to facilitate the raising or lowering involved in the said establishing of a pressure interface (See FIGS. 8A and 8B). Such mechanical actuator can involve, for example, one or more pneumatic components (52) (e.g. cylinders), hydraulic components (e.g. cylinders), solenoids, electrical motors, magnets (e.g. fixed magnets mechanically moved into place), or combinations thereof. In some embodiments, the mechanical actuation can be under computer control. In some embodiments, the mechanical actuation is augmented with manual control (e.g. using any of the means for mechanical control described above), for example, in order to provide a manual override. A user interface on the instrument can control this process.

Regardless of whether the actuation is manual or automatic, the system can, in some embodiments, further include one or more mechanisms for increasing the applied mechanical force. This may be desirable in order to provide sufficient force on the pressure interface in order to obtain a sufficient or sufficiently robust seal. Such mechanisms for increasing the applied mechanical force can include levers, cams, pneumatic or hydraulic amplifiers, or combinations thereof.

In some embodiments, the mechanical motion can be controlled and or constrained using various mechanical components or designs known in the art. These mechanical components or designs include, for example, rails, guide rots, pivots, cams, four-bar linkages, etc. Raising or lowering motion can, but need not. be linear. For example, a rotational motion (e.g. in the case of a pivot) or a compound motion (e.g. in the case of a linkage) are desirable in some embodiments.

Although the forgoing describes raising or lowering and features present on the top of bottom of various substrates, one with typical skill in the art would appreciate that the description can also be applied to lateral motions or motions along other axes (and not necessarily linear motions), and to features present on any sides or orientations. Additionally, although the forgoing implies that the one or more fluidic elements are disposed beneath the one or more pressure manifolds, one with typical skill in the art would appreciate that the said pressure manifolds may instead lie beneath the said fluidic elements (for example, the pressure interfaces may be disposed on the bottom surface of a perfusion disposable).

A current embodiment (illustrated in the attached figures) includes two mechanics, each of which permits 6 perfusion disposables to be interfaced with a pressure manifold (50) in a single motion. In this embodiment, the pressure manifolds are lowered (FIG. 8B) into contact with the perfusion disposables (or optionally in contact with pressure lids covering the perfusion disposables) using an electrically controlled pneumatic actuator. The force of the actuator is directed using a cam system, which also increases the applied force due to its mechanical advantage. The illustrated mechanism is also bi-stable, i.e. once the actuator pushes the manifold up or down it can be unpowered, while maintaining the position of the manifold. This can help with heat reduction.

E. Pressure Manifolds and Distribution Manifolds.

In many applications of the pressure-driven system, it is desirable to distribute one or more pressure sources to two or more fluidic elements (including, for example, fluidic chips, perfusion disposables, reservoirs, pressure lids, or combinations thereof). For example, it may be desirable for two or more perfusion disposables to share a single set of pressure regulators in order to reduce the number of regulators in the system (e.g. in contrast with providing a different set of regulators for each perfusion disposable).

In one aspect of the present disclosure, the instrument includes one or more distribution manifolds. The said distribution manifolds includes one or more fluidic conduit (e.g. gas channels or tubes) adapted to distribute one or more pressure sources to two or more fluidic elements (e.g. fluidic chips, perfusion disposables, reservoirs, pressure lids, or combination thereof). Correspondingly, the distribution manifold may include one or more pressure input ports, which may for example be adapted to communicate with one or more pressure regulators (each input port may communicate with a single or multiple regulators). The distribution manifold, in one embodiment, can also have pressure regulation components (valves, pressure sensors, pressure source) integrated into the manifold itself. Similarly, the distribution manifold may include two or more interfaces, which may for example be adapted to communicate with one or more fluidic elements. In some embodiments, the two or more interfaces include at least one region comprising an elastomeric or pliable material. Examples include gaskets, o-rings, etc. made of materials including silicone, SEBS, polypropylene, rubber, Viton, etc. Such regions comprising an elastomeric or pliable region can aid in providing or improving a fluidic seal. Such elastomeric or pliable regions can also be included in pressure manifolds that are not distribution manifolds to provide similar advantages.

In addition to distributing pressure that can be used, for example, to produce pressure-driven flow, the distribution manifold may distribute pressure used for other purposes, for example, to produce mechanical strain or compression (e.g. in actuating mechanical forces in organs-on-chips), to create gas flow within the fluidic element. Moreover, the distribution manifold may optionally distribute one or more liquids. Such liquids can include, for example, wash solutions, disinfectant solutions, working liquids (e.g. for liquid-handling or flow control purposes), tissue-culture media, test agents or compound, biological samples (e.g. blood), or combinations thereof. In some embodiments, the distribution manifold may comprise a working fluid, a membrane and/or a plunger disposed to conduct pressure. For example, a working fluid may be used to reduce the amount of gas required in order to establish a desired pressure, or to facilitate more precise volumetric control. A membrane, plunger and/or working fluid can be used to isolate fluids used in different pans of the distribution manifold (e.g. isolate 5% $CO_2$ tissue-culture gas on the "reservoir side" of the distribution manifold from dry air on the actuation side).

In many applications, it is desirable to enable proper Junction of the instrument even when fewer fluidic elements are engaged than the instrument can accept. For example, it is often desirable that an instrument that includes a distribution manifold designed to interface with six perfusion disposables still support proper operation of the instrument when four perfusion disposable are present. For example, it may be undesirable to gas to escape through the interfaces intended for the missing perfusion disposables, as such gas escape may reduce gas pressure or deplete gas supplies. Such considerations are relevant even without a distribution manifold (i.e. with a non-distributing pressure manifold).

According to one aspect of the present disclosure, a pressure manifold (or specifically a distribution manifold) can include one or more valves adapted to controllably shut-off one or more of the fluidic (e.g. gas) conduits included in the manifold. A variety of valves suitable are known in the art, including for example pinch valves, screw valve, needle valve, ball valves, spring-loaded valves, poppet valves, umbrella valves, Belleville valves, etc. In some embodiments, one or more of the valves are controlled by a user. For example, a user may configure the valves to match the configuration of perfusion disposables in use. In some embodiments, one or more of the valves are controlled electronically. For example, software may configure the valves according to knowledge of experimental settings or other information available to it. In some embodiments, one or more of the valves are controlled by sensing whether the intended fluidic element is present, for example, in order to shut off a gas line if the fluidic element is missing. Such sensing can involve electrical means (e.g. contact switches, conductors closing circuits), optical means (e.g. optical gates), magnetic means (e.g. magnetic switches), or mechanical means (e.g. levers, buttons). In some embodiments, one or more of the sensing elements affects one or more of the valves by means of interposed software or electronic hardware. In some embodiments, one or more of the sensing elements affects one or more of the valves directly (e.g. by mechanical coupling or by electrically signaling to the valve). As a specific example, the presence of a perfusion disposable can act to depress a protruding feature, which in turn affects the state of a valve. In some embodiments, such configuration lends itself well, for example, to pinch valves, spring valves, poppet valves, or umbrella valves, as the depressed protruding feature can act directly on the valve to augment flow.

In some embodiments, it is desirable or convenient to include the said one or more valves at one or more of the interfaces to the fluidic elements. This may be desirable, for example, since a number of successful valve designs are known that respond to a force present at their outlets. Examples of such valves include Schrader valves, Dunlop valves, Presta valves, umbrella valves, their modifications, and related valves. As a specific example, a Schrader valve may be integrated at an interface to a pressure lid such that when the pressure lid is present, it acts to depress the central stem of the Schrader valve, thereby allowing gas flow.

Valves suitable for inclusion in the interfaces to the fluidic element as described above often have their control feature (e.g. the pin of a Schrader valve) located in the middle of the valve. This, however, can pose a difficulty in some potential embodiments, since a corresponding feature should be provided on the fluidic element to depress such a central control feature. An alternative approach is described herein. The pressure manifold (50) or distribution can manifold can include a valve (59) such as a Schrader valve (or any listed above) and further include a shuttle (61). The said shuttle includes a first surface that faces the location of a potential fluidic element, and a second surface that faces the said valve. The first surface is designed to accept contact from the fluidic element at the desired location. For example, the first surface can be designed to accept contact from the periphery of a port that may be present on, e.g., a pressure lid (11). The second surface, in term, is design to mechanically engage the said valve's control surface, which may for example lie in the center of the valve. A further advantage of this approach is that the thickness of the shuttle can be adjusted, for example, to control at what distance from the fluidic element the valve will open.

The interface can be optionally covered at least in part by an elastic, pliable or deformable substrate, such as a pliable membrane (e.g. silicone membrane) (60). The presence of this elastic, pliable or deformable substrate can aid in the sealing of the fluidic element against the manifold (50). The elastic, pliable or deformable substrate can, for example, be a membrane, a gasket or a suitably shaped plug, and it may comprise, for example, silicone, SEBS, Viton, polypropylene, rubber, PTFE, etc. As illustrated, the elastic, pliable or deformable substrate can be held in place by capturing it with an additional component (e.g. a cover plate (63) in this example). However, the elastic, pliable or deformable substrate can also be retained in a variety of other ways, including for example by bonding, adhesion, welding, etc.

The desired function of the embodiments illustrated in part in FIG. 8B are hereby illustrated by example: a pressure lid (11) of a perfusion manifold assembly (10) possessing a ridge around its instrument interface is brought into contact with the pressure manifold (50). As the lid is moved closer to the valve, the lid's ridge begins forming a pressure seal against the manifold's silicone membrane. With the lid's advance, the shuttle gradually moves up and at some point begins depressing the central pin or poppet (65) of the Schrader valve (59). However, according to the example, the shuttle would be designed such that a sufficiently good gas seal is formed before the valve's pin is depressed enough to open the Schrader valve (59). Once the valve open (and ideally not before) gas is able to flow between the manifold (50) and pressure lid (11). In this example, Schrader valves sense the presence of each pressure-lid ridge independently, rather than sensing the presence of a perfusion disposable (or pressure lid) as a single unit. Such embodiments may provide a further advantage in that they may accept different configurations of pressure lids or perfusion disposables, for example, a configuration that employs 4 of the 5 illustrated ports.

One embodiment of the PD engaging face (54) of a pressure manifold (50) that is a distribution manifold and shows elastomeric regions, which act as gaskets to improve gas seal against the fluidic element. In a current embodiment, a gas seal can be formed by compressing these elastomeric regions against ridges present on the top of pressure lids (II), which are in turn disposed onto perfusion disposables (10). The exemplary distribution manifold (50) can distribute to each of six pressure lids pressure (positive or negative) used for enact pressure-driven flow as well as pressure (positive or negative) used to actuate mechanical stretch within the included organ-on-chip devices (in this example, each of these is disposed within a perfusion disposable, which is in turn covered with a pressure lid). The illustrated distribution manifold includes several Schrader-like valves.

As the manifold engages the PDs, the valve seals engage the sealing teeth or ridges on the top of the cover (see FIG. 2C) forming a seal for transferring pressurized gas from the manifold into the reservoir chambers. The poppet (65) acts as a backing to provide a rigid surface for the sealing tooth on the cover to compress the valve seal. This provides load transfer from the cover to the Schrader valve (59) to actuate it when a PD is in position. Simultaneously, the Schrader Valve (or similar type valve system) is actuated by the engagement to the PD Cover to gas flow from the pressure regulator into the PD. When no PD is in the respective position, the valve prevents any gas flow.

Figure 2A:
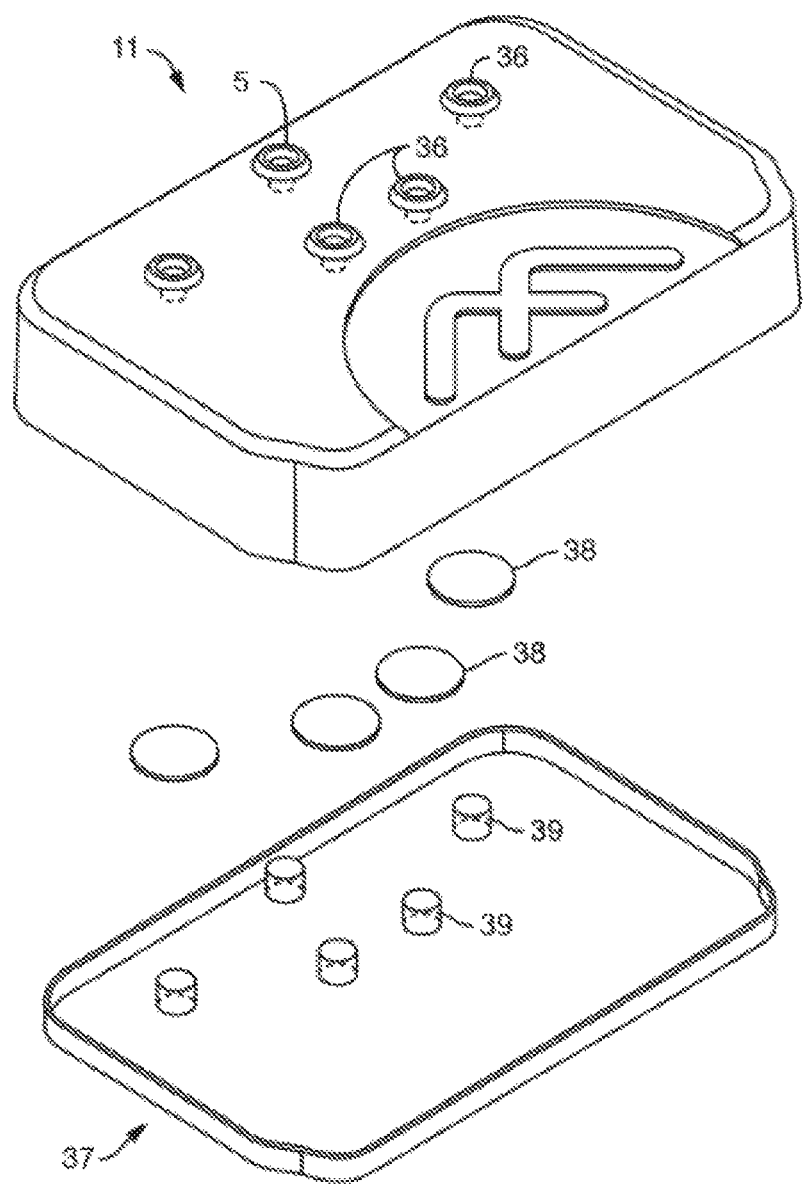
FIG. 2A is an exploded view of one embodiment of the cover assembly comprising a pressure cover or pressure lid. In the illustrated embodiment, the pressure lid comprises a plurality of ports (e.g. through-hole ports) associated with filters and corresponding holes in a gasket. The illustrated design of the holes in the gasket is intended to permit the gasket to aid in retaining the illustrated filters in position. In alternative embodiments, gasket openings may employ a shape different from openings in the lid. For example, the gasket can be shaped to follow the contour of one or more reservoirs with which it is intended to form a fluidic or pressure seal. In some embodiments, a plurality of gaskets may be employed. In some embodiments, the filters and/or gasket may be fixed using an adhesive, heat stacking, bonding (ultrasonic, solvent-assisted, laser welding), clamped, or captured by elements of the lid and/or an additional substrate. Although the illustrated pressure lid comprises through-hole ports, alternative embodiments comprise one or more channels that route at least one top-surface port to one or more bottom surface ports, which need not be directly underneath the top-surface port.
Figure 2B:
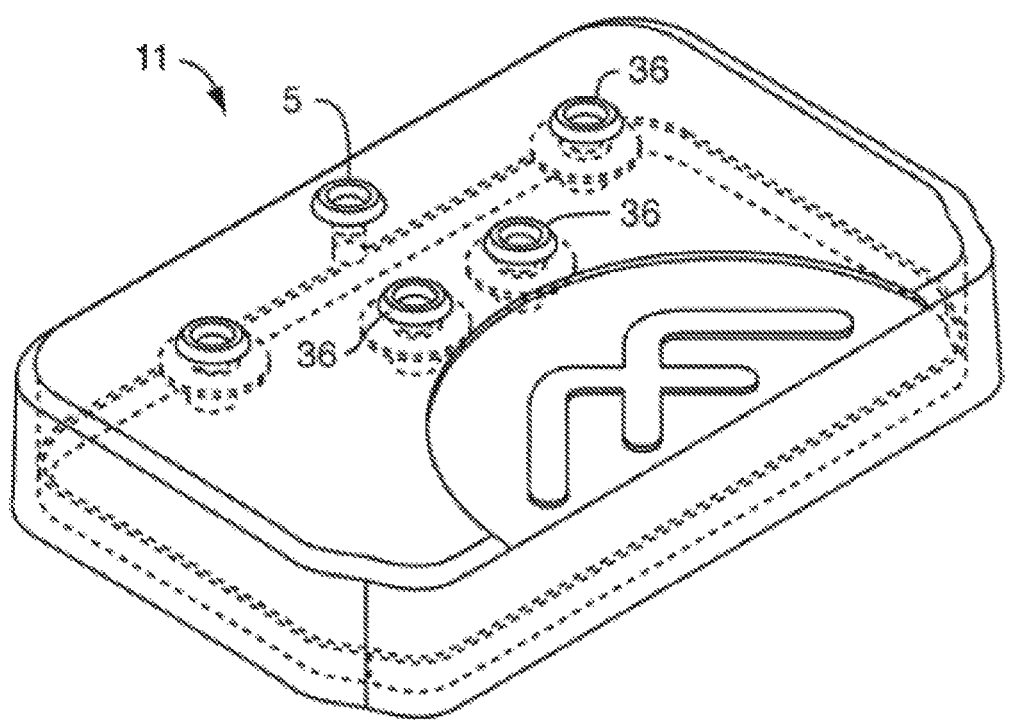
FIG. 2B shows the same embodiment of the cover assembly illustrated in FIG. 2A with the filters and gasket positioned within (and under) the cover.
Figures 1, 2C:
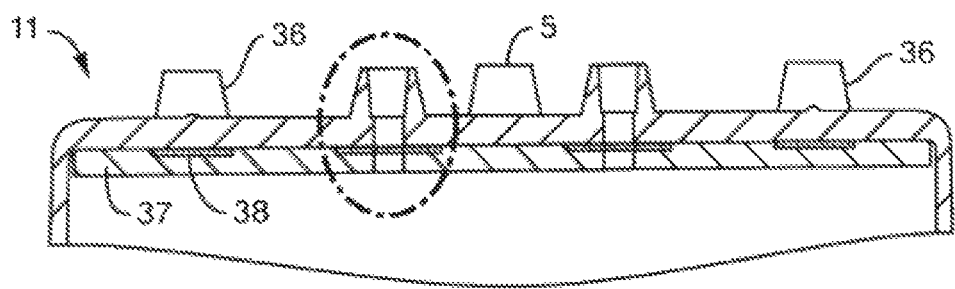
FIG. 2C-1 is a cross-section view of one embodiment of the cover assembly showing the ridges or sealing tooth that surrounds both the through-hole ports in the cover.
Figures 2, 2C:
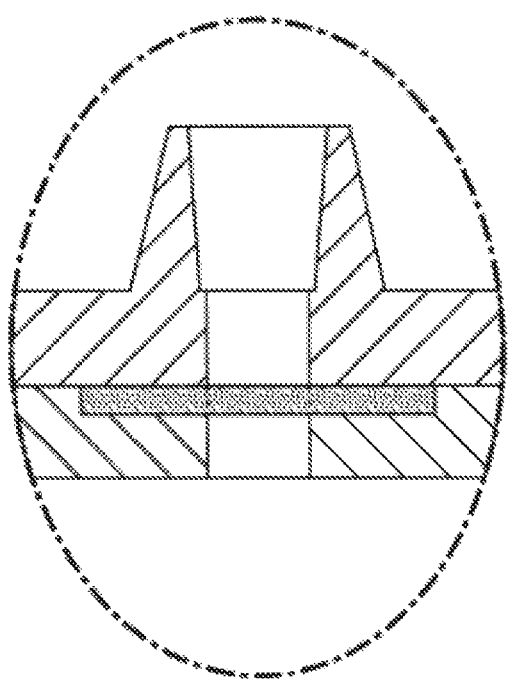
Figure 2D:
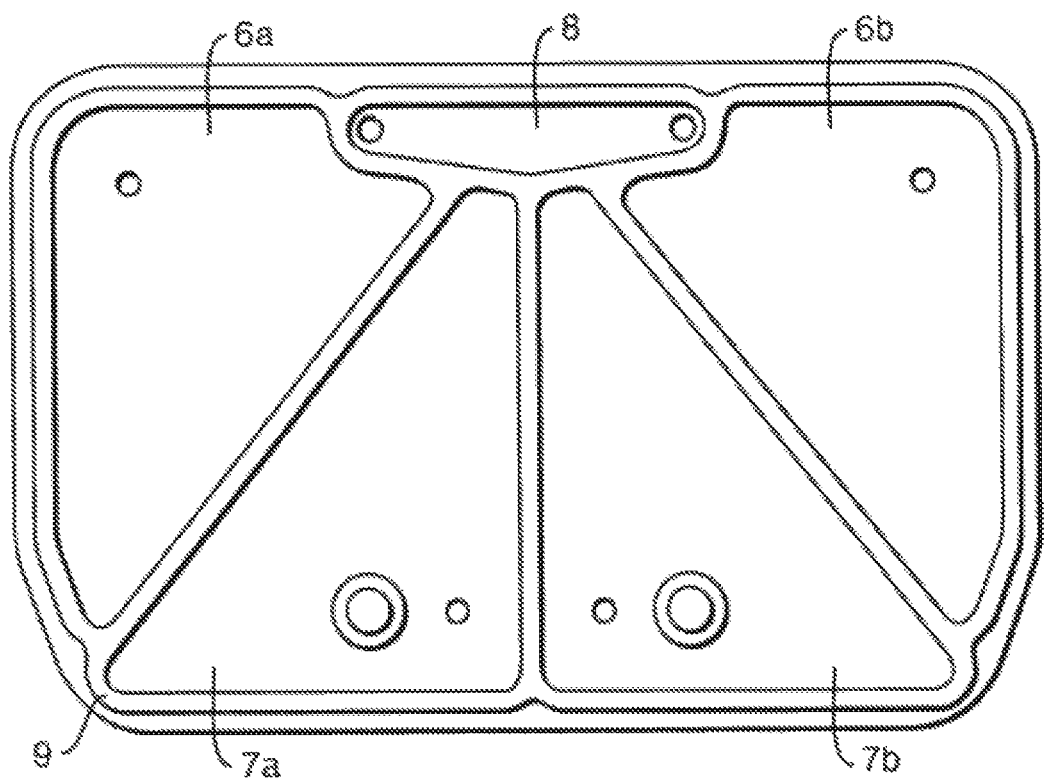
FIG. 2D is a top view of one embodiment of the reservoir chamber-cover assembly seal showing the sealing tooth, vacuum chamber and inlet and outlet chambers.

The spring shuttle (55) provides the load to the cover assembly (11) to create the reservoir chamber-cover assembly seals (e.g. pressure lid-to-reservoir seals) (FIG. 2D). In operation, there is a deflection of the valve seal and the displacement of the poppet (65) when the PD is engaged.

Alternatively, a lid compressor provides the load to the cover assembly to create the reservoir chamber-cover assembly seals (e.g. pressure lid-to-reservoir seals).

In one embodiment, each valve assembly has an optional spring, flexure or elastic component built in that allows for pressure to be applied to each seal independently. In one embodiment, the spring (or similar element) is an integral part of the valve function, but one can get additional function out of it by using it to apply pressure to the sealing tooth on the reservoir lid. The spring (or similar element) can work to restore the shuttle and to apply pressure against the fluidic element to provide or improve the gas seal. Independently applying this load to each sealing element on the lid results in a design that is more robust both to variations due to manufacturing tolerances, and how many PDs happen to be loaded into the instrument.

In some embodiments, one or more of the described valves are controlled by software or a user. For example, the user or software may aim to disconnect gas flow if a fluidic element (e.g. perfusion disposable) is present at the corresponding interface. This could be desired, for example, if the user suspects or the software or sensor detects that there is excess gas flow to the fluidic element, perhaps because the element is damaged. The pressure manifold (whether a distribution manifold or not) may further include sensors, for example, pressure sensors, flow sensors, etc.

F. Controlling Pressure and Flow.

In one embodiment, a flow rate of between 5 and 200 uL/hr, and more preferably between 10 and 60 uL/hr, is desired through the one or more microchannels of the device. In one embodiment, this flow rate is controlled by the applied gas pressure from the pressure manifold (described above). For example, when one applies between 0.5 and 1 kPa, this nominal pressure results, in one embodiment, in a flow rate of between 15 uL/hr and 30 uL/hr.

In addition to maintaining control over this gas pressure over time (and thereby maintain control over flow), in some embodiments, one should also address the gas pressure that may be applied by the process of engaging or disengaging the manifold against the perfusion disposable. That is to say, it is been observed, in a particular embodiment, that the step of engaging the manifold results in a pressure spike of as much as 100 kPa on the gas present within a reservoir included in the perfusion disposable. This can cause a spike in the flow rate and/or an undesired pressure on a coupled microfluidic device. In the particular case wherein the coupled microfluidic device comprises a membrane, an undesired pressure spike may deform the membrane, create trans-membrane flow and/or damage any included cells.

Without being bound by theory, the described pressure spikes can be caused because the mechanical force applied by the manifold to the pressure lid deforms one or more compliant materials included in the pressure lid or perfusion disposable (e.g. compressing any gaskets and the like). Such deformation can act to shrink the volume of gas present in the reservoir, increasing its pressure. The opposite effect leading to a negative spike in pressure may occur during manifold disengagement; one skilled in the art will appreciate that while this discussion primarily contemplates positive spikes that are typical to manifold engagement, analogous consideration may be given to negative pressure spikes that may be typical during manifold disengagement. Whether positive or negative, spikes can be particularly troublesome where the gas volume in the reservoir is low, which may occur when the volume of liquid in a reservoir is high (for example, in the preferred embodiment when more than 3 milliliters, and particularly when the volume is more than 5 milliliters). These engagement spikes may take time to dissipate, as the excess pressure should typically vent. In embodiments wherein the pressure lid includes a filter, this filter may provide the dominant resistance to the venting, dictating the dynamics of pressure-spike dissipation. In one embodiment, the present invention contemplates reducing the venting resistance in the system so as to avoid, reduce the magnitude and/or reduce the duration of such spikes. In on embodiment, the present invention contemplates selecting filters in order to mitigate the pressure spikes during cartridge insertion and removal.

In this regard, reference is made to FIG. 2. FIG. 2A is an exploded view of one embodiment of the cover assembly (11) comprising a cover or lid having a plurality of ports (e.g. through-hole ports) associated with filters (38) and corresponding holes (39) in a gasket. FIG. 2B shows the same embodiment of the cover assembly with the filters (38) and gasket positioned within (and under) the cover. In one embodiment, the filters for the outlet pressure ports are selected for low gas-flow resistance. For example, some embodiments employ 25 micron filters instead of 0.2 micron filters (used in the inlet pressure ports), in order to decrease resistance and cause the manifold-engagement related gas pressure (discussed above) to rapidly dissipate, avoiding a prolonged spike in the flow rate. In particular embodiments, filters with an average pore size of 25 um (commercially available from Porex, filter 4901) do not compromise sterility when ⅛ inch in thickness. These filters maintain sterility, despite their larger pore size (much larger than typical bacteria/spores), by creating a tortuous path through their thickness, which is significantly thicker than the previously mentioned filter membrane/sheets.

In some embodiments, the design of inlet and outlet pressure ports may need different treatment with regards to the venting resistance. For example, in embodiments wherein the perfusion disposable or microfluidic device comprises a resistor, pressure applied on the resistor side (whether the resister is placed upstream or downstream of a region of interest) typically does not act directly on the region of interest (which may, for example, include cells). This can be the case, for example, if liquid flow through the resistor generates a pressure drop. In contrast, pressure spikes on a side without the resistor (whether inlet or outlet) may act directly on the region of interest, as there may not be a sufficient pressure drop to provide some degree of insulation. In a particular example with a resistor on the inlet side of the region of interest, a pressure spike on the inlet may produce a corresponding spike in flow rate but minimal increase in the pressure experienced within the region of interest; in contrast, a pressure spike on the outlet may produce both a spike in flow rate and in experienced pressure. In some applications, for example where the microfluidic device includes a membrane, pressures in the regions of interest may be significantly more detrimental than a temporary spike in flow rate. Accordingly, in this example it may be advisable to include low-resistance filters in the outlet ports and include more typical (higher resistance) filters in the inlet ports, as these can provide advantages in (low regulation (discussed further in the present disclosure).

Having discussed the engagement/disengagement spike issue, the issue of controlling gas pressure, particularly in low-pressure ranges is now addressed. Some commercially available pressure regulators (or pressure controllers) advertise an addressable pressure range with a lower pressure limit that is greater than zero. For example the SMC ITV-0011 regulators are marketed for pressure control in the range of 1 to 100 kPa (it has been observed that their linearity is poor in the 0 to 1 kPa range). In some applications, it may be desirable to nevertheless attain flow rates that correspond to pressures below the commercially available regulator's specified or linear range. Moreover, the accuracy of commercially available pressure regulators is typically a percentage of full range, implying that control at the low end of pressure is characterized by a larger percentage of variability. In some applications this can translate into low accuracy or fidelity in pressure control towards the lower end of the usable range. In one embodiment, either or both of these challenges are addressed by a form of "pulse width modulation" included in a method for pressure actuation.

In this regard, reference is made to FIG. 6. In one embodiment, the culture module (30) comprises a removable tray (32) for positioning the assembly-chip combinations, a pressure surface (33), and pressure controllers (34). In one embodiment, the tray (32) is positioned on the culture module (30) and the tray (32) is moved up via a tray mechanism (35) to engage the pressure surface (33) of the culture module, i.e. the cover or lid (11) of the perfusion manifold assembly engages the pressure surface of the culture module. Rather than having the pressure controllers "on" all of the time, they are switched "on" and "off" (or between two or more setpoints) in a pattern. Accordingly, the switching pattern may be selected such that the average value of pressure acting liquid in one or more reservoirs corresponds to a desired value. Such approaches are analogous to the techniques of pulse-width modulation (PWM), pulse-density modulation (PDM), delta-sigma modulation (DSM) and similar techniques that are known in the field of electrical engineering. In the case of pulse-width modulation, for example, a regular switching period is selected. Within each period the pressure regular may be turned on for a set pressure for a desired duration and turned off for the remainder of the switching period. The longer the switch is on compared to the off periods, the higher the total average pressure supplied. The term "duty cycle" describes the proportion of "on" time to switching period; a low duty cycle corresponds to low pressure, because the pressure is off for most of the time. Duty cycle is expressed in percent, 100% being fully "on." By using this type of "pulse width modulation" with the pressure controllers, it has been found that the average gas pressure can be reliably maintained below 1 kPa, using a regulator that does not offer linear control in that range. In a particular embodiment, the pressure regulator is used in its typical "linear" mode for pressure between 1 kPa and 100 kPa, and switched to pulse-width modulation using an "on pressure" of 2 kPa and an "off pressure" of 0 kPa for average-pressure setpoints between 0 kPa and 1 kPa. In other examples, pulse-width, pulse-density or delta-sigma modulation may be used for controlling the average pressure between 0.3 and 0.8 kPa.

Although the disclosed method can involve applying a pulsatile pressure pattern to the pressure lid, it has been empirically found that the filters aid in smoothing the pressure incident on the liquid with the reservoir. Without being bound by theory, the degree of smoothing increases with the resistance of the filter to gas flow and with the volume of gas within the reservoir (which typically decreases the more liquid is present). Similarly, analogy to electrical circuits indicates that smoothing increases with shorter switching periods. Accordingly, one skilled in the art may select a degree of smoothing by selecting the resistance of the gas filter, setting a lower bound on the gas volume, and selecting a switching period or modulation pattern. The pressure regulator is capable of controllably regulating pressure at a sufficient rate to reproduce the designed pressure modulation pattern. In some embodiments, 0.2 um filters (Porex filter membrane) and a switching period of 10 seconds provides desired smoothing. In other embodiments, 0.4 um filters may be used.

II. Embodiments of Drop-to-Drop Connections

A drop-to-drop connection scheme is contemplated as one embodiment for putting a microfluidic device in fluidic communication with another microfluidic device, including but not limited to, putting a microfluidic device in fluidic communication with the perfusion manifold assembly. Putting devices in fluidic communication with each other can result in the formation of bubbles (40), where a first surface (87) comprising a first fluidic port (89) is aligned with a second surface (88) and a second fluidic port (90). In one embodiment, a drop-to-drop connection is used to reduce the chance of bubbles becoming trapped during connection. Air bubbles are particularly challenging in microfluidic geometries because they get pinned to surfaces and are hard to flush away with just fluid flow. They pose additional challenges in cell culture devices because they can damage cells through various means.

In one embodiment, droplets are formed on the surfaces of the devices in the areas around and on top of the fluidic vias (e.g. connections) or ports. When the surfaces come near each other during a connection, the droplet surfaces join without introducing any air bubbles. In practice, maintaining alignment and stability of the droplets during manual device manipulate is challenging. Additionally, in situations where the Bond number is high liquid tends to drain from devices quickly and in an unstable manner. A number of solutions are herein described to address the problems of both maintaining a stable droplet on a device surface and guiding the drop-to-drop engagement of two primed devices in a controlled and robust manner.

In one embodiment a microfluidic device (16) in the area of the via or port, wherein the droplet sits on a molded-in pedestal or mount (42) and covers the mouth of the port and protrudes above the port, and where the port is in fluidic communication with a microchannel.

It is not intended that the present invention be limited to a particular method for controlling the droplet size, orientation, or direction. In one embodiment, the present invention contemplates using (or making) engineered surfaces to form stable drops. Such surfaces can be inherently hydrophilic or hydrophobic, or can be treated to be hydrophilic or hydrophobic. It is not intended that the present invention be limited to any one technique. However, among the various methods of hydrophilic treatment (e.g. low-pressure oxygen plasma treatment, corona treatment, etc.), a cleaner technology is preferred to treat Poly(dimethylsiloxane) (PDMS) microfluidic devices. In one embodiment, the present invention contemplates using atmospheric RF plasma, so that hydrophilic surfaces can be created (on what is normally hydrophobic material). See Hong et al., "Hydrophilic Surface Modification of PDMS Using Atmospheric RF Plasma," *Journal of Physics: Conference Series* 34 (2006) 656-661 (Institute of Physics Publishing). In one embodiment, masks (41) are used together with such plasma treatments. For example, a mask can be adhered to regions of the surface (e.g. made of PDMS or other polymer) of the microfluidic device (16) prior to plasma treatment in order to prevent such regions from becoming hydrophilic (and thereby controlling what part of the PDMS chip become hydrophilic and what portions remain hydrophobic). After plasma treatment, the mask (41) can be removed (typically by simply peeling the mask off the surface). In yet another embodiment, the present invention contemplates the use of plasma surface treatment in a fluorinated environment to increase the hydrophobicity of the surface. See Avram et al., "Plasma Surface Modification for Selective Hydrophobic Control," *Romanian J, Information Science and Technology*, Vol. 11, Number 4, 2008, 409-422.

Alternatively, such surfaces can have geometric features or shapes that cause the droplet to form or behave in a desired manner. For example, a mating surface might have a projection, platform or pedestal (42) with a geometry that allows for a droplet of particular dimensions. A surface might also be topped with a structure surrounding the port from which the droplet projects, such as a gasket (43) or other mechanical seal, which fills the space between the two mating surfaces (i.e. one surface from the microfluidic device and one from the perfusion assembly), to prevent leakage while under compression.

Alternatively, a portion of the droplet can be positioned in a depression or recess (44), such that a portion of the droplet is below the mating surface (21) of the microfluidic device. In still another embodiment, adhesive patches or stickers (45) can be placed on the surface to create hydrophilic or hydrophobic regions on the mating surface of the microfluidic device.

In yet another embodiment, a combination of geometric features and surface treatments can be applied. For example, a hydrophobic pedestal or gasket might be used (or made) to permit smaller droplet sizes. Most elastomeric polymers used to make gaskets are hydrophobic. Such gaskets are commercially available, e.g. from Stockwell Eiastomerics, Inc. (Philadelphia Pa., USA). On the other hand, M&P Sealing machines high-quality products made from materials such as Polytetrafluoroethylene ("PTFE"), Perfluorolkoxy ("PFA"), or fluorinated Ethylene ("PEP"), including soft hydrophobic gaskets (Orange, Tex., USA). These are also contemplated in some embodiments. When other portions of the device (i.e. portions other than the pedestal or gasket) are treated (e.g. plasma treatment) to make them hydrophilic, a naturally hydrophobic pedestal or gasket can be protected with a mask during plasma treatment to keep it from becoming hydrophilic.

In one embodiment, the walls of the port (or at least a portion thereof leading up to the mating surface of the microfluidic device) are hydrophilic or made hydrophilic. In one embodiment, the walls of the corresponding port (or at least a portion thereof leading up to the mating surface of the perfusion assembly) are hydrophilic or made hydrophilic. In one embodiment, both the walls of the port of the microfluidic device and the corresponding port of the perfusion assembly (or portions thereof) are hydrophilic or made hydrophilic.

In one embodiment, the present invention contemplates that the surface is designed to retain a droplet that resists the weight of liquid in the reservoir. This allows the droplets that go on the top device (i.e. where a first device approaches a second device from above) to be easily created. This embodiment allows one to simply put a measured amount of liquid into the reservoir (e.g. 100 uL, 75 uL, 50 uL or some other amount), leading that liquid to flow to the port, form a droplet and stop on its own. It is not intended that this embodiment be limited to any particular amount of liquid; indeed, one does not need a precisely measured amount of liquid. It is sufficient to aim for a certain amount, as long as that amount is below a certain threshold (where the weight of the water overwhelms the droplet's surface tension and breaks through) in order to form a droplet by this method. It might be more or less convex depending on how much liquid is pushing down on it, but the spatial extent of the droplet should be the same.

It is not intended that the present invention be limited to one manner for drop-to-drop connecting of microfluidic devices. In one embodiment, a first microfluidic device, such as an organ on a chip microfluidic device comprising cells that mimic one or more functions of cells in an organ in the body (i.e. mimic one or more functions of cells in an organ in the body such as cell-cell interaction, cytokine expression, etc.), has a droplet projecting upward, while the corresponding droplet on a second microfluidic device projects downward. In another embodiment, the first microfluidic device, such as an organ on a chip microfluidic device comprising cells that mimic cells in an organ in the body or at least one function of an organ, has a droplet projecting downward, while the corresponding droplet on the second microfluidic device projects upward.

Gravity alone, aside from momentum arguments, also plays a role in stable droplet formation. For example, a chip that is laid flat on a table does not experience significant forces due to gravity. If that device is tipped, as part of the engagement procedure for example, fluid will flow from the higher to lower point. Therefore, orientation of the device might be considered another way to aide in the confinement of droplets, including which device has vias pointing upwards vs downwards.

An additional aspect of controlling droplet volume is the fluidic resistance of the device channels. If a device has small channels, for example, the fluidic resistance might be high enough to maintain a nearly constant droplet volume over time despite there being forces driving fluid flow out of the device (e.g. gravity or capillary force). This is true even in the case of high Bond number. Tuning fluidic resistance might be utilized as a singular method to "confine droplets" or in combination with other methods like controlling liquid pinning geometry or controlling the wetting properties of the surfaces; fluidic resistance would be used to control droplet volume, while controlling the welting properties of the surface would help control droplet placement.

DETAILED DESCRIPTION OF THE PREFERRED EMBODIMENTS

I. Embodiments of Microfluidic Devices

It is not intended that the present invention be limited by the nature of the microfluidic device. However, preferred microfluidic devices are described in U.S. Pat. No. 8,647,861, hereby incorporated by reference, and they are microfluidic "organ-on-chip" devices comprising living cells in microchannels, e.g. cells on membranes in microchannels exposed to culture fluid at a flow rate. The surfaces of the microchannels and/or the membrane can be coated with cell adhesive molecules to support the attachment of cells and promote their organization into tissues. Where a membrane is used, tissues can form on either the upper surface, the lower surface or both. In one embodiment, different cells are living on the upper and lower surfaces, thereby creating one or more tissue-tissue interfaces separated by the membrane. The membrane may be porous, flexible, elastic, or a combination thereof with pores large enough to permit exchange of gases and small chemicals, or large enough to permit migration and transchannel passage of large proteins, as well as whole living cells. In one embodiment, the membrane can selectively expand and retract in response to pressure or mechanical forces, thereby further physiologically simulating the mechanical force of a living tissue-tissue interface.

Figure 10A:
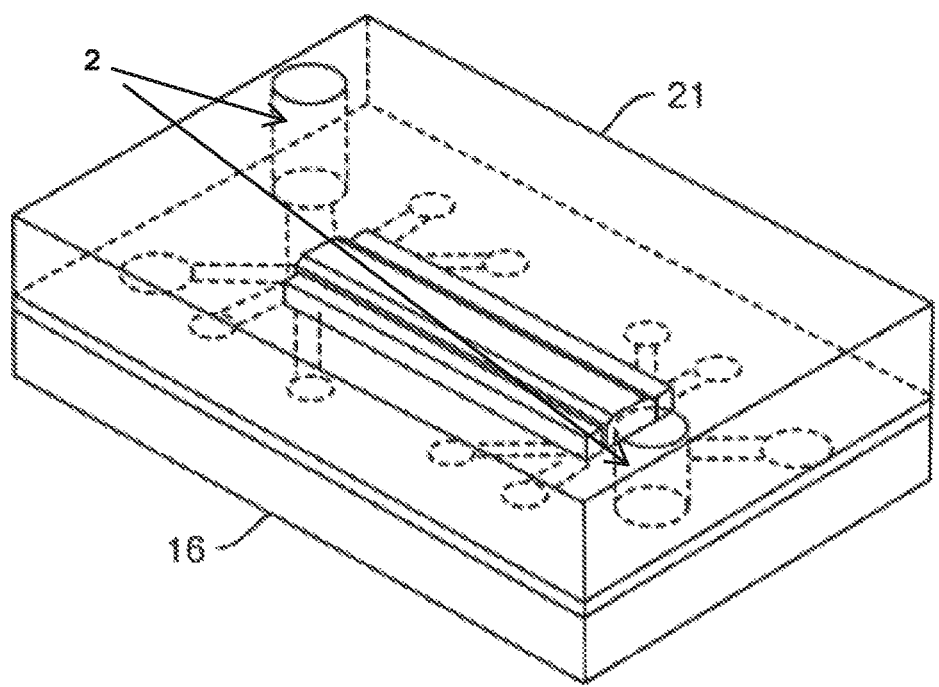
FIG. 10A-B shows a schematic of an illustrative microfluidic device or "organ-on-chip" device. The assembled device is schematically shown in FIG. 10A including a mating surface (21) of the microfluidic device (16) and a plurality of exemplary ports (2).
Figure 10B:
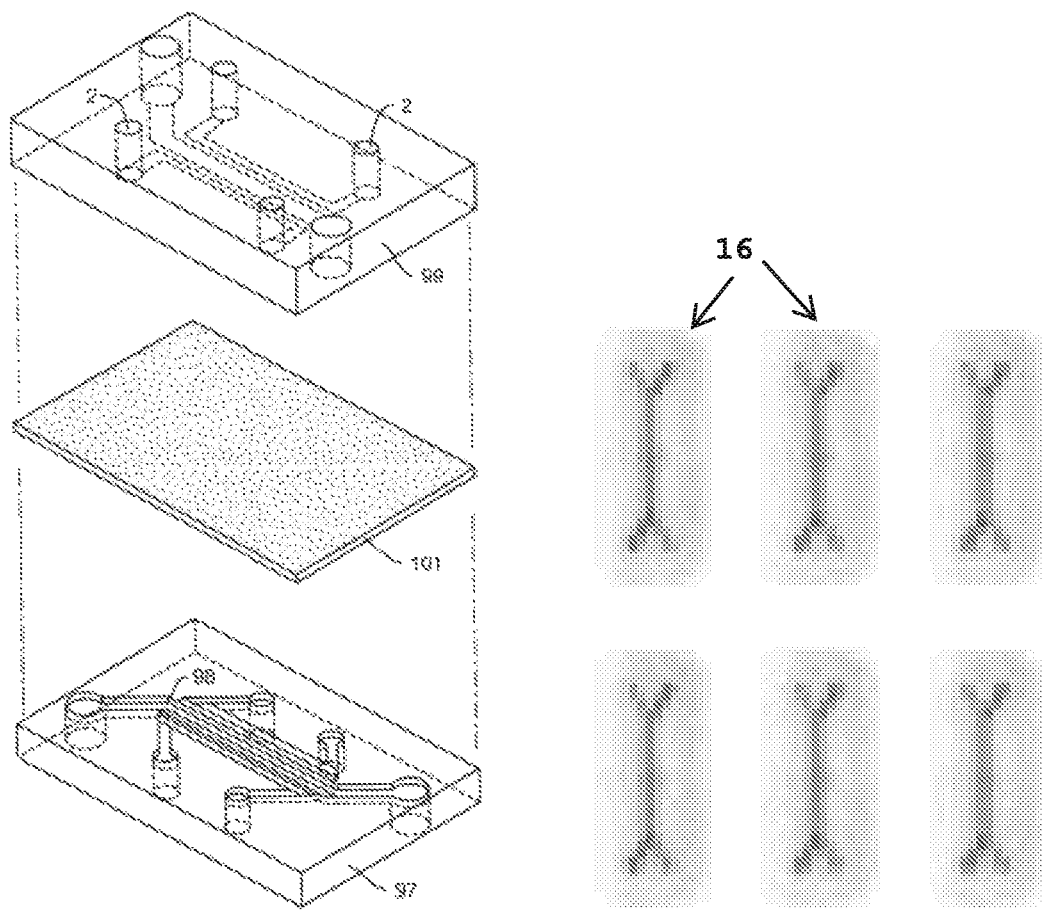

FIG. 10A-B shows a schematic of an illustrative microfluidic device or "organ-on-chip" device. The assembled device is schematically shown in FIG. 10A, which includes a plurality of ports (2). FIG. 10B shows an exploded view of the device of FIG. 10A, showing a bottom piece (97) having channels (98) in a parallel configuration, and a top piece (99) with a plurality of ports (2), with a tissue-tissue interface simulation region comprising a membrane (101) between the top (99) and bottom (97) pieces, where cell behavior and/or passage of gases, chemicals, molecules, particulates and cells are monitored. In an embodiment, an inlet fluid port and an outlet fluid port are in communication with the first central microchannel such that fluid can dynamically travel from the inlet fluid port to the outlet fluid port via the first central microchannel, independently of the second central microchannel. It is also contemplated that the fluid passing between the inlet and outlet fluid ports may be shared between the central microchannels. In either embodiment, characteristics of the fluid flow, such as flow rate and the like, passing through the first central microchannel is controllable independently of fluid flow characteristics through the second central microchannel and vice versa.

In one embodiment a three-channel device is used to determine cell behavior of cancer cells. Tumor cells are placed, for example, in the central microchannel surrounded on top and bottom by layers of stromal cells on the surfaces of the upper and lower membranes. Fluid such as cell culture medium or blood enters the vascular channel. Fluid such as cell culture medium or lymph enters the lymphatic channel. This configuration allows researchers to mimic and study tumor growth and invasion into blood and lymphatic vessels during cancer metastasis. The membranes may be porous or have grooves to allow cells to pass through the membranes.

II. Embodiments for Seeding Devices with Cells

In many of the embodiments described above, the microfluidic chip or other device comprises cells. In some embodiments, cells are seeded directly into the chip. However, in other embodiments, the chip is contained in a carrier, which in turn is mounted on a stand to facilitate cell seeding. In one embodiment, the seeding guide engages the carrier, which contains the micro fluidic chip, and holds the chip rigid side up (e.g. for top channel seeding) and upside down (e.g. for bottom channel seeding) in the various stages of seeding and/or coating (e.g. ECM coating), so as to improve aseptic technique. One embodiment of a stand (100) is assembled, i.e. by engaging two end caps (106, 107) with side panels (108, 109). One embodiment of a chip (16) and a earner (17) is engaged by the seeding guide, the seeding guide approaching the stand (100). One embodiment has six carriers (17) with chips, each engaged with a seeding guide, each seeding guide mounted on the stand (100). The seeding guide is adapted to accept a chip carrier (e.g. in a manner similar to how the skirt engages the chip carrier); after coating and/or seeding the same chip carrier can be (after disengaging from the seeding guide) linked to a perfusion manifold assembly. The seeding guide is designed to allow the chip to be held (whether right side up or upside down) such that its ports do not contact the tabletop or any other surface. This is in order to avoid the contamination of the chip through such contact. Additionally, the seeding guide or holder facilitates access to the chip through pipettes and/or needles and may optionally assist their insertion into chip ports using guide features.

In one embodiment, the present invention contemplates a method of seeding, comprising a) providing i) a chip at least partially contained in a carrier, ii) cells, iii) a seeding guide and iv) a stand with portions configured to accept at least one seeding guide in a stable mounted position; b) engaging said seeding guide with said carrier to create an engaged seeding guide, c) mounting said engaged seeding guide on said stand, and d) seeding said cells into said chip (e.g. with pipette tips) while said seeding guide (along with the carrier and chip) is in a stable mounted position. In one embodiment, the microfluidic device or chip comprises a top channel, a bottom channel, and a membrane separating at least a portion of said lop and bottom channels. In one embodiment, the microfluidic device or chip, after the seeding of step c) comprises cells on the membrane and/or in (or on) one or more of the channels (e.g. the top channel is seeded). In one embodiment of this method, a plurality of seeding guide are mounted on the stand, permitting a plurality of chips to be seeded with cells. The guide has a number of functions, including a) keeping the surface of a chip sterile during handling, b) guiding pipette tips properly into ports during seeding, c) clearly labeling the channels of the chip (e.g. differentiating between the top and bottom channels), and d) permitting the shipping of the chips with liquid in the channels (as well as shipping of chips with cells already seeded or functionalized with ECM). The stand also has a number of functions, including a) keeping the chip level to allow cells to distribute evenly across the membrane, b) allowing the guide to be flipped upside down for seeding of the bottom channel, and c) enabling users to carry and store many seeded chips at one time. Thus, in one embodiment, after the seeding of step c), the method continues with the steps of flipping the chip upside down and seeding the bottom channel.

III. Organs-On-Chips as a Platform for Studying Effects of Microgravity on Human Physiology: Blood-Brain Barrier-Chip in Health and Disease The Blood-Brain-Barrier (BBB), a barrier with very limited permeability, can be compromised in response to a variety of homeostatic challenges including toxins, microorganisms, circulating cells such as in cancer, and as an unwanted action of a number of therapeutics leading to brain pathology. Further, direct involvement of BBB to pathogenesis has been implicated for a number of diseases, which are still to be elucidated as the experimental approaches to study human BBB are limited. Through this study, we aim to build a robust Blood Brain Barrier (BBB) Chip model to provide a human ex vivo platform to study its functionality and biochemical signature in healthy and disease conditions.

Thus, contemplated embodiments include but are not limited to the development of the platforms for studying ischemic and hemorrhagic brain diseases and assessment of different therapeutics on BBB functionality. In one embodiment, developing neurons-on-chip platforms for the development of neurodegenerative diseases, brain injury, neurogenesis and the specific interaction of oligodendrocytes, microglia, astrocytes and neurons in brain homeostasis. In one embodiment, analyzing genomics (NGS) data from patients with multiple sclerosis and other neurological diseases with compromised BBB for testing of new biomarkers in the BBB-on-chip. In some embodiments, IPS endothelial cells will be used. Indeed, induced pluripotent stem cell-derived endothelial cells s including but not limited to iPSC-derived endothelial cells and neurons will be used in combination with primary astrocytes and pericytes, etc.

In addition, this model is contemplated for use in assessing gravity effects and stress hormones, as experienced by the human cells during flight conditions, on the BBB-Chip, in addition for use in identifying sensitive components of this organ, e.g. brain, while in space. We believe that the development of a well-characterized human BBB model, and its subsequent testing in space, should be done since the evidence suggests that: Simulated microgravity and hypergravity (both experienced during space flight) cause disruption in human endothelial cell layer integrity and associated inflammatory responses (Bellone et al., 2016), (Ramaswamy et al., 2016). Several neurodegenerative diseases including Alzheimer's and Parkinson's (Desai et al., 2007), (Gray and Woulfe, 2015), Multiple Sclerosis (MS) (Minagar and Alexander, 2003), ALS (Garbuzova-Davis et al., 2012), and neuropathologies such as Epilepsy (Ivens et al., 2007) have been associated with BBB dysfunction. Additionally, some of the long-term neural damages caused by traumatic brain injuries (TBI) and hypoxic ischemic insults are mediated by BBB dysfunction and inflammation (Chodobski et al., 2011), (Engelhardt et al., 2014); Astronauts returning to earth from spaceflight express a suppressed immune system (Crucian et al., 2013), (Pedersen et al., 1994). Additionally, elevated stress hormones have been found in astronauts during flight. Elevated stress hormones affect the immune system and the vascular endothelium, itself a significant contributor to immune function through complex biochemical signaling (Mai et al., 2013).

These findings, taken together, strongly call for the development of a robust in vitro system that can interrogate the effects of space travel on the human vasculature, such as the BBB-Chip. This chip system enables us to study the endothelium and also the contribution of each of the other supporting cells such as astrocytes and pericytes in BBB integrity in space. Growing evidence indicates each of their involvement in neurovascular pathologies (Ivens et al., 2007, Garbuzova-Davis et al., 2012, Cabezas et al., 2014) Garbuzova-Davis et al., 2012). The chip allows for the different cell types to interact in a modular, structural, and physiologically relevant manner, and includes microenvironment control of variables and inclusion of forces such as strain and shear stress. This combination of functionality and control is not attainable with other cell model systems.

Microfluidic Organs-on-chip technology enables the study of the precise contribution of each cell constituent in the physiological, in vivo relevant manner, while functions and responses of the tissue to homeostatic challenges will provide new avenues to study the impact of space conditions on the vascular system. Organs-on-chip technology as described herein, and in particular a BBB-Chip are contemplated for use, in part, to characterize (i) the potential impact of gravity changes on the endothelial barrier homeostasis, (ii) its response to inflammatory challenges and associated standard Food and Drug Administration (FDA) USA approved therapeutic and ultimately (iii) to identify the particular components of the BBB primarily affected by altered gravity and model the relevant interactions.

IV. Space Exploration

Space exploration imposes new challenges on human physiology and offers a unique opportunity to study human biology beyond the conditions found on Earth. There is growing evidence that conditions in space have an impact on cardiovascular health and the immune response in humans (Delp et al., 2016). Prior research has shown that some of the forces experienced during liftoff or simulated microgravity conditions have been associated with a decrease in tight junction proteins and barrier integrity in multiple endothelial models (Maier et al., 2015), (Bellone et al., 2016).

Interestingly, similar pathophysiological conditions have been previously associated to early stages of vasculopathies and neurodegenerative diseases such as multiple sclerosis (MS) (Hawkins 2005, Rosenberg, 2012). However, relatively little work has been done to understand the mechanisms that might contribute to this outcome. By leveraging engineering biomimetic organs-on-chips and vascular biology, the Blood Brain Barrier-Chip (BBB-Chip) that includes components of healthy brain vasculature along with parenchymal cells and neurons may be used m ISS experiments. One step in the proposal is to adapt and implement a BBB-Chip model in a novel space compatible instrument that will allow for automated organ maintenance, sampling and storage aboard the ISS, and downstream molecular analysts on Earth. The ultimate scope is to study the impact of microgravity and other potential stress factors associated with space travels on the BBB endothelial integrity and to identify potential mechanisms that underlie disease stales as well as therapeutic targets for recovery.

Specific Aim #1: Establish robust BBB-Chip platform for normal and inflamed states, compare endpoints and genomic profiles, and develop informative predictive models. Assess the functionality of BBB-Chip in space and compare with earth conditions ( ). Mechanical stimuli are fundamental modulators of endothelial functions in health and diseased conditions and the importance of physiological shear on BBB primary endothelial cells function and gene expression has been largely accepted. We propose to establish a new state-of-the-art model of the human BBB that comprises of stromal cells and neurons derived from iPSc introduced in a physiologically relevant architecture. The effect of inflammatory challenges on morphological characteristics, permeability, gene expression, protein and epigenetic profiles will be assessed.

Specific Aim #2: Modify Organ-on-Chip platforms and instrumentation for space-flight compatibility. (& UH3) This aim will begin the development of space hardware that allows for folly automated organ-chip experimentation on the ISS-NL. Modifying existing platforms for automated organ-chip experiments and integration into SpaceTango's TangoLab infrastructure on the ISS will enable remote control and data capture of experimental procedures. This infrastructure will allow for the environmental conditions necessary for Organ-chip culture, fluidic system for perfusing the BBB-Chip at physiologically relevant flow rates, effluent sampling system for biochemical analysis with high-temporal resolution upon return to earth, in-line sensing capabilities to monitor BBB integrity in real-time, and automated fixation protocols to proceed for analysis with immunofluorescent imaging and RNA analysis. In some embodiments, measurements will be taken of experimental conditions and recorded. In some embodiments, measurements will be taken and recorded automatically, e.g. continuous logging. Continuous logging refers to functions of software, as part of the software for the space hardware, that will be recording measurements throughout the experiment. For nonlimiting examples, the software will log the temperature in the various compartments of the hardware, the fluid pressure in the rigid manifold, the states of the valves and pumps, and the CO2 and humidity in the incubator area, etc.

Specific Aim 3. To simulate on earth each of the individual space cell-stressors in space and assess their contribution to the phenotype of the BBB-Chip in space flight (Specific Aim 1). Assess the inflammatory response of the BBB-Chip in space and its rescue by standard, FDA approved anti-inflammatory therapeutics. (UH3). This aim has two goals that we will first address through a series of experiments on earth to dissect the contribution of flight stressors, in particular hypoxia, hydrostatic pressure and hypergravity on the BBB-Chip. Next we will assess the responses of the inflamed BBB-Chip model, and compare with the inflammatory responses on earth. Along these lines, the efficacy of FDA approved drugs is contemplated for testing for success in rescuing BBB vasculature from inflammatory insults. In particular, in one embodiment, read-outs will be used to assess the inflammatory response of the Brain-Chip in space and its rescue by and FDA approved anti-inflammatory therapeutics. (UH3).

Space flights expose the organism to specific stressors, with hyper-gravity, microgravity, absence of hydrostatic pressure and hypoxia. Pathogenesis associated with these conditions has just started to be studied in detail, with the specific impact in the vasculature remaining greatly unknown. On the other side, conducting biological experiments in space has the particular advantages of removing environmental variables (i.e. gravity or fluidic pressure) that are constant on earth, but whose absence could potentially unveil novel disease mechanisms for target identification and drug discovery. The recent developments in Organ-on-chips technologies provide us with microphysiological systems (MPS) with unprecedented capabilities to study human biology and disease development ex vivo, as they recapitulate complex cell-to-cell interactions and organ-level physiological functions (Huh et al, 2010, Huh et al, 2012, Kim et al., 2012, Benam et al., 2015). Models generated using primary human cell sources, including human induced pluripotent cells (iPSc) differentiated to different cell types have been applied with success in the development of a human BBB-on-chip (Abstract, SFN, 2016 San Diego, Calif.). This proposal takes steps towards transforming the framework for understanding the effects of the space-specific environment on clinically relevant disease phenotypes, and pharmacological responses. The major innovative approaches of this proposal include a multidisciplinary approach in studying human disease ex vivo, and for establishing a new framework for disease modeling and drug discovery.

Organ-on-chip Hardware: An instrument is illustrated for allowing for the plug-and-play culture of Organ-Chips (FIG. 18A-C). It allows the user to control variables of the Organ-Chip microenvironment such as fluid flow rates, mechanical strain, and the frequency of the strain application using a simple computer interface. These instruments eliminate the need for the user to connect and disconnect tubing, reduce fluid dead-volumes to improve sampling resolution, and automates steps like priming the fluidics and removing undesirable bubbles—thereby increasing experiment throughput, reducing variability, and making the Organ-Chip technology accessible to a wide range of users, and for in flight automated operation.

A fully automated instrument with systems for fluorescent and phase contrast imaging, sample collection, pumping, mechanical actuation, and linking multiple organs together is contemplated for use (FIG. 18A-C). Many new technologies had to be created to enable low-volume pumping, high density valving (FIG. 18A-C), bubble management, and precise thermal management. The engineering know-how from developing these technologies will be extremely relevant in building space-ready hardware that will have many of the same stringent requirements.

Figure 19:
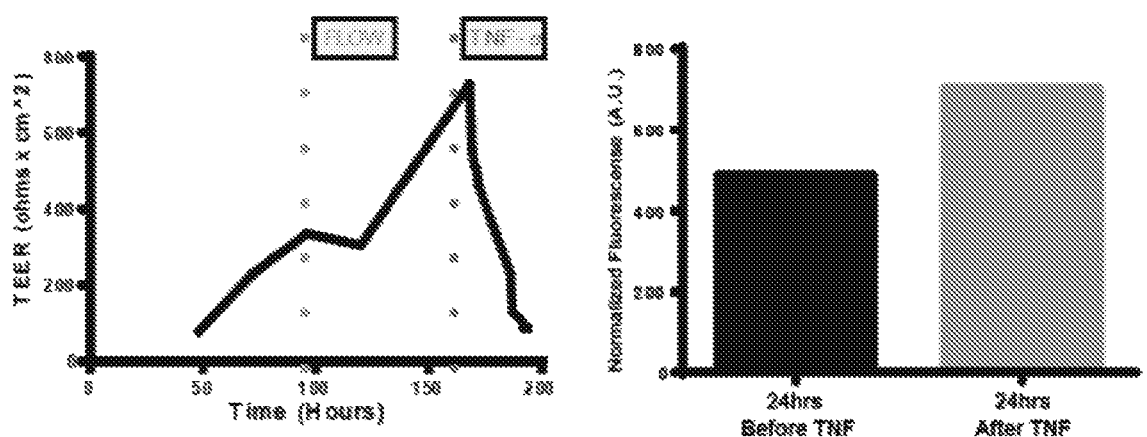
FIG. 19 shows exemplary real-time TEER measurements in a BBB-chip (left) showing a gradual increase in barrier function upon initiation of flow and then an abrupt drop after TNF-alpha challenge. The barrier function of the same BBB-chip measured by flowing a fluorescent molecule on one side of the chip and measuring how much crosses the endothelial cells (right). The resolution of this measurement is limited by the time it takes for a sufficient sample to flow through the chip.

Integration of in-line trans-endothelial electrical resistance (TEER) measurements on chips allows measurement of barrier function integrity of tissues continuously in real-time. Sensors are integrated into Organ-Chips so that these measurements can be made in real-time throughout an experiment. Thus, in some embodiments, abrupt changes in TEER measurements can be observed during inflammatory challenges to endothelial cells (FIG. 19). In this manner barrier integrity of vascular tissue can be measured with the high temporal resolution needed to look at the effects of hypergravity during launch or the time-progression of endothelial changes in the absence of gravity or hydrostatic pressure.

Figure 20A:
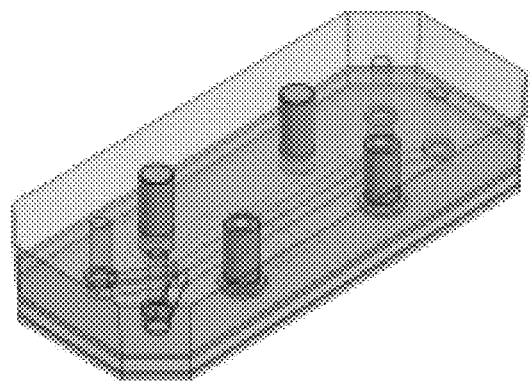
FIG. 20A-B illustrates exemplary devices as FIG. 20A an exemplary model of a TEER-Chip design (upper) utilizing electrodes oriented in a manner that allows electrical resistance of the cells on the membrane to be measured in real-time.
Figure 20B:
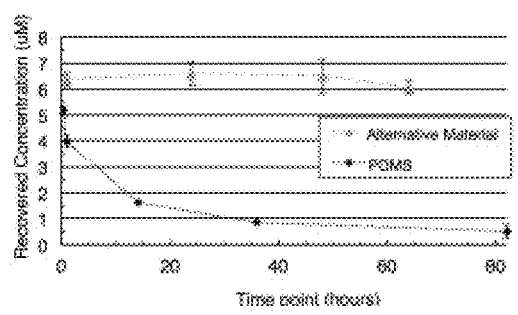
Figure 21:
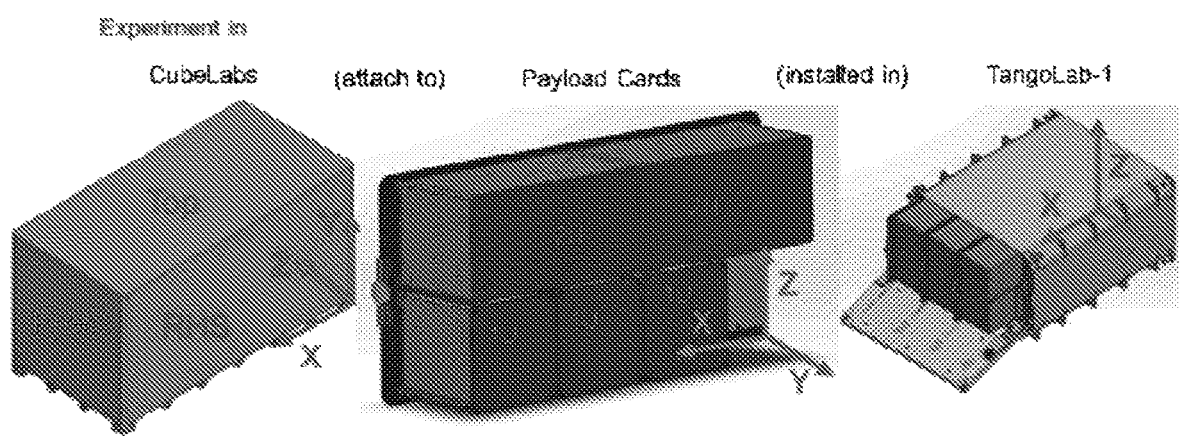
FIG. 21 illustrates exemplary devices an exemplary SpaceTango's modular CubeLab platform. The CubeLab is the individual unit used to contain an experiment. CubeLabs are identified by size in units with a 1U being a (100 mm$^3$) cube, as a further example a 2U as 200 mm. CubeLabs sizes can be reconfigured based on experiment requirements. The payload card is the mechanical and electrical interface between CubeLabs and the TangoLab-1. Each Payload Card connects 7U worth of CubeLabs. Each card has seven Lab Management Cards (LMCs), one for each U of CubeLab and one toplevel flight computer.

In designing these chip and instrument systems, wherever possible, alternative materials may be used that significantly reduce the absorption of small molecules. FIG. 20A-B, shows preliminary data from an assay measuring the absorption of the small-molecules from media into one of an alternative material over time. This data indicates that alternative material resists absorption of many molecules that PDMS was shown to absorb.

Space Hardware: TangoLab-1 facility (Space Tango, Inc., 333 E Short St. Lexington, Ky. 40507; www.spacetango.com/) is a reconfigurable experiment ecosystem designed for microgravity R&D and pilot manufacturing aboard the ISS. Hardware development for the proposed experiments will be developed using the TangoLab infrastructure (Space Tango, Inc., 333 E Short St. Lexington, Ky. 40507; www.spacetango.com/). The facility refers to a single EXPRESS rack locker volume that provides mechanical, electrical and network interfacing. It can hold up to 21U of CubeLabs, 3 Payload Cards with 7U of CubeLabs each, with the fourth Payload Card slot is internally used by Space Tango, Inc. Internal guide rails make sure each Payload Card can be smoothly installed and seated properly ensuring a solid connection with the facility power and data connections. Currently Space Tango is has CubeLab custom modules for cell culture, plant biology and material science studies on the TangoLab platform. With the Orbital CRS7 launch in Q2 of 2017 Space Tango will be implementing a CubeLab for a tissue mimetic study that allows for cell culture environmental conditions and fine control of fluid delivery.

Figure 22:
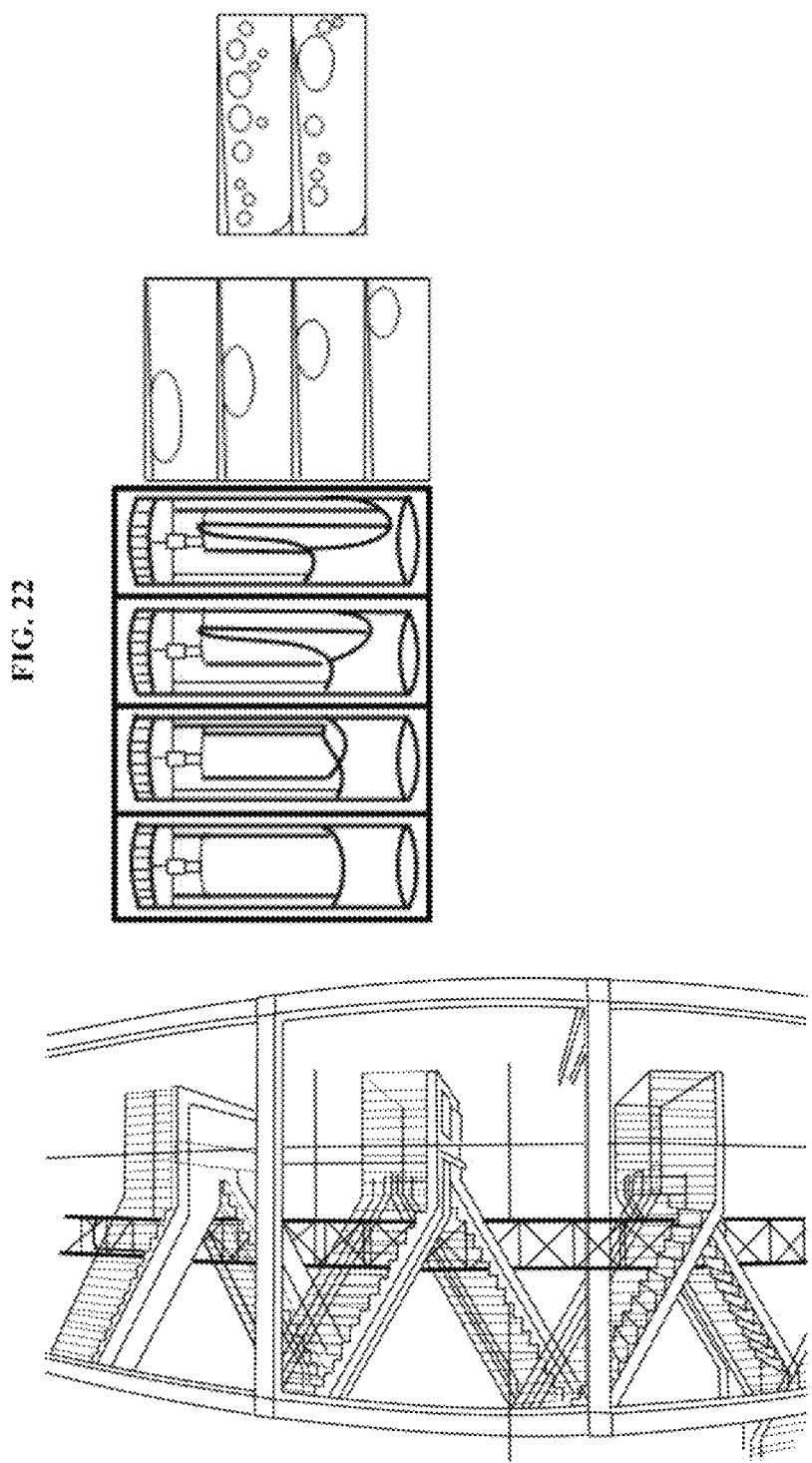
FIG. 22 shows an exemplary (left) Microgravity drop tower facility utilized by IRPI that offers 2.1 seconds of microgravity experiment time for validating fluid system robustness. IRPI Capillary Fluid Experiment-Vane Gap vessel (top center) on the ISS for investigating the orientation of fluids in complex reservoirs. Capillary Fluid Experiment-Interior Corner Flow (top right) on the ISS for studying the passive separation of bubbles from liquid in microgravity.

The design process for what is increasingly referred to as (microgravity) capillary fluidics has been dramatically compressed by the convergence of new analytic tools developed from recent ISS experimentation, rapid prototyping in the form of transparent 3D printing, and ready access to a high rate drop lower facility (FIG. 22). IRPI (IRPI, LLC, 11535 SW 67$^{th}$ Ave Portland, Oreg. 97223www.irpillc.com may provide capillary conduits, containers and devices are contemplated to have incorporated unique geometries for the passive positioning, separation, and control fluid phases in this system. Drop tower tests on scale and/or full-scale sub/systems are capable of establishing high technology readiness levels on components of the system for what basically provides the 'plumbing' function. In this way verification in a relevant environment preflight is contemplated for providing a high level of reliability.

A. Approach.

Specific Aim #1: Establish robust BBB-Chip platform for normal and inflamed states, compare endpoints and genomic profiles, and develop informative predictive models. Assess the functionality of BBB-Chip in space and compare with earth conditions.

Rationale: There is a lack of human data ex vivo, from a physiologically relevant platform to study the pathogenesis of compromised BBB and drug development. Such a model could also mimic the complex environment astronauts are exposed to, such as the sudden acceleration during launch, an event that involves reduced perfusion of blood to the brain and temporary hypoxia. Within a few moments of entering orbit, microgravity causes the loss of hydrostatic pressure and body fluids redistribute from the lower end of the body to the brain. In vitro studies have demonstrated that microgravity also leads to changes in the production and expression of vasoactive and inflammatory mediators and adhesion molecules that could have a negative impact on the BBB integrity and expression of molecular transporters. However, studies performed on animal models have not yet clarified whether these observations are indicative of a pro-inflammatory condition eventually leading to edema or rather a peculiar adaptation of endothelial cells to the extraterrestrial environment (Sofronova et al., 2015).

Thus, different biomarkers of vascular disorders and neurodegenerative diseases from flight experiments are contemplated for use to compare them to control simulations on earth. This will allow comparison to forces experienced by the BBB in space, and allow an understanding of impacts of hyper-gravity, hypoxia and reduced hydrostatic pressure on the human BBB vasculature in terms of tissue integrity and function of molecular mechanisms involved in drug delivery to the brain. In aim 2, these stresses will be mimicked individually on terrestrial experiments to understand how they each contribute to vascular dysfunction. Notably the possibility that some of the above-mentioned factors could promote or exacerbate vascular dysfunction represents a unique opportunity for discovering novel therapeutic targets whose role in disease might have been masked by the forces of the earth environment. Thus, a platform is contemplated for using normal and diseased BBB using technology, including microphysiological systems, for characterizing the effect of space flight environment on brain microvasculature, in terms of tissue architecture, functionality and transcriptomic profiling.

Figure 14:
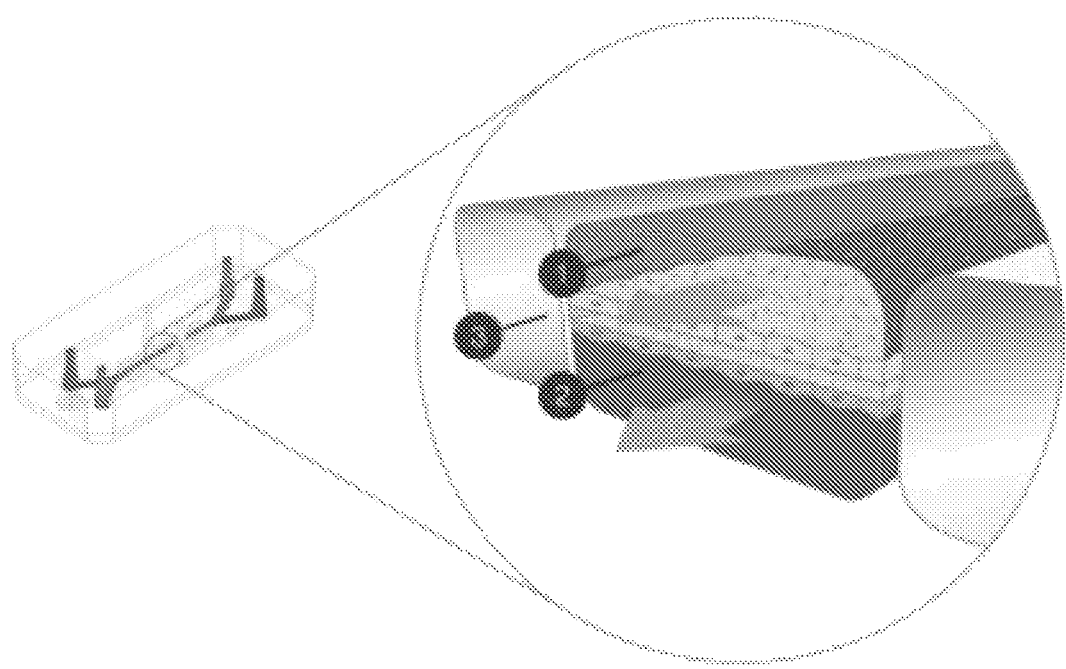
FIG. 14 shows an exemplary BBB-on-chip developed with human iPS-derived endothelial cells, pericytes and astrocytes. An Organ-Chip comprised of two microchannels (Labeled 1 & 2) separated by a porous flexible-membrane. The material is functionalized with specific extracellular matrix and cells are seeded into the different channels. In many models endothelial cells are seeded in the bottom compartment (2) and epithelial cells in the top compartment (1) to emulate the basic functioning unit of an organ. However in some embodiments, models may have epithelial or other parenchymal cells in a channel without endothelial cells in the other channel. Vacuum pressure may be applied to the side channels (3) to mechanical stretch the membrane. Fluids can be continuously pumped through the channels to mimic shear forces, bring in nutrients, and wash away waste.
Figure 16:
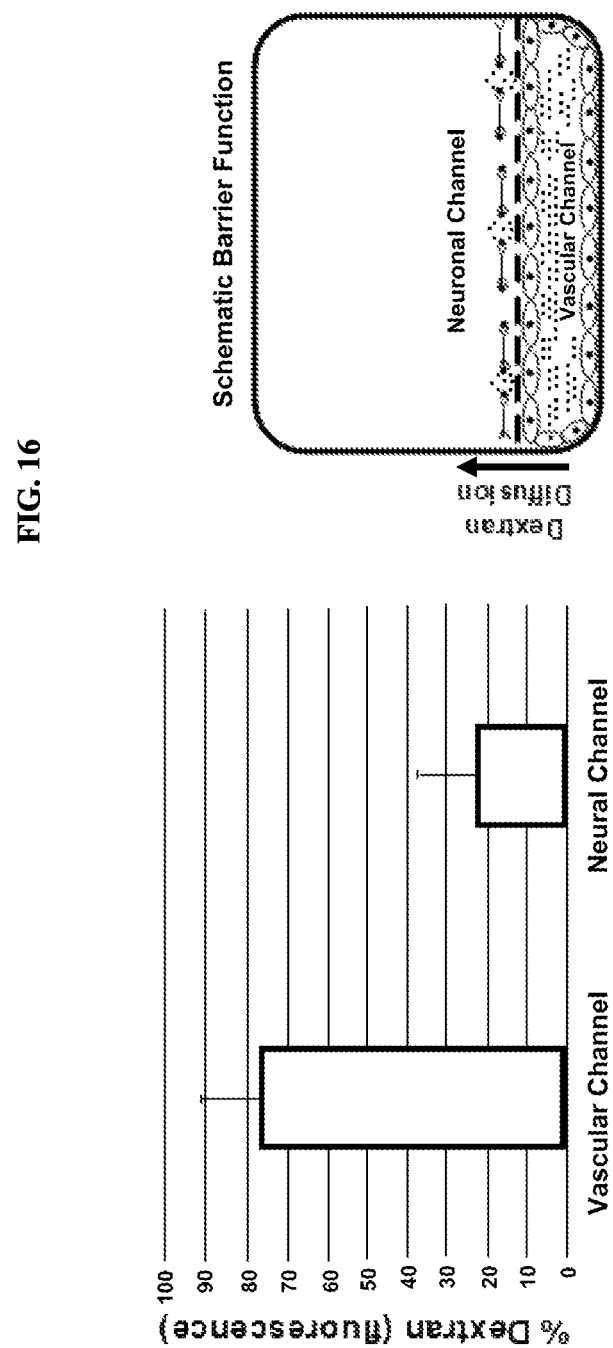
FIG. 16 shows an exemplary chart demonstrating barrier function of the BBB-on-chip as assessed with fluorescent dextran (4 kDa) (left) and an exemplary illustration of a microfluidic BBB-on-chip (right).
Figure 17A:
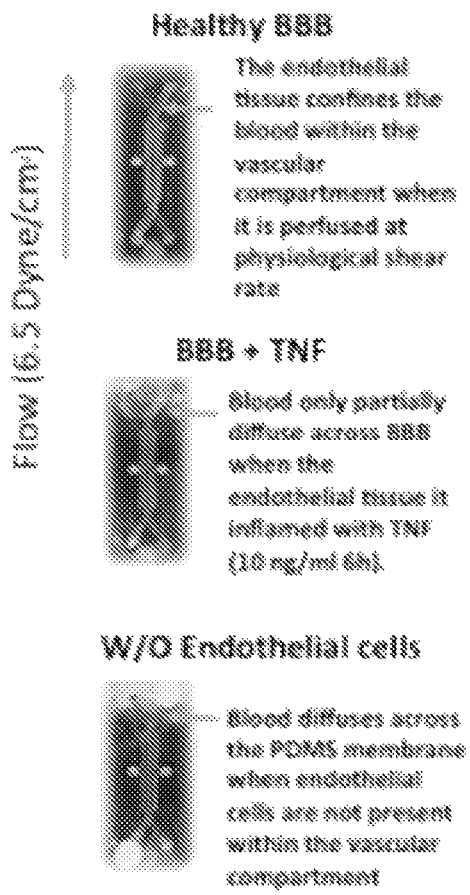
FIG. 17A-D shows an exemplary BBB-Chip with whole blood. In the presence of a healthy and intact endothelium, the vascular channel can be perfused with human whole blood without leaking into the brain compartment, FIG. 17A, TNF disrupt the barrier function and vascular leakage can be assessed by measuring the relative diffusion of fluorescently labeled dextran from the vascular to the brain compartment.
Figure 17B:
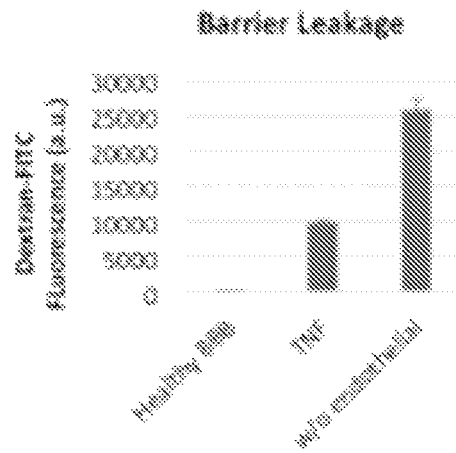
Figure 17C:
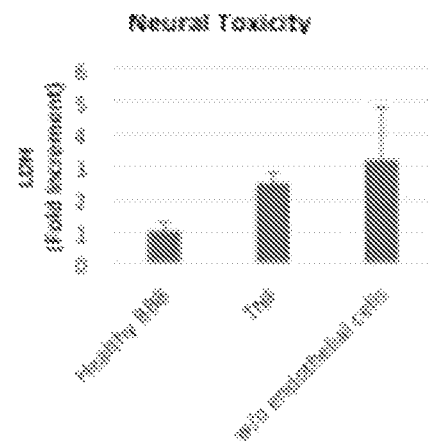
Figure 17D:
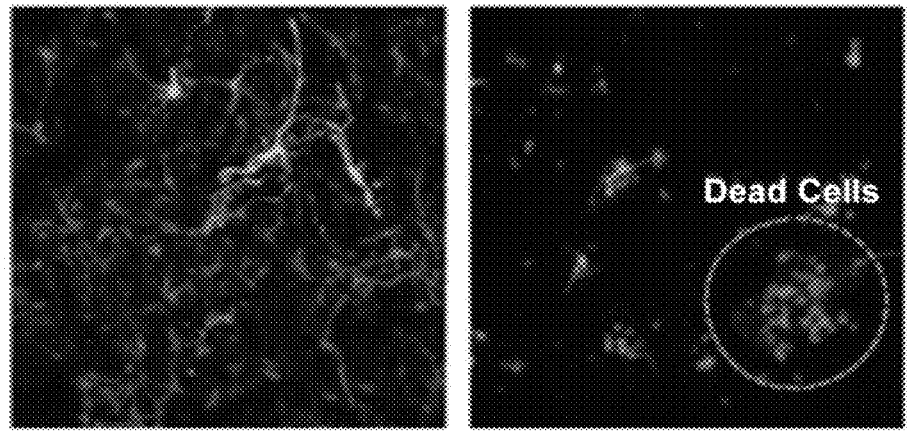

Strategy: The lack of an appropriate cell source of hBMEC has been the main limiting factor to developing a robust in vitro model of the human blood brain barrier. However, iPSc can be used to produce a large amount of mature endothelial cells expressing typical markers of adult HBMECs, forming a light cellular monolayer and displaying selective molecular barrier functionality (Abstract, SFN, San Diego 2016). Thus, pluripotent stem cells (iPSc)-derived human brain-micro vascular endothelial cells (hBMEC) in combination with primary astrocytes, pericytes and iPSc-derived neurons, will be used to consolidate a model of a BBB-Chip. To allow for physiologically relevant combinations of the cells, the hBMEC will be placed in the bottom channel of the chip, and the astrocytes, pericytes, and neurons in the top channel of the chip (FIG. 14). The cell types will be able to communicate chemically and physically through the porous membrane that separates the top and bottom channels. Organ-functions including endothelial tissue integrity, directional transport of soluble proteins, as well as protection from plasma-induced neurotoxicity will be monitored for up to or at least 15 days. Next, the BBB-Chip will be challenged with inflammatory cytokines that simulate the in vivo diseased state. Data from normal and inflamed states will be analyzed and used to develop a predictive model, in great demand in the field to reveal the specific points for efficient therapeutic interventions.

Automated space hardware will be validated (as described in detail in Aim 2) for studies on the BBB-Chip in space flight conditions.

Cell source: In some embodiments, iPSc will be purchased from the Cedars Sinai medical center in Los Angeles (USA) where cells have been previously reprogrammed, expanded and characterized. Primary human Astrocytes and Pericytes are purchased from ScienceCells (Cat. #1800, #1200).

Aim 1a. Developing and Characterizing the BBB-Chip: cells will be plated, put on flow the next day, and will be maintained in the same conditions for 2 weeks. At different time points (d1, d3, d7, d12 and d15): Qualitative and quantitative characterization of BBB endothelial cells will be done by immunostaining and imaging of cells growing in the BBB-Chip, as well as protein extraction and Western blot of the following markers: Glut-1, VE-Cadherin, Claudin-5, Occludin and PgP; Vascular leakage will be measured as the vascular-to-brain diffusion of fluorescent fluid phase markers dextran (3 Kda) and Lucifer yellow (450 Da) and fluorescence will be detected via spectrophotometry; Gene expression of typical BBB endothelial cell markers will be done via RT-PCR for different transporters involved in both drug transport and resistance such as PgP, MDR1, Transferrin Receptor and Glut-1; The clinically used "Q-Alb" index depicting the vascular-to-brain diffusion ratio of albumin will be assessed; The vascular-to-brain diffusion ratio of IgG and Transferrin will be measured via ELISA; Viability of the BBB-Chip will be assessed via MTT reduction assay (Zhang et al., 2005) and lactose dehydrogenase (LDH) measurements in the medium; Mechanical stretching of the BBB-Chip will be tested at strains ranging from 0 to 12%; Biochemical stimulation will be performed via perfusion of the vascular chamber with 10 ng/ml IL-1beta.

For some conditions, media-sampling will be performed every 16 h for 3 days and secreted soluble factors will be detected via ELISA and include soluble markers involved in traumatic brain injury (TBI), multiple sclerosis (MS) or ischemia as described in Table 1, here below.

TABLE 1

Disease Biomarkers References.

| Disease | Biomarkers | References |
|---------|------------|------------|
| TBI | IL-1B | (Liu et al., 1993); (Wang et al., 1997) |
| MS | ICAM-1, V-CAM, IL-1B | Heidary et al., 2014); (Petersen et al., 1998); (Dore-Duffy et al., 1995) |
| Ischemia | IL-IB, IL-17, IL-23, IFNγ, IL-6, TNFα | (Yilmaz, 2006); (Shichita et al, 2009); (Lakhan et al, 2009) |

Aim 1b. Biological validation of space hardware with terrestrial experiments on the BBB-Chip. Exemplary experiments are outlined in Aim 1a, using exemplary space-hardware system outlined in Aim 2. These experiments are contemplated as a dry-run of the space flight experiments where the data collected will allow us determine whether the space hardware performs differently than standard instrumentation.

B. Study Design.

Experiments will be performed in parallel on both current instrumentation and hardware developed for space experiments (in part, outlined in Specific Aim 2).

Readouts will include assessment of barrier function and vascular-to-brain albumin translocation as well as RNA extraction and transcriptome analysis of molecular transporters involved in brain homeostasis and drug delivery.

Exemplary Endpoints: The BBB-Chip model needs to display expression of typical transporter proteins and remain viable for a minimum of 7 days; iPSc derived neurons do not over-proliferate and invade the vascular compartment while on chip for 2 weeks.

Aim 1c. Test the effects of space conditions on BBB-Chip. Exemplary experiments on the BBB-Chip in space is contemplated using the space hardware validated in Aim 1b. The effects of space conditions will be studied by fixing half the BBB-Chip immediately after the hypergravity launch event (n=6 chips) and culturing the BBB-Chip in space for a minimum of 7 days (n=6 chips). Samples will be taken daily throughout the 7-day space experiment to look at BBB function. Controls will be conducted using identical space hardware on ground, running the same environmental conditions measured with sensors in the space experiment. The following readouts will be conducted on experimental samples: Qualitative and quantitative characterization of BBB endothelial cells will be done by immunostaining and imaging of cells growing in the BBB-Chip, as well as protein extraction and Western blot of the following markers. Glut-1, VE-Cadherin, Claudin-5, Occludin and PgP; Vascular leakage will be measured as the vascular-to-brain diffusion of fluorescent fluid phase markers dextran (3 Kda) and Lucifer yellow (450 Da) and fluorescence will be detected via spectrophotometry; Gene expression of typical BBB endothelial cell markers will be done via RT-PCR for different transporters involved in both drug transport and resistance such as PgP, MDR1, Transferrin Receptor and Glut-1; The clinically used "Q-Alb" index depicting the vascular-to-brain diffusion ratio of albumin will be assessed; The vascular-to-brain diffusion ratio of IgG and Transferrin will be measured via ELISA; Viability of the BBB-Chip will be assessed via MTT reduction assay LDH measurements in the medium.

Alternative approaches: The selective transport of the endothelial barrier is a function of the BBB. If this function is lost before the planned 7 days endpoint, appropriate mitigation strategies may be used such as: Optimization of HBMECs differentiation: This can be achieved by defining a robust selective step during the iPSc differentiation protocol. Sequential steps of FACS sorting might be used in order to select an ultra-pure (>95%) population of endothelial cells expressing 3 markers typically found within the brain microvasculature (Claudin-5, VE-Cadherin, Glut-1). Alternatively, the stability of endothelial cell functions might be achieved using selective antibiotics such as puromycin; Reducing the neural proliferation rate: Maturation of iPSc derived neurons can be achieved by growing the neural progenitors in the dish for a few weeks, as they slow down their proliferation rate when they reach a certain level of maturation.

Specific Aim 1d. Data Analysis and Modeling.

For each experiment conducted (Specific Aim 1a-c) a large number of heterogeneous data measurements will be collected, e.g. readouts, related to biomarkers, transcriptomics and proteomics profiling from the effluent, imaging of the cells, TEER, etc. Each of these experiments is defined by the combination of the BBB-Chip setup and the conditions applied, where the "BBB model setup" is determined by the types of cells used to form the BBB on the chip, and "conditions applied" corresponds to the specific stressors used. The variables in this data matrix will be homogenized and correlated so that the most information bearing variables will be identified i.e. those that for a given BBB-Chip setup change significantly across conditions, and those that for a given stress condition change significantly across BBB-Chip setups. This sensitivity analysis, in conjunction with what is known from the literature, will allow us to develop hypotheses as to how a condition, perturbation, or a change in the combination of cell types present in the chip is expected to affect the BBB model's functionality. These hypotheses will be translated into a mathematical model whose most sensitive parameter will be estimated using part of the available data, and cross-validated using the rest of the data to avoid over-fitting. The calibrated mathematical model will then be used to generalize and predict the quality of BBB-Chip's function based on permeability responses to induced toxicity, for novel experiments performed in silico and previously unseen by the model.

Moreover, the in silico model, e.g. mathematical modeling, computer modeling or computer simulation, will be used to investigate the effects of co-factors for which there exist some mechanistic understanding on the influence they exert (i.e. on cell differentiation/maturation), but which there is not extensive experimental data. A model using data matrix resulting from the smaller number of experiments to be performed in space, may be used in an attempt to understand the changes in biology under microgravity conditions by identifying the parameters that change the most among the best fit earth and space models and decode the mechanisms that may drive these changes. Overall, combining bioinformatics data analysis and predictive modeling is expected to provide a coherent view of the outcomes of the whole study and ideas for new interesting directions for further research.

Specific Aim 2: Modify Organ-Chip platforms for spaceflight compatibility in a CubeLab. Modification of Organ-Chips and support instrumentation may be done in order to be compatible with the microgravity environment of the ISS using the SpaceTango CubeLab platform. This will include the automation of experimental procedures (pumping, sampling, dosing, in-line sensing, and fixation) to minimize the requirements for astronaut time.

Technical Feasibility: The proposed work will utilize the TangoLab-1 facility on the International Space Station. The experiment itself will be housed within a 4U CubeLab module and attached to a payload card on orbit before installation in the TangoLab-1 (FIG. 20B (lower)). Logistics: The TangoLab-1 facility is currently installed on ISS in EXPRESS Rack 4, position 8 in the Japanese Experiment Module (JEM). The expected operations required from the astronauts will be minimal, as they will be needed for routine installation and removal. For installation they should unpack the payload cards, retrieve any CubeLabs which flew up unattached m Cold or Soft Stowage, attach to payload cards, and then install into the TangoLab-1 facility. The removal process to return the experiment to earth is essentially the installation process in reverse.

Hazards: At current design and understanding the hazards of most concern would be the toxicology assessments of the reagents, cells and other materials flown. Currently Space Tango is flying materials with Tox level 1 and BSL of 2M, this requires two levels of independent containment that CubeLab MRKII designs can achieve and have been verified through testing. Special attention will be considered for compatibility of materials so any inadvertent mixing during operations will not create gas that could result in pressure buildup within the CubeLab. Chemical compatibility assessments are a standard input from Space Tango to NASA for flights. Other common hazards of wiring sizing, power limitation, EMI/EMC and astronaut egress are accomplished at the TangoLab-1 facility level and outlined in its specific hazard report.

Data Flow: TangoLab-1 and CubeLab modules installed within the facility utilizing the Ku-FWD system for data communications. This allows for remote commanding terrestrially which greatly reduces astronaut inputs and frees up the researchers and users to control their experiments. Commands are sent from the Space Tango operations center in Lexington Ky., USA. Data from experiments is downlinked to the same center but is then displayed on a web-based customer portal so stakeholders, no matter their location, can monitor their work on ISS if they have internet or cell access.

Time Frame: An expected timeframe from project kickoff to flight is approximately one year with the proposed work.

Project kickoff is used here as the point at which technical, science objectives and requirements are defined. It is anticipated that much of the hardware used for this study will be reflights, this requires a 622 reflight verification which is less cumbersome than completely new hardware through the Payload Safety Review Panel (PSRP). Once on orbit it is anticipated the experiment will fly up and down on the same SpaceX mission allowing for approximately 5 weeks of time on orbit.

Specific Aim 2a: Development of an automated fluidic system allowing for physiologically relevant fluid shear stress, recirculation of media, storage of input media, sample collection, and dosing. This will be the backbone of the space hardware that allows functions within a normal experiment to be automated. This will add new functionality to the current platform in that samples from Organ-Chip effluent can be taken and stored automatically with high temporal resolution. Additionally, automated dosing will allow for the modulation of input media at a time resolution required for studies in multi-day drug dosing or cyclic inflammatory insults.

Design Approach: Integrating pumping, routing tubing, and valving into a common fluidic manifold is contemplated. Advantages include in part: substituting flexible silicone tubing that tends to have high small-molecule absorption with a low drug absorbing rigid material, such as described herein, (FIG. 8), the reduction of fluid interfaces reduces the risk for leaking and bubble accumulation, integration of components reduces dead-volume by removing large volume commercial fluid connections and therefore increases temporal resolution of sampling, and integration of fluidics will decrease the complexity of tubing/cable routing in the CubeLab and can be implemented in a more space-efficient manner. The developed fluidic system will allow for: reservoirs for cold storage of fresh input media and output effluent; the continuous perfusion of media through the chip at physiologically relevant shear stress levels; the switching of different input medias for inflammatory challenges; the switching of different input reagents for automated fixation of the chips to allow for immunofluorescent imaging, including but not limited to the extraction of RNA for analysis back on earth; and automated sampling and storage of chip effluent for biochemical analysis back on earth.

We will monitor and transmit to earth the performance and status of pumps and valves wherever possible. This will allows us to ensure that the experiment ran as expected. Additionally, if minor abnormalities are detected, then intervention by changing flow conditions or valve states may be done, i.e. controlled, from earth. In situations where intervention is not possible then the exact conditions may be recreated using space hardware for on earth as controls for comparison to ensure that the earth and space data can be compared for space variables, and not simply deviations in a protocol.

Alternative Approaches: Media reservoirs for space hardware can be challenging as capillary forces dominate in microgravity and fluid can reorient depending on the geometry of the container. This reorientation can cause the introduction of air into the fluidic system that can cause irreparable damage to the cell layers. In the absence of buoyancy-induced convection, fluid phases, bubbles in particular, can wreak havoc in even the simplest of flows (Halvorson 2005), (Robinson 2010), (Nimon 2011). Mathematical frameworks, design intuition, and validated computational modeling software based are contemplated for use, such as described in, for examples, Jenson et al., 2014, Chen et al., 2012, Weislogel et al., 2011, herein incorporated by reference). Some practical implementations of this work are fluid reservoir designs that ensure fluid remains m its anticipated location regardless of gravity orientation. This is needed for space-hardware since cell culture media will be transitioning from large reservoirs in g (gravity), to large reservoirs in micro-g, to microfluidics in micro-g, to sample collection in micro-g, which will then be frozen.

There are many transitions in these steps, and they should occur without the introduction of cell-damaging bubbles into any of the fluidics.

Another challenge will be transitioning media from storage conditions (4° C.) to the culture conditions (37° C.) required during perfusion of the Organ-Chip. Liquids can hold less dissolved gases at higher temperature, which results in the nucleation of bubbles from excess gas during media heating. This can be partially mitigated by ensuring the media is preconditioned to a lower gas concentration than it contains at 37° C. In practice this may be hard to do perfectly, and fully degassing the media is not an option since cells need dissolved oxygen and CO2 in their media to survive. However, bubble traps (14), sec FIG. 1I for one example, may be inserted into the system to mitigate the risk of bubbles nucleating in the system during temperature changes. Geometries for passively separating gas and liquid phases hum bubbly flows ore contemplated for use, such as configured in FIG. 11. Thus information on phase separation in microgravity may be used to develop bubble traps that work efficiently both on ground and in space.

Specific Aim 2b: Develop environmental control for Organ-Chip culture, media and sample storage. The automated platform will require multiple compartments to allow for an incubated and gas-controlled environment for the Organ-Chip, and cold storage for input media and Organ-Chip effluent samples. The ability to immediately store samples at 4° C. will allow for measurements of biomarkers back on earth. The developed environment control system will allow for: the storage of input media and chip effluent at 4° C.; the maintenance of Organ-Chip culture area at 37° C. and 5% $CO_2$; the entire module to be frozen at −80° C. at the end of the experiment.

Several options are being considered in the storage of media at 4° C. Present designs route samples into a separate compartment which itself is transferred to 4° C. refrigerators on ISS for storage by the astronauts. However, this design requires regular astronaut operations and power down of the Space Tango facility (to prevent Electromagnetic Interference when the door is open). Currently under design is an automated system that will include an insulated storage section that will chill the storage tanks. This architecture is preferred as no astronaut input is needed and maintains the preferred automation over the duration of experimentation. Maintenance of the culture area at 37° C. will be achieved with simple flat heaters, temperature sensors, and a PID control loop, commercially available. Temperature measurements will be logged throughout the experiment to ensure there are no abnormal fluctuations that might cause chip failure. In some embodiments, humidity may not be needed in the CubeLab since fluids in the Organ-Chip system are sealed from their surroundings/environment.

Alternative Approaches: The management of multiple temperatures within the volumetric confines of a 2U CubeLab will be quite challenging. The control of condensation at interfaces will be of supreme importance. In some embodiments, the two environments within a CubeLab, may be alternatively employ a neighboring CubeLab to act as a cold storage facility and route the samples here with tubing. Freezing of samples at the end of the experiment can also pose challenges due to the expansion of fluid during freezing and the embrittlement of plastic reservoirs at cold temperatures. In some embodiments, flexible sample collection reservoirs may be used to allow for the expansion of samples during freezing.

Aim 2c: Development of integrated chip electrodes and electronics for the measurement of transendothelial electrical resistance (TEER). (UH3) A space compatible TEER chip would have to be redesigned to fit into the size constraints of the CubeLab 2U module. Additional steps will need to be taken to ensure that this chip can be produced on an appropriate scale and have repeatable readings between chips and within a single chip over extended periods of time. The steps to a space-compatible TEER chip are as follows: Outsource the manufacturing of the TEER electrodes to meet the demand of chips from the experimental design; Verify that electrodes function electrically as required • Test the biocompatibility of the outsourced electrode material; Assembly full TEER-Chips and test for integrity against leaking or delamination; Obtain TEER measurements of empty chips (n=6) over 7 days; Biologically validate TEER-Chips with BBB cells, showing a time-dependent response to an inflammatory challenge.

In some embodiments, a custom potentiostat that can fit into the confines of the CubeLab dimensions may be required. The electronics will be integrated into the CubeLabs data communication system so that measurements can be observed on Earth in real-time. The TEER functionality adds an additional benefit of being a very sensitive sensor for measuring bubbles in the chip. Therefore when bubbles have entered the system they will be detected so that corrective action may be taken, either manually from the control system on earth or through an automated protocol.

During the first space flight the proper function of space-hardware, and log any issues will be monitored. For the second space flight, an iterated version of this hardware may be developed to address any issues uncovered, i.e. that occurred or were at risk of occurring on the first flight.

Specific Aim 3. To simulate on earth each of the individual space cell-stressors in space and assess their contribution to the phenotype of the BBB-Chip in space flight (Specific Aim 1). Assess the inflammatory response of the BBB-Chip in space and its rescue by standard, FDA approved anti-inflammatory therapeutics. (UH3).

Rationale; Space missions impose a number of stressors on the human body. In particular the circulatory system needs to rapidly adjust to accommodate to changes in metabolic needs during the different stages of the space flight. During the liftoff astronauts are exposed to sudden acceleration (hyper-gravity) and the associated temporary hypoxia it causes. Further, in space blood flow is not subjected to the hydrostatic pressure normally present on earth. Whether the reduced hydrostatic pressure can affect the endothelial transport of nutrients or diffusion of other molecules has not yet been investigated. Hyper-gravity, hypoxia, hydrostatic blood pressure, and stress hormones release are factors that impact the body homeostasis of astronauts and are also putative causes of vascular inflammation.

Our overall strategy is to: (1) perform experiments on earth to de-couple hyper-gravity, hypoxia, hydrostatic pressure, and stress hormone-associated impact on BBB-Chip functionality (2) validate the inflamed BBB-Chip model and the efficacy of a standard FDA-approved drug in reducing brain edema and (3) do systematic and comparative data analysis and validation with the model to be developed in Aim 1.

Aim 3a: Characterization of the responses of the BBB-Chip to hypoxia, hypergravity and absence of hydrostatic pressure in terrestrial experiments. Hypoxia can be simulated in vitro by removing dissolved gases from media before perfusion through the chip. In order to simulate the acceleration that astronauts are exposed during liftoff, the BBB-Chip will be centrifuged at 3 g for 10 minutes, in normoxic or hypoxic conditions. To test the hypothesis that the combination of stress factors associated with the space flight could exacerbate an eventual inflammatory condition, 3 chips will be incubated with IL-1β (100 ng/ml, 4 hours) before being exposed to hypergravity and hypoxia. After centrifugation 3 chips per condition will be used to investigate the immediate effect of hypergavity in normoxic or hypoxic conditions (T0).

Three more chips per condition will be perfused with standard cell growth media for one or two weeks in order to investigate eventual long-term effects of the hypergravity and hypoxia on the system (T1). Media concentration of cortisol will be adjusted to reflect the in vivo stress-induced cortisol increase or levels in basal states. Experiments will be repeated 3 times to obtain statistically significant data. The lack of hydrostatic pressure in space will be assessed though terrestrial characterization of molecular transport in chips lacking hydrostatic pressure via redesigning the reservoir positioning relative to the Organ-Chip. Medium will be sampled from the effluents every 24 hours for 2 weeks for analysis of related circulating markers (as described in 1 above); organ-chips will be sacrificed after 3 days, 1 week and 2 weeks post seeding. Data will be analyzed systematically and run through an exemplary model developed in Aim 1 for identification of main points in the process.

Aim 3b. To assess the inflammatory responses of BBB-Chip in space and to validate the automated instrument (aim 2) for drug testing. Inflammation will be induced in BBB-Chip during space flight as described in Aim 1 and related endpoints will be characterized as in Aim 1. In some embodiments, Dexamethasone effects on IL-1β-induced inflammation on the BBB-Chips may be determined. Dexamethasone is a well-known antiedemic and anti-inflammatory drug approved by the FDA. Dexamethasone will be tested at clinically relevant doses ranging between 2-15 ng/ml. Thus, following induction of inflammation of the BBB-Chip (treatment with 100 ng/ml IL-1β, for 4 hours) will be put on Dexamethasone treatment.

V. Barrier Function Will be Monitored in Real-Time Through the Use of TEER

Endpoints for experiments in Aim 3, including but not limited to: Protein extraction and analysis of apoptosis markers: Caspase 3, PARP Cytochrome C (for 3A); RT-PCR of markers associated to inflammatory response and vascular leakage: NF-kB, ICAM1, E-Selectin, P-Selectin, IL-8, IL-1B, IL-8; Gene expression of markers associated to barrier function and transports: Glut-1, VE-Cadherin, Claudin-5, Occludin, PgP and Transferrin Receptor; Barrier function measurement via Lucifer yellow (450 Da) and dextran (3 kDa); Measurement of vascular-to-brain diffusion of Albumin (Alb-Q index), IgG and fibrinogen levels; Transport of transferrin transport from the vascular to the brain compartment and vice versa.

Recapitulating this phenotype is contemplated to simulate each of the main space stressors for the cells in experiments on earth. If the phenotype is not recreated, factors other than the primary stressors are likely involved.

Contemplated Exemplary Developments and Data Collection.

BBB-Chip viability maintenance (morphology/LDH assay) and functionality (barrier function assay) for a minimum of 7 days on existing instrumentation; Space hardware validation on earth showing operation of fluidic and thermal functions for a minimum of 7 days without failure; BBB-Chip viability maintenance (morphology/LDH assay) and functionality (barrier function assay) for a minimum of 7 days on space hardware in terrestrial experiments In some embodiments, taking into consideration the limited number of chips and experiments that may be run in space conditions, cells from male donors may be used for one set of experiments in order to avoid sex related differences. In some embodiments, cells from female donors may be used. Sex related differences in BBB integrity in response to challenges were reported. Several lines of evidence suggest that the reported gender differences in vascular and neural diseases may be associated to sex hormones differences.

Estrogens, in particular 17-Estradiol, have been reported to increase vascular endothelial growth factor-induced (Chi et al., 2004; Burek et al., 2014) leakiness of the blood-brain barrier in the cerebral cortex.

Recently, a comparison of male and female murine responses to peripheral LPS challenge revealed a short-term inflammation-induced deficit in BBB integrity in males that was not apparent in young females, but was notable in older, reproductively senescent females (Maggioli et al., 2016). The choice of cells from male donors was done in order to decrease the variability within females due to differences in phase of the reproductive cycle or in reproductive function, such as between women in pre- or postmenopausal state (Bake et al., 2004).

VI. Automated Platform

Examples of microfluidic chips, e.g. products, that includes integrated flow control, stretching, and fresh media/effluent storage are described herein, at least in part, in addition to descriptions in WO2017035484 (PCT/US2016/049033), herein incorporated by reference in its entirety. FIG. 18A-C shows exemplary components for an integrated automatic system.

However, the integrated system described herein, has open liquid interfaces that are contemplated to be hard to control during the multiple transitions in gravity (1-g, hyper-g, and micro-g). Additionally, the current system's footprint is too large to fit into a 2U CubeLab. CubeLab has an infrastructure for power (3.3V, 5V, 12V for 10 W total power), communication, and temperature control, and contemplated for use in providing a power (e.g. electrical) infrastructure. For these reason, in some embodiments the fluidic architecture may be redesigned to ensure reliability in different gravity conditions, to reduce the overall footprint, and to automate sampling and fixation steps that are currently done manually.

Additionally, Space Tango has already flown latching fixed volume pumps and is in process of approving piezo electric types for flight on SpaceX CRS-12 in August 2017. This gives a range of capability for fluidic movement using the TangoLab architecture. Regarding environmental control: incubation temperatures are reached via TangoLab ambient temperature with resistive heaters. For cooling Space Tango will be utilizing a highly insulated cooler coupled with an endothermic reaction to hold the 4 C within a CubeLab. This system will be tested on ISS on the same CRS-12 flight.

Microchannels may be manufactured in different polymers, pumping and valving technologies (custom and off-shelf) for integrated microfluidic systems, and in some embodiments, using the power and communications infrastructure that already exists in the CubeLab. Standard organ-chip and current attachment methods will be used, in part, for connecting the chip to the fluidic architecture, such as described herein. This has multiple advantages; this chip is produced by professional manufacturers to ISO 9001 quality standards at volumes of over 1000's chips/month (this volume is also scalable to higher numbers if required), it is an established product with extremely good reliability and repeatability being utilized by numerous research groups across multiple Organ types, including a current BBB-chip model as a chip design this re-optimizing conditions for a new custom chip, and the chip-to-fluidics attachment method has been carefully developed over three years to maintain a reliable and bubble-free seal and allow for seeding workflows that minimize damage to cells and generate consistent cell seeding densities.

Off-the-shelf surface mount valve and pump components will be used where applicable, for connecting to an integrated micromachined fluidic manifold allowing for pumping, sampling, and fixation of a microfluidic chip. The off-the-shelf components have the advantage of shorter development time and excellent reliable and repeatability, but are disadvantaged by their larger footprint and the inherent introduction of dead-volume by surface mount components. A second approach will aim to integrate pumping and valving components into the fluidic manifold through various methods well-established in the academic literature (Quake 2002, Nature 001:10.1126/science.1076996, Hinojosa 2012 US Patent Application 20150306596A1, Wang et al 2005, Biomedical Microdevices doi: 10.1007/s 10544-005-6073-z, herein incorporated by reference in its entirety), which are beginning to gain traction in industry applications. The methods that will be considered are Quake valves, hydrogel valves, electromechanical actuators, etc.

Advantages of embodiments of the present inventions described herein, include but are not limited to reduced footprint, lower dead-volume, and fewer control actuators, but comes at the cost of increased manufacturing complexity, longer development time, and potential for reduced reliability. A fail-fast approach is contemplated for evaluating the two approaches for reliability, repeatability, and ability to meet the requirements of space-travel. Actuator components that are compatible with safety regulations and CubeLab's existing power and electronics infrastructure to ensure ease of integration are contemplated for use.

Figure 11:
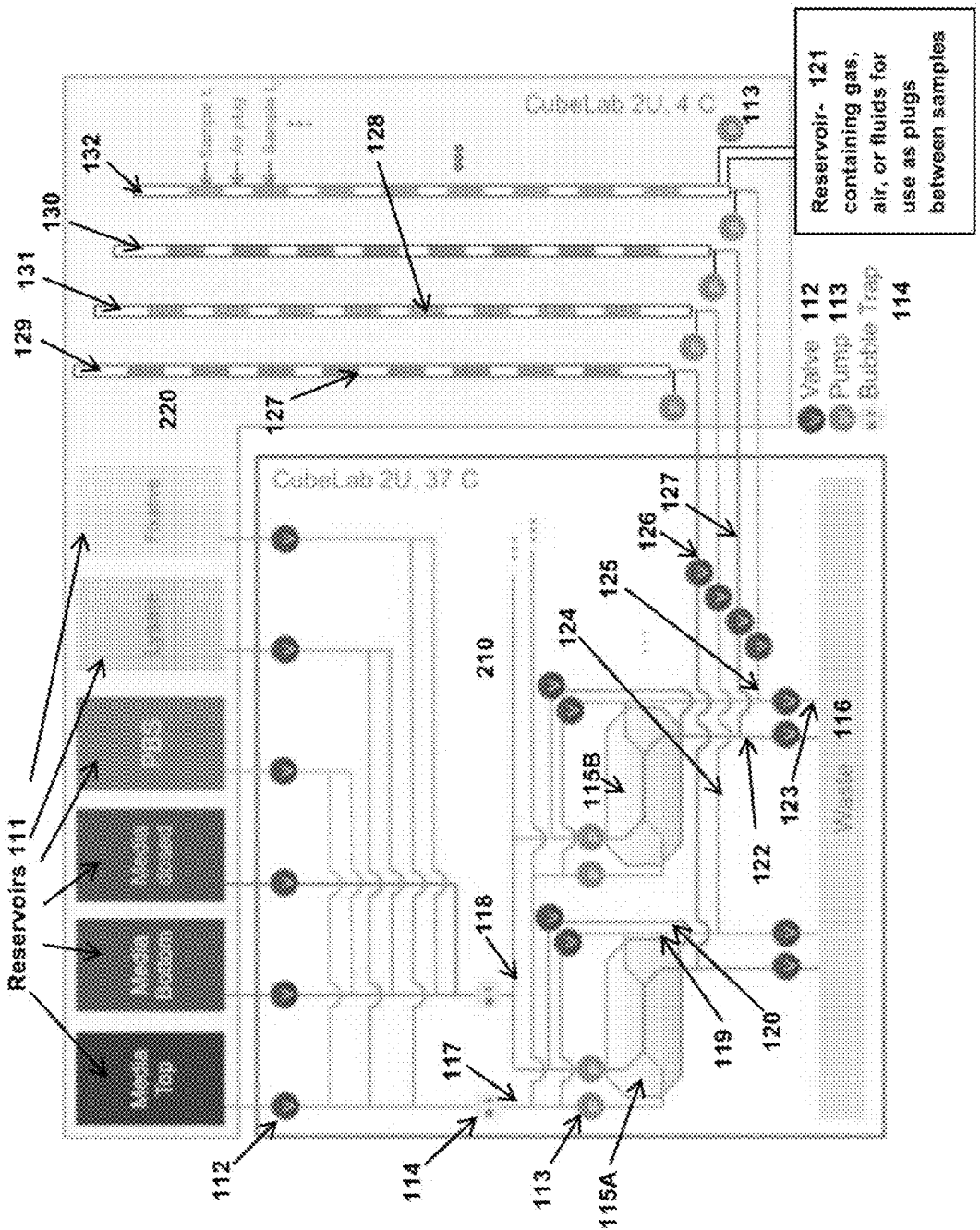
FIG. 11 shows an exemplary schematic illustration of one embodiment of a wireframe, for use in space and/or terrestrial experiments, showing an exemplary fluidic and thermal system diagram. The fluidics include valves (112) and pumps (P) (such as 113), along with (optional) bubble traps (114) that can be orchestrated to allow for the automated delivery of fluids from reservoirs (111) through exemplary upper channel fluidic connectors (117) and lower channel fluidic connectors (118) including but not limited to media, including recirculation of media (from effluent, upper channel (119) or lower channel (120), as incoming fluid into a chip—in some embodiments using additional fluidic connectors) introduction of dosed media, reagents for fixation of the chip for terrestrial immunohistochemistry, and reagents for RNA extraction for terrestrial analysis. In one embodiment, two separate microfluidic chips (115A and 115B) are shown in fluidic communication with reservoirs (111) above (blue squares at the top). For recirculation, effluent fluid may be diverted to an outlet reservoir. Thus, reservoirs may include inlet and outlet reservoirs for recirculation, such that at least one pair of inlet and outlet reservoirs are in fluidic communication, comprising a check valve and a shortcut channel as in FIG. 46A-D, in addition to other components in a pressure manifold, e.g. pod. Sampling conduits are in fluidic communication with the microfluidic devices (e.g. 129 identifying one of the sampling conduits for effluent fluid that exited the lower channel (red area 127) and lower areas 131 through channel 124 for samples for the first chip 115A; 131 identifying one of the sampling conduits for effluent fluid that exits the bottom channel (red area 127) for the chip 115A) are shown containing samples (red and blue areas with samples collected over time (e.g. t(time)1, t2, etc) separated by plugs, e.g. air or fluids (white spaces). Upper channel fluid effluent 124 and lower channel effluent 126 may enter sampling conduits 129 and 131, respectively.

The fluidic reservoirs to support this infrastructure will be designed based upon design of fluid reservoirs for space-travel and used on the space station. The specific design direction will be informed by the chosen pump style, footprint constraints, cold storage constraints, manufacturing options for biocompatible and low-drug absorbing materials, etc. In one embodiment, the sample reservoirs will build-off a microfluidic sampling concept (FIG. 11). In short, each organ-chip channel outlet can be sent to one of three channels; waste reservoir, recirculation channel, or a sample channel (e.g. SC-sampling conduit). The sample channel is a long circuitous microbore capillary tubing ubiquitous in mass spectrometers due to their low compound absorption/adsorption and their low dead-volume. In some embodiments, this type of tubing may be used as a way to collect samples as effluent from the organ-chip. When the sample valve is switched "on" effluent from the organ-chip flows into the sample reservoir/lube until the desired volume is collected. The sample volume is driven by the pump flow rate, and the required volume for a given time point (driven by assays) sets the time needed for sample collection. After the appropriate volume of sample has been collected, the sample valve is switched off and air (or immiscible fluid) is injected into the sample reservoir/tube to ensure each sample is discrete in time and does not diffuse into samples from other time points. This methodology will allow for high-temporal sampling resolution, without the size and added complexity of hundreds of sample reservoirs or bulky switching valves. It also allows for the sample reservoir/tubing to be routed to a separate thermal compartment in an adjacent CubeLab that will allow for storage of the effluent at 4 C.

At the end of the experiment valves will be switched to allow for reagents to be pumped through the chip for either fixation of chips for immunohistochemistry or for lysing the cells and collecting RNA in the sample reservoirs. After this final operation, the sample storage unit will be transferred to 80° C. freezer on the ISS while the organ-chip module will be storage at 4° C. Both modules will return to earth on the SpaceX Dragon Module where they will be analyzed. After Dragon splashdown, the capsule takes approximately 24 hours to reach shore via barge. The samples will be maintained at −80° C. until turnover to Space Tango at the unpacking location. At this point samples will be transferred to a cyro shipper for shipment to a location providing data analysis. The fixed organ-chips will be stained and imaged using a Zeiss Confocal Microscope LSM 880, as one example. The discrete samples from the sample reservoir tubing will be aliquoted to 96-well plates and analyzed on an exemplary Meso Scale Discovery ELISA system, Life Technology qPCR, or a plate spectrophotometer.

The TangoLab facility CubeLab modules allow for foil control and monitoring of pump, heater, cooling, imaging and other control systems. This gives the PI foil clarity of the state of their work while operating on ISS. Telemetry is currently downloaded once per day manually at the Space Tango offices and distributed. However, a Delay Tolerant Network (DTN) will be implemented on the SpaceX CRS-12 mission allowing near streaming of data for approximately 80% of the day. There are occasional satellite black outs due to the orbital mechanics between the ISS and the geostationary satellites used for data downloads.

A system diagram outlining a potential fluidic and thermal architecture is shown in FIGS. 11 and 18A-C.

VII. Polymer Compound Absorption

In some embodiments, polydimethylsiloxane (PDMS) is an exemplary polymer for use in microfluidic chips described herein. However, in other embodiments, alternative materials for providing microfluidic chips may be desired. PDMS absorbs certain compounds, such as drugs, thus potentially interfering with some drug testing on microfluidic chips. Thus, in some embodiments, a non-drug absorbing chip is desired.

A. Non-Drug Absorbing Chip.

In some embodiments, it is contemplated to provide material(s) to replace polydimethylsiloxane (PDMS) is another polymer or a hard plastic material. Examples of alternative materials for using with PDMS or in place of PDMS, include but are not limited to Cyclo Olefin Polymer (COP) (such as Zeonor 1420R, which is commercially available) and SEBS, described further herein.

TABLE 2

The absorption of different compounds with varying physiochemical properties into PDMS, two alternative flexible materials, and an alternative rigid material. Compound Absorption Summary Table.

| Compound | MW | loaP | PDMS Partition | Flex 2 Partition | Flex 2 Partition | Rigid Partition |
|---|---|---|---|---|---|---|
| Compound 1 | 321 | 2.1 | Minimal* | Minimal* | Minimal* | Minimal* |
| Compound 2 | 188 | 0.4 | 3* | Minimal* | Minimal* | Minimal* |
| Compound 3 | 326 | 4.3 | 201 | 4 | — | Minimal |
| Compound 4 | 285 | 2.8 | 25 | 11 | 5 | Minimal |
| Compound 5 | 277 | 4.9 | >1000 | 175 | 50 | Minimal |

*High noise/variability in the data.

PDMS Drug Absorption and Alternative Materials.

The plan on when and how to replace the use of PDMS microfluidic chips with microfluidic chips manufactured with an alternative material(s) may be dependent on application. In the case of biologics PDMS typically does not present a problem with some exemptions. As one example, in the case of using small molecules, mathematical modeling may be used to address drug absorption onto PDMS. However, there are certain classes of small molecules that due to their physiochemical properties present a challenge with compound loss that is too extensive. For studies involving the types of compounds that significantly absorb into PDMS there is a need to replace PDMS with an alternative material. This does come with the additional challenge of finding an appropriate material that is biocompatible, manufacturable, optically clear, and flexible (for some applications). These materials come with new material properties such as low gas diffusivity properties (e.g. lower than PDMS) or low surface energy for surface modifications.

Therefore, many alternative materials that are both flexible and rigid were tested. For many of the organ-chips mechanical strain was not necessary and therefore a rigid material can suffice, e.g. Liver-Chip (mechanical stretch is shown to be detrimental, it is the shear stress that is the relevant mechanical force. Therefore, a rigid Chip will suffice. Materials are subject to drug absorption studies using compounds with a range of physiochemical parameters. A sampling of those studies is shown in Table 2 for both PDMS and alternative rigid and flexible materials. Materials are also evaluated for cytotoxicity. Issues such as material's reduced ability for oxygen diffusion or different surface properties for ECM attachment are dealt with during the organ optimization phase. In the example below the optimization readouts are functional assays such as the ability for the Liver-chip to metabolize compounds or produce Albumin. The Liver-chip serves as an excellent organ for optimization as the hepatic epithelial and endothelial are exquisitely sensitive to toxic compounds. In addition, hepatocytes are highly metabolic and therefore very sensitive to changes in the transport of dissolved oxygen.

Figure 12:
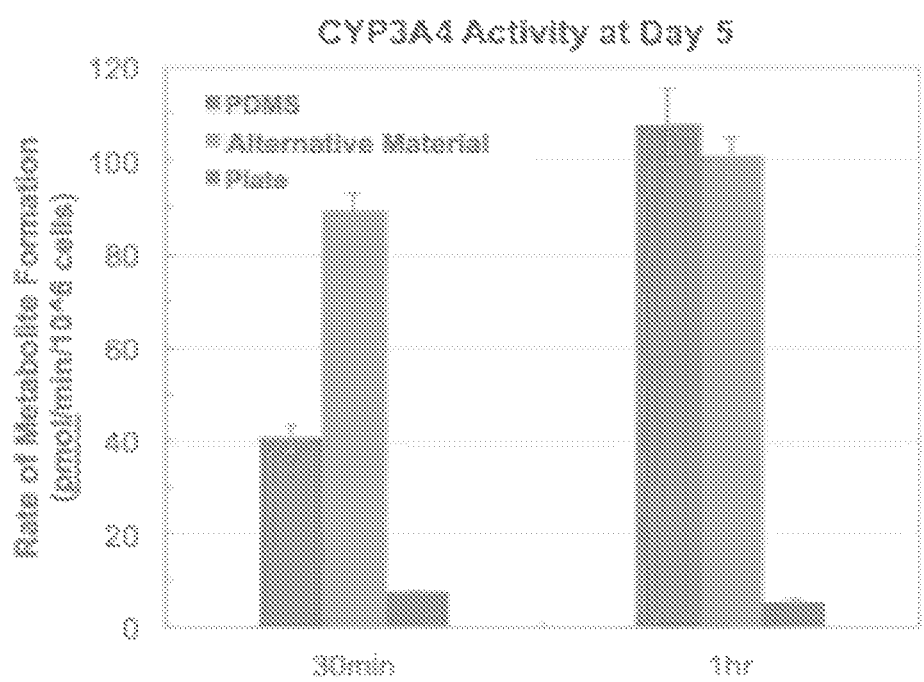
FIG. 12 shows an exemplary metabolite formation in a Liver-chip for both a PDMS Liver-chip, alternative rigid Liver-chip, and static plate showing that Organ-chips made from alternative rigid materials are performing at the same level or better than PDMS chips.
Figure 13:
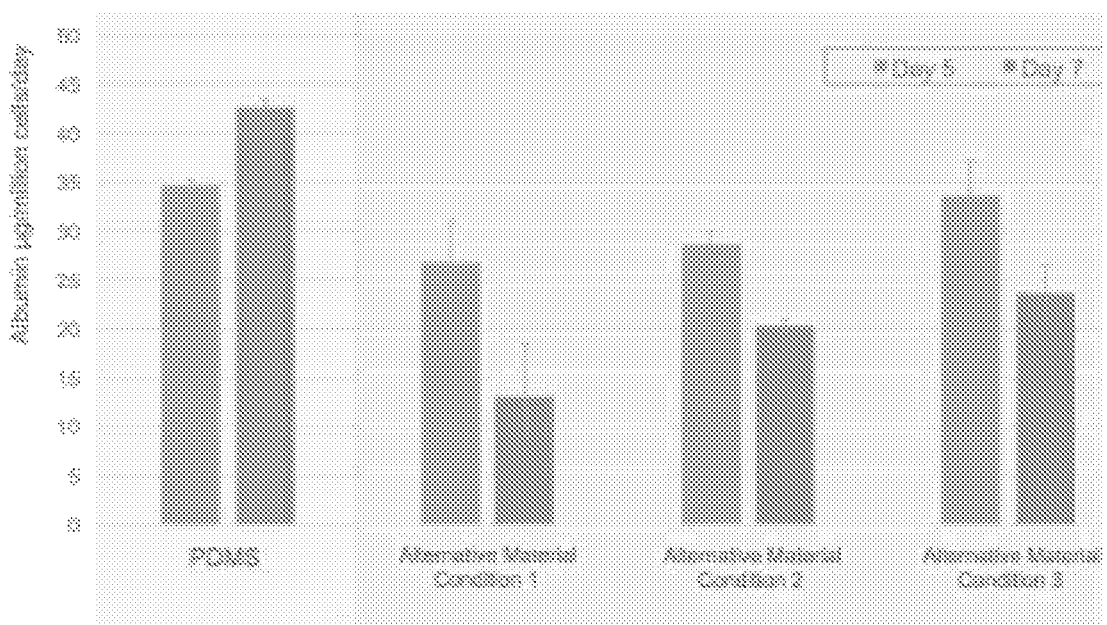
FIG. 13 shows an exemplary Liver-chip albumin production in a PDMS Liver-chip and alternative rigid Liver-chip material for different conditions of dissolved oxygen mass transport.

FIG. 12 shows that the Liver-Chip fabricated with the alternative material maintains drug metabolizing capacity (major function of the liver) shown by CYP3A4 activity at similar levels as in Chips made with PDMS. FIG. 13 shows that when a standard PDMS chip is used, a reduction in albumin production (condition 1) possibly due to a reduction in dissolved oxygen flux from the less gas permeable chip material. However, by changing the mass transport of oxygen through increased convection (FIG. 13, condition 3) sufficient gas may be provided to the cells even with less gas permeable chip materials. This type of optimization process is carried out for any organ transitioning to an alternative material chip.

B. Exemplary Recirculation Surprisingly Increases Production of Secreted Proteins From Cells On-Chip.

In some embodiments, microfluidic Liver-Chip data, provides proof of concept data for allowing the ability to solve the challenges with PDMS and alternative materials. In addition, it provides proof-of-concept data to demonstrate the ability to optimize Chip design and conditions to address oxygen tension, flexibility, and drug absorption.

Because PDMS absorbed test compounds, including test drugs, Liver-Chips were provided on Cyclo-olefin-polymer (COP) microfluidic chips, as described herein, as it was contemplated that less compound would be absorbed by COP surfaces. Therefore for comparison, duplicate hepatocyte cell and endothelial cell samples were seeded onto PDMS microfluidic chips for comparing to COP chips for drug dosing and media fluid recirculation experiments.

Further, delivery of oxygen to the cells in an otherwise gas impermeable system, such as COP microfluidic chips in some embodiments, is desired. In contrast, PDMS chips are gas permeable. Thus, in some embodiments, media exposure to atmospheric oxygen occurs in the reservoir before the first pass of fluid over the cells in a microchannel. After contacting oxygen-consuming cells, effluent fluid is oxygen depleted. Thus, in some embodiments, reciprocation is designed to include reoxygenation of the nutrient media before returning media into the microchannel to contact the cells. In some embodiments, wherein effluent fluid is oxygen depleted, e.g. media, the fluid is reoxygenated prior to recirculation. In some embodiments when oxygen reoxygenation does not occur in recirculated fluids, the cells may consume the majority of oxygen in the channel/in the media upon the first and subsequent passes, thus without an additional source of oxygen, the media will become hypoxic resulting in cell death depending upon the length of time cells are in contact with hypoxic media and the relative amount of oxygen deprivation compared to the amount the cells need to thrive.

Figure 44A:
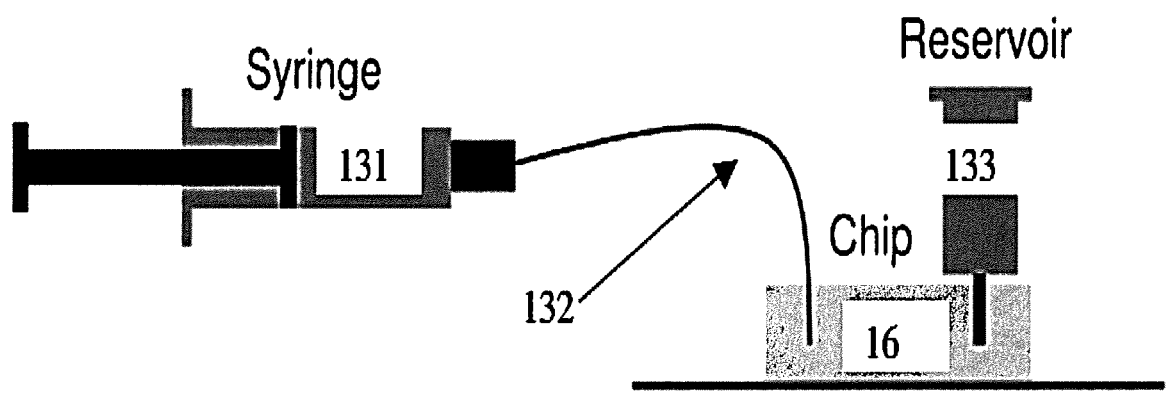
Figure 45A:
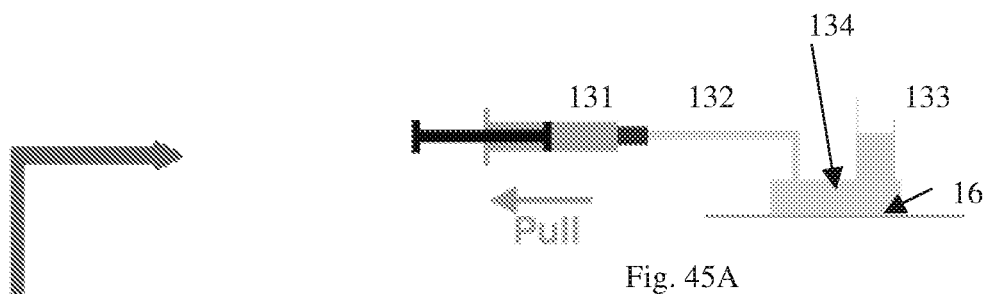
FIG. 45A-C shows exemplary schematic diagrams for one embodiment of a Non Drug Absorbing Study Design: Pragmatic Approach.
Figure 45B:
Figure 45C:
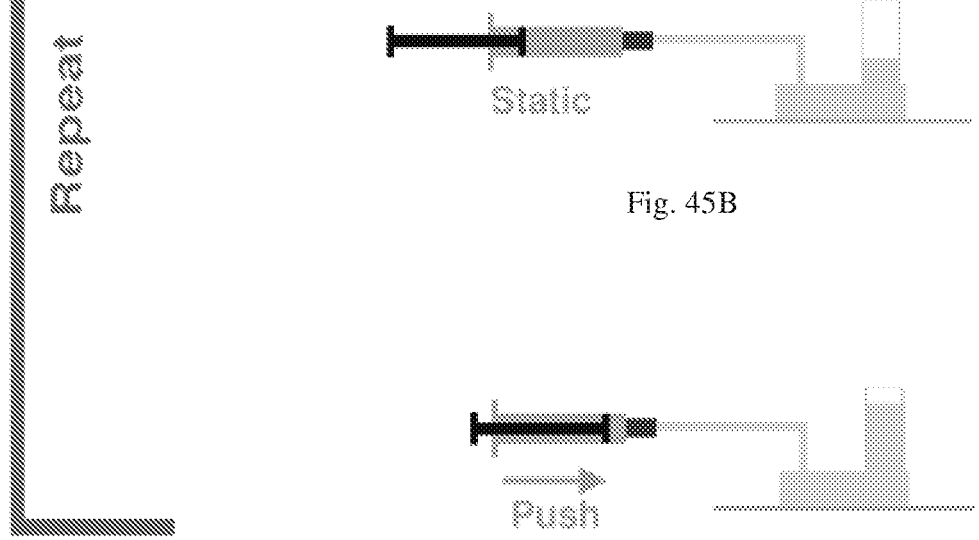

Thus, in one embodiment, the drug testing (i.e. dosing) method included exemplary recirculation steps shown in FIG. 45A-C using exemplary recirculation devices shown in FIG. 44A-C, for recirculation of effluent fluid, i.e. nutrient media.

FIG. 44A-C illustrates and shows photographs of embodiments for recirculation (reciprocation) and introduction of a test compound into a microfluidic chip as one embodiment of a non-drug absorbing setup (e.g. device). Setup: for ensuring adequate oxygenation; is non-drug absorbing; and decreases system volume. FIG. 44A shows an illustration of one embodiment of a syringe (131) fluidically connected by tubing (132) to a microchannel of a microfluidic chip (16) in turn (fluidically connected to a reservoir (133). FIG. 44B shows a photograph image of one embodiment of a syringe (131) fluidically connected by tubing (132) to a microchannel of a microfluidic chip (100) in turn fluidically connected to a reservoir (133). FIG. 44C shows a photograph image of one embodiment of a Chip with both channels attached to a reservoir and attachments for syringes fluidically connected by tubing (132) to a microchannel of a microfluidic chip (16) in turn fluidically connected to a reservoir (133).

FIG. 45A-C shows exemplary schematic diagrams for one embodiment of a Non Drug Absorbing Study Design: Pragmatic Approach. FIG. 45A shows one embodiment for a Pull Mode—Recirculate as Step 1: Pull 30 µL of media into the chip, exposing cells to freshly oxygenated media. A syringe (131) fluidically connected by tubing (132) to a microchannel (134) of a microfluidic chip (16) in turn fluidically connected to a reservoir (133). FIG. 45B shows one embodiment for exposing chips, i.e. cells, to a test compound as Step 2: Incubate for 1 minute, allowing exposure of cells to a test compound. FIG. 45C shows one embodiment for a Push Mode—Oxygen Exposure. Step 3: Push 30 µL of media into outlet, exposing media to oxygen. Then repeat Steps 1-3 as desired.

More specifically, before dosing (day 5 and earlier) the flow rate was 150 uL/hr in both the top and bottom channels. In some embodiments, the lower channel was seeded with endothelial cells. In some embodiments, both channels were recirculated t reciprocated simultaneously. On day 6 (for 24 hrs) the flow rate was changed as outlined in FIG. 45A-C for dosing the human hepatocytes with test compounds, i.e. cocktail of 0.5 uM Diazepam and 0.5 uM Amitriptyline (2 drugs at the same time). The flow rate during step 1 was 3600 uL hr in one direction for 30 s, 0 uL/hr during step 2 for 1 min, and 3600 uL/hr in the opposite direction for step 3 for 30 s (which was immediately followed by step 1 again and repeated for 24 hrs).

Data was collected on day 7. Albumin production in addition to cell death, e.g. ETHD-1 staining for permeabilized, i.e. dying/dead cells, was measured on day 7.

C. COP Liver-Chip Shows Comparable (High) Albumin Production to PDMS Liver-Chip.

Figure 47C:
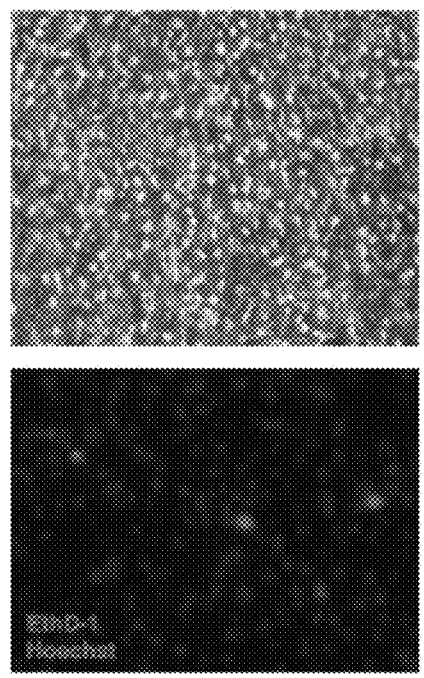
FIG. 47C shows micrographs of liver cells on-chip on Day 7. Upper image is a bright field image while the lower image shows a colored immunofluorescent micrograph of dead cells stained with EthD-1 (red) and Hoechst stained nuclei (blue).

Surprisingly, after analyzing the albumin data it was discovered that liver cells on both PDMS and COP microfluidic chips showed comparable (high) albumin production, see. FIG. 47A. Further, in order to rule-out production from dying cells, hepatocytes were stained with EtHD-1 on both chips, see FIG. 47C, showing a representative field of a healthy hepatocyte cell monolayer with the expected scattered dying or dead cells. In fact, for the first lime, albumin production was unexpectedly measured within a physiologically relevant range indicating an increase in metabolic function of the liver cells. Although the cells were dosed with the test drug cocktail, the drugs did not appear to be influencing the increase in metabolic function caused by the recirculation method. In fact, additional albumin samples were collected and measured after returning the chips to single-pass/uni-directional flow (after reciprocating for 24 hrs), see results below.

D. Reciprocation Appears to Dramatically and Significantly Increase Albumin Production from Hepatic Cells in Both the PDMS and COP Liver-Chip.

Even more surprising was the discovery that the rate of albumin production increased dramatically both in comparison to previous experiments and also in comparison to the same chips from earlier in the experiment, see FIG. 47B, where the 150 uL/hr refers to albumin production in the same chip before reciprocation.

Thus, rapid reciprocation described herein caused a dramatic increase in albumin production compared to the same microfluidic Live On-Chip when fluid (i.e. nutrient media) was restored to flowing in one direction (i.e. one pass of the media) at 150 uL/hr. This result was so surprising additional experiments were done. Thus, in at least one embodiment, the chip was evaluated to find out whether it "returned" to lower rates of albumin production when the single direction fluid flow was used on the same cells that had been subject to reciprocating flow.

Albumin was measured from PDMS microfluidic Liver on-chip effluent before reciprocation (days 5 & 6), after reciprocation (day 8), and then after returning to single pass flow. After sampling the effluent on Day 6, fluid was reciprocated for 24 hrs while dosing cells with lorazepam/antipyrine at 0.5 uM during reciprocation, see FIG. 47A. Again, surprisingly, the hepatic cells on-chip returned to producing lower levels of albumin after returning to the single pass flow rate, see FIG. 47B. Further, in the Day 8 sample, using reciprocating fluid flow at 3600 UL/hr, albumin production was measured on the high end of physiologically relevant range.

FIG. 47A-B shows graphs demonstrating hepatocyte viability and function as albumin production (ug/million cells/day) when media is recirculated. COP Liver-Chip shows comparable (high) albumin production to PDMS Liver-Chip after dosing with compounds during reciprocation. Comparative chips were not dosed. Chips were "perfused" with media each day during the experiment including both single-pass flow and reciprocation.

FIG. 47A shows exemplary data graphs comparing albumin production after 7 days of dosing. Static plates and microfluidic chips, constructed with PDMS or COP, are compared by several test conditions over time, albumin production after dosing with no recirculation, i.e. a single pass flow at 150 ul/hr. on Day 5 was compared to Day 7 albumin production with reciprocating flow 3600 uL/hr.

FIG. 47B shows exemplary data graphs comparing albumin production after dosing PDMS chips under conditions of a single pass flow at 150 ul/hr. on Days 5 and 6, then Day 8 production with reciprocating fluid flow at 3600 uL/hr compared to a single pass flow at 150 ul/hr. on Day 9.

FIG. 47C shows micrographs of liver cells on-chip on Day 7. Upper image is a bright field image while the lower image shows a colored immunofluorescent micrograph of dead cells stained with EthD-1 (red) and Hoechst stained nuclei (blue). Albumin measured before reciprocation (day 5) and after reciprocation (day 7) in the same chips (reciprocated for 24 hrs on day 6), see FIG. 47A-B.

These exemplary results support a linkage between the reciprocation protocol resulting in significantly increased albumin production and further support reversibility of these high levels to lower levels of albumin production on-chip. Thus, albumin production may be controlled within the same Liver On-Chip, such that when low-level albumin production is desired single pass nutrient media fluid flow may be used. When higher levels of albumen production are desired from the same Liver On-Chip then recirculation methods may be used to boost production levels. It is contemplated that by changing the length of recirculation time, that specific levels of albumen production from a Liver On-Chip may be obtained, i.e. tuned, using recirculation times up to 2 hrs; up to 6 hrs; up to 12 hrs; up to 24 hrs; up to 48 hrs; up to 72 hrs or more.

Thus, some embodiments are contemplated to use microfluidic chips/devices without effluent fluid recirculation. In other embodiments, microfluidic chips/devices are contemplated for use with recirculation devices, see exemplary FIG. 44A-C and FIG. 45A-C. In other embodiments, microfluidic chips/devices are contemplated for use with recirculation devices in an incubation pod, see exemplary FIG. 46A-E. As nonlimiting examples, exemplary pods are described in US20170055522, herein incorporated by reference in its entirely.

Thus, in some embodiments, such recirculation devices are automated. In fact, additional embodiments are contemplated for recirculation devices, as described and shown in FIG. 46A-D. More specifically, a recirculation device as part of a pod operates by applying pressure to the inlet reservoir pushing fluid through tubing then through a microchannel in the chip where the effluent fluid enters the outlet reservoir. A shortcut channel is located in between the inlet and outlet reservoir has a check-valve that is closed for passing fluid through the chip to the outlet reservoir. To move fluid from the outlet to the inlet reservoir for recirculation, the outlet reservoir is then pressurized for pushing the fluid through a shortcut channel and the now open check-valve. The majority of fluid moves into the inlet reservoir as the path of least resistance through the open check valve. However, if in some embodiments it is decided that too much fluid is moving backwards through the fluid resistor of the backplane, then a check valve may be placed to prevent the effluent fluid from flowing back through the effluent port of the microfluidic chip.

Figure 46A:
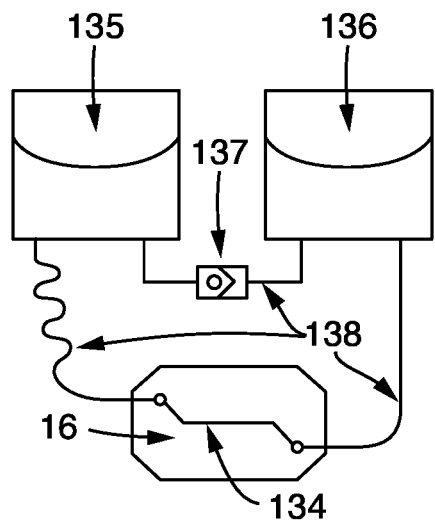
FIG. 46A-E shows illustrations and diagrams for exemplary embodiments providing recirculation for chips incubated within a pod.
Figure 46B:
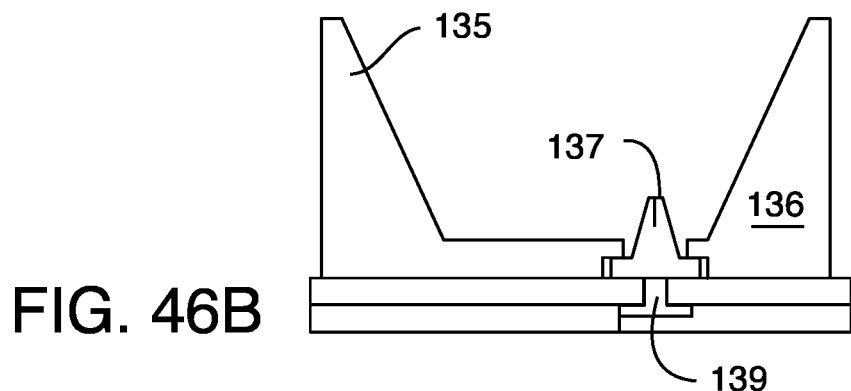
Figure 46C:
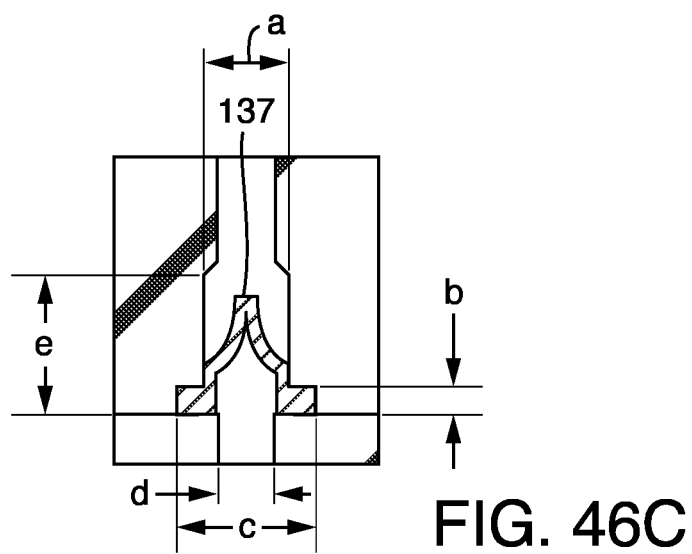
Figure 46D:
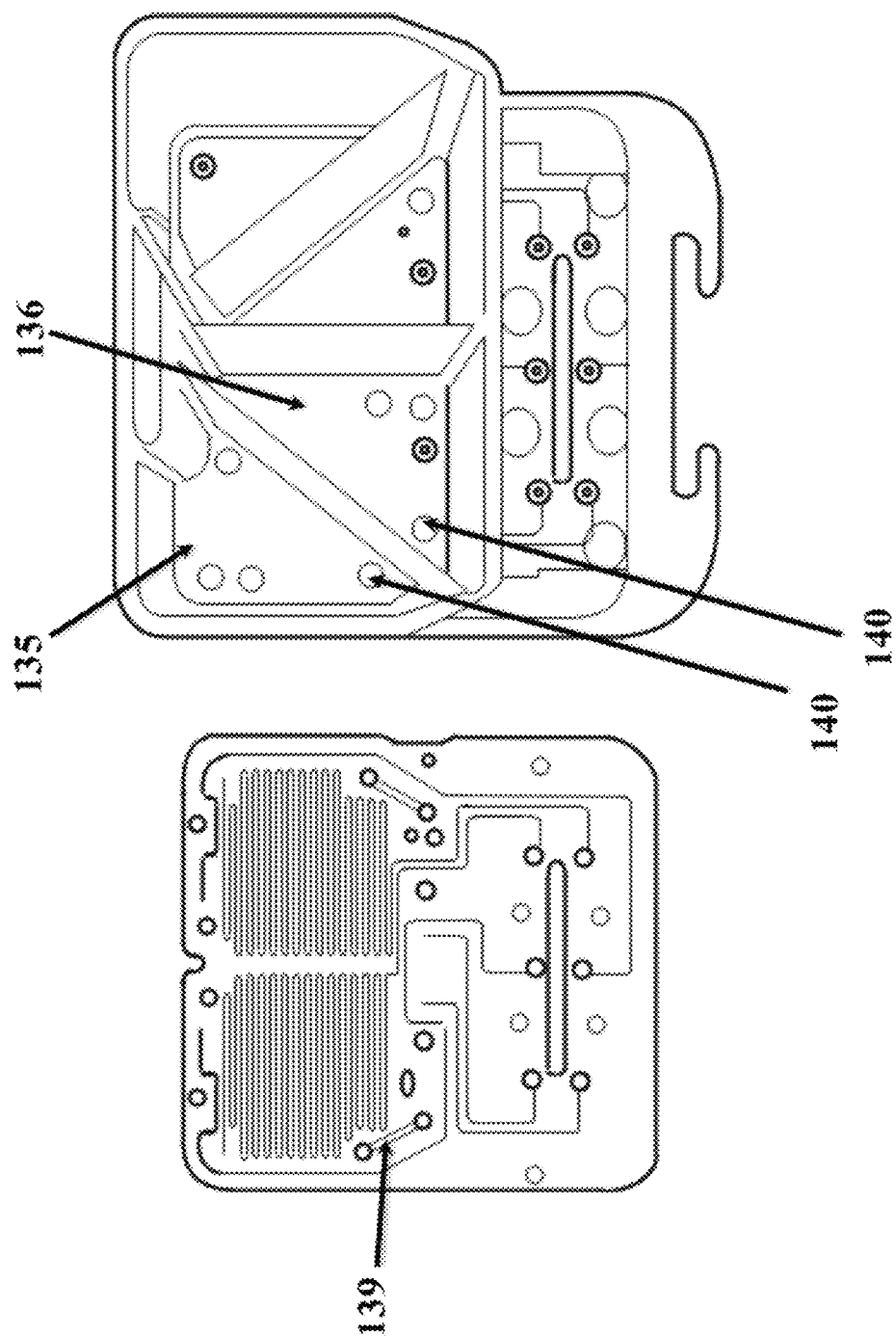
Figure 46E:
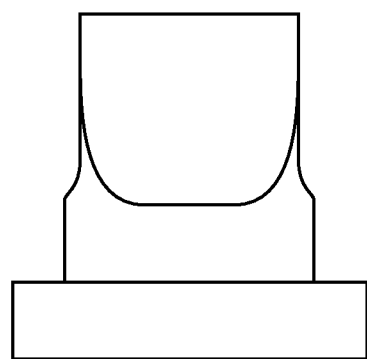

FIG. 46A-E shows illustrations and diagrams for exemplary embodiments providing recirculation for chips incubated within a pod. FIG. 46A Inlet reservoir (135); outlet reservoir (136); check valve (137): lines indicate tubing (138) fluidically connecting reservoirs with one channel (70) in a microfluidic chip (16). FIG. 46B shows a more detailed illustration of one embodiment for incorporation of a check Valve into a Pod. Inlet reservoir (135); outlet reservoir (136); check valve (137); Shortcut channel in Pod fluid layer (139). FIG. 46C shows an illustration of an engineering drawing for one embodiment of a check valve (137) as an exemplary Duckbill Check Valve. FIG. 46D shows exemplary photographs of pod reservoirs. Inlet reservoir (135); outlet reservoir (136); Shortcut channel in Pod fluid layer (139); Shortcut channel vias into reservoirs (140). FIG. 46E shows an illustration of a side view of the check valve in FIG. 46C. Dimension a of FIG. 46C may be between 2.03 and 2.10 mm (.080 and 0.083 in) in one embodiment. Dimension b of FIG. 46C may be between 0.6 and 0.7 mm (0.022 and 0.026 in) in one embodiment. Dimension c of FIG. 46C may be at a minimum 3.1 mm in diameter (0.122 in) in one embodiment. Dimension d of FIG. 46C may be at a minimum of 1.4 mm in diameter (0.055 in) in one embodiment. Dimension e of FIG. 46C maybe a minimum 3.3 mm(0.130 in) in one embodiment.

In summary, 150 uL/hr flow rate resulted in low albumin production for one embodiment of a Liver on-chip seeded with human hepatocytes in the upper channel and endothelial cells in the lower channel. Reciprocation as described herein, significantly improved albumin production in both PDMS and COP microfluidic chips. Therefore, in some embodiments, reciprocation is contemplated to increase function of cells seeded onto microfluidic chips as described herein. In other words, it is not meant to limit the type of microfluidic chip device for use with recirculation of effluent media. In fact, it is not meant to limit the use of such recirculation devices and methods to microfluidic Liver On-chips, such that other organ on-chips are contemplated for use including but not limited to Brain On-chips, etc.

VIII. Exemplary Chip Manufacturing

Conditions for bonding the capping layer (FIG. 2, element 13) to the backplane (14) were examined. Extruded SEBS sheets were bonded to a hot embossed plate. The SEBS sheets were designed to act as the capping layer to the channels that are formed in the COP via the hot embossing process and as a fluid and gas gasketing to mating parts. The testing showed that the 1 mm thick SEBS was better as a fluid seal between the reservoirs and the backplane. The hot embossed plates were fabricated from Zeonor 1420R. The SEBS materials used were, but not limited to: A. Thickness: 1 mm, Material: Kraton G1643, Mfg Process: extrusion and B. Thickness: 0.2 mm, Material: Kraton G1643+5% Polypropylene, Mfg Process: extrusion.

An oven process was used in comparison to a laminator. The laminator produced marginal to not adequate bonding. However, the oven process revealed the following in Table 3.

TABLE 3

Exemplary Material Characteristics.

| | 0.2 mm SEBS | 1 mm SEBS |
|---|---|---|
| Material Thickness | | |
| Bonding Temp (° C.) | 80 | 80 |
| Bonding Time | 1 hr-24 hr | |
| Clamping Pressure | None | 0.5 kg Applied through a silicone coated acrylic plate Necessary for conformal lamination/good bond production |
| Bond Quality | 1 hr: good bond 24 hr: excellent bond | Good bond |
| Anisotropic Effects | None noticeable | Yes. Requires clamping pressure to be held for ~30 min during cooling |

In some embodiments, the fluidic layer is sealed with a film. This film may be polymeric, metallic, biological or a combination thereof (e.g. A laminate of multiple materials). Examples of materials include polypropylene, SEBS, COP, PET, PMMA, aluminum, etc. Specifically, the film may be elastomeric. The film may be affixed to the fluidic layer by means of an adhesive agent, thermal lamination, laser welding, clamping, and other methods known in the art. The film may further be used to affix and potentially fluidically interconnect additional components to the fluidic layer. For example, the film may be used to adhere one or more reservoirs to the fluidic layer. In an example embodiment, the film is a thermal lamination film that includes EVA or EMA. In the example embodiment, the film may be first laminated against the fluidic layer using a thermal treatment and then, using a second thermal treatment, adheres one or more reservoirs to the fluidic layer. In a different embodiment, the film includes SEBS, which is known to be bondable to a variety of materials including polystyrene, COP, polypropylene, etc., either using a thermal treatment or with the help of one or more solvents. In this example, the SEBS film may be laminated to a fluidic layer (using thermal treatment or with the help of solvent) and using a second treatment, bond one or more reservoirs to the fluidic layers. There are multiple potential advantages to using a film that is elastomeric, deformable, or pliable, or film that reflows during the bonding process. These advantages include, for example: potentially conforming to the fluidic layer or other bonded component (e.g. reservoirs), thereby relaxing manufacturing tolerance (e.g. on the flatness or planarity of the manufactured parts), potentially simplifying the required parallelism or alignment during bonding (e.g. because the said film may deform to absorb errors in parallelism), and acting as a gasket to create a fluidic seal, for example, between the fluidic backplane and reservoirs. SEBS is especially advantageous as a bonding film, since it can bond under moderate temperatures (typically under 100 C) while not significantly reflowing. Reflowing may be undesirable as it poses a risk of filling in and blocking fluidic channels. By not significantly reflowing, SEBS can better maintain the dimensions and structure of fluidic channels and other features in the fluidic layer compared to materials that reflow (e.g. traditional thermal lamination films). Film thickness can range from 10 um to 5 mm in different embodiments. The film may include various fluidic ports or channels. The film need not be flat and can take on a variety of three-dimensional shapes.

IX. The Following Include Some Exemplary Contemplated Embodiments

Develop and Validate Fluidic System for Automated Experiments that is Compatible with CubeLab Size Constraints, Power and Communications Infrastructure.

In this example, show that hardware can pump reliably (+/−5% of set flow rate for 10 days), valves operate and provide fixation reagents at appropriate volume and flow rates, discrete samples can be obtained and recovered at the end of the experiment. A continuous flow rate is preferred for organ-chips to maintain consistent function and viability.

Prolonged periods of significant reduced flow or increased flow will influence organ-chip readouts, thus there is a need to ensure that a readout is changing due to an experimental variable and not a hardware malfunction. The 10-day minimum will cover 3 days it takes to go from loading biological components on CubeLab on earth to ISS with at least an additional 7 days for experimentation on ISS.

Develop and Validate Thermal Management System that is Compatible with CubeLab Size, Power and Communications Infrastructure.

In this example, show that hardware can maintain temperature of +/−0.5° C. for culture area, and +/−4° C. for reagent storage area for 10 days. Mammalian cells are sensitive to changes in temperature, so major deviations may be detrimental to viability.

The tolerance on temperature is based on the variability measured on standard tissue culture incubators routinely used for culturing organ-chips.

Integrate and Validate Thermal, Fluidic, and Organ-Chip Subsystems into CubeLab.

In this example, show that integrated system can pump reliably (+/−15% of set flow rate), valves operate and provide fixation reagents at appropriate volume and flow rates, discrete samples can be obtained and recovered at the end of the experiment, and culture temperature is stable (+/−0.5° C.) and reagent storage stable (+/−5° C.) for 10 days. To conduct an experiment on the ISS, the integrated hardware will be first tested so it can perform its functions in terrestrial tests.

Conduct First Space Experiment on BBB-Chip Comparing Hypergravity, Microgravity, and Terrestrial Gravity Conditions.

In this example, show an experiment that runs without hardware malfunctions (defined in Example #4, and recorded throughout experiment using on-board sensors for temperature and operating state of pumps and valves) and data are collected throughout experiment. Samples (frozen effluent, frozen cell lysate, and fixed chips) are collected upon return to earth and able to be analyzed. The hardware should run without flaws to accurately determine if BBB-chip results are due to space variables.

Iterate Space Hardware Based on Learnings from First Flight

In this example, success will be dependent on the design iteration (if any) require changes. Issues may arise during the first flight that will warrant changes to the design of the space hardware for the second flight. These issues may be addressed so long as doing so does not influence the capability to compare data between the first and second flights.

Feasibility Study of Effect of Space Stressors on BBB-Chip on Earth.

In this example, show terrestrial studies can be conducted with space-like variables of hydrostatic pressure and hypoxia. To allow us to decouple the effects of different space variables Development and Characterization of Inflamed BBB-Chip in Space.

In this example, show inflamed BBB-Chip runs as described in Example #6 and endpoints are in the same range as upon experimentation on earth. Deviation in the endpoints are contemplated for further evaluation to elucidate the underlying mechanisms, i.e. specific space parameters) implicated.

Exposure of the BBB-Chip to inflammatory stressors may unmask the impact of specific space-induced stressors, that could be missed in normal states due to the ability of the cells to adapt to mild stressors, particularly when applied for limited time period.

Model Validation

In this example, quantify the extent to which the model developed can recapitulate the BBB behavior based on the results of experiments to be performed on earth under a single space stressor condition, i.e. hypoxia, hypergravity, or absence of hydrostatic pressure, as described in Aim3a.

This is necessary to assess to what extent the collected data of the study suggest that simultaneous application of space stressors exert orthogonal or combined effects on the BBB cells under normal and inflammation conditions.

This is contemplated to allow the recalibration of the model to improve its predictive power under different gravity conditions.

Modify CubeLab for Space Stressor Terrestrial Experiments.

In this example, show-confirm with pressure sensors that experimental setups to simulate no hydrostatic forces maintain no hydrostatic pressure (+/−200 Pa). Confirm with oxygen sensors that hypoxic chips can maintain 0% (+0.5%) dissolved oxygen content for duration of treatment. To decouple the effect of different space stressors they should be decoupled in terrestrial experiments. The tolerances presented here are based on limitations on hardware design.

Conduct Second Space Experiment on BBB-Chip Inducing Inflammation and Attempting to Rescue with Dexamethasone.

In this example, show hardware runs without flaws to accurately determine if BBB-chip results are due to space variables.

Flight Certify Space Hardware and Other Components.

In some embodiments, hardware and systems described herein, are contemplated for use under flight conditions. In some embodiments, cells are grown or maintained under flight conditions in order to determine whether modifications are necessary for successful completion of experiments.

Low Temperature Storage.

Temperatures encountered over the course of spaceflight, i.e. takeoff through landing, and aboard ISS, include low temperature conditions, e.g. $-80°$ C., for up to 12 weeks, or more, depending upon the length of space travel. Therefore, $-80°$ C. storage conditions are added to capabilities for $4°$ C. storage and transition temperatures, and sample temperatures of $37°$ C. onboard space craft and ISS. Samples on-chips are fixed, and/or lysed, then stored at $-80°$ C. Samples at $37°$ C. may be samples under incubation or during at least a part of the assay, readout. Reagents such as media, buffer, lysis buffer, fixative, etc., in addition to being stored at $4°$ C., also go through a $-80°$ C. time period, e.g., prior to landing.

Figure 23:
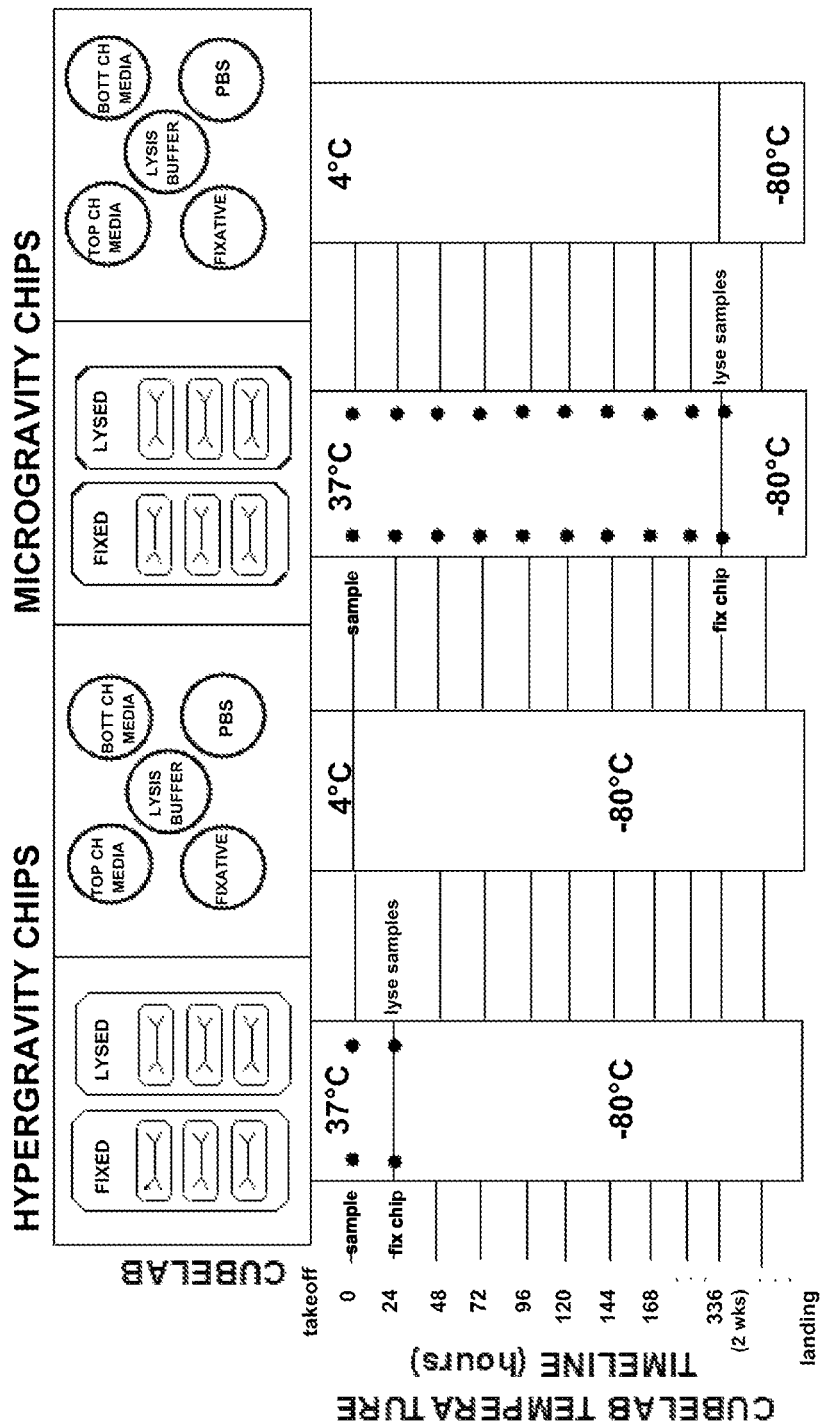
FIG. 23 Shows an exemplary thermal timeline showing temperatures of chips, reagents, and samples over the course of the flight.

Thus, in some embodiments, methods described herein, include low temperature conditions, e.g. $-80°$ C., as shown in exemplary FIG. 23.

X. Hypergravity Chips

FIG. 23 shows an exemplary thermal timeline showing temperatures of chips, reagents, and samples over the course of the flight. For another example, thermal design parameters are contemplated to include: Chip culture temperature ($37°$ C.); Media storage ($4°$ C.); Effluent storage ($4°$ C.); Chip storage, including unfixed chips, fixed chips, and lysed chips, etc., temperature during return to earth (between $4°$ C. or $-80°$ C.).

Thus, in some embodiments, Hypergravity Chips are fixed then stored after takeoff. In some embodiments, Microgravity Chips are sampled daily and fixed at >10 days. In some embodiments, Microgravity Chips are automatically sampled daily and fixed at >10 days. In some embodiments, chips frozen at $-80°$ C., are brought to $4°$ C. or ambient temperature, e.g. room temperature, then stained with antibodies.

Furthermore, fixation of cells on chips were modified due in part to long storage conditions at $-80°$ C. In part due to the long term storage at $-80°$ C., fixatives were tested for capabilities to retain antigen structure upon thawing for accurate staining of specific molecules, e.g. E-cadherin, showing little or no background staining.

Figure 24:
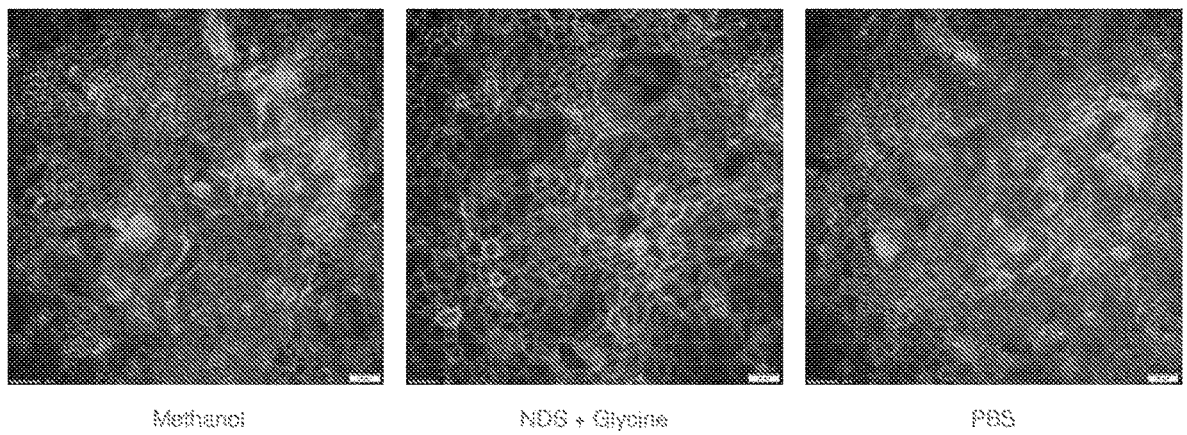
FIG. 24 Shows an exemplary staining of specific protein markers remains viable after methanol fixation and storage at −80° C. for 1 month. E-cadherin (green) staining of alveolar chips, HAECs. Fixatives compared were MeOH (left) NDS+Glycine (middle) and buffer control (right), i.e. PBS.

FIG. 24 shows an exemplary Staining of specific protein markers remains viable after methanol fixation and storage at $-80°$ C. for 1 month. E-cadherin (green) staining of alveolar chips, HAECs. Fixatives compared were MeOH (left) NDS+Glycine (middle) and buffer control (right), i.e. PBS.

Figure 25:
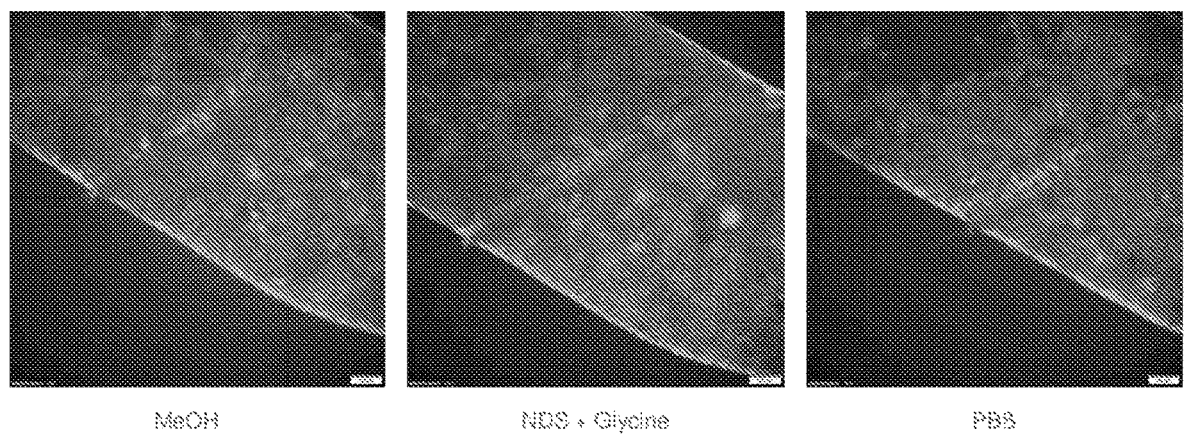
FIG. 25 Shows an exemplary minimal background staining or noise after methanol fixation and storage at −80° C. E-cadherin (green) staining of alveolar chips, HAECs. Fixatives compared were MeOH (left) NDS+Glycine (middle) and buffer control (right), i.e. PBS.
Figure 28A:
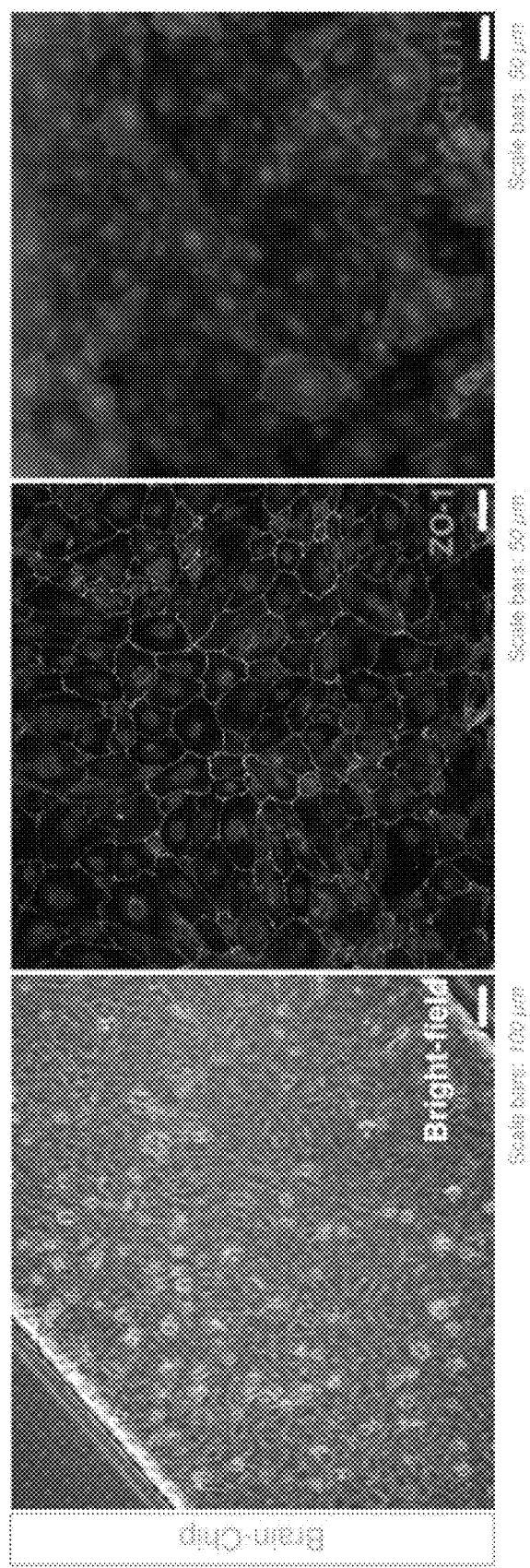
FIG. 28A-B Shows exemplary immunofluorescent micrographs from embodiments of a Brain-Chip and BBB chip showing cell morphology in the vascular channel. iPS-derived HBMECs demonstrate relevant tight junction proteins (e.g. Zonula occludens-1: ZO-1) and brain endothelium-specific marker (e.g. Glucose transporter 1: GLUT1). Nuclei are shown in blue. Bright-field Scale bar: 100 µm (left) ZO-1 Scale bars: 50 µm (middle) GLUT1 Scale bars: 50 µm (right).
Figure 28B:
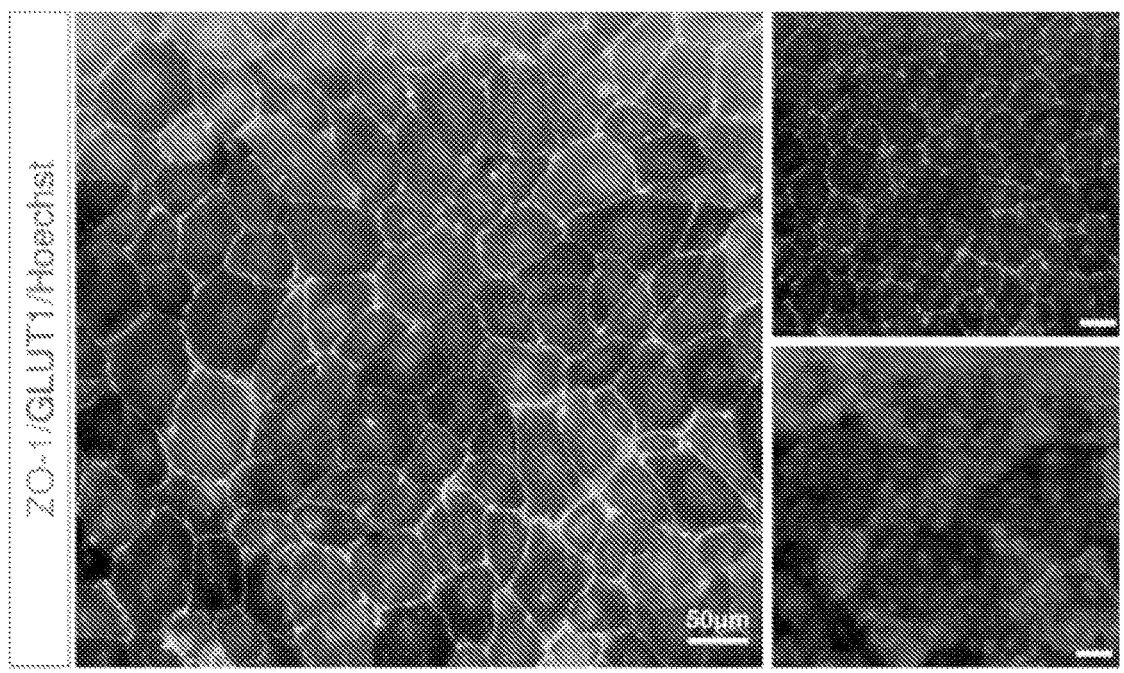
Figure 28C:
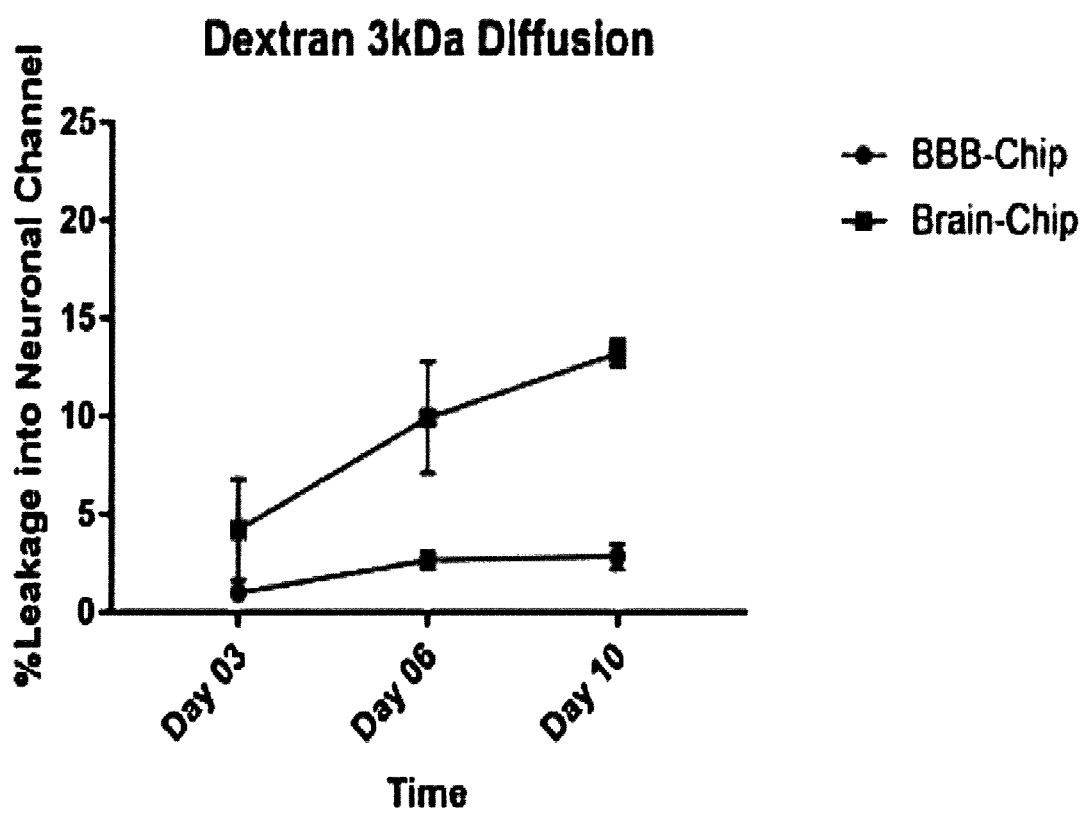
FIG. 28C Under optimized culture conditions, these iHBMECs maintain their function for a prolonged period of time and form an effective blood-brain barrier on-Chip, as measured by quantifying the diffusion of a small (3 kDa), fluorescently labeled Dextran molecule loaded into the vascular channel and under flow overnight.
Figure 29A:
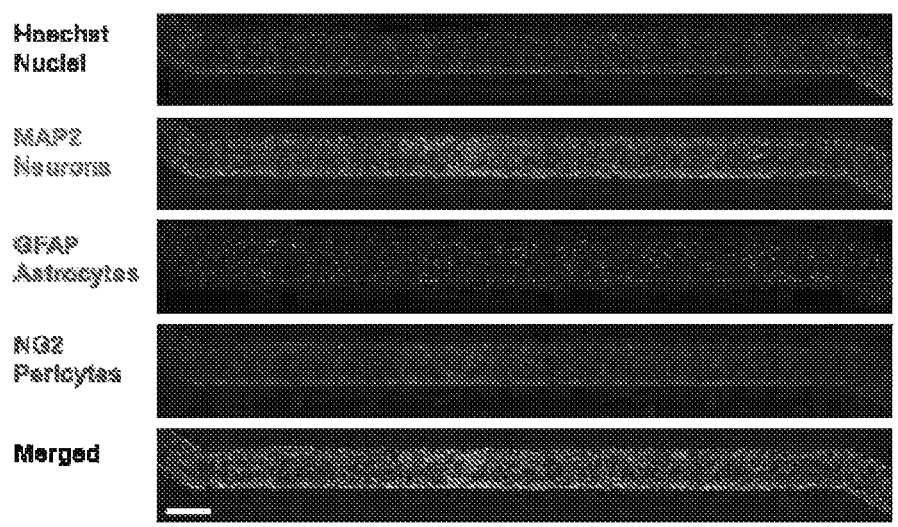
FIG. 29A-B Embodiments of the Neuronal Channel showing exemplary Cell Morphology. Cortical neurons, astrocytes and pericytes express cell-specific markers as shown in micrographs of the neural channel on the Brain-Chip. hPSC-derived neuronal cultures in direct contact with astrocytes and pericytes after 10 days of flow (i.e. under flowing fluids).
Figure 29B:
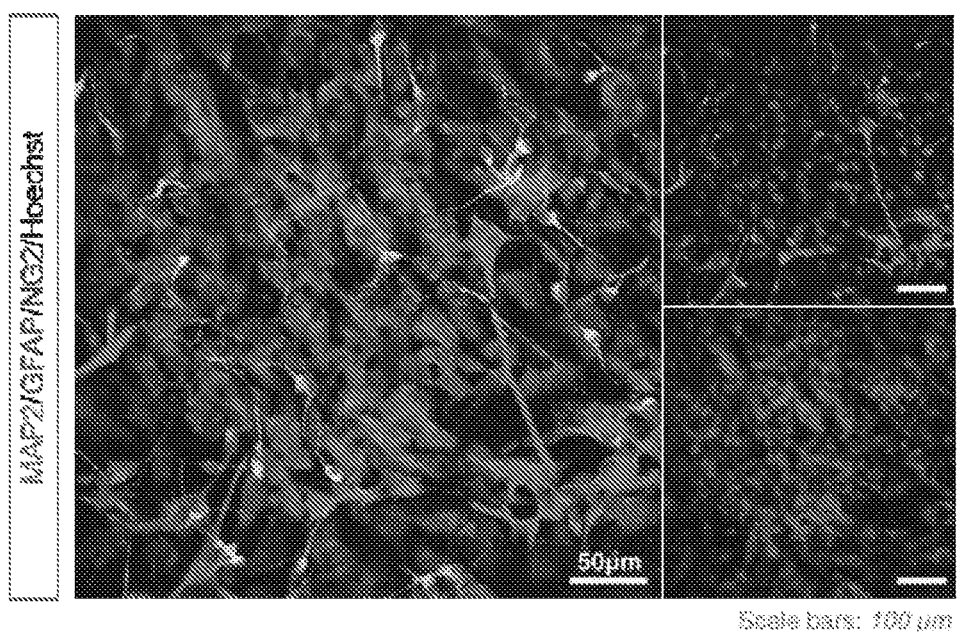
Figure 30A:
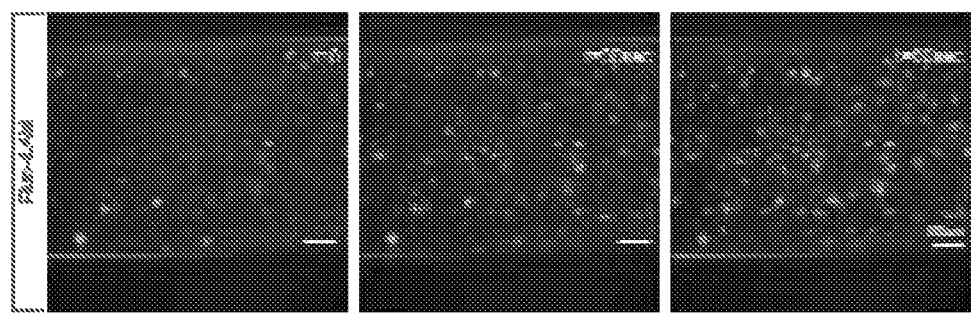
FIG. 30A-C Exemplary Effect of Vascular Flow on the Neuronal Activity. Vascular flow corresponds to an increase in neuronal activity as Functional Characterization of Human iPSC-derived Neurons on-Chip.
Figure 30B:
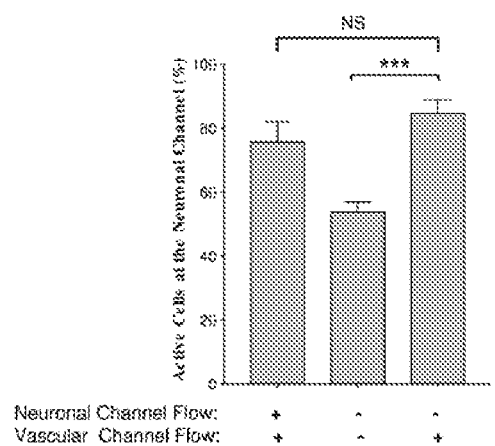
Figure 30C:
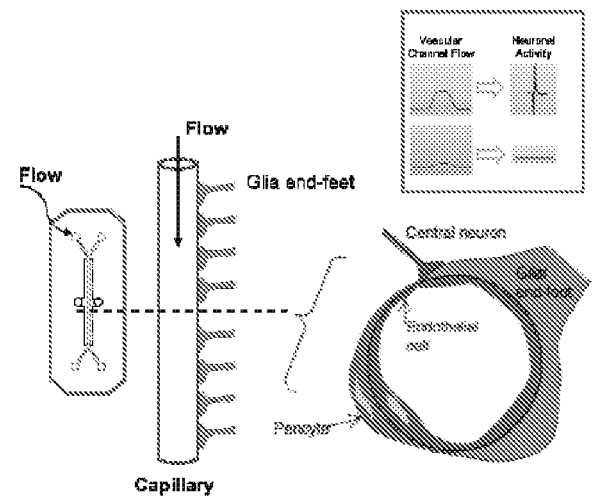
Figures 31A, 31B:
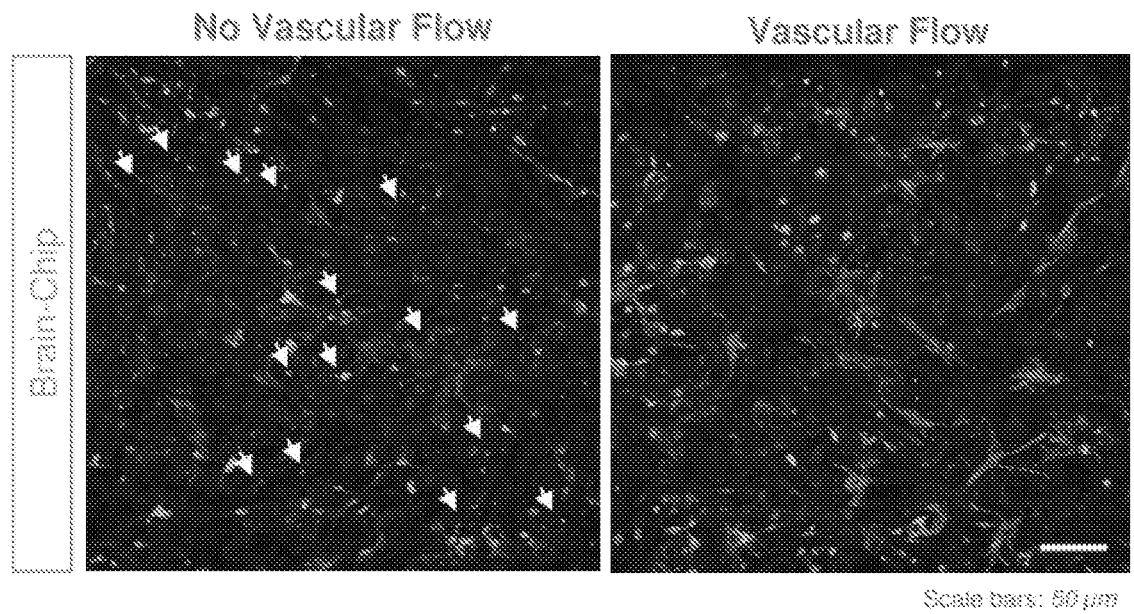
FIG. 31A-C Effect of Vascular Flow on Neuronal Cell Survival. Vascular flow corresponds to a decrease in apoptotic cell death in the neuronal channel. One embodiment of a Brain-Chip is shown with variables and stained with specific markers of neurons, glia and pericytes, localized with a marker of apoptosis (TUNEL-red).
Figure 31C:
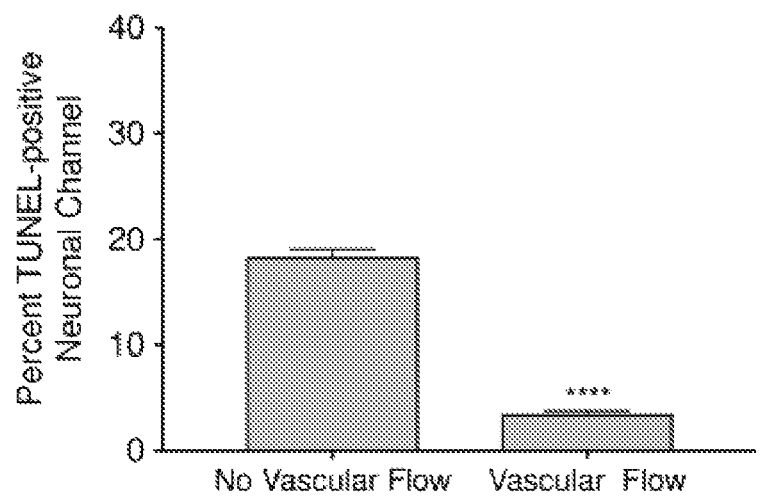
Figure 32A:
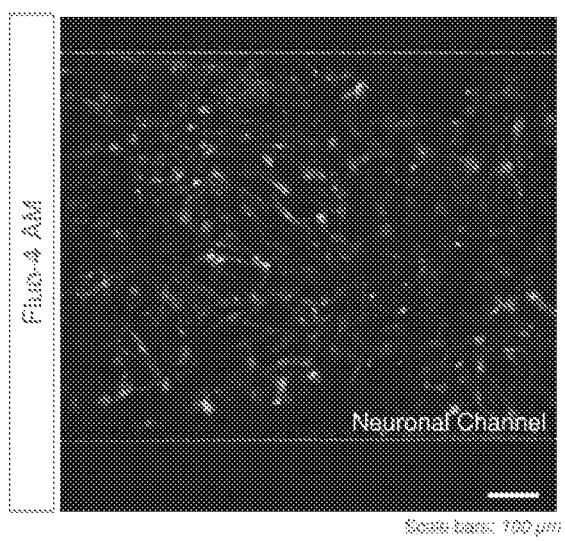
FIG. 32A-B One example of functional characterization of the human Brain-chip.
Figure 32B:
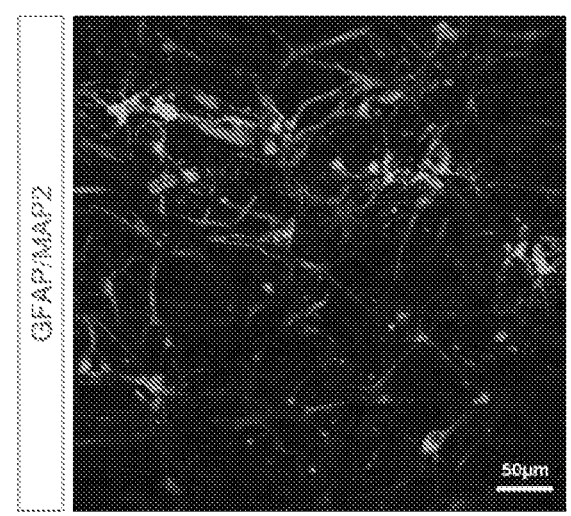
Figure 33:
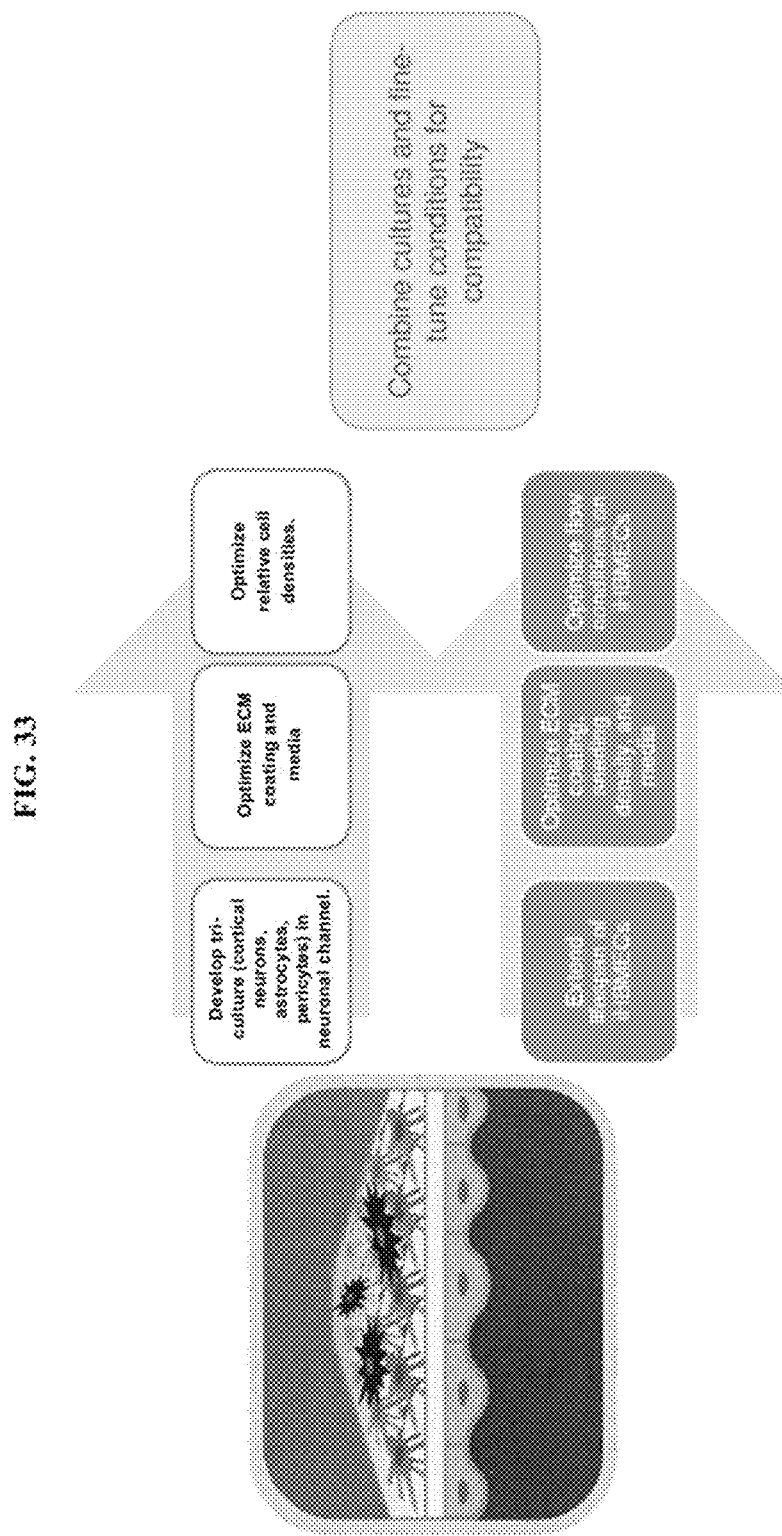
FIG. 33 Exemplary BBB-Chip Optimization Strategy. Optimize conditions in the neuronal channel: Develop triculture (cortical neurons, astrocytes, and pericytes in the neuronal channel); optimize ECM coating and media: optimize relative cell densities. Optimize conditions in the vascular channel: Extend lifespan of iHBMECs; continue to optimize ECM coating, seeding density, and media; optimize flow conditions on iHBMECs. Then combine cultures and fine-tune conditions for compatibility.

FIG. 25 shows an exemplary minimal Background staining or noise after methanol fixation and storage at $-80°$ C. E-cadherin (green) staining of alveolar chips, HAECs. Fixatives compared were MeOH (left) NDS+Glycine (middle) and buffer control (right), i.e. PBS.

Moreover, methods described herein were modified in part due to constraints of ISS. Therefore, fixation of chips were modified due in part to limitation of automation and cold storage options on ISS; Fluid recirculation was incorporated to allow for physiological shear stress without requiring large fluidic reservoirs; Space hardware is contemplated to have new materials and components that may influence biological function. For comparisons, terrestrial parallel methods are modified accordingly.

XI. Recirculation

When using recirculating culture, e.g. for experiments as shown herein, a measured volume of culture media is recirculated through channels of the microfluidic chips, also referred to as recirculation through chips. Whereas in comparison to non-recirculating perfusion, i.e. single pass, the culture media is perfused through the system, including through the microchannels, and directed directly to waste or at least a portion directed to effluent sample collection conduits, e.g. FIG. 11. Thus, in non-recirculating culture, secreted factors and waste products generated by cells and tissues on chips are permanently removed from the microchannels. Unlike single pass perfusion, secreted factors and waste products in recirculating cultures are diluted into the total culture media volume of a media reservoir (although in some embodiments a second reservoir for recirculation is used instead) and recirculated back to the cells in the microchannels. In some embodiments, effluent fluid from one microchannel is recirculated. In some embodiments, effluent fluid from two or more microchannels is recirculated. In some embodiments, effluent fluid from a microchannel is recirculated into the same microchannel it was collected from, e.g. the upper channel effluent is recirculated back to the upper channel of the same chip. In some embodiments, effluent fluid from one microchannel is recirculated into another microchannel, e.g. the upper channel effluent is recirculated into the upper channel of another chip. Similarly for the lower channel, or additional channels. In some embodiments, effluent fluid from a microchannel is recirculated into a different microchannel, e.g. the upper channel effluent is recirculated into a lower channel of the same chip, or into a different chip.

A. Purposes of Recirculation.

For certain embodiments, recirculation of fluids, (e.g. all of it, a portion of it, etc.) including but not limited to nutrient media, provides advantages over a single pass of fluid through microfluidic channels of chips.

Some advantages over non-recirculating perfusion, include but are not limited to: using lower amounts of fluid, such as media, i.e. recirculation of fluid lowers fluid consumption, e.g. from reservoirs, at least ⅕ less or greater reductions in amounts; while recirculation of fluids is contemplated to result in the increase in concentration of low concentrations of biologicals, e.g. cellular metabolites, to a high enough concentration for detection, such as quantified/measured; etc. Recirculation may provide biological advantages, such that cells secrete or provide additional molecules that may beneficially alter population dynamics or cell functions, which in some embodiments, recirculation minimizes biological sample dilution thus allowing for accumulation of biologicals including but not limited to: cellular metabolites, including autocrine signaling factors; drug metabolism responses, such as drug metabolites produced by liver chips, i.e. hepatocytes; increasing protein production by cells, such as liver albumin production, discovered as described herein; control of shear where high shear=a large amount of media for single pass, unlike recirculation, allows for independent control of mass transport and shear stress, etc.

Further, additional advantages are related to biological relevance, including but not limited to: providing a method for mimicking blood recirculation in the body; creating a more physiologically relevant microenvironment including allowing for the accumulation of cell signaling factors (autocrine signaling), cellular waste compounds, and other cellular factors; and allows for creation of physiologically relevant fluidic shear via a higher flow rate, without using a high, i.e. large volume of media, including technically unobtainable amounts of media volume to obtain a desired fluidic shear rate for a single pass system.

B. Discontinuous Recirculation.

In some embodiments including discontinuous recirculation, fluid, e.g. media, is sent (fluidically directed) through a microfluidic chip into an outlet reservoir. At a designated time-point, used media from the outlet reservoir is placed into the inlet reservoir, manually, by fluidic connection, by automatic fluidic connections, for pumping through the chip as recirculated fluid. In some embodiments, transfer of media from the outlet to the inlet reservoir (such as in a pod) can be done by means of a shortcut channel connecting the two reservoirs. In this embodiment, the shortcut channel contains a valve that is closed during normal operation, but is open during the media transfer step. In a pressure driven system the valve can be a one-way check valve as depicted by arrow 137 in FIG. 46A. In a different implementation media can be transferred from one reservoir to another by means of a liquid handling robot. One benefit of discontinuous recirculation is that flow through the chip may be maintained in the same direction, similar to flow of fluids through vasculature in the human body. In some embodiments, a uni-directional flow results in cells' aligning their attachment integrins in the direction of flow such that changing flow directions might cause changes in cells that are not desired for particular types of experiments, such a flowing immune cells over endothelial cells where alignment of integrins may be involved in cell attachment.

In some embodiments, an additional "secondary reservoir" as discussed herein, may be added between the main, e.g., input, media reservoir and the chip so that media that is pulled through shortcut channel is held in the secondary reservoir and does not enter the main reservoir. The use of a secondary reservoir for fluids entering microfluidic chips has at least one advantage of not diluting effluent fluid, e.g. containing generated cell-signaling compounds, into the main reservoir. Additional advantages include the use of a certain configuration of valves and fluidic connections that would direct recirculated fluid back to designated chips, while the main reservoir would supply unused fluid for the same chip, when desired, with valves bypassing the secondary reservoir, in addition to having valves allowing specific amounts of unused fluid into the secondary reservoir; and would allow unused fluid for use with more than one microfluidic chip by limiting the use of the recirculated fluid to specific chips. Thus, bypassing the main reservoir, avoids excess dilution of, and control of the amounts of delivery of autocrine signals, drug doses, or other soluble factors from the recirculated fluid.

C. Bi-Direction Recirculation.

Bi-direction recirculation, in contrast to single direction recirculation as described for discontinuous recirculation, refers to media is pumped through the chip. In some embodiments, such as when you media is depleted in a reservoir, the pump direction is switched such that media is now pumped from the outlet port back to the inlet port via the chip fluidics (as opposed to a shortcut channel). In some embodiments, the pump direction is switched such that media exciting the outlet port is pumped back through the chip microchannels towards the inlet port via the chip fluidics, then the pump direction is switched again to pump fluid back through the chip.

D. Replenishment

Discontinuous recirculation may also be asymmetric, meaning that less media is pulled from the outlet to the inlet reservoir during a recirculation step. As a result, some amount of fresh (unused) media may be introduced in the next infusion through the chip. Therefore in some embodiments, replenishment and recirculation may be used to independently control shear stress and mass transport within chip.

XII. BBB-Chip Validation

The challenge of providing appropriate dissolved oxygen transport should be significantly easier for the BBB-chip as appropriate conditions for other metabolically active cells are known. However, further methods are contemplated to alter the surface of the PDMS to prevent drug absorption but retain the flexibility and oxygen permeability of the material. See, non-drug absorbing devices and methods described herein.

The plan for introducing low compound absorbing materials into the space hardware is, in part, outlined here: Any new components custom designed for this project (i.e. fluidic manifold, sample tubing, reservoirs) will utilize materials identified as having low compound absorption properties (Table 2, materials referred to as Flex 1, Flex 2, and Rigid). Off-the-shelf components will also be selected for proper material compatibility wherever possible. Initial studies will continue to utilize a well-established PDMS chip for the reliability, reproducibility, and robustness considerations outlined previously. Additionally, the BBB-chip will be challenged in the phase by IL-1beta, a protein whose size should not allow for absorption. Alternative inflammation inducer to be used, would be TNF alpha, a protein of similar size to IL1beta; For the UH3 phase the TEER functionality will be engineered into the BBB-chip. Thus, alternative materials, such as COP, may be used for construction/manufacture of this new chip when candidate drug strongly absorbs into the PDMS material. For drugs that moderately absorb into the PDMS materials, mathematically models may be used to account for the defined loss of compound. 3D COMSOL models were designed that take into account the geometry of microfluidic chips, as described herein, the connective mass transport due to flow, and the diffusion of compounds through the chip materials and liquid, see, FIG. 12.

In some embodiments, TEER measurements will be taken while monitoring the state of pumps, valves, temperature, and acceleration during experiments, for one example, by remote monitoring.

If necessary, one or more of: a fluidic architecture designed for microgravity, a fluidic system for sampling and sample collection by remote monitoring, and designs for compactness, etc. may be modified for compatibility to the limited confinements of a Cube. For one example of increasing compactness, input reservoirs may be grouped, and there may be an option of sending effluent output to the sampling system or to a common waste reservoir (to save on occupancy space).

A. Data Shows that Viability of the BBB-On-Chip is Extended Beyond One Week, i.e. Beyond 7 Days.

Data shows cells in a BBB-chip survive beyond 7 days, occasionally up to 10-12 days. Thus, in some embodiments, developing methods for extended survival are contemplated by optimization of the differentiation of the iPS-derived endothelial cells.

PDMS (silicon elastomer) membrane with 7 um pores allows for cell-cell (astrocytes/HBMECs) interaction beyond secreted factors alone. TEER was integrated into Organs-on-chips and subsequent analyzed (Odijk et al, 2015, Lab Chip).

While most of the dextran is confined within the vascular compartment, others report about ⅙ of the dextran diffuses into the brain compartment of their chip. In this system, the fluorescent signal of the 4 Kda-Dextran is barely detected in the brain compartment. In fact just 0.5-1% of the total dextran is actually detected in the brain compartment, indicating the model described herein is much closer to the in vivo condition, i.e. physiology of a human brain.

Biologically Validate Integrated Space Hardware with BBB-Chip Culture for 7-Days.

In this example, show that a BBB-Chip with neurons included, demonstrated cell survival—at least 80% live cells throughout the chip (measured by tiled imaging and quantification of total fluorescence signal) and maturation as per IHC with specific markers (ZO1, Glut1, GFAP, alphaSMA and beta III Tubulin, and demonstrated barrier function defined as; less than 10% leakage of Dextran 4 kDa, less than 20% IgG or Alb leakage individually as normalized to basal media contents, and at least 40% transport of Transferrin.

B. Establishment of BBB-Chip with Human iPS-Derived Endothelial Cells, Primary Pericytes and Astrocytes and Confirmation of Physiological, Limited Permeability and Barrier Integrity Using Fluorescent Dextran and Transport of IgG.

Neurons and astrocytes will be co-stained with the nuclear dye Hoechst as a read-out for cell viability. For the live/dead cell staining assay acceptance criteria require at least 80% alive cells in any field of view—2 independent blinded observers will quantify the entire chip through tiled imaging. Since these assays do not need to sacrifice chips, in some embodiments, both cell viability and organ-function may be monitored every other day for 2 weeks.

For barrier characterization baselines for use may include: (a) less than 10% leakage of Dextran 4 kDa, and less than 20% IgG or Alb leakage individually as normalized to basal media contents and/or (b) at least 40% transport of Transferrin, immunohistochemistry (IHC) will be performed for a qualitative, rather than quantitative analysis of the barrier by staining for ZO-1, VE-Cadherin, Claudin-5, PECAM-1, typical markers used for assessing epithelial tight junction formation and integrity of the microvascular endothelial layer. The neuronal population will be characterized by morphological criteria (axon formation, neurite outgrowth measurements) and immunocytochemistry (staining with β-III Tubulin as a neuron-specific marker and for specific identity characterization such as with antibodies for GABA, Acetylcholine, etc.) and assessment of voltage dependent ion channels through Cn2+ imaging. The intracellular calcium concentration in the cytoplasm should be ~50-100 nM and rise following stimulation (Vehicle (external solution-in mM: NaCl 140, KCl 5, MgCl2 2, HEPES 10, D-glucose 10, CaCl20 and KCl (45 or 85 mM) or glutamate (200 μM) solutions will be applied to test the calcium events in both neuron and astrocyte cultures.) to levels ten times higher than base line (Berridge et al., 2000).

Astrocytes should be confirmed to grow in a controlled manner, i.e. without overgrowing the neural cultures in order to maintain the in vivo representative cellular composition of between 1:8 to 1:2 astrocyte:neuron (1:4 has been described for astrocytes to neural precursor cells, Kuijlaars J, Scientific Reports 6, 2016), determined during plating and at frequent intervals (every 2-3 days) over the culture period. Aside from their unique morphology, astrocytes will be distinguished by their expression of the intermediate filament GFAP.

To specifically study apoptosis in neurons and glia in co-culture, specific biomarkers of neurons and glia, m part as described above, may be stained in order to identify localization with a marker of apoptosis, such as terminal deoxynucleotidyl transferase-based dUTP nick-end labeling (TUNEL).

In some embodiments, demonstration of a tight barrier with cells involved in this organ in humans, at the right topology and with sustained functionality for a minimum of 10 days, is desired as a goal of this study.

C. Development of Inflamed BBB-Chip.

In this example, show demonstration of dose- and time-dependent increased permeability of the BBB-Chip following exposure to TNF alpha or IL1 beta.

Readouts will include disruption of tight junctions and loss of the associated barrier function demonstrated by increased permeability (As in Example SI above: Greater than 10% Dextran leakage; Greater than 20% IgG and/or Alb leakage; Greater than 20% increase in "gap areas" as compared to control when imaging cell-cell junctions), neuronal death/apoptosis as described in Example 1.

Show statistically significant changes in specific markers demonstrating exposure of cortical neurons to stressors as assessed by live/dead cells assay and IHC, where appropriate, with specific markers. Before studying inflammation in space experiments, terrestrial experiments using contemplated space systems may be developed and validated.

D. Data Analysis of Earth BBB-Chip Experiments.

In this example, show a successful analysis will result in the identification and rank ordering of the most informative variables (features) that can discriminate reliably between biological conditions (normal vs. inflamed state) as well as between environmental state (earth vs space gravity vs hypergravity conditions) for a given biological condition. This analysis will consider variables measured in the heterogeneous data sources (genomics, proteomics, biomarkers etc.) collected based on BBB-chip experiments to be conducted on the earth before the space flights (as detailed in Aim1d) This analysis is necessary to establish a baseline for comparing against same experimental conditions in space and understand what parameters are affected and to what extent by the changes in gravity conditions.

Establishing this baseline is a prerequisite for developing and validating models for the space effects on endpoints.

E. Development and Calibration of Models with BBB-Chip, First Flight Data.

Analysis of first flight data and identification of differences of BBB-chip behavior as compared to same earth experiments (Example #7) for the control and inflammation conditions. Parsimonious modeling of how the observed changes depend on the altered gravity conditions.

First flight data analysis and comparison to the earth results analysis under same conditions is required to build a model that captures the essential differences of BBB-chip behavior in space. Parsimonious modeling is known to increase the predictive value of the models.

Integrate TEER Functionality into BBB-Chip and CubeLab.

In this example, show that TEER chips and potentiostat can give steady readings (+/−100 ohms×cm$^2$) over 7 days in a CubeLab without leaking.

A typical inflammation challenge in a BBB-chip will change the TEER reading on the order of 1000 ohms×cm$^2$. A tolerance of +/−100 ohms×cm$^2$ on a blank chip (hardware variability) will allow us to have one order of magnitude greater signal to noise ratio in this readout of tissue barrier integrity.

F. Cell Viability: Increasing Flow Improves Vascular Viability.

In this example, cell viability was measured under at least 4 four types of flow conditions.

Exemplary experimental design. Condition 1: Chips at D2 (day 2): fluid flowed at 60 ul/hr and maintained for 4 or 10 days. (Control 1). Condition 2: Chips at D2: fluid flowed at 60 ul/hr for 48 hours; then increased to 600 ul/hr for 48 hrs. Condition 3; Chips at D2: fluid flowed at 60 ul/hr for 48 hrs; increased to 600 ul/hr for 48 hrs; then increased to 900 ul/hr for 4 days. Condition 4: Chips at D2: fluid flowed at 1 ml/hr for 24 hours. In some experiments, effluent fluid from at least one channel was recirculated; see descriptions of materials and methods for recirculation of effluent as described herein.

Figure 35:
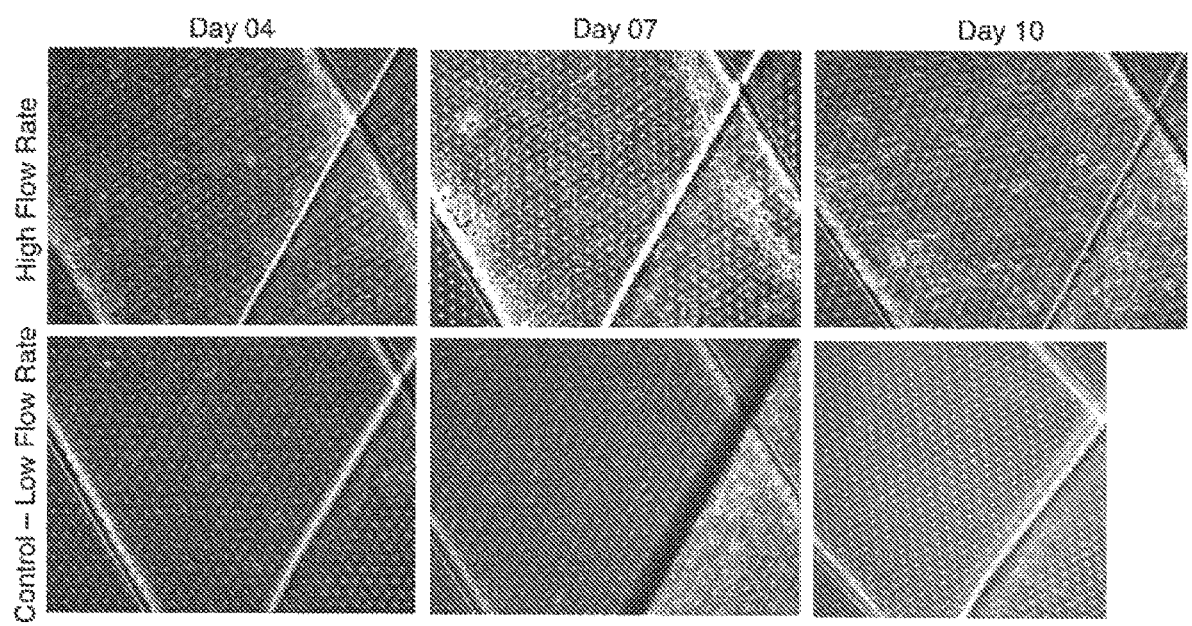
FIG. 35 Exemplary Morphology (brightfield) comparing High flow rate (600-900 ul/hr) and recirculation in upper panels, compared to low flow rate controls (no flow) in lower panels for maintaining iHBMEC morphology and viability in the vascular channel. Day 04; Day 07; and Day 10 images showing numerous cells on Day 10 under high flow compared to a few cells by Day 10 under low flow.

FIG. 35 Exemplary Morphology (bright-field) comparing High flow rate (600-900 ul/hr) and recirculation in upper panels, compared to low flow rate/controls (no flow) in lower panels for maintaining iHBMEC morphology and viability in the vascular channel. Day 04; Day 07; and Day 10 images showing numerous cells on Day 10 under high flow compared to a few cells by Day 10 under low flow.

Figure 36:
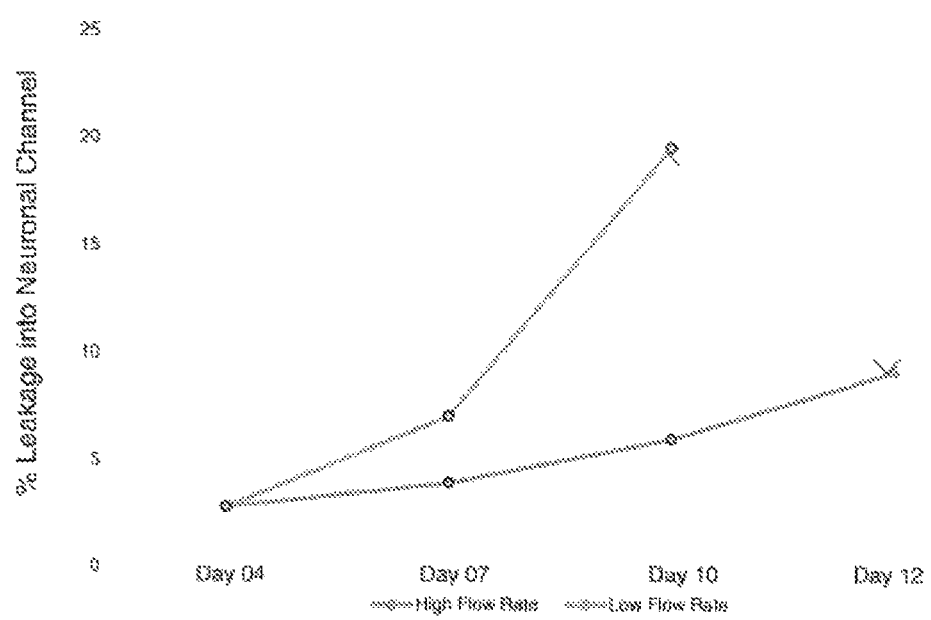
FIG. 36 Exemplary graph demonstrating barrier function using 3 kDa Dextran. High flow rate (600-900 ul/hr) and recirculation facilitates maintenance of barrier function in the BBB-Chip as shown by a lower percent leakage of Dextran into the neuronal channel (lower line) over time, Day 4-Day 10.
Figures 37A, 37B, 37C:
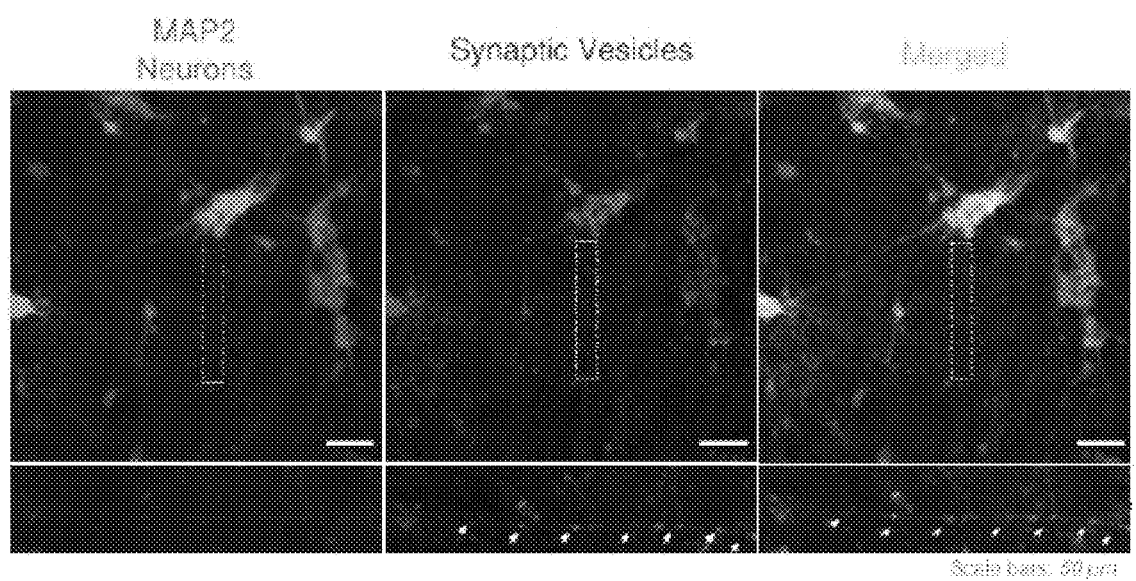
FIG. 37A-C Labeling the Presynaptic Terminals. Synaptic vesicles can be visualized in the axon terminals of glutamatergic neurons on the Brain-Chip.

Therefore it was discovered that without high levels of flow in the vascular channel there are few to zero neuronal cells living in the neuronal channel by Day 10 of incubation. See, FIG. 36. Therefore, an exemplary protocol was designed as follows: Start cultures in microfluidic chips by adding endothelial cells to the vascular channel allowing them to attach to the bottom, top and sides of the channel without using flow or by using low flow up to 60 ul/hr. Then begin increasing flow on day 4, alternatively day 3 or day 5, from 60 ul/hr up to 600 ul/hr, then up to 900 ul/hr. In fact, an increase in viability, i.e. active cells, in the neuronal channel are shown under high flow, see, FIG. 36A. Further, by recirculating media, i.e. a recirculating culture, enhances this effect.

In recirculating culture, a given volume of effluent culture media (e.g. all of it, a portion of it, etc.) is recirculated, whereas in non-recirculating perfusion, the culture media is perfused through the system and sent to directly to waste, in some embodiments. Secreted factors and waste products in recirculating cultures are recirculated back to the cells, whereas in non-recirculating culture, the secreted factors and waste products are permanently removed.

G. Sampling Effluent and Readouts on Effluent Sampling.

The invention further relates to samples obtained from effluent, i.e. sampling the fluid exiting a microfluidic device as described herein. Thus, the microfluidic devices further comprises a sampling conduit for collecting (or removing) samples of effluent fluids, where effluent fluids may or may not include detached cells, secreted proteins and the like, in one embodiment, the microfluidic device comprises a top channel and bottom channel separated by a membrane. In some embodiments, effluent may be collected from media leaving the top channel. In some embodiments, effluent may be collected from media leaving the bottom channel. In some embodiments, effluent sampling is by hand. In some embodiments, the invention comprises an effluent sampling system. See, FIG. 11 for an illustration of one embodiment showing sampling conduits in fluidic communication with microfluidic devices for sample collections (and testing).

Samples may be collected over time, for example, different time-points separated by seconds, up to minutes, up to hours, up to days apart depending upon the desired readout for an experiment. Samples may be labeled in part as sample t1, sample t2, etc, see FIG. 11. One embodiment for separating sequential sample collection is to induce an air plug in between the desired sample amounts. Sample amounts may be in nanoliters, ul up to ml in amounts. One embodiment for sampling is based on the ICE CORE approach. For example, in one embodiment, sampling is continuous sampling (i.e. no gaps to reduce or eliminate mixing between samples). For microfluidics mixing is limited by laminar flow, and diffusive mixing occurs. In one embodiment, sampling is discontinuous (use gaps to avoid mixing), such as a. Use AIR (T-junction to introduce air, could also use other immiscible fluids); and/or b. Use Mass Spec tubing (hydrophilic capillary tubes, hydrophilic can also work, however an increase in length of an air gap will be used to ensure liquid films from sample plugs do not contaminate neighboring plugs.

Exemplary readouts on effluent sampling will include readouts described herein, and including but not limited to: RNA analysis; immunohistochemistry; barrier function; inflammatory cytokine signals; transepithelial/transendothelial electric resistance (TEER) (associated with UH3), etc. In particular, UG3 Analysis will compare Brain-Chip phenotypes between hypergravity, microgravity, and terrestrial conditions in addition to response to compounds, such as drugs, for reversing undesirable responses to a change in conditions. Analysis will also compare the inflammation response of the Brain-Chip between terrestrial and space conditions, as well as its rescue by anti-inflammatory drugs.

Drug Testing.

Microfluidic devices described herein may be used for testing compounds including but not limited to compounds know to affect in vivo neuronal activity, in vitro neuronal activity, neuronal signaling inhibitors, drugs, drug candidates, etc. In some embodiments, a compound is a glutamateric signaling inhibiting compound.

Thus, in some embodiments, a compound is added to a fluid for flowing through a microfluidic device described herein. A fluid for use with a compound includes but is not limited to media intended for the vascular channel (bottom), media intended for the neuronal channel, (top), phosphate buffered saline (PBS), etc. In some embodiments, a reservoir containing a fluid comprising a compound for testing is added to the microfluidic system (assembly). Further, said reservoir may be connected to a valve for controlling the amount of fluid flowing in a conduit between the reservoir and the channel for entering the microfluidic channel. The valve may be controlled automatically or manually. Even further, a pump may be connected to control the flow of fluid containing compound into the microchannels.

Pharmacological Targeting of the Glutamatergic Neurons On-Chip.

In this example, the ability to modulate neuronal function with known neurotransmitters receptor antagonists was demonstrated. Specifically, NMDA and AMPA receptor inhibition (DAP5 and CNQX respectively) reduced the percentage of active neurons by blocking the influx of calcium in glutamatergic neurons on the Brain-Chip.

Figures 38A, 38B:
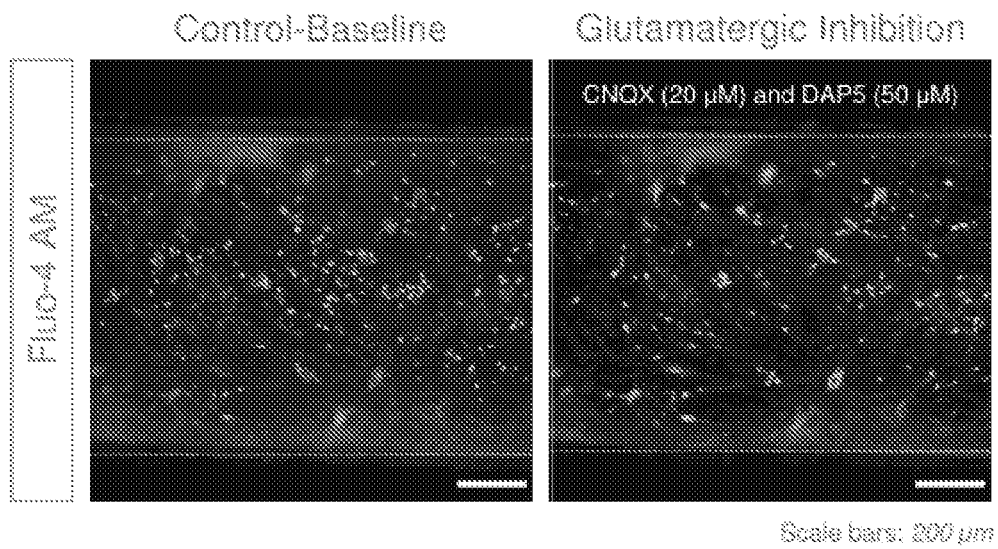
FIG. 38A-C Pharmacological Targeting of the Glutamatergic Neurons in the Brain-Chip. Combination of NMDA and AMPA (α-amino-3-hydroxy-5-methyl-4-isoxazolepropionic acid) receptor inhibition blocks the influx of calcium in glutamatergic neurons on the Brain-Chip as demonstrated using a florescent Fluo-4 AM (green). Exemplary modulation of neuronal function using known neurotransmitters receptor antagonists are shown here.
Figure 38C:
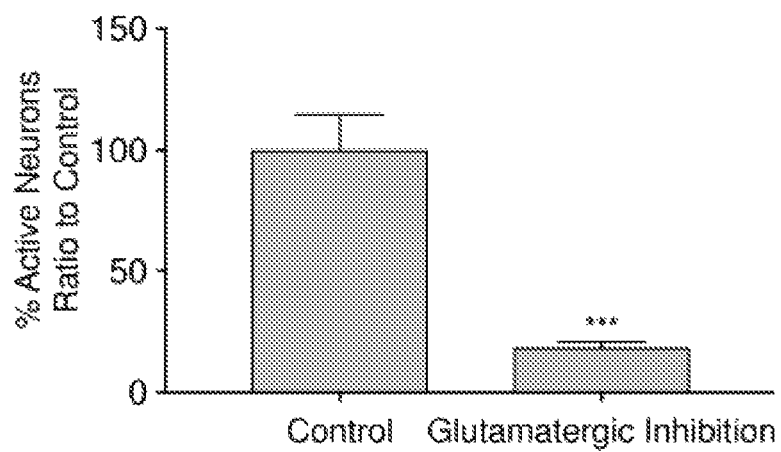
Figure 39A:
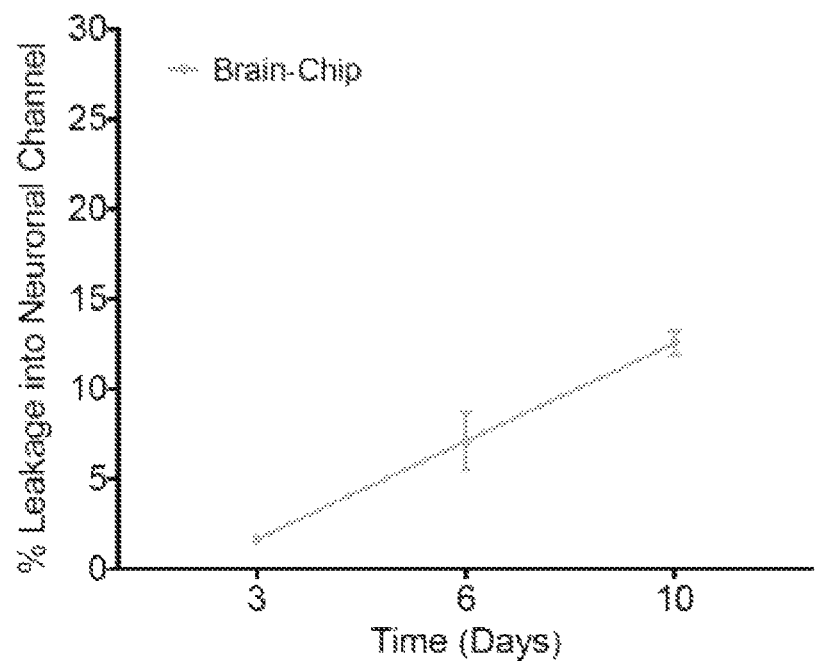
FIG. 39A-B Barrier Function on the Brain-Chip. Low permeability, i.e. a loss of permeability, across the BBB over time, FIG. 39A. Low permeability across the BBB corresponds to reduced expression of tissue-specific tight junction proteins, e.g. ZO-1 (yellow) in the iPS-derived HBMECs, FIG. 39B. Scale bar=50 μm.
Figure 39B:
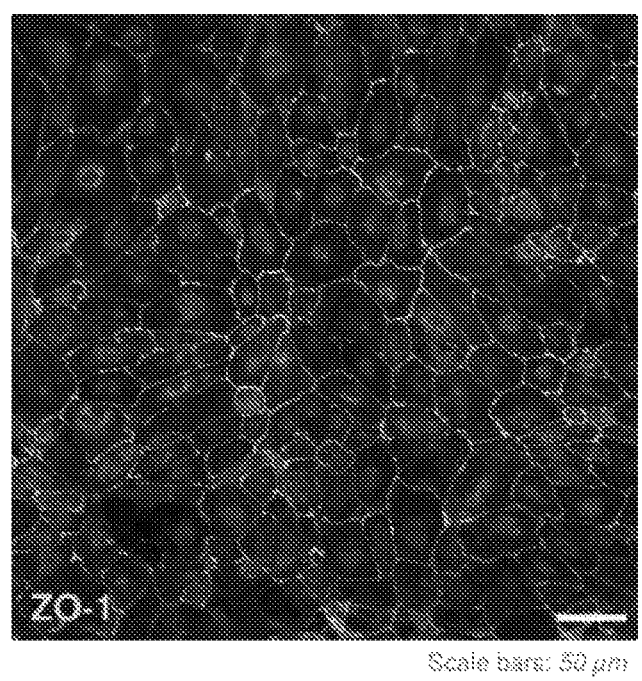
Figure 40:
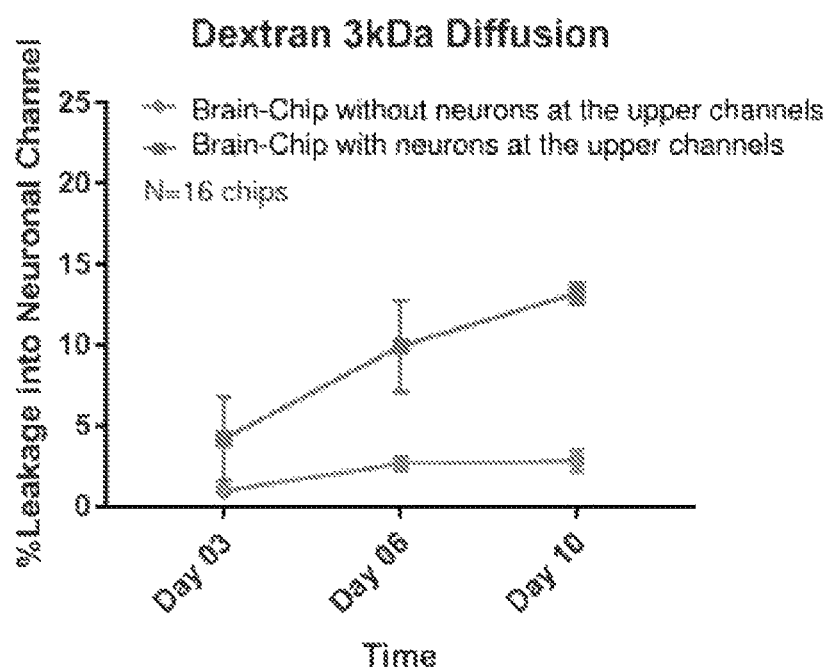
FIG. 40 Comparison of barrier functions between Brain chips with and without neurons in the upper channel. Low permeability across the BBB on Chip in line with the expression of specific tight junction proteins. BBB function is associated with neurodegeneration and onset of dementia FIG. 41A-B BBB-Chip: Selective Barrier Function. BBB-Chip shows physiologically relevant diffusion of typical blood biomarkers.
Figure 41A:
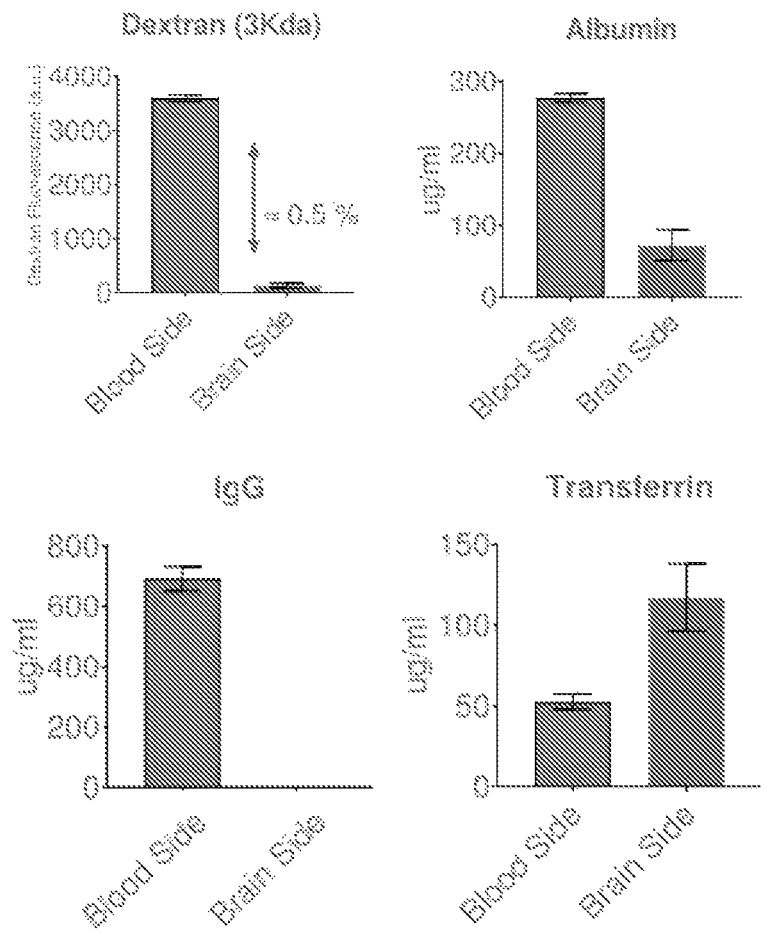
FIG. 41A Diffusion of markers from the blood side (vasculature channel) to Brain side (neuronal channel) are shown for Dextran—3 Kda; Albumin and IgG) in comparison to selective transport of transferrin.
Figure 41B:
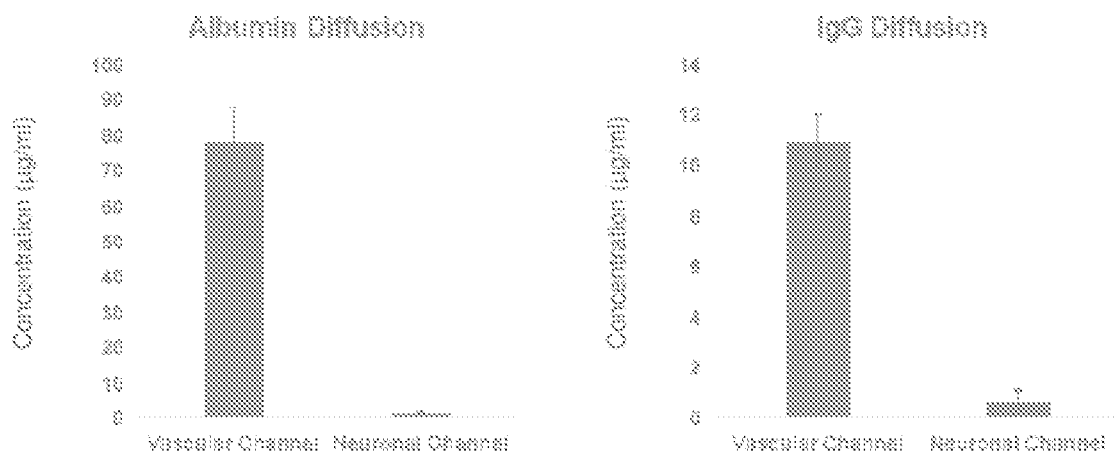
FIG. 41B Shows similar experiments where lower amounts of markers shown, albumin and IgG, were added to the vascular channel.
Figure 42:
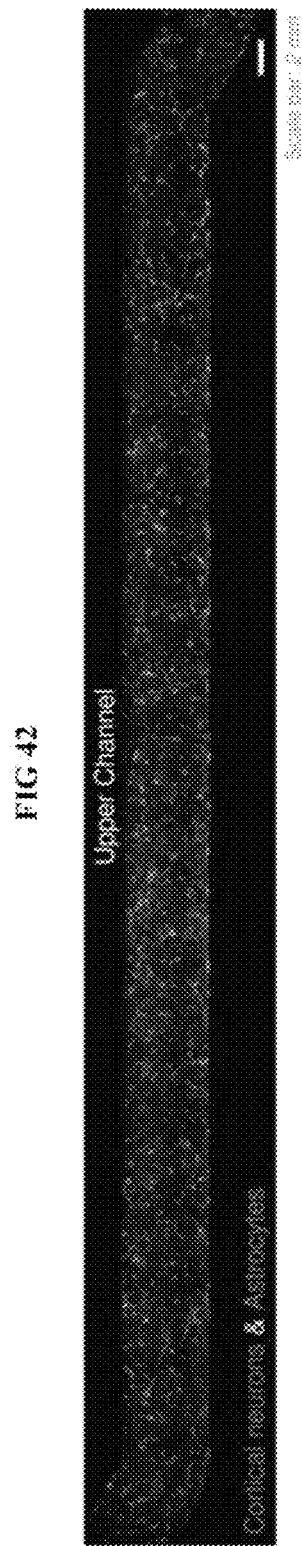
FIG. 42 shows exemplary low power micrograph of cells in upper Channel. Cortical neurons (green) and Astrocytes (magenta). Scale bar=2 mm.

FIG. 38A-C Pharmacological Targeting of the Glutamatergic Neurons in the Brain-Chip. Combination of NMDA and AMPA (α-amino-3-hydroxy-5-methyl-4-isoxazolepropionic acid) receptor inhibition blocks the influx of calcium in glutamaterigic neurons on the Brain-Chip as demonstrated using a florescent Fluo-4 AM (green). Exemplary modulation of neuronal function using known neurotransmitters receptor antagonists are shown here. FIG. 38A is a graph demonstrating control-baseline staining for Fluo-4AM neuronal activity. FIG. 38B shows staining for Fluo-4AM neuronal activity under Glutamatergic Inhibition with a combination of NMDA and AMPA receptor inhibition (DAP5 (blocks NMDAR) and CNQX (blocks AMPAR) respectively) which reduced the percentage of active neurons by blocking the influx of calcium in glutamaterigic neurons on the Brain-Chip as compared to a control (baseline) without inhibitors, FIG. 38A. Scale bars=200 µm.

FIG. 38C is an exemplary graph showing around 100% active neurons in controls while less than 25% show activity after addition of inhibitors.

In Alzheimer's disease, however, excess glutamate can be released from damaged cells, leading to chronic overexposure to calcium, which can speed up cell damage. Attachment of glutamate to cell surface "docking sites" called NMDA receptors permits calcium to enter the cell. In this regard, selective inhibition of NMDARs-mediated excitotoxicity alone may help to slow down the progression of synaptic disruption in AD. These insights help us to develop new and potentially more effective compounds as therapeutics for AD. One of these compounds is Memantine. Memantine, the fifth Alzheimer's drug, is an NMDA (N-methyl-D-aspartate) receptor antagonist, which works by regulating the activity of glutamate, a neurotransmitter in the brain involved in learning and memory. Thus, in some embodiments, a drug, such as Memantine, may be added to microfluidic Brain chips for use in drug testing, pre-clinical testing, individualized medicine, etc.

Additional contemplated validation of BBB-on-chip components, or other Organ chips, include but are not limited to embodiments of the following: BBB-chip should maintain viability (at least 80% of total cells stain "live" (or less than 20% stain dead) and daily LDH assay shows a release <40% of the positive control (whole chip lysate)) for a minimum of 10 days. Barrier function of BBB-chip should be maintained for a minimum of 10 days (maintenance defined as less than 20% of vascular dextran 4 kDa should be detected in neural compartment, less than 20% vascular IgG and albumin should be detected in the neural compartment, and at least 40% of vascular transferrin should be transported to the neural compartment). These criteria should be met on both terrestrial hardware and on the space-compatible hardware. Space hardware validation on earth showing operation of fluidic and thermal functions for a minimum of 10 days without failure. Success is defined as system can pump reliably (+/−15% of set flow rate), valves operate and provide fixation reagents at appropriate volume and flow rates, discrete samples can be obtained and recovered at the end of the experiment, and culture temperature is stable (+/−0.5 C) and reagent storage stable (+/−4 C); Completion of Example 9, with the ability to analyze frozen fluid samples, cell lysate, and fixed chips for the assays outlined in Aim 1c upon return to earth. Observation of abnormal BBB functionality (outside the bounds describe in Example 1) in the hypergravity and/or microgravity conditions, but not in terrestrial controls.

Brain-Chip: Summary.

Brain-(On-)Chip supports the survival and interaction of iPSC-derived glutamatergic neurons and brain endothelial cells, human primary astrocytes and pericytes over a 10-day time period. Recapitulates features observed at the human cerebral cortex in vivo: Glia to neuron ratio of about 3:1. Cerebral blood flow contributes to neuronal activity and survival. Brain-Chip shows low levels of macromolecular permeability after 10 days. Recirculating vascular flow: enables more physiological shear stress while minimizing the amount of media used in space hardware. Fixation protocols: Have to be modified to accommodate cold storage limitations on the ISS. Dosing, sampling, and fixation protocols will be done by automated fluidic system. Timing and flow parameters are being optimized for repeatable and reliable results.

XIII. Exemplary Generation of Neurons and Exemplary Sources of Cells

It is not intended to limit the method by which neurons are generated or obtained. In one embodiment, neuronal cells are generated by forced expression of at least one gene in a nonneuronal cell. In one embodiment, neuronal cells are generated by transforming nonneuronal cells, such as iPS, PS, etc., with a vector that overexpresses a gene for inducing a change in phenotype.

A. Exemplary Sources of Cells.

Some cells and reagents contemplated for use in experiments are commercially available. Examples of commercials sources for cells include but are not limited to: Pluripotent stem cell (iPSC)-derived Glutamatergic (GABAergic induced neurons (iNs)); astroglia; Human SynFire Neurons from NeuCyte, 1230 BordeauxDr. Sunnyvale, Calif. 94089, USA. For purchasing commercially generated cells, whenever possible sufficient single lots of cells will be purchased to run at least one year of experiments. Preliminary tests will be conducted on any new lot of Matrigel or batch of cells, whether purchased or grown, including differentiated cells.

In some embodiments, iPSc-derived endothelial cells will be grown on transwell and trans endothelial resistance (TER) will be measured 48 h post seeding. Batches of cells that show TER values above 1000 Ohm/cm$^2$ will be used for subsequent chip experiments. To compare different batches of cells on-chip, barrier function (Dextran 4 Kda; will be measured to confirm less than 10% leakage (vascular-to-brain diffusion) for healthy cells.

B. Exemplary Generation of Neurons.

It is not intended to limit the method by which neurons are generated or obtained. In one embodiment, neuronal cells are generated by forced expression of at least one gene in a nonneuronal cell. In one embodiment, neuronal cells are generated by transforming nonneuronal cells, such as iPS, PS, etc., with a vector that overexpresses a gene for inducing a change in phenotype.

C. Directed Differentiation of Neurons.

The methods described herein include direct-reprogrammed neurons to generate a distinct neuron population for us on microfluidic chips. Direct reprogramming includes but is not limited to direct conversion of nonneuronal cells to functional neurons by inducing a neuronal fate.

In some embodiments, direct-reprogrammed neurons methods include: 1) generating iPS-iN cells or ES-iN cells starting from iPS cell (or ES cell), then differentiating neurons without creating an organoid (for one example, by adding transcription factors that take the iPS cell directly into the specific neuron fate). Reference, see exemplary methods in: Zhang, et al., "Rapid Single-Step Induction of Functional Neurons from Human Pluripotent Stem Cells." Neuron, 78(5): 785-798 and supplemental content (2013), herein incorporated by reference in its entirety, and 2) starting from a somatic cell (typically a fibroblast) and programming it into a neuron WITHOUT going through an iPS stage. Reference: (Chanda, et al., "Generation of induced neuronal cells by the single reprogramming factor ASCL1." Stem Cell Reports. 3(2):282-96.2014, herein incorporated by reference in its entirety.

Advantages of using direct-programmed neurons and their distinct populations include: enabling biological studies that is specific to that neuron type (e.g. glutamatargic, gabanergic, inhibitory vs. stimulatory neurons); allowing flexibility in designing microfluidic chip populations, such that tailored mixtures of neuron populations comprising specific neurons to tune the model (e.g. generate an in vivo-like population, generate a pathologic population of one or more types of chosen neurons, etc.); direct-reprogrammed neurons appears to allow the spontaneous formation of neural networks more readily; apparently the best neural networks are formed by an appropriate mix of stimulatory and inhibitory neurons, for recreation and tuning due to the access to specific neuronal populations.

D. Example (A) of Generating iN Cells.

Human ESCs and iPSCs can be converted into functional iN cells with nearly 100% yield and purity in less than 2 weeks by forced expression of a single transcription factor. The resulting ES-iN or iPS-iN cells exhibit quantitatively reproducible properties independent of the cell line of origin, form mature pre- and postsynaptic specializations, etc. In one embodiment, Neurogenin-2 overexpression rapidly transforms ESCs and iPSCs into neurons. Alternatively, NeuroD1 expression transforms human ESCs and iPSCs into neurons.

Thus, lentiviral expression of at least one gene for directing differentiation is used for transformation and expression in nonneuronal cells. Examples of lentiviral vectors for Ngn2-mediated conversion (and NeuroD1 conversion) of ESCs and iPSCs to iN cells, are described in Zhang, et al., "Rapid Single-Step Induction of Functional Neurons from Human Pluripotent Stem Cells." Neuron, 78(5): 785 798 and supplemental content (2013), herein incorporated by reference in its entirety.

For example, nonneuronal cells are transduced with (1) a virus expressing rtTA and (2) either a single additional virus expressing an Ngn2/EGFP/puromycin resistance gene as a fusion protein linked by P2A and T2A sequences, or with two viruses that separately express Ngn2/puromycin resistance gene and EGFP. iN cells are clearly identifiable already on day 6. See, FIG. 43B for an exemplary timeline.

E. Generation of iN Cells from Human ES and iPS Cells.

Figure 43A:
FIG. 43A-B shows exemplary schematic diagrams for FIG. 43A a lentiviral construct for forcing (inducing) expression of a lineage-inducing gene and FIG. 43B an exemplary timeline for generating specific iN cells.
Figure 43B:
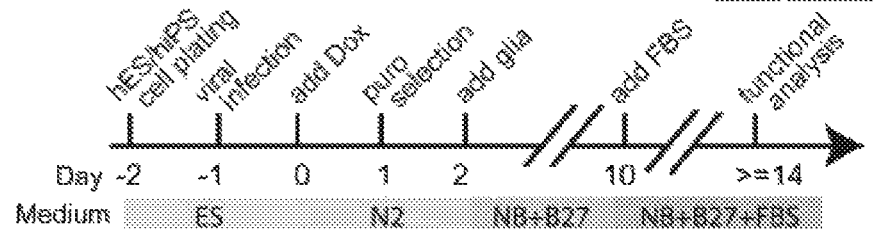

As one example, ES and iPS cells were treated with Accutase (Innovative Cell Technologies) and plated as dissociated cells in 24 well plates (H1: 1×104 cells/well; iPS cells: 1.5×104 cells/well) on day −2 (FIG. 43B). Cells were plated on matrigel—(BD Biosciences)-coated coverslips inmTeSR™ 1 containing 2 µM thiazovivin (Bio Vision). On day −1, lentivirus prepared as described above (0.3 µl/well of 24 well plate) was added in fresh mTeSR™ 1 medium containing polybrene (8 µg/µl, Sigma). On day 0, the culture medium was replaced with N2/DMEM/F12/NEAA (Invitrogen) containing human BDNF (10 µg/l, PeproTech), human NT-3 (10 µg/l, PeproTech) and mouse laminin (0.2 mg/l, Invitrogen). Doxycycline (2 g/l, Clontech) was added on day 0 to induce TetO gene expression, and retained in the medium until the end of the experiment. On day 1, a 2 h puromycin selection (1 mg/l) period was started. On day 2, mouse glia cells were added in Neurobasal medium supplemented with B27/Glutamax (Invitrogen) containing BDNF, and NT3; Ara-C (2 g/l, Sigma) was added to the medium to inhibit astrocyte proliferation. After day 2, 50% of the medium in each well was exchanged every 2 days. FBS (2.5%) was added to the culture medium on day 10 to support astrocyte viability, and iN cells were assayed on day 14 or 21 in most experiments.

The efficiency of conversion of ES and iPS cells into iN cells was calculated by two approaches from counts of cell densities in four random fields on each coverslip: (1) as the percentage of EGFP-positive lentivirally-transduced cells that also express MAP2 or NeuN; (2) as the percentage of starting cells that become NeuN-positive.

The potential use of ESC- or iPSC-derived iN cells for monitoring drug activities, studying human synaptic plasticity, or modeling human disease states, Monitoring activity-dependent $Ca^{2+}$ transients in entire populations of iN cells using the genetically expressed $Ca^{2+}$ sensor gCamp6M, which is an advanced version of gCamp5.

F. Generation of Lentiviral Vectors for Use in Generating iN Cells.

Lentiviruses for forcing gene expression may be produced as described (Pang et al., 2010) in HEK293T cells (ATCC, VA) by co-transfection with three helper plasmids (pRSV-REV, pMDLg/pRRE and vesicular stomatitis virus G protein expression vector) (12 µg of lentiviral vector DNA and 6 µg of each of the helper plasmid DNA per 75 cm culture area) using calcium phosphate (Chen and Okayama, 1987). Lentiviruses were harvested with the medium 46 hr after transfection, pelleted by centrifugation (49,000×g for 90 min), resuspended in MEM, aliquoted, and snap-frozen in liquid N2. Virus preparations with >90% infection efficiency as assessed by EGFP expression or puromycin resistance were used for experiments. For details of lentiviral constructs, see Supplementary Methods, Zhang, et al., "Rapid Single-Step Induction of Functional Neurons from Human Pluripotent Stem Cells." Neuron, 78(5): 785-798 and supplemental content (2013), herein incorporated by reference in its entirety. One example of a lentiviral vector is shown in FIG. 43A.

Further, data generated from the direct-reprogrammed glutamatergic neurons as shown herein, using a variation on method (1), iPS-derived neurons. These iN neurons are indeed glutamatergic, shown by use of a drug that specifically blocks such neurons.

Human ES cells may be obtained from WiCell Research Resources (Wicell, WI); the iPS #1 line was derived from dermal fibroblasts of a Dystrophic epidermolysis bullosa patient carrying homozygous mutations in COL7A1, while the iPS #2 line was derived from dermal fibroblast of a sickle cell anemia patient and genetically corrected by homologous recombination (Sebastiano et al., 2011). Both iPS lines were generated by infecting with a floxed polycistronic lentiviral reprogramming vector followed by Cre-mediated loop-out of the reprogramming factors (Sommer et al., 2009). ES and iPS cells were maintained as feeder-free cells in mTeSR™ 1 medium (Stem Cell Technologies; Xu et al., 2010).

G. Example (B) of Generating iN Cells.

Alternatively, human fibroblasts can be directly converted into induced neuronal (iN) cells, in addition to human embryonic stem cells. As one example, a reprogramming factor is a transcription factor, such as an early bHLH factors, ASCL1. Such generated cells produce neuronal gene-expression profile at later time points similar to that of NGN2- or BAM-mediated iN cells.

H. Generation of HESC-iN Cells.

As one example, H9 hESCs were maintained under feeder-free conditions in mTeSR media (STEMCELL Technologies). Media was changed every day. When cell density reached 70%-80% confluence, colonies were dissociated using accutase (STEMCELL Technologies) and plated onto Matrigel (BD Biosciences)-coated plates at a 1:6 dilution. During passaging, the media was supplemented with 2 mM thiazovivin overnight. For hESC-iN formation, dissociated single cells were plated at a density of ↑ 2.5-3×105 cells per 35 mm2 well. Lentivirus infections (with an additional EGFP-expressing virus) and transgene induction were performed similarly to as described for the fibroblast-iN production, using N3 media. Puromycin selection continued from day 2-6 postinfection, with media changes every other day. On day 7, cells were dissociated into single cells using PBS-EDTA (0.5 mM) and seeded onto mouse glia. The next day, media was replaced with Neurobasal media (Neurobasal [invitrogen], L-glut [Invitrogen], B27 [Invitrogen], penicillin/streptomycin [invitrogen], doxycycline [2 mg/ml], BDNF [10 ng/ml] [PeproTech], GDNF [20 ng/ml] [PeproTech], and Ara-C). Media was half-exchanged every 3-4 days.

New batches of antibodies will be authenticated, including but not limited to the following biomarkers: Glut1 (Abeam ab15309; http://www.abcam.com/glucose-transporter-glut1-antibody-ab15309.html). Will be validated by performing WB using known positive control, HepG2 whole cell lysate (ab7900; http://www.abcam.com/HepG2-whole-cell-lysate-ab7900.html) and compared with negative control, human skeletal muscle tissue lysate—total protein (ab29330, http://www.abcam.com/human-skeletal-muscle-tissue-lysate-total-protein-ab29330.html); ZO-1 (Thermofisher Scientific ZO1-1A12; www.thermofisher.com/antibody/product/ZO-1-Antibody-clone-ZO1-1A12-Monoclonal/33-9100); validated by performing immunocytochemistry on known positive control, human Caco-2 cells and compared with negative control, murine 3T3 fibroblast cells (NIH3T3); Beta III Tubulin (Abeam ab18207; www.abcam.com/beta-III-Tubulin-antibody-ab18207.html); validated by performing WB on known positive control, human brain tissue lysate total protein (ab29466; www.abcam.com/human-brain-tissue-lysate-total-protein-ab29466.html) and compared with negative control, whole cell lysates of HUVECs (www.fishersci.com/shop/products/huvec-human-umbilical-vein-whole-cell-lysate-non-denatured-abnova-200-g/89014394); GFAP (Abeam ab10062; www.abcam.com/gfap-antibody-gf5-ab10062.html); contemplated to be validated by performing immunocytochemistry on known positive control, murine glial cells, and compared with negative control, human endothelial cells—HUVECs; αSMA (Abeam ab5694; www.abcam.com/alpha-smooth-muscle-actin-antibody-ab5694.html)—Will be validated by performing WB against known positive controls, HEK293 cell lysates or NIH3T3 cell lysates and compared with negative control, whole cell lysates of HUVECs (www.fishersci.com/shop/products/huvec-human-umbilical-vein-whole-cell-lysate-non-denatured-abnova-200-g/89014394).

Induction of inflammation on the BBB-chip. As one example, inflammation will be induced by challenge with exemplary either TNF alpha or IL-1beta, or combination of inflammatory cytokines, both potent and physiologically-relevant inflammatory stressors, while acting by engagement of different receptors and activation of separate pathways.

EXPERIMENTAL

Some cells and reagents contemplated for use in experiments are commercially available. Examples of commercials sources for cells include but are not limited to: Pluripotent stem cell (iPSC)-derived Glutamatergic (GABAergic induced neurons (iNs)); astroglia; Human SynFire Neurons from NeuCyte, 1230 BordeauxDr. Sunnyvale, Calif. 94089, USA. For purchasing commercially generated cells, whenever possible sufficient single lots of cells will be purchased to run at least one year of experiments. Preliminary tests will be conducted on any new lot of Matrigel or batch of cells, whether purchased or grown, including differentiated cells.

In some embodiments, iPSc-derived endothelial cells will be grown on transwell and trans endothelial resistance (TEER) will be measured 48 h post seeding. Batches of cells that show TEER values above 1000 Ohm/cm$^2$ will be used for subsequent chip experiments. To compare different batches of cells on-chip, we will measure barrier function (Dextran 4 Kda) and confirm less than 10% leakage (vascular-to-brain diffusion).

Exemplary Generation of Neurons.

It is not intended to limit the method by which neurons are generated or obtained. In one embodiment, neuronal cells are generated by forced expression of at least one gene in a nonneuronal cell. In one embodiment, neuronal cells are generated by transforming nonneuronal cells, such as iPS, PS, etc., with a vector that overexpresses a gene for inducing a change in phenotype.

Directed Differentiation of Neurons.

The methods described herein include direct-reprogrammed neurons to generate a distinct neuron population for us on microfluidic chips. Direct reprogramming includes but is not limited to direct conversion of nonneuronal cells to functional neurons by inducing a neuronal fate.

In some embodiments, direct-reprogrammed neurons methods include: I) generating iPS-iN cells or ES-iN cells starting from iPS cell (or ES cell), then differentiating neurons without creating an organoid (for one example, by adding transcription factors that take the iPS cell directly into the specific neuron fate). Reference, see exemplary methods in: Zhang, et al., "Rapid Single-Step Induction of Functional Neurons from Human Pluripotent Stem Cells." Neuron, 78(5): 785-798 and supplemental content (2013), herein incorporated by reference in its entirety, and 2) starting from a somatic cell (typically a fibroblast) and programming it into a neuron WITHOUT going through an iPS stage. Reference: (Chanda, et al., "Generation of induced neuronal cells by the single reprogramming factor ASCL1." Stem Cell Reports. 3(2):282-96. 2014, herein incorporated by reference in its entirety.

Advantages of using direct-programmed neurons and their distinct populations include: enabling biological studies that is specific to that neuron type (e.g. glutamatargic, gabanergic, inhibitory vs. stimulatory neurons); allowing flexibility in designing microfluidic chip populations, such that we can tailor mix neuron populations of specific neurons to tune the model (e.g. generate an in vivo-like population, generate a pathologic population of one or more types of chosen neurons, etc.); direct-reprogrammed neurons appears to allow the spontaneous formation of neural networks more readily; apparently the best neural networks are formed by an appropriate mix of stimulatory and inhibitory neurons, which we can recreate and tune due to the access to specific neuronal populations.

Example (A) of Generating iN Cells

Human ESCs and iPSCs can be converted into functional iN cells with nearly 100% yield and purity in less than 2 weeks by forced expression of a single transcription factor.

The resulting ES-iN or iPS-iN cells exhibit quantitatively reproducible properties independent of the cell line of origin, form mature pre- and postsynaptic specializations, etc. In one embodiment, Neurogenin-2 overexpression rapidly transforms ESCs and iPSCs into neurons. Alternatively, NeuroD1 expression transforms human ESCs and iPSCs into neurons.

Thus, lentiviral expression of at least one gene for directing differentiation is used for transformation and expression in nonneuronal cells. Examples of lentiviral vectors for Ngn2-mediated conversion (and NeuroD1 conversion) of ESCs and iPSCs to iN cells, are described in Zhang, et al., "Rapid Single-Step Induction of Functional Neurons from Human Pluripotent Stem Cells." Neuron, 78(5): 785-798 and supplemental content (2013), herein incorporated by reference in its entirety.

For example, nonneuronal cells are transduced with (1) a virus expressing rtTA and (2) either a single additional virus expressing an Ngn2/EGFP/puromycin resistance gene as a fusion protein linked by P2A and T2A sequences, or with two viruses that separately express Ngn2/puromycin resistance gene and EGFP. iN cells are clearly identifiable already on day 6. See, FIG. 43B for an exemplary timeline.

Generation of iN Cells from Human ES and iPS Cells.

As one example, ES and iPS cells were treated with Accutase (Innovative Cell Technologies) and plated as dissociated cells in 24 well plates (H1: 1×104 cells/well; iPS cells: 1.5×104 cells/well) on day −2 (FIG. 43B). Cells were plated on matrigel—(BD Biosciences)—coated coverslips inmTeSR™ 1 containing 2 µM thiazovivin (Bio Vision). On day −1, lentivirus prepared as described above (0.3 µl/well of 24 well plate) was added in fresh mTeSR™ 1 medium containing polybrene (8 µg/µl, Sigma). On day 0, the culture medium was replaced with N2/DMEM/F12/NEAA (Invitrogen) containing human BDNF (10 µg/l, PeproTech), human NT-3 (10 µg/l, PeproTech) and mouse laminin (0.2 mg/l, Invitrogen). Doxycycline (2 g/l, Clontech) was added on day 0 to induce TetO gene expression, and retained in the medium until the end of the experiment. On day 1, a 2 h puromycin selection (1 mg/l) period was started. On day 2, mouse glia cells were added in Neurobasal medium supplemented with B27 Glutamax (Invitrogen) containing BDNF, and NT3; Ara-C (2 g/l, Sigma) was added to the medium to inhibit astrocyte proliferation. After day 2, 50% of the medium in each well was exchanged every 2 days. FBS (2.5%) was added to the culture medium on day 10 to support astrocyte viability, and iN cells were assayed on day 14 or 21 in most experiments.

The efficiency of conversion of ES and iPS cells into iN cells was calculated by two approaches from counts of cell densities in four random fields on each coverslip: (1) as the percentage of EGFP-positive lentivirally-transduced cells that also express MAP2 or NeuN; (2) as the percentage of starting cells that become NeuN-positive.

The potential use of ESC- or iPSC-derived iN cells for monitoring drug activities, studying human synaptic plasticity, or modeling human disease states, Monitoring activity-dependent $Ca^{2+}$ transients in entire populations of iN cells using the genetically expressed $Ca^{2+}$ sensor gCamp6M, which is an advanced version of gCamp5.

Generation of Lentiviral Vectors for Use in Generating iN Cells.

Lentiviruses for forcing gene expression may be produced as described (Pang et al., 2010) in HEK293T cells (ATCC, VA) by co-transfection with three helper plasmids (pRSV-REV, pMDLg/pRRE and vesicular stomatitis virus G protein expression vector) (12 µg of lentiviral vector DNA and 6 µg of each of the helper plasmid DNA per 75 cm culture area) using calcium phosphate (Chen and Okayama, 1987). Lentiviruses were harvested with the medium 46 hr after transfection, pelleted by centrifugation (49,000×g for 90 min), resuspended in MEM, aliquoted, and snap-frozen in liquid N2. Virus preparations with >90% infection efficiency as assessed by EGFP expression or puromycin resistance were used for experiments. For details of lentiviral constructs, see Supplementary Methods, Zhang, et al., "Rapid Single-Step Induction of Functional Neurons from Human Pluripotent Stem Cells." Neuron, 78(5): 785-798 and supplemental content (2013), herein incorporated by reference in its entirely. One example of a lentiviral vector is shown in FIG. 43A.

Further, data generated from the direct-reprogrammed glutamatergic neurons as shown herein, using a variation on method (1), iPS-derived neurons. These iN neurons are indeed glutamatergic, shown by use of a drug that specifically blocks such neurons.

Human ES cells may be obtained from WiCell Research Resources (Wicell, WI); the iPS #1 line was derived from dermal fibroblasts of a Dystrophic epidermolysis bullosa patient carrying homozygous mutations in COL7A1, while the iPS #2 line was derived from dermal fibroblast of a sickle cell anemia patient and genetically corrected by homologous recombination (Sebastiano et al., 2011). Both iPS lines were generated by infecting with a floxed polycistronic lentiviral reprogramming vector followed by Cre-mediated loop-out of the reprogramming factors (Sommer et al., 2009). ES and iPS cells were maintained as feeder-free cells in mTeSR™ 1 medium (Stem Cell Technologies; Xu et al., 2010).

Example (B) of Generating iN Cells

Alternatively, human fibroblasts can be directly converted into induced neuronal (iN) cells, in addition to human embryonic stem cells. As one example, a reprogramming factor is a transcription factor, such as an early bHLH factors, ASCL1. Such generated cells produce neuronal gene-expression profile at later time points similar to that of NGN2- or BAM-mediated iN cells.

Generation of H ESC-iN Cells.

As one example, H9 hESCs were maintained under feeder-free conditions in mTeSR media (STEMCELL Technologies). Media was changed every day. When cell density reached 70%-80% confluence, colonies were dissociated using accutase (STEMCELL Technologies) and plated onto Matrigel (BD Biosciences)-coated plates at a 1:6 dilution. During passaging, the media was supplemented with 2 mM thiazovivin overnight. For hESC-iN formation, dissociated single cells were plated at a density of ↑ 2.5-3×105 cells per 35 mm2 well. Lentivirus infections (with an additional EGFP-expressing virus) and transgene induction were performed similarly to as described for the fibroblast-iN production, using N3 media. Puromycin selection continued from day 2-6 postinfection, with media changes every other day. On day 7, cells were dissociated into single cells using PBS-EDTA (0.5 mM) and seeded onto mouse glia. The next day, media was replaced with Neurobasal media (Neurobasal [Invitrogen], L-glut (Invitrogen), B27 [Invitrogen], penicillin/streptomycin [Invitrogen], doxycycline [2 mg/ml], BDNF [10 ng/ml][PeproTech], GDNF [20 ng/ml] [PeproTech], and Ara-C). Media was half-exchanged every 3-4 days.

We will authenticate new batches of antibodies with the following, but not limited to these biomarkers: Glut1 (Abcam ab15309; www.abcam.com/glucose-transporterglut1-antibody-ab15309.html); validated by performing WB using known positive control, HepG2 whole cell lysate (ab7900; www.abcam.com/HepG2-whole-cell-lysate-ab7900.html) and compared with negative control, human skeletal muscle tissue lysate total protein (ab29330, http://www.abcam.com/human-skeletal-muscle-tissue-lysate-total-protein-ab29330.html); ZO-1 (Thermofisher Scientific ZO1-1A12; www.thermofisher.com/antibody/product/ZO-1-Antibody-clone-ZO1-1A12-Monoclonal/33-9100); validated by performing immunocytochemistry on known positive control, human Caco-2 cells and compared with negative control, murine 3T3 fibroblast cells (NIH3T3); Beta III Tubulin (Abeam ab18207; http://www.abcam.com/beta-III-Tubulin-antibody-ab18207.html)—Will be validated by performing WB on known positive control, human brain tissue lysate—total protein (ab29466; http://www.abcam.com/human-brain-tissue-lysate-total-protein-ab29466.html) and compared with negative control, whole cell lysates of HUVECs (www.fishersci.com/shop/products/huvec-human-umbilical-vein-whole-cell-lysate-non-denatured-abnova-200-g/89014394); GFAP (Abeam ab10062; http://www.abcam.com/gfap-antibody-gf5-ab10062.html)—Will be validated by performing immunocytochemistry on known positive control, murine glial cells, and compared with negative control, human endothelial cells—HUVECs: αSMA (Abeam ab5694; http://www.abcam.com/alpha-smooth-muscle-actin-antibody-ab5694.html)—Will be validated by performing WB against known positive controls, HEK293 cell lysates or NIH3T3 cell lysates and compared with negative control, whole cell lysates of HUVECs (www.fishersci.com/shop/producls/huvec-human-umbilical-vein-whole-cell-lysate-non-denatured-abnova-200-g/89014394).

Induction of inflammation on the BBB-chip. As one example, we will induce inflammation by challenge with either TNF alpha or IL1beta, both potent and physiologically-relevant inflammatory stressors, while acting by engagement of different receptors and activation of separate pathways.

BBB-Chip was Maintained Past 7 Days.

We have preliminary evidence showing survival beyond 7 days, 10-12, occasionally. In some embodiments, we contemplate developing methods for extended survival, by optimization of the differentiation of the iPS-derived endothelial cells.

We are using a PDMS (silicon elastomer) membrane with 7 um pores what allows for cell-cell (astrocytes/HBMECs) interaction beyond secreted factors alone. The different material and porosity make difficult to compare the TER values among the two systems. Also, it is not clear how the Vanderbilt team measured TER (FIG. 7 in their manuscript). The measured values they report (above 30000 ohm/cm$^2$) are not physiologically relevant when compared to previous papers showing that TER values measured in vivo in rats reach values as high as 1500 6000 ohm/cm$^2$. We have previously reported the challenges of integrating TER into Organs-on-chips and the subsequent analysis (Odijk et al. 2015, Lab Chip, DOI: 10.1039/c41c01219d) which may contribute to this significant deviation. Interestingly in FIG. 5 of the paper the authors shown dextran diffusion using molecules of 70 and $0 Kda, of much larger MW than the 4 Kda routinely used.

While most of the dextran is confined within the vascular compartment, other reports indicate that about ⅙ of the dextran diffuses into the brain compartment of their chip. In the system described herein, the fluorescent signal of the 4 Kda-Dextran in the brain compartment can barely be detected. In fact just 0.5-1% of the total dextran is actually detected in the brain compartment; therefore this model is much closer to the in vivo condition, i.e. physiology, in humans.

Exemplary Chip Manufacturing

Conditions for bonding the capping layer (FIG. 2, element 13) to the backplane (14) were examined. Extruded SEBS sheets were bonded to a hot embossed plate. The SEES sheets were designed to act as the capping layer to the channels that are formed in the COP via the hot embossing process and as a fluid and gas gasketing to mating parts. The testing showed that the 1 mm thick SEBS was better as a fluid seal between the reservoirs and the backplane. The hot embossed plates were fabricated from Zeonor 1420R. The SEBS materials used were, but not limited to: A. Thickness: 1 mm, Material: Kraton G1643, Mfg Process: extrusion and B. Thickness: 0.2 mm, Material: Kraton G1643+5% Polypropylene, Mfg Process: extrusion.

An oven process was used in comparison to a laminator. The laminator produced marginal to not adequate bonding. However, the oven process revealed the following in Table 3.

TABLE 3

| Material Thickness | 0.2 mm SEBS | 1 mm SEBS |
| --- | --- | --- |
| Bonding Temp (° C.) | 80 | 80 |
| Bonding Time | 1 hr-24 hr | |
| Clamping Pressure | None | 0.5 kg<br>Applied through a silicone coated acrylic plate<br>Necessary for conformal lamination/good bond production |
| Bond Quality | 1 hr: good bond<br>24 hr: excellent bond | Good bond |
| Anisotropic Effects | None noticeable | Yes. Requires clamping pressure to be held for ~30 min during cooling |

In some embodiments, the fluidic layer is sealed with a film. This film may be polymeric, metallic, biological or a combination thereof (e.g. A laminate of multiple materials). Examples of materials include polypropylene, SEBS, COP, PET, PMMA, aluminum, etc. Specifically, the film may be elastomeric. The film may be affixed to the fluidic layer by means of an adhesive agent, thermal lamination, laser welding, clamping, and other methods known in the art. The film may further be used to affix and potentially fluidically interconnect additional components to the fluidic layer. For example, the film may be used to adhere one or more reservoirs to the fluidic layer. In an example embodiment, the film is a thermal lamination film that includes EVA or EMA. In the example embodiment, the film may be first laminated against the fluidic layer using a thermal treatment and then, using a second thermal treatment, adheres one or more reservoirs to the fluidic layer. In a different embodiment, the film includes SEBS, which is known to be bondable to a variety of materials including polystyrene, COP, polypropylene, etc., either using a thermal treatment or with the help of one or more solvents. In this example, the SEBS film may be laminated to a fluidic layer (using thermal treatment or with the help of solvent) and using a second treatment, bond one or more reservoirs to the fluidic layers. There are multiple potential advantages to using a film that is elastomeric, deformable, or pliable, or film that reflows during the bonding process. These advantages include, for example: potentially conforming to the fluidic layer or other bonded component (e.g. reservoirs), thereby relaxing manufacturing tolerance (e.g. on the flatness or planarity of the manufactured parts), potentially simplifying the required parallelism or alignment during bonding (e.g. because the said film may deform to absorb errors in parallelism), and acting as a gasket to create a fluidic seal, for example, between the fluidic backplane and reservoirs. SEBS is especially advantageous as a bonding film, since it can bond under moderate temperatures (typically under 100 C) while not significantly reflowing. Reflowing may be undesirable as it poses a risk of filling in and blocking fluidic channels. By not significantly reflowing, SEBS can better maintain the dimensions and structure of fluidic channels and other features in the fluidic layer compared to materials that reflow (e.g. traditional thermal lamination films). Film thickness can range from 10 um to 5 mm in different embodiments. The film may include various fluidic ports or channels. The film need not be flat and can take on a variety of three-dimensional shapes.

Example 1

Establishment of BBB-Chip with Human iPS-Derived Endothelial Cells, Primary Pericytes and Astrocytes and Confirmation of Physiological, Limited Permeability and Barrier Integrity Using Fluorescent Dextran and Transport of IgG Neurons and astrocytes will be co-stained with the nuclear dye Hoechst as a read-out for cell viability. For the live/dead cell staining assay acceptance criteria require at least 80% alive cells in any field of view—2 independent blinded observers will quantify the entire chip through tiled imaging. Since these assays do not need to sacrifice chips, we count on monitoring both cell viability and organ-function every other day for 2 weeks.

For barrier characterization we aim for (a) less than 10% leakage of Dextran 4 kDa, and less than 20% IgG or Alb leakage individually as normalized to basal media contents (b) at least 40% transport of Transferrin. Immunohistochemistry (IHC) will be performed for a qualitative, rather than quantitative analysis of the barrier by staining for ZO-1, VE-Cadherin, Claudin-5, PECAM-1, typical markers used for assessing epithelial tight junction formation and integrity of the micro vascular endothelial layer. The neuronal population will be characterized by morphological criteria (axon formation, neurite outgrowth measurements) and immunocytochemistry (staining with β-III Tubulin as a neuron-specific marker and for specific identity characterization such as with antibodies for GABA, Acetylcholine, etc.) and assessment of voltage dependent ion channels through Ca2+ imaging. The intracellular calcium concentration in the cytoplasm should be ~50-100 nM and rise following stimulation (Vehicle (external solution-in mM: NaCl 140, KCl 5, MgCl2 2, HEPES 10, D-glucose 10, CaCl20 and KCl (45 or 85 mM) or glutamate (200 µM) solutions will be applied to test the calcium events in both neuron and astrocyte cultures.) to levels ten times higher than base line (Berridge et al., 2000).

Astrocytes should be confirmed to grow in a controlled manner, i.e. without overgrowing the neural cultures in order to maintain the in vivo representative cellular composition of between 1:8 to 1:2 astrocyte:neuron (1:4 has been described for astrocytes to neural precursor cells, Kuijlaars J, Scientific Reports 6, 2016), determined during plating and at frequent intervals (every 2-3 days) over the culture period. Aside from their unique morphology, astrocytes will be distinguished by their expression of the intermediate filament GFAP.

To specifically study apoptosis in neurons and glia in co-culture, we will stain with specific markers of neurons and glia as described above localized with a marker of apoptosis, such as terminal deoxynucleotidyl transferase-based dUTP nick-end labeling (TUNEL).

In some embodiments, demonstration of a tight barrier with cells involved in this organ in humans, at the right topology and with sustained functionality for a minimum of 10 days, is desired as a goal of this study.

Example 2

Develop and Validate Fluidic System for Automated Experiments that is Compatible with CubeLab Size Constraints, Power and Communications Infrastructure In this example, show that hardware can pump reliably (+/−15% of set flow rate for 10 days), valves operate and provide fixation reagents at appropriate volume and flow rates, discrete samples can be obtained and recovered at the end of the experiment. A continuous flow rate is preferred for organ-chips to maintain consistent function and viability. Prolonged periods of significant reduced flow or increased flow will influence organ-chip-readouts, and we need to be able to ensure that a readout is changing due to an experimental variable and not a hardware malfunction. The 10 day minimum will cover 3 days it takes to go from loading biology on CubeLab on earth to ISS with an additional 7 days for experimentation on IBS.

Example 3

Develop and Validate Thermal Management System that is Compatible with CubeLab Size, Power and Communications Infrastructure In this example, show that hardware can maintain temperature of +/−0.5° C. for culture area, and +/−4° C. for reagent storage area tor up to 10 days. Mammalian cells are sensitive to changes in temperature, so major deviations may be detrimental to viability.

The tolerance on temperature is based on the variability measured on standard tissue culture incubators routinely used for culturing organ-chips.

Example 4

Integrate and Validate Thermal, Fluidic, and Organ-Chip Subsystems into CubeLab

In this example, show that integrated system can pump reliably (+/−15% of set flow rate), valves operate and provide fixation reagents at appropriate volume and flow rates, discrete samples can be obtained and recovered at the end of the experiment, and culture temperature is stable (+/−0.5° C.) and reagent storage stable (+/−5° C.) for 10 days. To conduct an experiment on the ISS we will need to ensure that the integrated hardware can perform its functions in terrestrial tests.

Example 5

Biologically Validate Integrated Space Hardware with BBB-Chip Culture for 7-Days In this example, show that a BBB-Chip with neurons included, demonstrated cell survival—at least 80% live cells throughout the chip (measured by tiled imaging and quantification of total fluorescence signal) and maturation as per IHC with specific markers (ZO1, Glut1, GFAP, alphaSMA and beta III Tubulin, and demonstrated barrier function defined as: less than 10% leakage of Dextran 4 kDa, less than 20% IgG or Alb leakage individually as normalized to basal media contents, and at least 40% transport of Transferrin.

We should ensure that the BBB-chip maintains the same viability and function when cultured in the space hardware or existing instrumentation, in part, and for example, as described herein.

Example 6

Development of Inflamed BBB-Chip

In this example, show demonstration of dose- and time-dependent increased permeability of the BBB-Chip following exposure to TNF alpha or IL1 beta.

Readouts will include disruption of tight junctions and loss of the associated barrier function as demonstrated by increased permeability (As in Example #1 above: Greater than 10% Dextran leakage; Greater than 20% IgG and/or Alb leakage; Greater than 20% increase in "gap areas" as compared to control when imaging cell-cell junctions), neuronal death/apoptosis as described in Example 1.

Show statistically significant changes in specific markers demonstrating exposure of cortical neurons to stressors as assessed by live/dead cells assay and IHC, where appropriate, with specific markers. Before we can study inflammation in space experiments, we need to develop and validate the system in terrestrial experiments.

Example 7

Data Analysis of Earth BBB-Chip Experiments

In this example, show a successful analysis will result in the identification and rank ordering of the most informative variables (features) that can discriminate reliably between biological conditions (normal vs. inflamed state) as well as between environmental state (earth vs space gravity vs hypergravity conditions) for a given biological condition. This analysis will consider variables measured in the heterogeneous data sources (genomics, proteomics, biomarkers etc.) collected based on BBB-chip experiments to be conducted on the earth before the space flights (as detailed in Aim1d) This analysis is necessary to establish a baseline for comparing against same experimental conditions in space and understand what parameters are affected and to what extent by the changes in gravity conditions.

Establishing this baseline is a prerequisite for developing and validating models for the space effects on endpoints.

Example 8

Conduct First Space Experiment on BBB-Chip Comparing Hypergravity, Microgravity, and Terrestrial Gravity Conditions In this example, show an experiment that runs without hardware malfunctions (defined in Example #4, and recorded throughout experiment using on-board sensors for temperature and operating state of pumps and valves) and data are collected throughout experiment. Samples (frozen effluent, frozen cell lysate, and fixed chips) are collected upon return to earth and able to be analyzed.

The hardware needs to run without flows to accurately determine if BBB-chip results are due to space variables.

Example 9

Development and Calibration of Models with BBB-Chip, First Flight Data

Analysts of first flight data and identification of differences of BBB-chip behavior as compared to same earth experiments (Example #7) for the control and inflammation conditions. Parsimonious modeling of how the observed changes depend on the altered gravity conditions.

First flight data analysis and comparison to the earth results analysis under same conditions is required to build a model that captures the essential differences of BBB-chip behavior in space. Parsimonious modeling is known to increase the predictive value of the models.

Example 10

Integrate TEER Functionality into BBB-Chip and CubeLab

In this example, show that TEER chips and potentiostat can give steady readings (+/−100 ohms*cm$^2$) over 7 days in a CubeLab without leaking.

A typical inflammation challenge in a BBB-chip will change the TEER reading on the order of 1000 ohms×cm$^2$. A tolerance of +/−100 ohms×cm$^2$ on a blank chip (hardware variability) will allow us to have one order of magnitude greater signal to noise ratio in this readout of tissue barrier integrity.

Example 11

Iterate Space Hardware Based on Learnings from First Flight

In this example, success will be dependent on the design iteration (if any) require changes.

Issues may arise during the first flight that will warrant changes to the design of the space hardware for the second flight. These issues may be addressed so long as doing so does not influence the capability to compare data between the first and second flights.

Example 12

Feasibility Study of Effect of Space Stressors on BBB-Chip on Earth

In this example, show terrestrial studies can be conducted with space-like variables of hydrostatic pressure and hypoxia.

To allow us to decouple the effects of different space variables

Example 13

Development and Characterization of Inflamed BBB-Chip in Space

In this example, show inflamed BBB-Chip runs as described in Example #6 and endpoints are in the same range as upon experimentation on earth. Deviation in the endpoints are contemplated for further evaluation to elucidate the underlying mechanisms, i.e. specific space parameters) implicated.

Exposure of the BBB-Chip to inflammatory stressors may unmask the impact of specific space-induced stressors, that could be missed in normal states due to the ability of the cells to adapt to mild stressors, particularly when applied for limited time period.

Example 14

Model Validation

In this example, quantify the extent to which the model developed can recapitulate the BBB behavior based on the results of experiments to be performed on earth under a single space stressor condition, i.e. hypoxia, hypergravity, or absence of hydrostatic pressure, as described in Aim3a.

This is necessary to assess to what extent the collected data of the study suggest that simultaneous application of space stressors exert orthogonal or combined effects on the BBB cells under normal and inflammation conditions.

This will also allow the recalibration of the model to improve its predictive power under different gravity conditions.

Example 15

Modify CubeLab for Space Stressor Terrestrial Experiments

In this example, show confirm with pressure sensors that experimental setups to simulate no hydrostatic forces maintain no hydrostatic pressure (+/−200 Pa). Confirm with oxygen sensors that hypoxic chips can maintain 0% (+0.5%) dissolved oxygen content for duration of treatment. To decouple the effect of different space stressors we should try to decouple them in terrestrial experiments. The tolerances presented here are based on limitations on hardware design.

Example 16

Conduct Second Space Experiment on BBB-Chip Inducing Inflammation and Attempting to Rescue with Dexamethasone In this example, show hardware runs without flaws to accurately determine if BBB-chip results are due to space variables.

Example 17

Flight Certify Space Hardware and Other Components

In some embodiments, hardware and systems described herein, are contemplated for use under flight conditions. In some embodiments, cells are grown or maintained under flight conditions in order to determine whether modifications are necessary for successful completion of experiments.

Example 18

Low Temperature Storage

Temperatures encountered over the course of spaceflight, i.e. takeoff through landing, and aboard ISS, include low temperature conditions, e.g. −80° C., for up to 12 weeks, or more, depending upon the length of space travel. Therefore, −80° C. storage conditions are added to capabilities for 4° C. storage and transition temperatures, and sample temperatures of 37° C. onboard space craft and ISS. Samples on-chips are fixed, and/or lysed, then stored at −80° C. Samples at 37° C. may be samples under incubation or during at least a part of the assay, readout. Reagents such as media, buffer, lysis buffer, fixative, etc., in addition to being stored at 4° C., also go through a −80° C. time period, e.g., prior to landing.

Thus, in some embodiments, methods described herein, include low temperature conditions, e.g. −80° C., as shown in exemplary FIG. 23.

FIG. 23 shows an exemplary Thermal timeline showing temperatures of chips, reagents, and samples over the course of the flight.

For another example, thermal design parameters are contemplated to include: Chip culture temperature (37° C.); Media storage (4° C.); Effluent storage (4° C.); Chip storage, including unfixed chips, fixed chips, and lysed chips, etc., temperature during return to earth (between 4° C. or −80° C.).

Thus, in some embodiments, Hypergravity Chips are fixed then stored after takeoff. In some embodiments, Microgravity Chips are sampled daily and fixed at >10 days. In some embodiments, Microgravity Chips are automatically sampled daily and fixed at >10 days. In some embodiments, chips frozen at −80° C., are brought to 4C or ambient temperature, e.g. room temperature, then stained with antibodies.

Furthermore, fixation of cells on chips were modified due in part to long storage conditions at −80° C. In part due to the long term storage at −80° C. fixatives were tested for capabilities to retain antigen structure upon thawing for accurate staining of specific molecules, e.g. E-cadherin, showing little or no background staining.

FIG. 24 Shows an exemplary Staining of specific protein markers remains viable after methanol fixation and storage at −80° C. for 1 month. E-cadherin (green) staining of alveolar chips, HAECs. Fixatives compared were MeOH (left) NDS+Glycine (middle) and buffer control (right), i.e. PBS.

FIG. 25 Shows an exemplary minimal Background staining or noise after methanol fixation and storage at −80° C. E-cadherin (green) staining of alveolar chips, HAECs. Fixatives compared were MeOH (left) NDS+Glycine (middle) and buffer control (right), i.e. PBS.

Moreover, methods described herein were modified in part due to constraints of ISS. Therefore, fixation of chips were modified due in part to limitation of automation and cold storage options on ISS; Fluid recirculation was incorporated to allow for physiological shear stress without requiring large fluidic reservoirs; Space hardware is contemplated to have new materials and components that may influence biological function. For comparisons, terrestrial parallel methods are modified accordingly.

Example 19

In this example, cell viability was measured under four types of flow conditions.

Exemplary experimental design. Condition 1: Chips at D2: Flowed at 60 ul/hr and maintained for 4 or 10 days. (Control 1). Condition 2: Chips at D2: Flowed at 60 ul/hr for 48 hours; then increased to 600 ul/hr for 48 hrs. Condition 3: Chips at D2: Flowed at 60 ul/hr for 48 hrs; increased to 600 ul/hr for 48 hrs; then increased to 900 ul/hr for 4 days. Condition 4: Chips at D2: Flowed at 1 ml/hr for 24 hours.

Figure 34:
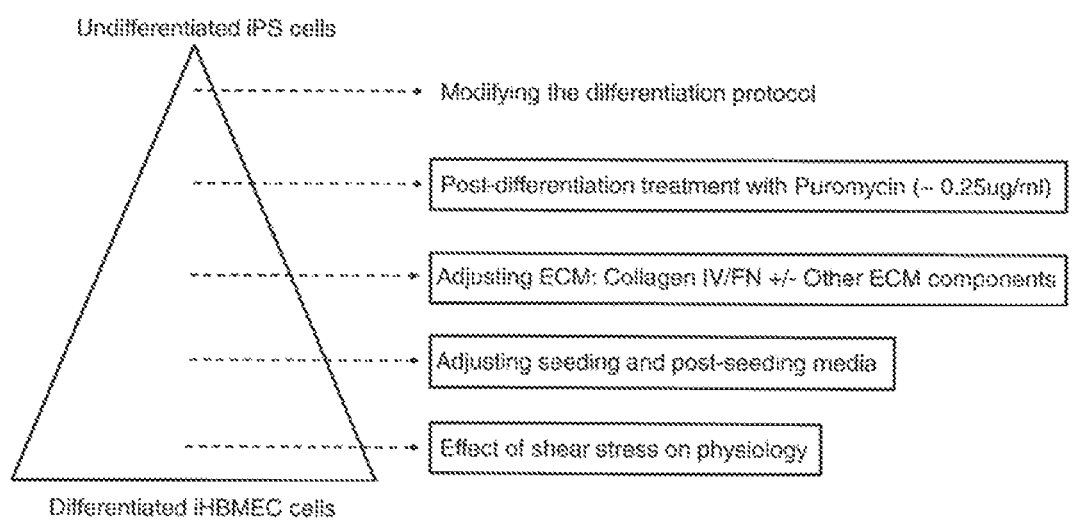
FIG. 34 Exemplary strategy to prolong lifespan of iPS derived HBMECs (i.e. Undifferentiated iPS cells induced to differentiated iHBMEC cells): includes but is not limited to variables such as modifying the differentiation protocol; post-differentiation treatment with Puromycin (approximately 0.25 ug/ml); adjusting ECM: Collagen IV/FN+/− other ECM components; adjusting seeding and post-seeding media; and Effect of shear stress on physiology.

FIG. 34 Exemplary Morphology (brightfield) comparing High flow rate (600-900 ul/hr) and recirculation in upper panels, compared to low flow rate/controls (no flow) in lower panels for maintaining iHBMEC morphology and viability in the vascular channel. Day 04; Day 07; and Day 10 images showing numerous cells on Day 10 under high flow compared to a few cells by Day 10 under low flow.

Example 20

Pharmacological Targeting of the Glutamatergic Neurons On-Chip

In this example, we demonstrated the ability to modulate neuronal function with known neurotransmitters receptor antagonists. Specifically, NMDA and AMPA receptor inhibition (DAP5 and CNQX respectively) reduced the percentage of active neurons by blocking the influx of calcium in glutamatergic neurons on the Brain-Chip.

FIG. 38A-C Pharmacological Targeting of the Glutamatergic Neurons in the Brain-Chip. Combination of NMDA and AMPA receptor inhibition blocks the influx of calcium in glutamaterigic neurons on the Brain-Chip as demonstrated using a florescent Fluo-4 AM (green). Exemplary modulation of neuronal function using known neurotransmitters receptor antagonists are shown here. FIG. 38B, NMDA and AMPA receptor inhibition (DAP5 (blocks NMDAR) and CNQX (blocks AMPAR) respectively) reduced the percentage of active neurons by blocking the influx of calcium in glutamaterigic neurons on the Brain-Chip as compared to a control (baseline) without inhibitors, FIG. 38A. Scale bars=200 µm. FIG. 38C is an exemplary graph showing around 100% active neurons in controls while less than 25% show activity after addition of inhibitors.

Example 21

Hepatocyte Viability and Function of microfluidic Liver On-Chips under fluid flow, single pass and recirculating, comparing PDMS to COP microfluidic chips.

In this example, reciprocation increased albumin production. Human hepatocytes. Static control.

Exemplary Recirculation Surprisingly Increases Production of Secreted Proteins from Cells On-Chip.

Because PDMS absorbed test compounds, including test drugs, Liver-Chips were provided on Cyclo-olefin-polymer (COP) microfluidic chips, as described herein, as it was contemplated that less compound would be absorbed by COP surfaces. Therefore for comparison, duplicate hepatocyte cell and endothelial cell samples were seeded onto PDMS microfluidic chips for comparing to COP chips for drug dosing and media fluid recirculation experiments.

Further, delivery of oxygen to the cells in an otherwise gas impermeable system, such as COP microfluidic chips in some embodiments, is desired, in contrast, PDMS chips are gas permeable. Thus, in some embodiments, media exposure to atmospheric oxygen occurs in the reservoir before the first pass of fluid over the cells in a microchannel. After contacting oxygen-consuming cells, effluent fluid is oxygen depleted. Thus, in some embodiments, reciprocation is designed to include reoxygenation of the nutrient media before returning media into the microchannel to contact the cells. In some embodiments, wherein effluent fluid is oxygen depleted, e.g. media, the fluid is reoxygenated prior to recirculation. In some embodiments when oxygen reoxygenation does not occur in recirculated fluids, the cells may consume the majority of oxygen in the channel/in the media upon the first and subsequent passes, thus without an additional source of oxygen, the media will become hypoxic resulting in cell death depending upon the length of time cells are in contact with hypoxic media and the relative amount of oxygen deprivation compared to the amount the cells need to thrive.

Thus, in one embodiment, the drug testing (i.e. dosing) method included exemplary recirculation steps shown in FIG. 45A-C using exemplary recirculation devices shown in FIG. 44A-C, for recirculation of effluent fluid, i.e. nutrient media.

FIG. 44A-C illustrates and shows photographs of embodiments for recirculation (reciprocation) and introduction of a test compound into a microfluidic chip as one embodiment of a non-drug absorbing setup (e.g. device). Setup: for ensuring adequate oxygenation; is non-drug absorbing; and decreases system volume. FIG. 44A shows an illustration of one embodiment of a syringe (131) fluidically connected by tubing (132) to a microchannel of a microfluidic chip (16) in turn fluidically connected to a reservoir (133). FIG. 44B shows a photograph image of one embodiment of a syringe (131) fluidically connected by tubing (132) to a microchannel of a microfluidic chip (100) in turn fluidically connected to a reservoir (133). FIG. 44C shows a photograph image of one embodiment of a Chip with both channels attached to a reservoir and attachments for syringes fluidically connected by tubing (132) to a microchannel of a microfluidic chip (16) in turn fluidically connected to a reservoir (133).

FIG. 45A-C shows exemplary schematic diagrams for one embodiment of a Non Drug Absorbing Study Design: Pragmatic Approach. FIG. 45A shows one embodiment for a Pull Mode—Recirculate as Step 1: Pull 30 µL of media into the chip, exposing cells to freshly oxygenated media. A syringe (131) fluidically connected by tubing (132) to a microchannel (134) of a microfluidic chip (16) in turn fluidically connected to a reservoir (133). FIG. 45B shows one embodiment for exposing chips, i.e. cells, to a test compound as Step 2: Incubate for 1 minute, allowing exposure of cells to a test compound. FIG. 45C shows one embodiment for a Push Mode—Oxygen Exposure. Step 3: Push 30 µL of media into outlet, exposing media to oxygen. Then repeat Steps 1-3 as desired.

Data was collected on day 7. Albumin production in addition to cell death, e.g. ETHD-1 staining for permeabilized, i.e. dying/dead cells, was measured on day 7.

More specifically, before dosing (day 5 and earlier) the flow rate was 150 uL/hr in both the top and bottom channels. In some embodiments, the lower channel was seeded with endothelial cells. In some embodiments, both channels were recirculated/reciprocated simultaneously. On day 6 (for 24 hrs) the flow rate was changed as outlined in FIG. 45A-C for dosing the human hepatocytes with test compounds, i.e. cocktail of 0.5 uM Diazepam and 0.5 uM Amitriptyline (2 drugs at the same time). The flow rate during step 1 was 3600 uL/hr in one direction for 30 s, 0 uL/hr during step 2 for 1 min, and 3600 uL/hr in the opposite direction for step 3 for 30 s (which was immediately followed by step 1 again and repeated for 24 hrs).

Static plate control: The protocol used was the standard liver hepatocyte plate control protocol—media is replaced every 2 days (same media as chip) and chips were dosed with compound at the same concentration on day 6.

COP Liver-Chip Shows Comparable (High) Albumin Production to PDMS Liver-Chip.

COP chip initially under 150 uL/hr flow in one direction, followed by reciprocating flow for 24 hrs. EthD-1 staining was performed after rinsing chips. Surprisingly, after analyzing the albumin data it was discovered that liver cells on both PDMS and COP microfluidic chips showed comparable (high) albumin production, see, FIG. 47A. Further, in order to rule-out production from dying cells, hepatocytes were stained with EthD-1 on both chips, see FIG. 47C, showing a representative field of a healthy hepatocyte cell monolayer with the expected scattered dying or dead cells. In fact, for the first time, albumin production was unexpectedly measured within a physiologically relevant range indicating an increase in metabolic function of the liver cells. Although the cells were dosed with the test drug cocktail, the drugs did not appear to be influencing the increase in metabolic function caused by the recirculation method. In fact, additional albumin samples were collected and measured after returning the chips to single-pass/uni-directional flow (after reciprocating for 24 hrs), see results below.

Reciprocation Appears to Dramatically and Significantly Increase Albumin Production from Hepatic Cells in Both the PDMS and COP Liver-Chip.

Even more surprising was the discovery that the rate of albumin production increased dramatically both in comparison to previous experiments and also in comparison to the same chips from earlier in the experiment, see, FIG. 47A where the 150 uL/hr refers to albumin production in the same chip before reciprocation).

Thus, rapid reciprocation described herein caused a dramatic increase in albumin production compared to the same microfluidic Live On-Chip when fluid (i.e. nutrient media) was restored to flowing in one direction (i.e. one pass of the media) at 150 uL/hr. This result was so surprising additional experiments were done. Thus, in at least one embodiment, the chip was evaluated to find out whether it "returned" to lower rates of albumin production when the single direction fluid flow was used on the same cells that had been subject to reciprocating flow.

Albumin was measured from PDMS microfluidic Liver on-chip effluent before reciprocation (days 5 & 6), after reciprocation (day 8), and then after returning to single pass flow. After sampling the effluent on Day 6, fluid was reciprocated for 24 hrs while dosing cells with lorazepam/antipyrine at 0.5 uM during reciprocation, see. FIG. 47A. Again, surprisingly, the hepatic cells on-chip returned to producing lower levels of albumin after returning to the single pass flow rate, see FIG. 47B. Further, in the Day 8 sample, using reciprocating fluid flow at 3600 UL/hr, albumin production was measured on the high end of physiologically relevant range.

FIG. 47A-B shows graphs demonstrating hepatocyte viability and function as albumin production (ug/million cells/day) when media is recirculated. COP Liver-Chip shows comparable (high) albumin production to PDMS Liver-Chip after dosing with compounds during reciprocation. Comparative chips were not dosed. Chips were "perfused" with media each day during the experiment including both single-pass flow and reciprocation.

FIG. 47A shows exemplary data graphs comparing albumin production after 7 days of dosing. Static plates and microfluidic chips, constructed with PDMS or COP, are compared by several test conditions over time, albumin production after dosing with no recirculation, i.e. a single pass flow at 150 ul/hr. on Day 5 was compared to Day 7 albumin production with reciprocating flow 3600 uL/hr.

FIG. 47B shows exemplary data graphs comparing albumin production after dosing PDMS chips under conditions of a single pass flow at 150 ul/hr. on Days 5 and 6, then Day 8 production with reciprocating fluid flow at 3600 uL/hr compared to a single pass flow at 150 ul/hr. on Day 9.

FIG. 47C shows micrographs of liver cells on-chip on Day 7. Upper image is a bright field image while the lower image shows a colored immunofluorescent micrograph of dead cells stained with EthD-1 (red) and Hoechst stained nuclei (blue). Albumin measured before reciprocation (day 5) and after reciprocation (day 7) in the same chips (reciprocated for 24 hrs on day 6), see FIG. 47A-B.

These exemplary results support a linkage between the reciprocation protocol resulting in significantly increased albumin production and further support reversibility of these high levels to lower levels of albumin production on-chip. Thus, albumin production may be controlled within the same Liver On-Chip, such that when low-level albumin production is desired single pass nutrient media fluid flow may be used. When higher levels of albumen production are desired from the same Liver On-Chip then recirculation methods may be used to boost production levels. It is contemplated that by changing the length of recirculation time, that specific levels of albumen production from a Liver On-Chip may be obtained, i.e. tuned, using recirculation times up to 2 hrs; up to 6 hrs; up to 12 hrs; up to 24 hrs; up to 48 hrs; up to 72 hrs or more.

Thus, some embodiments are contemplated to use microfluidic chips/devices without effluent fluid recirculation. In other embodiments, microfluidic chips devices are contemplated for use with recirculation devices, see exemplary FIG. 44A-C and FIG. 45A-C. In other embodiments, microfluidic chips/devices are contemplated for use with recirculation devices in an incubation pod, see exemplary FIG. 46A-E. As nonlimiting examples, exemplary pods are described in US20170055522, herein incorporated by reference in its entirety.

Thus, in some embodiments, such recirculation devices are automated. In fact, additional embodiments are contemplated for recirculation devices, as described and shown in FIG. 46A-D. More specifically, a recirculation device as part of a pod operates by applying pressure to the inlet reservoir pushing fluid through tubing then through a microchannel in the chip where the effluent fluid enters the outlet reservoir. A shortcut channel is located in between the inlet and outlet reservoir has a check-valve that is closed for passing fluid through the chip to the outlet reservoir. To move fluid from the outlet to the inlet reservoir for recirculation, the outlet reservoir is then pressurized for pushing the fluid through a shortcut channel and the now open check-valve. The majority of fluid moves into the inlet reservoir as the path of least resistance through the open check valve. However, if in some embodiments it is decided that too much fluid is moving backwards through the fluid resistor of the backplane, then a check valve may be placed to prevent the effluent fluid from flowing back through the effluent port of the microfluidic chip.

FIG. 46A-E shows illustrations and diagrams for exemplary embodiments providing recirculation for chips incubated within a pod. FIG. 46A Inlet reservoir (135); outlet reservoir (136); check valve (137); lines indicate tubing (138) fluidically connecting reservoirs with one channel (70) in a microfluidic chip (16). FIG. 46B shows a more detailed illustration of one embodiment for incorporation of a check Valve into a Pod. Inlet reservoir (135); outlet reservoir (136); check valve (137); Shortcut channel in Pod fluid layer (139). FIG. 46C shows an illustration of an engineering drawing for one embodiment of a check valve (137) as an exemplary Duckbill Check Valve. FIG. 46D shows exemplary photographs of pod reservoirs. Inlet reservoir (135); outlet reservoir (136); Shortcut channel in Pod fluid layer (139); Shortcut channel vias into reservoirs (140). FIG. 46E shows an illustration of a side view of the check valve in FIG. 46C. Dimension a of FIG. 46C may be between 2.03 and 2.10 mm (.080 and 0.083 in) in one embodiment. Dimension b of FIG. 46C may be between 0.6 and 0.7 mm (0.022 and 0.026 in) in one embodiment. Dimensimon c of FIG. 46C may be at a minimum 3.1 mm in diameter (0.122 in) in one embodiment. Dimension d of FIG. 46C may be at a minimum of 1.4 mm in diameter (0.055 in) in one embodiment. Dimension e of FIG. 46C may be a minimum 3.3 mm(0.130 in) in one embodiment.

In summary, 150 uL/hr flow rate resulted in low albumin production for one embodiment of a Liver on-chip seeded with human hepatocytes in the upper channel and endothelial cells in the lower channel. Reciprocation as described herein, significantly improved albumin production in both PDMS and COP microfluidic chips. Therefore, in some embodiments, reciprocation is contemplated to increase function of cells seeded onto microfluidic chips as described herein. In other words, it is not meant to limit the type of microfluidic chip device for use with recirculation of effluent media. In fact, it is not meant to limit the use of such recirculation devices and methods to microfluidic Liver On-chips, such that other organ on-chips are contemplated for use including but not limited to Brain On-chips, etc.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in biochemistry, chemistry, microbiology, molecular biology, space biology, engineering and medicine, or related fields are intended to be within the scope of the following claims.

The invention claimed is:

1. A method of recirculating culture media through microfluidic devices, comprising:
    1) providing an assembly, comprising
        a) one or more reservoirs comprising cell culture media in fluidic communication with one or more microfluidic devices, said one or more microfluidic devices comprising
            i) first and second channels attached mammalian cells on a surface of said first or second channels and
            ii) inlet and outlet ports associated with said first and second channels, said inlet and outlet ports in fluidic communication with a recirculation pathway, said cells perfused with fluid; and
    2) causing culture media in said one or more reservoirs to flow into said one or more microfluidic devices, thereby causing fluid to exit as effluent from said outlet port of said first or second channels of one or more microfluidic devices, enter said recirculation pathway and directly enter an inlet port of said first or second channel, so that said effluent becomes incoming fluid.

2. The method of claim 1, wherein said surface is a microchannel.

3. The method of claim 1, wherein said surface is a membrane.

4. A method of recirculating culture media through a microfluidic device, comprising:
    a) providing an assembly, comprising
        i) an inlet reservoir and ii) an outlet reservoir connected by iii) a shortcut channel, said shortcut channel containing iv) a single valve, and said inlet and outlet reservoirs in fluidic communication with v) a microfluidic device, said inlet reservoir comprising fluid, said microfluidic device comprising inlet and outlet ports, one of said ports linked to one of said reservoirs through a resistor; and
    b) causing fluid in said inlet reservoir to flow into said inlet port of said microfluidic device while said valve is closed, thereby causing fluid to exit said outlet port of said one or more microfluidic devices and enter said outlet reservoir as recirculated fluid;
    c) causing said valve to open, thereby permitting said recirculated fluid in said outlet reservoir to move through said shortcut channel to said inlet reservoir; and
    d) causing said valve to close;
    e) flowing said recirculated fluid in said inlet reservoir into said inlet port of said microfluidic device.

5. The method of claim 4, wherein said fluid is moved in step b) with pressure.

6. The method of claim 4, wherein said single valve is a one-way check valve.

7. The method of claim 4, wherein the majority of fluid in step c) moves into the inlet reservoir through the open check valve as the path of least resistance.

8. The method of claim 4, wherein said microfluidic device further comprises cells.

* * * * *